United States Patent
Harvey et al.

(10) Patent No.: US 11,795,464 B2
(45) Date of Patent: *Oct. 24, 2023

(54) INDUCIBLE PRODUCTION-PHASE PROMOTERS FOR COORDINATED HETEROLOGOUS EXPRESSION IN YEAST

(71) Applicant: The Board of Trustees of the Leland Stanford Junior University, Stanford, CA (US)

(72) Inventors: Colin Harvey, Mountain View, CA (US); Ulrich Schlecht, Sunnyvale, CA (US); Maureen Elizabeth Hillenmeyer, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 791 days.

This patent is subject to a terminal disclaimer.

(21) Appl. No.: 16/796,851

(22) Filed: Feb. 20, 2020

(65) Prior Publication Data

US 2020/0291411 A1 Sep. 17, 2020

Related U.S. Application Data

(63) Continuation of application No. 15/469,452, filed on Mar. 24, 2017, now Pat. No. 10,612,032.

(60) Provisional application No. 62/313,108, filed on Mar. 24, 2016.

(51) Int. Cl.
| | |
|---|---|
| *C12N 15/81* | (2006.01) |
| *C12N 15/11* | (2006.01) |
| *C12N 1/19* | (2006.01) |
| *C12N 15/63* | (2006.01) |

(52) U.S. Cl.
CPC ........... *C12N 15/81* (2013.01); *C12N 15/635* (2013.01)

(58) Field of Classification Search
None
See application file for complete search history.

(56) References Cited

U.S. PATENT DOCUMENTS

| | | | |
|---|---|---|---|
| 4,876,197 | A | 10/1989 | Burke et al. |
| 5,672,491 | A | 9/1997 | Khosla et al. |
| 6,358,733 | B1 | 3/2002 | Motwani et al. |
| 7,172,886 | B2 | 2/2007 | Keasling et al. |
| 9,512,431 | B2 | 12/2016 | Temme et al. |
| 10,612,032 | B2 | 4/2020 | Harvey et al. |
| 2004/0171154 | A1 | 9/2004 | Storici et al. |
| 2007/0061084 | A1 | 3/2007 | Farnet et al. |
| 2007/0224208 | A1 | 9/2007 | Guo et al. |
| 2010/0272698 | A1 | 10/2010 | Stateva et al. |
| 2012/0045809 | A1 | 2/2012 | Buelter |
| 2013/0237435 | A1 | 9/2013 | Machida et al. |
| 2014/0273144 | A1 | 9/2014 | Hawkins |
| 2014/0342416 | A1 | 11/2014 | Jansen et al. |
| 2015/0275200 | A1 | 10/2015 | Jayaprakash et al. |
| 2015/0310168 | A1 | 10/2015 | Machida et al. |
| 2016/0213767 | A1 | 7/2016 | King et al. |
| 2017/0022532 | A1 | 1/2017 | Seyedsayamdost |
| 2017/0275635 | A1 | 9/2017 | Harvey et al. |
| 2018/0355020 | A1 | 12/2018 | Anchel |
| 2020/0040347 | A1 | 2/2020 | Naughton et al. |
| 2021/0230611 | A1 | 7/2021 | Naughton et al. |

FOREIGN PATENT DOCUMENTS

| | | |
|---|---|---|
| CN | 110268057 A | 9/2019 |
| EP | 3541936 A2 | 9/2019 |
| HK | 40011835 A | 7/2020 |
| MX | 2019005701 A | 10/2019 |
| WO | 1992013963 A1 | 8/1992 |
| WO | 2018094110 A2 | 5/2018 |
| WO | 2018094110 A3 | 8/2018 |
| WO | 2019055816 A1 | 3/2019 |

OTHER PUBLICATIONS

Gasmi et al, The Switch from Fermentation to Respiration in *Saccharomyces cerevisiae* Is Regulated by the Ert1 Transcriptional Activator/Repressor, Genetics, vol. 198, 547-560 Oct. 2014.*
Shen et al, Development and characterization of a vector set with regulated promoters for systematic metabolic engineering in *Saccharomyces cerevisiae*, Yeast 2012; 29: 495-503.*
Weinhandl et al, Carbon source dependent promoters in yeasts, Microbial Cell Factories 2014, pp. 1-17.*
Vickers et al, Dual gene expression cassette vectors with antibiotic selection markers for engineering in *Saccharomyces cerevisiae*, 2013, pp. 1-10.*
Young et al, Evolution of a glucose-regulated ADH gene in the genus *Saccharomyces*, Gene 245 (2000) 299-309.*
Partow et al, Characterization of different promoters for designing a new expression vector in *Saccharomyces cerevisiae*, 2010, pp. 955-964.*
O'Brien et al., "Computational identification and analysis of orphan assembly-line polyketide synthases", The Journal of Antibiotics, 2014, vol. 67, pp. 89-97, published online Dec. 4, 2013, doi:10.1038/ja.2013.125.
FBP1/YLR377C Sequence, downloaded Jul. 31, 2019, 7 pgs.
S.cerevisiae chromosome XI reading frame ORF YKR097w, downloaded Jul. 31, 2019, 2 pgs.
UniProtKB, pp. 1-3, downloaded Jan. 22, 2019.

(Continued)

*Primary Examiner* — Maria Marvich
(74) *Attorney, Agent, or Firm* — KPPB LLP

(57) ABSTRACT

Inducible promoters for the coordinated expression of at least one heterologous gene in yeast and methods of using them are disclosed. In particular, the invention relates to sets of inducible promoters derived from *S. cerevisiae* and related species that can be induced in the presence of nonfermentable carbon sources.

15 Claims, 16 Drawing Sheets
(13 of 16 Drawing Sheet(s) Filed in Color)
Specification includes a Sequence Listing.

(56) References Cited

OTHER PUBLICATIONS

Baym et al., "Inexpensive Multiplexed Library Preparation for Megabase-Sized Genomes", PLoS One, vol. 10, No. 5, May 22, 2015, 15 pgs., doi: 10.1037/journal.pone.0128036.
Blin et al., "antiSMASH 2.0—a versatile platform for genome mining of secondary metabolite producers", Nucleic Acids Research, vol. 41, Jun. 3, 2013, W204-W212, doi:10.1093/nar/gk1449.
Botstein et al., "Yeast: an experimental organism for 21$^{st}$ century biology", Genetics, vol. 189, No. 3, Nov. 1, 2011, pp. 695-704.
Bowman, Brian R., "Rapid Engineering of Secondary Metabolite Gene Clusters in the Genomic Era. Presentation", SIMB. Warp Drive Bio. Aug. 2015. 26 pages.
Brachmann et al., "Designer deletion strains derived from *Saccharomyces cerevisiae* S288C: A useful set of strains and plasmids for PCR-mediated gene disruption and other applications", Yeast, vol. 14, Jan. 30, 1998, pp. 115-132.
Gaisne et al., "A 'natural' mutation in *Saccharomyces cerevisiae* strains derived from S288c affects the complex regulatory gene HAP1 (CYP1)", Current Genetics, Oct. 1999, vol. 36, pp. 195-200.
Gertz et al., "Composition-based statistics and translated nucleotide searches: Improving the TBLASTN module of BLAST", BMC Biology, Dec. 7, 2006, vol. 4, No. 41, 14 pgs., doi:10.1186/1741-7007-4-41.
Li et al., "Comprehensive curation and analysis of fungal biosynthetic gene clusters of published natural products", Fungal Genetics and Biology, vol. 89, Apr. 2016, pp. 18-28, doi: doi: 10.1016/j.fgb.2016.01.012.
Robinson, Keith, "Surveying Thousands of Actinomycete Genomes for Novel Biosynthetic Clusters", Presentation. Society of Industrial Microbiology and Biotechnology Annual Meeting, New Orleans. Warp Drive Bio., 2016, v.05.16, 20 pgs.
Storici et al., "The Delitto Perfetto Approach to In Vivo Site-Directed Mutagenesis and Chromosome Rearrangements with Synthetic Oligonucleotides in Yeast", Methods in Enzymology, vol. 409, 2006, pp. 329-345, DOI: 10.1016/S0076-6879(05)09149-1.
"*Saccharomyces cerevisiae*", American Type Culture Collection (ATCC) Product Sheet, 208288, 2017, 2 pgs.
"*Saccharomyces cerevisiae*", American Type Culture Collection (ATCC) Product Sheet, 4001213, 2016, 2 pgs.
Belli et al., "An activator/repressor dual system allows tight tetracycline-regulated gene expression in budding yeast", Nucleic Acids Research, vol. 26, No. 4, 1998, pp. 942-947.
Botstein et al., "Yeast as a Model Organism", Science, vol. 277, No. 5330, Aug. 29, 1997, pp. 1259-1260.
Buijs et al., "Advanced biofuel production by the yeast *Saccharomyces cerevisiae*", Current Opinion in Chemical Biology, vol. 17, No. 3, Jun. 2013, Electronic Publication: Apr. 27, 2013, pp. 480-488.
Chooi et al., "A Cytochrome P450 Serves as an Unexpected Terpene Cyclase during Fungal Meroterpenoid Biosynthesis", Journal of the American Chemical Society, vol. 135, No. 45, Nov. 13, 2013, 12 pgs.
Christianson et al., "Multifunctional yeast high-copy-number shuttle vectors", Gene, vol. 110, No. 1, Jan. 2, 1992, pp. 119-122.
Da Silva et al., "Introduction and expression of genes for metabolic engineering applications in *Saccharomyces cerevisiae*", FEMS Yeast Research, vol. 12, No. 2, Mar. 1, 2012, pp. 197-214.
Daran-Lapujade et al., "Role of Transcriptional Regulation in Controlling Fluxes in Central Carbon Metabolism of *Saccharomyces cerevisiae*", The Journal of Biological Chemistry, vol. 279, No. 10, Mar. 5, 2004, pp. 9125-9138.
De Kok et al., "Rapid and Reliable DNA Assembly via Ligase Cycling Reaction", ACS Synthetic Biology, vol. 3, No. 2, Feb. 21, 2014, Electronic Publication: Jan. 15, 2014, pp. 97-106.
Dimitrov et al., "Polymorphisms in multiple genes contribute to the spontaneous mitochondrial genome instability of *Saccharomyces cerevisiae* S288C strains", Genetics 183, 2008, pp. 365-383.
Galanie et al., "Complete biosynthesis of opioids in yeast", Science, vol. 349, No. 6252, Sep. 4, 2015, pp. 1095-1100.
Gibson et al., "Chemical synthesis of the mouse mitochondrial genome", Nature Methods, vol. 7, No. 11, Nov. 2010, pp. 901-903.
Gibson et al., "Enzymatic assembly of DNA molecules up to several hundred kilobases", Nature Methods, vol. 6, No. 5, May 2009, pp. 343-345.
Gietz et al., "High-efficiency yeast transformation using the LiAc/SS carrier DNA/PEG method", Nature Protocols, vol. 2, No. 1, 2007, pp. 31-34.
Guo et al., "Recent advances in genome mining of secondary metabolites in Aspergillus terreus", Frontiers in Microbiology, Dec. 23, 2014, vol. 5, Article 717, 13 pgs., doi: 10.3389/fmicb.2014.00717.
Hinnen et al., "Transformation of yeast", Proceedings of the National Academy of Sciences of the United States of America, vol. 75, No. 4, Apr. 1978, pp. 1929-1933.
Horecka et al., "The 50:50 method for PCR-based seamless genome editing in yeast", Yeast, Mar. 2014, Published Online: Nov. 29, 2013, vol. 31, No. 3, pp. 103-112, DOI:10.1002/yea.2992.
Johnston et al., "Sequences That Regulate the Divergent GAL1-GAL10 Promoter in *Saccharomyces cerevisiae*", Molecular and Cellular Biology, vol. 4, No. 8, Aug. 1984, pp. 1440-1448.
Kim et al., "Cloning large natural product gene clusters from the environment: Piecing environmental DNA gene clusters back together with TAR", Biopolymers, Sep. 2010, First Published: Jun. 23, 2010, vol. 93, No. 9, pp. 833-844, https://doi.org/10.1002/bip.21450.
Kim et al., "Screening of Yeast Diauxic Promoters for Production of Foreign Proteins", Journal of Microbiology and Biotechnology, vol. 16, No. 9, 2006, pp. 1459-1463.
Kuijpers et al., "A versatile, efficient strategy for assembly of multi-fragment expression vectors in *Saccharomyces cerevisiae* using 60 bp synthetic, recombination sequences", Microbial Cell Factories, vol. 12, No. 47, May 10, 2013, 13 pgs.
Lee et al., "A Highly Characterized Yeast Toolkit for Modular, Multipart Assembly", ACS Synthetic Biology, vol. 4, No. 9, Apr. 14, 2015, pp. 975-986.
Lee et al., "Evaluation of the *Saccharomyces cerevisiae* ADH2 promoter for protein synthesis", Yeast, vol. 22, No. 6, Apr. 30, 2005, First Published: Apr. 22, 2005, pp. 431-440.
Liang et al., "Coordinated induction of multi-gene pathways in *Saccharomyces cerevisiae*", Nucleic Acids Research, vol. 41, No. 4, 2013, Published online: Dec. 22, 2012, 10 pgs.
Medema et al., "antiSMASH: rapid identification, annotation and analysis of secondary metabolite biosynthesis gene clusters in bacterial and fungal genome sequences", Nucleic Acids Research, Jul. 1, 2011, First Published: Jun. 14, 2011, vol. 39, No. suppl 2, pp. W339-W346, https://doi.org/10.1093/nar/gkr466.
Montiel et al., "Yeast homologous recombination-based promoter engineering for the activation of silent natural product biosynthetic gene clusters", Proc Natl Acad Sci U S A, Jul. 21, 2015, vol. 112, No. 29, pp. 8953-8958.
Mumberg et al., "Yeast vectors for the controlled expression of heterologous proteins in different genetic backgrounds", Gene, vol. 156, No. 1, Apr. 14, 1995, pp. 119-122.
Negritto et al., "Influence of DNA Sequence Identity on Efficiency of Targeted Gene Replacement", Molecular and Cellular Biology, vol. 17, No. 1, Jan. 1997, pp. 278-286.
Peng et al., "Controlling heterologous gene expression in yeast cell factories on different carbon substrates and across the diauxic shift: a comparison on yeast promoter activities", Microbial Cell Factories, vol. 14, No. 91, Jun. 26, 2015, 11 pgs.
Pscheidt et al., "Yeast cell factories for fine chemical and API production", Microbial Cell Factories, vol. 7, No. 25, Aug. 7, 2008, 36 pgs.
Reeves et al., "Genes for the Biosynthesis of the Fungal Polyketides Hypothemycin from Hypomyces subiculosus and Radicicol from Pochonia chlamydosporia", Applied and Environmental Microbiology, vol. 74, No. 16, Aug. 2008, pp. 5121-5129.
Ro et al., "Production of the antimalarial drug precursor artemisinic acid in engineered yeast", Nature, vol. 440, No. 7086, Apr. 13, 2006, pp. 940-943.
Scannell et al., "The Awesome Power of Yeast Evolutionary Genetics: New Genome Sequences and Strain Resources for the *Sac-

(56) References Cited

OTHER PUBLICATIONS charomyces sensu stricto Genus", G3: Genes, Genomes, Genetics, vol. 1, No. 1, Jun. 2011, pp. 11-25.

Shao et al., "DNA assembler, an in vivo genetic method for rapid construction of biochemical pathways", Nucleic Acids Research, vol. 37, No. 2, Feb. 2009, Published Online: Dec. 12, 2008, 10 pgs.

Smith et al., "A method for high-throughput production of sequence-verified DNA libraries and strain collections", Molecular Systems Biology, Feb. 1, 2017, vol. 13, No. 2, Article 913, 15 Pgs., DOI 10.15252/msb.20167233.

Steen et al., "Metabolic engineering of *Saccharomyces cerevisiae* for the production of n-butanol", Microbial Cell Factories, vol. 7, No. 36, Dec. 3, 2008, 8 pgs.

Stinchcomb et al., "Isolation and characterisation of a yeast chromosomal replicator", Nature, vol. 282, Nov. 1, 1979, pp. 39-43.

Studier et al., "Protein production by auto-induction in high-density shaking cultures", Protein Expression and Purification, vol. 41, No. 1, May 2005, pp. 207-234.

Sun et al., "Cloning and Characterization of a Panel of Constitutive Promoters for Applications in Pathway Engineering in *Saccharomyces cerevisiae*", Biotechnology and Bioengineering, vol. 109, No. 8, Aug. 2012, Electronic Publication: Mar. 15, 2012, pp. 2082-2092.

Tang et al., "Discovery of Unclustered Fungal Indole Diterpene Biosynthetic Pathways through Combinatorial Pathway Reassembly in Engineered Yeast", Journal of the American Chemical Society, vol. 137, No. 43, Nov. 4, 2015, pp. 13724-13727.

Weber et al., "antiSMASH 3.0—a comprehensive resource for the genome mining of biosynthetic gene clusters", Nucleic Acids Research, Jul. 1, 2015, vol. 43, No. W1, pp. W237-W243.

Weinhandl et al., "Carbon source dependent promoters in yeasts", Microbial Cell Factories, vol. 13, No. 5, Jan. 9, 2014, 17 pgs.

Xu et al., "Bidirectional promoters generate pervasive transcription in yeast", Nature, vol. 457, No. 7232, Feb. 19, 2009, Published Online: Jan. 25, 2009, pp. 1033-1037.

Yu et al., "Adjacent Upstream Activation Sequence Elements Synergistically Regulate Transcription of ADH2 in *Saccharomyces cerevisiae*", Molecular and Cellular Biology, vol. 9, No. 1, Jan. 1989, pp. 34-42.

Buren et al., "Formation of Nitrogenase NifDK Tetramers in the Mitochondria of *Saccharomyces cerevisiae*", ACS Synthetic Biology, Feb. 21, 2017, vol. 6, No. 6, pp. 1043-1055, DOI: 10.1021/acssynbio.6b00371.

Deutschbauer et al., "Quantitative trait loci mapped to single-nucleotide resolution in yeast", Nature Genetics, Nov. 6, 2005, vol. 37, pp. 1333-1340, DOI: https://doi.org/10.1038/ng1674.

Jones, "Tackling the protease problem in *Saccharomyces cerevisiae*", Methods in Enzymology, 1991, vol. 194, pp. 428-453, https://doi.org/10.1016/0076-6879(91)94034-A.

Keller et al., "Translating biosynthetic gene clusters into fungal armor and weaponry", Nature Chemical Biology, Aug. 18, 2016, vol. 11, pp. 671-677, DOI: https://doi.org/10.1038/nchembio.1897.

Labbe et al., "Copper ion inducible and repressible promoter systems in yeast", Methods in Enzymology, 1999, vol. 306, pp. 145-153, https://doi.org/10.1016/S0076-6879(99)06010-3.

Lee et al., "Determination of the extent of phosphopantethelnylation of polyketide synthases expressed in *Escherichia coli* and *Saccharomyces cerevisiae*", Analytical Biochemistry, Nov. 1, 2009, vol. 394, No. 1, pp. 75-80, https://doi.org/10.1016/j.ab.2009.07.010.

Liu et al., "Rapid customised operon assembly by yeast recombinational cloning", Applied Microbiology and Biotechnology, Jun. 2017, vol. 101, No. 11, pp. 4569-4580, DOI: https://doi.org/10.1007/s00253-017-8213-9.

Mattoon et al., "Effects of hap mutations on heme and cytochrome formation in yeast", Current Genetics, Feb. 1990, vol. 17, No. 2, pp. 179-183, DOI: https://doi.org/10.1007/BF00312865.

Ostergaard et al., "Physiological studies in aerobic batch cultivations of *Saccharomyces cerevisiae* strains harboring the MEL1 gene", Biotechnology and Bioengineering, May 5, 2000, First Published: Mar. 31, 2000, vol. 68, No. 3, pp. 2.52-259, https://doi.org/10.1002/(SICI)1097-0290(20000505)68:3<252::AID-BIT3>3.0.CO;2-K.

Ronicke et al., "Use of conditional promoters for expression of heterologous proteins in *Saccharomyces cerevisiae*", Methods in Enzymology, 1997, vol. 283, pp. 313-322, https://doi.org/10.1016/S0076-6879(97)83025-X.

Rutledge et al., "Discovery of microbial natural products by activation of silent biosynthetic gene clusters", Nature Reviews Microbiology, Aug. 2015, vol. 13, No. 8, pp. 509-523, DOI: https://doi.org/10.1038/nrmicro3496.

Blin et al., "The AntiSMASH Database, a Comprehensive Database of Microbial Secondary Metabolite Biosynthetic Gene Clusters", Nucleic Acids Research, 2017, 45 (D1), pp. D555-D559.

Najmanova et al., "Sequence Analysis of Porothramycin Biosynthetic Gene Cluster", Folia Microbiologica, 2014, 59 (6), pp. 543-552.

"Cloning vector sequence (*E. coli*/yeast/phage P1) ADH2 gene, promoter; beta-lactamase gene; TRP1 gene; CYC1 gene, terminator; and two replication origins", GenBank Accession No. L11060. Version No. L11060.1. Record created Jul. 26, 1993. 3 pages. Retrieved May 17, 2023 at URLL: https://www.ncbi.nlm.nih.gov/nuccore/L11060.

"ICL1 isocitrate lyase 1 [ *Saccharomyces cerevisiae* S288C ]", Gene ID: 856794. Updated Apr. 14, 2023. 5 pages. Retrieved May 17, 2023 at URL: https://www.ncbi.nlm.nih.gov/gene/856794.

"S. Cerevisiae promoter region of PCK1 gene", GenBank Accession No. X68938 S46233. Version No. X68938.1. Updated Aug. 11, 2005. 1 page. Retrieved May 17, 2023 at URL: https://www.ncbi.nlm.nih.gov/nuccore/X68938.

"*Saccharomyces bayanus* alcohol dehydrogenase isozyme 2 gene, partial cds", GenBank Accession No. AF218306. Version No. AF218306.1. Record created Mar. 16, 2000. 2 pages. Retrieved May 17, 2023 at URL: https://www.ncbi.nlm.nih.gov/nuccore/AF218306.

"*Saccharomyces cerevisiae* strain B1 malate synthase (MLS1) gene, partial cds", GenBank Accession No. AY942279. Version No. AY942279.1. Record created Jun. 28, 2005. 2 pages. Retrieved May 17, 2023 at URL: https://www.ncbi.nlm.nih.gov/nuccore/AY942279.

"*Saccharomyces cerevisiae* YJM1202 chromosome XIV sequence", GenBank Accession No. CP005533. Version No. CP005533.2. Updated May 23, 2016. 286 pages. Retrieved May 17, 2023 at URL: https://www.ncbi.nlm.nih.gov/nuccore/CP005533.

Alanjary et al., "The Antibiotic Resistant Target Seeker (ARTS), an Exploration Engine for Antibiotic Cluster Prioritization and Novel Drug Target Discovery", Nucleic Acids Research 2017, 45 (W1), W42-W48.

Breinbauer et al., "From Protein Domains to Drug Candidates-Natural Products as Guiding Principles in the Design and Synthesis of Compound Libraries", Angewandte Chemie International Edition 2002, 41 (16), 2878-2890.

Koonin et al., "Chapter 2 Evolutionary Concept in Genetics and Genomics", Sequence-Evolution-Function: Computational Approaches in Comparative Genomics. Boston: KluwerAcademic; 2003.

Medema et al., "Minimum Information about a Biosynthetic Gene cluster", Nature Chemical Biology, 2015, vol. 11, pp. 625-631.

Reeck et al., ""Homology" in Proteins and Nucleic Acids: A Terminology Muddle and a Way out of It", Cell, Aug. 28, 1987, vol. 50, 667.

Weber et al., "The Secondary Metabolite Bioinformatics Portal: Computational Tools to Facilitate Synthetic Biology of Secondary Metabolite Production", Synthetic and Systems Biotechnology 2016, 1 (2), 69-79.

* cited by examiner

INDUCIBLE PRODUCTION-PHASE PROMOTERS FOR COORDINATED HETEROLOGOUS EXPRESSION IN YEAST

CROSS REFERENCE TO RELATED APPLICATIONS

This current application is a continuation of U.S. patent application Ser. No. 15/469,452, filed Mar. 24, 2017, entitled "Inducible Production-Phase Promoters for Coordinated Heterologous Expression in Yeast" to Harvey et al., which claims priority under 35 U.S.C. 119(e) to U.S. Provisional Application Ser. No. 62/313,108, filed Mar. 24, 2016, the disclosures of which are each incorporated herein by reference in its entirety.

STATEMENT REGARDING FEDERALLY SPONSORED RESEARCH OR DEVELOPMENT

This invention was made with Government support under contract GM110706 awarded by the National Institutes of Health. The Government has certain rights in the invention.

REFERENCE TO A SEQUENCE LISTING SUBMITTED ELECTRONICALLY VIA EFS-WEB

The instant application contains a Sequence Listing which has been filed electronically in ASCII format and is hereby incorporated by reference in its entirety. Said ASCII copy, created on Jun. 3, 2020, is named "05041CONseqlist_ST25.txt" and is 104 bytes in size.

FIELD OF THE INVENTION

The invention is generally directed to systems and constructs for heterologous expression in yeast, and more specifically to a set of inducible promoters that can be combined for coordinated expression of multiple genes and methods related to their construction and use.

BACKGROUND

*Saccharomyces* (*S.*) is a genus of fungi composed of different yeast species. The genus can be divided into two further subgenera *S. sensu stricto* and *S. sensu lato*. The former have relatively similar characteristics, including the ability to interbreed, exhibiting uniform karyotype of sixteen chromosomes, and their use in the fermentation industry. The later are more diverse and heterogeneous. Of particular importance is the *S. cerevisiae* species within the *S. sensu stricto* subgenus, which is a popular model organism used for genetic research.

The yeast *S. cerevisiae* is a powerful host for the heterologous expression of biosynthetic systems, including production of biofuels, commodity chemicals, and small molecule drugs. The yeast's genetic tractability, ease of culture at both small and large scale, and a suite of well-characterized genetic tools make it a desirable system for heterologous expression. Occasionally, production systems require coordinated expression of two or more heterologous genes. Coordinated expression systems in bacteria (e.g., *E. coli*) has long exploited the operon structure of bacterial gene clusters (e.g., lac operon), allowing a single promoter to control the expression of multiple genes. The construction of synthetic operons therefore allows a single inducible promoter to control the timing and strength of expression of an entire synthetic system. In yeast, many heterologous-expression systems do not rely on the operon system, but instead rely on a one-promoter, one-gene paradigm. Accordingly, multi-gene heterologous expression in most yeast strains is performed using multiple expression cassettes with a well-characterized promoter and terminator, each on a single expression vector (e.g., plasmid DNA) (See D. Mumberg, R. Muller, and M. Funk *Gene* 156:119-22, 1995, which is incorporated herein by reference). With traditional restriction-ligation cloning, it is also possible to recycle a promoter on a single plasmid by the serial cloning of multiple genes (M. C. Tang, et al., *J Am Chem Soc* 137:13724-27, 1995).

SUMMARY OF THE INVENTION

Many embodiments of the invention are directed to a DNA molecule composition comprising at least one exogenous DNA vector comprising at least two different production-phase promoters; wherein the two production-phase promoters are each capable of repressing heterologous expression of an exogenous gene in a *Saccharomyces cerevisiae* cell when the *S. cerevisiae* cell predominantly exhibits anaerobic energy metabolism; and wherein the two production-phase promoters are each also capable of inducing heterologous expression of the exogenous gene in the *S. cerevisiae* cell when the *S. cerevisiae* cell predominantly exhibits aerobic energy metabolism.

In further embodiments the at least one exogenous DNA vector further comprising a heterologous gene; wherein the heterologous gene Sequence is derived from a species other than *S. cerevisiae*; and wherein the heterologous gene is situated proximately downstream of one of the two production promoters such that the heterologous gene expression can be repressed and induced by the production promoter that is proximately upstream from the heterologous gene.

In more embodiments, the anaerobic energy metabolism is defined by the catabolism of a fermentable carbon source.

In further more embodiments, the fermentable carbon source is glucose or dextrose.

In even further more embodiments, the aerobic energy metabolism is defined by the catabolism of a nonfermentable carbon source.

In even further more embodiments, the nonfermentable carbon source is ethanol or glycerol.

In even further more embodiments, the DNA molecule compositions further comprise a *S. cerevisiae* cell, wherein the exogenous DNA vector exists within the *S. cerevisiae* cell.

In even further more embodiments, at least one of the at least two production phase promoters comprises a sequence of an endogenous production-phase promoter of *S. cerevisiae*.

In even further more embodiments, the production-phase promoter is substantially similar to a sequence selected from the group consisting of the *S. cerevisiae* ADH2 promoter (Seq. ID No. 1), *S. cerevisiae* PCK1 promoter (Seq. ID No. 2), the *S. cerevisiae* MLS1 promoter (Seq. ID No. 3), the *S. cerevisiae* ICU promoter (Seq. ID No. 4), the *S. cerevisiae* YLR307C-A promoter (Seq. ID No. 5), the *S. cerevisiae* YGRO67C promoter (Seq. ID No. 6), the *S. cerevisiae* IDP2 promoter (Seq. ID No. 7), the *S. cerevisiae* ADY2 promoter (Seq. ID No. 8), the *S. cerevisiae* GAC1 promoter (Seq. ID No. 9), the *S. cerevisiae* ECM13 promoter (Seq. ID No. 10), the *S. cerevisiae* FAT3 promoter (Seq. ID No. 11), the *S. cerevisiae* PUT1 promoter (Seq. ID No. 12), the *S. cerevisiae* NQM1 promoter (Seq. ID No. 13), the *S. cerevisiae* SFC1 promoter (Seq. ID No. 14), the *S. cerevisiae* JEN1 promoter (Seq. ID No. 15), the *S. cerevisiae* SIP18 promoter (Seq. ID No. 16), the *S. cerevisiae* ATO2 promoter (Seq. ID No. 17), the *S. cerevisiae* YIG1 promoter (Seq. ID No. 18), and the *S. cerevisiae* FBP1 promoter (Seq. ID No. 19).

In even further more embodiments, at least one of the at least two production phase promoters comprises a Sequence of an exogenous production-phase promoter of *S. cerevisiae*.

In even further more embodiments, the production-phase promoter is substantially similar to a sequence selected from the group consisting of the *S. paradoxus* ADH2 promoter (Seq. ID No. 36), the *S. kudriavzevii* ADH2 promoter (Seq. ID No. 37), *S. bayanus* ADH2 promoter (Seq. ID No.38), *S. paradoxus* PCK1 promoter (Seq. ID No. 41), the *S. kudriavzevii* PCK1 promoter (Seq. ID No. 42), *S. bayanus* PCK1 promoter (Seq. ID No. 43), *S. paradoxus* MLS1 promoter (Seq. ID No. 44), the *S. kudriavzevii* MLS1 promoter (Seq. ID No. 45), *S. bayanus* MLS1 promoter (Seq. ID No. 46), *S. paradoxus* ICL1 promoter (Seq. ID No. 47), the *S. kudriavzevii* ICL1 promoter (Seq. ID No. 48), and *S. bayanus* ICL1 promoter (Seq. ID No. 49).

Many embodiments are directed to at least one exogenous DNA vector comprising a production-phase promoter, wherein the production-phase promoter is substantially similar to a sequence selected from the group consisting of the *S. cerevisiae* PCK1 promoter (Seq. ID No. 2), the *S. cerevisiae* MLS1 promoter (Seq. ID No. 3), the *S. cerevisiae* ICL1 promoter (Seq. ID No. 4), the *S. cerevisiae* YLR307C-A promoter (Seq. ID No. 5), the *S. cerevisiae* YGRO67C promoter (Seq. ID No. 6), the *S. cerevisiae* IDP2 promoter (Seq. ID No. 7), the *S. cerevisiae* ADY2 promoter (Seq. ID No. 8), the *S. cerevisiae* GAC1 promoter (Seq. ID No. 9), the *S. cerevisiae* ECM13 promoter (Seq. ID No. 10), the *S. cerevisiae* FAT3 promoter (Seq. ID No. 11), the *S. cerevisiae* PUT1 promoter (Seq. ID No. 12), the *S. cerevisiae* NQM1 promoter (Seq. ID No. 13), the *S. cerevisiae* SFC1 promoter (Seq. ID No. 14), the *S. cerevisiae* JEN1 promoter (Seq. ID No. 15), the *S. cerevisiae* SIP18 promoter (Seq. ID No. 16), the *S. cerevisiae* ATO2 promoter (Seq. ID No. 17), the *S. cerevisiae* YIG1 promoter (Seq. ID No. 18), the *S. cerevisiae* FBP1 promoter (Seq. ID No. 19), the *S. paradoxus* ADH2 promoter (Seq. ID No. 36), the *S. kudriavzevii* ADH2 promoter (Seq. ID No. 37), *S. bayanus* ADH2 promoter (Seq. ID No.38), *S. paradoxus* PCK1 promoter (Seq. ID No. 41), the *S. kudriavzevii* PCK1 promoter (Seq. ID No. 42), *S. bayanus* PCK1 promoter (Seq. ID No. 43), *S. paradoxus* MLS1 promoter (Seq. ID No. 44), the *S. kudriavzevii* MLS1 promoter (Seq. ID No. 45), *S. bayanus* MLS1 promoter (Seq. ID No. 46), *S. paradoxus* ICL1 promoter (Seq. ID No. 47), the *S. kudriavzevii* ICL1 promoter (Seq. ID No. 48), and *S. bayanus* ICL1 promoter (Seq. ID No. 49).

In further embodiments, the selected production-phase promoter is substantially similar to the *S. cerevisiae* PCK1 promoter sequence (Seq. ID No. 2).

In more embodiments, the selected production-phase promoter is substantially similar to the *S. cerevisiae* MLS1 promoter sequence (Seq. ID No. 3).

In further more embodiments, the selected production-phase promoter is substantially similar to the *S. cerevisiae* ICL1 promoter sequence (Seq. ID No. 4).

In even further more embodiments, the selected production-phase promoter is substantially similar to a sequence selected from the group consisting of the *S. paradoxus* ADH2 promoter (Seq. ID No. 36), the *S. kudriavzevii* ADH2 promoter (Seq. ID No. 37), and *S. bayanus* ADH2 promoter (Seq. ID No. 38).

In even further more embodiments, the selected the production-phase promoter is substantially similar to a sequence selected from the group consisting of *S. paradoxus* PCK1 promoter (Seq. ID No. 41), the *S. kudriavzevii* PCK1 promoter (Seq. ID No. 42), *S. bayanus* PCK1 promoter (Seq. ID No. 43), *S. paradoxus* MLS1 promoter (Seq. ID No. 44), the *S. kudriavzevii* MLS1 promoter (Seq. ID No. 45), *S. bayanus* MLS1 promoter (Seq. ID No. 46), *S. paradoxus* ICL1 promoter (Seq. ID No. 47), the *S. kudriavzevii* ICL1 promoter (Seq. ID No. 48), and *S. bayanus* ICL1 promoter (Seq. ID No. 49).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The description will be more fully understood with reference to the following figures and data graphs, which are presented as exemplary embodiments of the invention and should not be construed as a complete recitation of the scope of the invention.

BRIEF DESCRIPTION OF THE SEQUENCE LISTING

The current disclosure incorporates a sequence listing in accordance with the WIPO Standard ST.25. The Sequence listing embodies sixty-six nucleic acid sequences (Seq ID Nos, 1-66), which are referenced in Table 3 and throughout the specification.

DETAILED DESCRIPTION

Turning now to the drawings and data, embodiments of the invention are generally directed to systems and constructs of heterologous expression during the production phase of yeast. In many of these embodiments, the expression system involves coordinated expression of multiple heterologous genes. More embodiments are directed to production-phase promoter systems having promoters that are inducible upon an event in the yeast's growth or by the nutrients and supplements provided to the yeast. Specifically, a number of embodiments are directed to the promoters that are capable of being repressed in the presence of glucose and/or dextrose. In more embodiments, the promoters are capable of being induced in the presence of glycerol and/or ethanol. In additional embodiments, at least one production-phase promoter exists within an exogenous DNA vector, such as (but not limited to), for example, a shuttle vector, cloning vector, and/or expression vector. Embodiments are also directed to the use of expression vectors for the expression of heterologous genes in a yeast expression system.

Controlled gene expression is desirable in heterologous expression systems. For example, it would be desirable to express heterologous genes for production during a longer stable phase. Accordingly, decoupling the anaerobic growth and aerobic production phases of a culture allows the yeast to grow to high density prior to introducing the metabolic stress of expressing unnaturally high amounts of heterologous protein. In accordance with many embodiments, the anaerobic growth phase is defined by the yeast culture's energy metabolism in which the yeast cells predominantly catabolize fermentable carbon sources (e.g., glucose and/or dextrose), and a high growth rate (i.e., short doubling-time). In contrast, and in accordance with several embodiments, the aerobic production phase is defined by the yeast culture's energy metabolism in which the yeast cells predominantly catabolize nonfermentable carbon sources (e.g., ethanol and/or glycerol), and a steady growth rate (i.e., long doubling-time). Accordingly, each yeast cell's energy metabolism is binary and dependent on the local concentration of the carbon source.

Figure 1A:
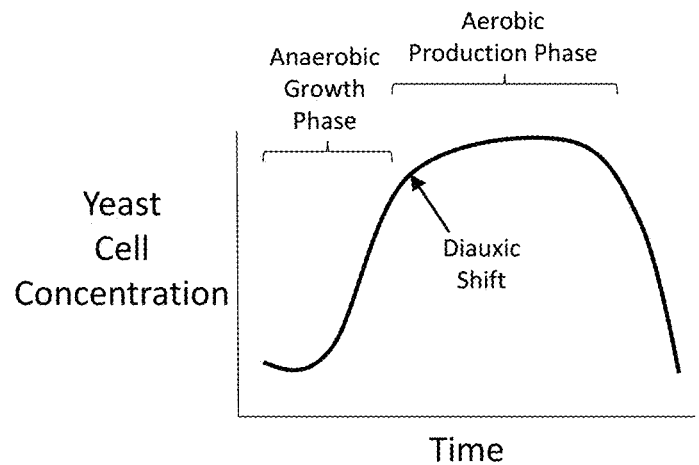
FIG. 1A illustrates a yeast phase chart displaying yeast cell concentration in relation to time to provide reference for various embodiments of the invention.

FIG. 1A depicts the phases of a yeast culture when provided a fermentable sugar, such as glucose or dextrose sugar, at a concentration of around 2-4% as its main carbon source. Initially, a yeast culture will predominantly catabolize the fermentable sugar, which correlates with an exponential growth with very high doubling rates. The growth phase typically lasts approximately 4-10 hours. During this phase, the catabolism of the fermentable sources results in the production of ethanol and glycerol.

Figure 1B:
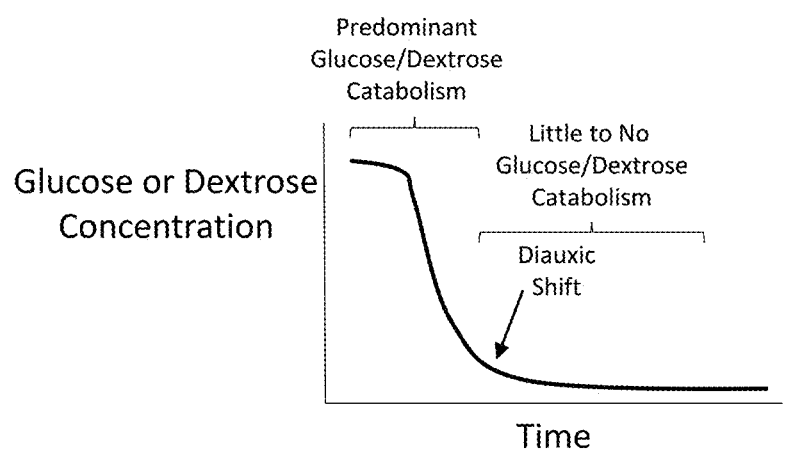
FIG. 1B illustrates a yeast phase chart displaying glucose concentration in relation to time to provide reference for various embodiments of the invention.

Once glucose becomes scarce, the growth of a yeast culture passes a diauxic shift and begins to predominantly catabolize nonfermentable carbon sources (e.g., ethanol and/or glycerol) (FIG. 1B). The predominant catabolism of nonfermentable carbon source correlates with a longer and more stable production phase that can last for several days, or even weeks in an industrial-like setting (FIG. 1A). During the production phase, yeast cultures reach and maintain a high concentration, but have a much lower doubling time (FIG. 1A). Due to the decrease in doubling rate, yeast cultures no longer expend a great amount of energy and resources on rapid growth and thus can reallocate that energy and those resources to other biological activities, including heterologous expression. Accordingly, it is hypothesized that limiting the transcription of heterologous genes to the production phase would allow a yeast culture to reach a high, healthy confluency that would in turn allow better heterologous protein expression and biosynthetic production.

In yeast, transcriptional regulation can be achieved in several ways, including inducement by chemical substrates (e.g., copper or methionine), the tetON/OFF system, and promoters engineered to bind unnatural hybrid transcription factors. Perhaps the most commonly employed inducible promoters are the promoters controlled by the endogenous GAL4 transcription factor. GAL4 promoters are strongly repressed in glucose, and upon switching to galactose as a carbon source, strong induction of transcription is observed (M. Johnston and R. W. Davis, *Mol. Cell Biol.* 4:1440-48, 1984, the disclosure of which is incorporated herein by reference). While this system leads to high-level transcription, only four galactose-responsive promoters are known, and galactose is both a more expensive and a less efficient carbon source as compared to glucose (S. Ostergaard, et al., *Biotechnol. Bioeng.* 68:252-59, 2000, the disclosure of which is incorporated herein by reference).

Other carbon-source dependent promoters have also been used for heterologous gene expression. The *S. cerevisiae* ADH2 gene exhibits significant derepression upon depletion of glucose as well as strong induction by either glycerol or ethanol (K. M. Lee & N. A. DeSilva Yeast. 22:431-40, 2005, the disclosure of which is incorporated herein by reference). Once induced, genes driven by the ADH2 promoter (pADH2) display expression levels equivalent to those driven by highly expressed constitutive counterparts. This induction profile was found to work in heterologous expression studies, as the system auto-induces upon glucose depletion in the late stages of fermentative growth after cells have undergone diauxic shift. The ADH2 promoter has been used extensively for yeast heterologous expression studies, resulting in high-level expression of several heterologous biosynthetic proteins (For example, see C. D. Reeves, et al., Appl. Environ. Microbiol. 74:5121-29, 2008, the disclosure of which is incorporated herein by reference).

Figure 1C:
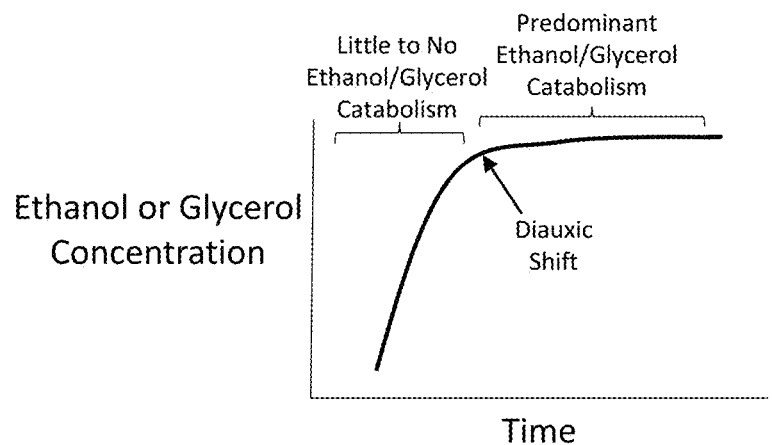
FIG. 1C illustrates a yeast phase chart displaying ethanol or glycerol concentration in relation to time to provide reference for various embodiments of the invention.

As shown in FIG. 1C, the concentration of ethanol and glycerol increases as glucose and dextrose sugar decreases, due to anaerobic glycolysis (i.e., breaking down the fermentable sugar) and subsequent fermentation (i.e., converting the broken-down glucose into alcohol) and glycerol biosynthesis (i.e., converting the broken-down glucose into glycerol). Upon fermentable sugar depletion, yeast cultures undergo a diauxic shift and begin to use ethanol and glycerol as a carbon source instead of glucose. A diauxic shift, as understood in the art, is defined as a point in time when an organism switches consumption of one source for energy, to another source. This shift requires significant changes to a yeast culture's gene-expression pattern. Accordingly, it is hypothesized that higher concentrations of ethanol, (i.e., ~2-4%) and or glycerol (i.e., ~2%) could be used to stimulate promoters that either directly or indirectly respond to these concentrations (See FIGS. 1A and 1C).

Various embodiments of the invention are based on the discovery of inducible promoters that can be used for the coordinated expression of multiple genes (e.g., gene cluster pathway) in Saccharomyces yeast. Described below are sets of inducible promoters from S. cerevisiae and related species that are inactive during anaerobic growth, activating transcription only after a diauxic shift when glucose is near-depleted and the yeast cells are respiring (i.e., the production phase). As portrayed in various embodiments, various production-phase promoters are auto-inducing and allow automatic decoupling of the growth and production phases of a culture and thus initiate heterologous expression without the need for exogenous inducers. It should be noted, however, that many embodiments of the invention include production-phase promoters that are also inducible in the presence of nonfermentable carbon-sources (e.g., ethanol and/or glycerol) supplied to the yeast. As such, multiple embodiments employ recombinant production-phase promoters that act much like constitutive promoters when the host yeast cultures are constantly maintained in ethanol- and/or glycerol-containing media.

Once activated, the strength of various production-phase promoters can vary as much as 50-fold in accordance with numerous embodiments of the invention. The strongest production-phase promoters stimulate heterologous expression greater than that observed from strong constitutive promoters. The production-phase promoters could be employed in many different applications in which high expression of multiple genes is beneficial. Accordingly, the promoters can be used, for example, in multiple subunit protein production or for the production of biosynthetic compounds that are produced by multiple proteins within a pathway. Discussed in an exemplary embodiment below, embodiments of the invention are used to express multiple proteins involved in production of indole diterpene compound product. When compared to constitutive promoters, the production-phase promoters produced greater than a 2-fold increase in titer of the exemplary diterpene natural products. In other exemplary embodiments, it was found that the production-phase promoter system outperformed constitutive promoters by over 80-fold. Thus, these promoters can enable heterologous expression of biosynthetic systems in yeast.

The practice of several embodiments of the present invention will employ, unless otherwise indicated, conventional methods of chemistry, biochemistry, and molecular biology and recombinant DNA techniques within the skill of the art. Such techniques are explained fully in the literature. See, e.g., A. L. Lehninger, Biochemistry (Worth Publishers, Inc., 30 current addition); Sambrook, et al., Molecular Cloning: A Laboratory Manual (3$^{rd}$ Edition, 2001); Methods In Enzymology (S. Colowick and N. Kaplan eds., Academic Press, Inc.).

Inducible Production-Phase Promoters for Heterologous Expression in Yeast

In accordance with several embodiments of the invention, inducible production-phase promoters can be constructed into exogenous expression vectors for production of at least one protein in Saccharomyces yeast. In many embodiments, the constructed expression vectors have multiple inducible production-phase promoters in order to express multiple heterologous genes.

Several embodiments are directed to production-phase promoters and DNA vectors incorporating these promoters. Promoters, in general, are defined as a noncoding portion of DNA sequence situated proximately upstream of a gene to regulate and promote its expression. Typically, in S. cerevisiae and similar species, the promoter of a gene can be found within 500-bp upstream of a gene's translation start codon.

In accordance with several embodiments, production-phase promoters have two defining characteristics. First, production-phase promoters are capable of repressing heterologous expression of a gene in S. cerevisiae and similar species when the yeast is exhibiting anaerobic energy metabolism. As described previously, yeast exhibit anaerobic metabolism in the presence of a nontrivial concentration of fermentable carbon sources such as, for example, glucose or dextrose. In addition, production-phase promoters are also capable of inducing heterologous expression of a gene in S. cerevisiae and similar species when the yeast is exhibiting aerobic energy metabolism. As described previously, yeast exhibit aerobic metabolism when fermentable carbon sources are near depleted and the yeast cells switch to a catabolism of nonfermentable carbon sources such as glycerol or ethanol. These characteristics correspond to the phase charts in FIGS. 1A-1C. Tables 1 and 2 provide several examples of production-phase promoters in accordance with several embodiments. Table 3 provides sequences that correspond with the promoters and the incorporated sequence listing.

The production-phase promoters can be characterized based on their level of transgene expression relative to each other and to constitutive promoters. As described in an exemplary embodiment below, it was found that the sequence of endogenous promoters of the S. cerevisiae genes ADH2, PCK1, MLS1, and ICL1 exhibited high-level expression and thus can be characterized as strong production-phase promoters (Table 1). Sequences of the endogenous promoters of the S. cerevisiae genes YLR307C-A, ORF-YGRO67C IDP2, ADY2, CACI, ECM13, and FATS exhibited mid-level expression and thus can be characterized as semi-strong production phase promoters (Table 1). In addition, sequences of the endogenous promoters of the S. cerevisiae genes PUT1, NQM1, SFC1, JEN1, SIP18, ATO2, YIG1, and FBP1 exhibited low-level expression and thus can be characterized as weak production-phase promoters (Table 1).

TABLE 1

Production-Phase Promoters Expression Phenotype

| Gene Name | Systematic Name | Expression Phenotype | Sequence ID Number |
|---|---|---|---|
| ADH2 | YMR303C | Strong | 1 |
| PCK1 | YKR097W | Strong | 2 |
| MLS1 | YNL117W | Strong | 3 |
| ICL1 | YER065C | Strong | 4 |
| YLR307C-A | YLR307C-A | Semi-Strong | 5 |
| YGR067C | YGR067C | Semi-Strong | 6 |
| IDP2 | YLR174W | Semi-Strong | 7 |
| ADY2 | YCR010C | Semi-Strong | 8 |
| GAC1 | YOR178C | Semi-Strong | 9 |
| ECM13 | YBL043W | Semi-Strong | 10 |
| FAT3 | YKL187C | Semi-Strong | 11 |
| PUT1 | YLR142W | Weak | 12 |
| NQM1 | YGR043C | Weak | 13 |
| SFC1 | YJR095W | Weak | 14 |
| JEN1 | YKL217W | Weak | 15 |
| SIP18 | YMR175W | Weak | 16 |
| ATO2 | YNR002C | Weak | 17 |
| YIG1 | YPL201C | Weak | 18 |
| FBP1 | YLR377C | Weak | 19 |

The closely related *S. sensu stricto* species have similar genetics and growth characteristics. Accordingly, the phase charts provided in FIGS. 1A-1C apply generally to *S. sensu stricto* species. Table 2 provides a list of strong production-phase exogenous promoters of similarly related species in accordance with numerous embodiments of the invention.

TABLE 2

Strong Production-Phase Promoters of *S. sensu stricto* species

| Species | Gene Name | Sequence ID Number |
|---|---|---|
| S. paradoxus | ADH2 | 36 |
| S. kudriavzevii | ADH2 | 37 |
| S. bayanus | ADH2 | 38 |
| S. paradoxus | PCK1 | 41 |
| S. kudriavzevii | PCK1 | 42 |
| S. bayanus | PCK1 | 43 |
| S. paradoxus | MLS1 | 44 |
| S. kudriavzevii | MLS1 | 45 |
| S. bayanus | MLS1 | 46 |
| S. paradoxus | ICL1 | 47 |
| S. kudriavzevii | ICL1 | 48 |
| S. bayanus | ICL1 | 49 |

It should be noted that substantially similar sequences to the production-promoter sequences are expected to regulate heterologous expression in *S. cerevisiae* and achieve similar results. Accordingly, a substantially similar sequence of a production-phase promoter, in accordance with numerous embodiments, is any sequence with a high homology such that when regulating heterologous expression in *S. cerevisiae* that it achieves substantially similar results. For example, in an exemplary embodiment below, it was found that the ADH2 promoter of *S. bayanus* is only 61% homologous, yet achieved strong heterologous expression in *S. cerevisiae*, similar to the endogenous ADH2 promoter.

Figure 2A:
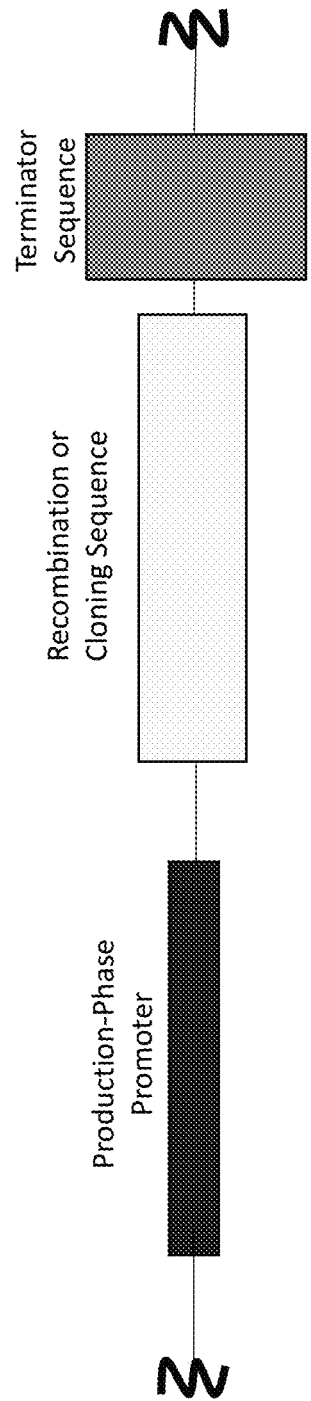
FIG. 2A illustrates a DNA vector having a production-phase promoter in accordance with an embodiment of the invention.

In FIG. 2A, an exemplary schematic of a section of an exogenous DNA vector (e.g., cloning vector, expression vector, and/or shuttle vector) having a production-phase promoter sequence embedded within. A vector is capable of transferring nucleic acid sequences to target cells (e.g., yeast). Typical DNA vectors include, but are not limited to, plasmid or viral constructs. DNA vectors are also meant to include a kit of various linear DNA fragments that are to be recombined to form a plasmid or other functional construct, as is common in yeast homologous recombination methods (See e.g., Z. Shao, H. Zhao & H. Zhao, 2009, *Nucleic Acids Research* 37:e16, 2009, the disclosure of which is incorporated herein by reference). Often, embodiments of cloning vectors will incorporate other sequences in addition to the production-phase promoter. As depicted in FIG. 2A, the exemplary cloning vector has a terminator sequence and cloning/recombination sequence in addition to the production-phase promoter, each of which can assist with expression vector construction. Furthermore, other sequences necessary for growth and amplification can be incorporated into the promoter vector. Embodiments of these sequences may include, for example, at least one appropriate origin of replication, at least one selectable marker, and/or at least one auxotrophic marker. It should be noted, however, that various embodiments of the invention are not required to contain cloning, terminator, or either sequences. For example, embodiments of a typical shuttle vector may only contain the production-phase promoter sequence along with the necessary sequences for amplification in a biological system.

For purposes of this application, an exogenous DNA vector is any DNA vector that was constructed, at least in part, exogenously. Accordingly, DNA vectors that are assembled using the yeast's own cell machinery (e.g., yeast homologous recombination) would still be considered exogenous if any of the DNA molecules transduced within yeast for recombination contain exogenous sequence or were produced by a non-host methodology, such as, for example, chemical synthesis, PCR amplification, or bacterial amplification.

Figure 2B:
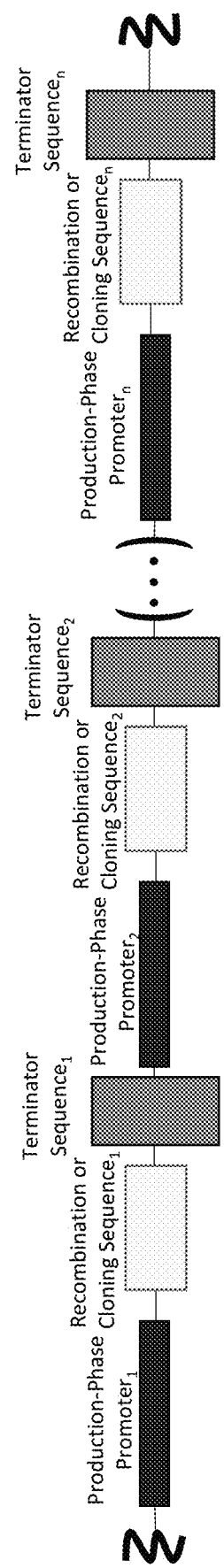
FIG. 2B illustrates a DNA vector having multiple production-phase promoters in accordance with an embodiment of the invention.

As shown in FIG. 2B, various embodiments of the invention are directed to DNA vectors having multiple production-phase promoters. In these various embodiments, multiple different production-phase promoters are incorporated, preferably each having a unique sequence and derived from a different gene and/or *S. sensu stricto* species. Having unique promoter sequences can prevent complications that can arise during product production in yeast, such as, for example, unwanted DNA recombination at sites similar to the promoter sequences that render the DNA vector constructs undesirable. In many embodiments, the DNA vector has at least two production-phase promoters and up to a number that still yields the vector useful. As the size of the DNA vector increases, the utility may decrease, as larger vectors may become unwieldly for the intended organism to handle. For example, plasmids for amplification in *E. coli* are often somewhere between 2,000 and 10,000 base pairs (bp) but can handle up to 20,000 bp or so. Likewise, plasmids for amplification and growth in yeast can vary from approximately 10,000 to 30,000 bp. Viral vectors, on the other hand, often have a limited construct size and thus may require a more precise vector size. Thus, depending on vector and intended use, the number of production-phase promoters within a DNA vector will vary.

Although FIG. 2B depicts recombination sites, cloning sites, and terminator sequences, it should be noted that these sequences may or may not be included in various embodiments of DNA vectors having multiple production-phase promoters. The incorporation of these sequences or other various sequence is often dependent on the purpose of the DNA vector. For example, cloning vectors may not include a terminator sequence if that sequence is to be incorporated into an expression construct at another stage of assembly.

Figure 3A:
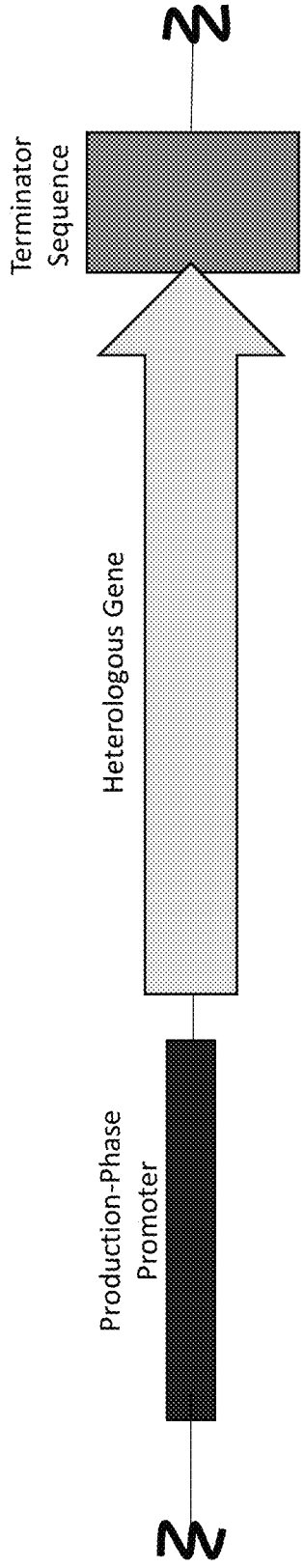
FIG. 3A illustrates a DNA expression vector having a production-phase promoter within an expression cassette in accordance with an embodiment of the invention.

FIG. 3A depicts an exemplary heterologous expression vector having a production-phase promoter for expression in yeast, in accordance with various embodiments of the invention. Expression constructs contain an expression cassette that minimally has a promoter, a heterologous gene, and a terminator sequence in order to produce an RNA molecule in an appropriate host. Expression cassette in accordance with numerous embodiments will have a production-phase promoter situated proximately upstream of a heterologous gene of which the promoter is to regulate expression. It should be understood, that the precise location of the production-phase promoter upstream of the heterologous gene may vary, but the promoter must be within a certain proximity to adequately function.

In many embodiments of the invention, a heterologous gene is any gene driven by a production-phase promoter, wherein the heterologous gene is different than the endogenous gene that the promoter regulates within its endogenous genome. Accordingly, a *S. cerevisiae* production-phase promoter could regulate another *S. cerevisiae* gene provided that the gene to be regulated is not the gene endogenously regulated. For example, the *S. cerevisiae* ADH2 promoter should not regulate the *S. cerevisiae* ADH2 gene; however, the *S. cerevisiae* ADH2 promoter can regulate any other *S. cerevisiae* gene or the ADH2 gene from any other species. Often, in accordance with many embodiments, the heterologous gene is from a different species than the species from which the production-promoter sequence was obtained.

Although not depicted, various embodiments of expression cassettes may include other sequences, such as, for example, intron sequences, Kozak-like sequences, and/or protein tag sequences (e.g., 6x-His) that may or may not improve expression, production, and/or purification. In yeast, various embodiments of expression vectors will also minimally have a yeast origin of replication (e.g., 2-micron) and an auxotrophic marker (e.g., URA3) in addition to the expression cassette. Other nonessential sequences may also be included, such as, for example, bacterial origins of replication and/or bacterial selection markers that would render the expression capable of amplification in a bacterial host in addition to a yeast host. Accordingly, various embodiments of expression vectors would include the essential sequences for heterologous expression in yeast and other various embodiments would include additional nonessential sequences.

In accordance with various embodiments, a DNA vector having a production-phase promoter expression cassette can be transformed into a yeast cell. Or alternatively, and in accordance with numerous embodiments, a DNA vector having a production-phase promoter expression cassette can be assembled within yeast using homologous recombination techniques. Once existing within a yeast cell, the production-phase promoter can regulate the expression of a heterologous gene in accordance with the yeast cell's energy metabolism. As described previously, and in accordance with many embodiments, production-phase promoters repress heterologous expression when the yeast cell is in an anaerobic energy metabolic state. Alternatively, and in accordance with a number of embodiments, production-phase promoters induce heterologous expression when the yeast cell is in an aerobic energy metabolic state.

Figure 3B:
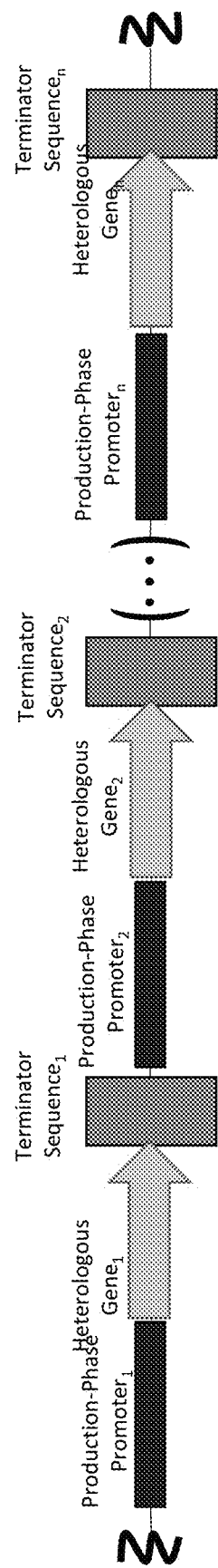
FIG. 3B illustrates a DNA expression vector having multiple production-phase promoters, each within an expression cassette in accordance with an embodiment of the invention.

Depicted in FIG. 3B are alternative exemplary heterologous expression vectors having multiple production-phase promoters for expression of multiple genes in yeast in accordance with numerous embodiments. In these embodiments, the expression vectors will include at least two expression cassettes, each with a unique promoter, gene, and terminator sequence in order to prevent unwanted recombination. The number of expression cassettes will vary based on vector construct design and application. For heterologous expression in *S. cerevisiae*, it has been found that plasmid expression vectors of approximately 30,000 bp are still tolerated. Thus, vectors containing up to seven production-phase promoter expression cassettes can be incorporated into an expression vector and have been found to be able to maintain adequate gene expression and protein production. Larger vectors with more expression cassettes may be tolerated.

Although FIG. 3B depicts multiple expression cassettes sequentially in the same orientation 5' to 3', it should be understood that the combination of two or more expression cassettes is not limited to sequential linear organization in the same orientation. Expression cassettes in accordance with many embodiments exist within the expression vector in any orientation and in any sequential order. Furthermore, it should be understood that other sequence elements of an expression vector (e.g., auxotrophic marker) may be among and/or between the multiple expression cassettes. Optimal vector design is likely to depend on various factors, such as, for example, optimizing the location of the auxotrophic marker to enable the final expression vector to include each expression cassette to be incorporated.

DNA heterologous expression vectors are a class of DNA vectors, and thus the description of general DNA vectors above also applies to the expression vectors. Accordingly, many embodiments of the expression vectors are formulated into a plasmid vector, a viral vector, or a kit of linear DNA fragments to be recombined into a plasmid by yeast homologous recombination. In several of these embodiments, the end-product vector contains at least one expression cassette having a production-phase promoter. It should be understood, that in addition to the at least one production-phase promoter, some vector embodiments incorporate expression cassettes that include other promoters, such as (but not limited to), constitutive promoters that maintain high expression during the growth and production phases.

The various embodiments of heterologous expression vectors having at least one production-phase promoter can be used in numerous applications. For example, high expression in the production phase can lead to better, prolonged expression, as compared to constitutive promoters. In many applications, the end product is a protein from a single gene or a protein complex of multiple genes to be purified from the culture. For these applications, high, prolonged expression using production-phase promoters can lead to better yields of proteins. Furthermore, when the heterologous protein is toxic to the host yeast cells, the use of production-phase promoters prevents the expression of the toxic protein during growth phase, allowing the yeast to reach a healthy confluency before mass protein production.

The production-phase promoter vectors can also benefit the production of a biosynthetic compound from a gene cluster. Many products derived from various natural species are produced from a cluster of genes with sequential enzymatic activity. For example, the antibiotic emindole SB is produced from a cluster of four genes that is expressed in *Aspergillus tubingensis*. To reproduce this gene cluster in a yeast production model, a production-promoter vector system with four different expression cassettes could work. This system would allow the yeast to reach a healthy confluency before the energy-draining expression of four heterologous proteins begin, leading to better overall yields of the antibiotic product. In fact, experimental results provided in an exemplary embodiment described below demonstrate that a production-phase promoter vector outperformed a constitutive promoter vector approximately 2-fold to produce the emindole SB product.

Figure 4:
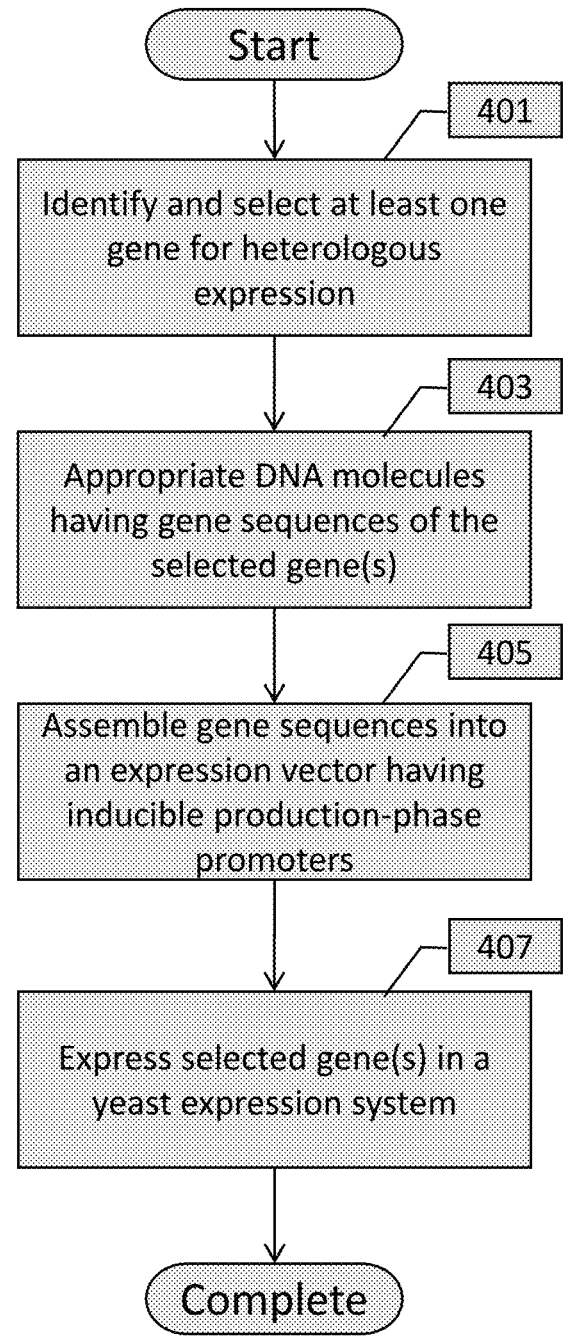
FIG. 4 illustrates a method to construct and utilize production-phase promoter DNA vectors in accordance with various embodiments of the invention.

FIG. 4 depicts an exemplary process (Process 400) to implement various embodiments of production-phase promoters. To begin, Process 400 identifies and selects at least one gene for heterologous expression in yeast (401). The choice of gene(s) for expression would depend on the desired outcome. For example, to produce a biosynthetic compound, one would likely select to express all the genes within a biosynthetic gene cluster of a particular organism. Once the gene(s) have been selected, Process 400 then appropriates DNA molecules having the coding sequence of the selected genes (403). As is well known in the art, there are many ways to appropriate DNA molecules, which include chemical synthesis, extraction directly from the biological source, or amplification of a gene by polymerase chain reaction (PCR).

Process 400 then uses the appropriated DNA molecules to assemble these molecules into an expression vector having production-phase promoters (405). There are many ways to assemble DNA expression vectors that are well known in the art, which include popular methodologies such as homologous recombination and restriction digestion with subsequent ligation. After assembly, the resultant expression vectors can be expressed in *Saccharomyces* yeast to obtain the desired outcome (407).

EXEMPLARY EMBODIMENTS

Biological data supports the systems and constructs of production-phase promoter DNA vectors and applications thereof. Provided below are several examples of incorporating production-phase promoters into DNA vectors. Many of these vectors were used to produce biosynthetic products from multi-gene clusters derived from various fungal species. Compared to a constitutive promoter system, a production-phase promoter system in accordance with various embodiments produced several fold greater product.
Production Phase Promoter Expression Analysis Because the ADH2 promoter (Seq. ID No. 1) has properties of a production-phase promoter, a panel of promoter sequences was compared to the ADH2 promoter to identify other production-phase promoters. To begin, endogenous *S. cerevisiae* genes were identified that appeared co-regulated with ADH2 in a previous genome-wide transcription study (Z. Xu. et al., Nature 457:1033-37, 2009, the disclosure of which is incorporated herein by reference). In this study, transcription of yeast genes was quantified during mid-exponential growth in several types of growth media. Of the 5171 ORFs examined, 35 appeared co-regulated with ADH2, with co-regulation defined as a greater than two-fold increase in expression with a non-fermentable carbon source (ethanol in a yeast-peptone-ethanol (YPE) media) as compared to a fermentable carbon source (dextrose in a yeast-peptone-dextrose (YPD) media). Because these data were collected at a single time point and assessed transcription of genes in their native context, their ability to co-regulate heterologous genes in a production-phase promoter system required further validation and characterization.

A detailed characterization of the ability of 34 selected promoters to control expression of heterologous genes was performed. A promoter was defined as the shorter of (a) 500 bp upstream of the start codon, or (b) the entire 5' intergenic region. Each promoter was cloned upstream of the gene for monomeric enhanced GFP (eGFP) and integrated each of the resulting cassettes in a single copy at the ho locus of individual strains. Control strains were included in which strong constitutive FBA1 and TDH3 promoters were cloned upstream of eGFP in an identical manner. The 35 promoter sequences can be found in Table 3. (Seq. ID Nos. 2-35).

Figure 5:
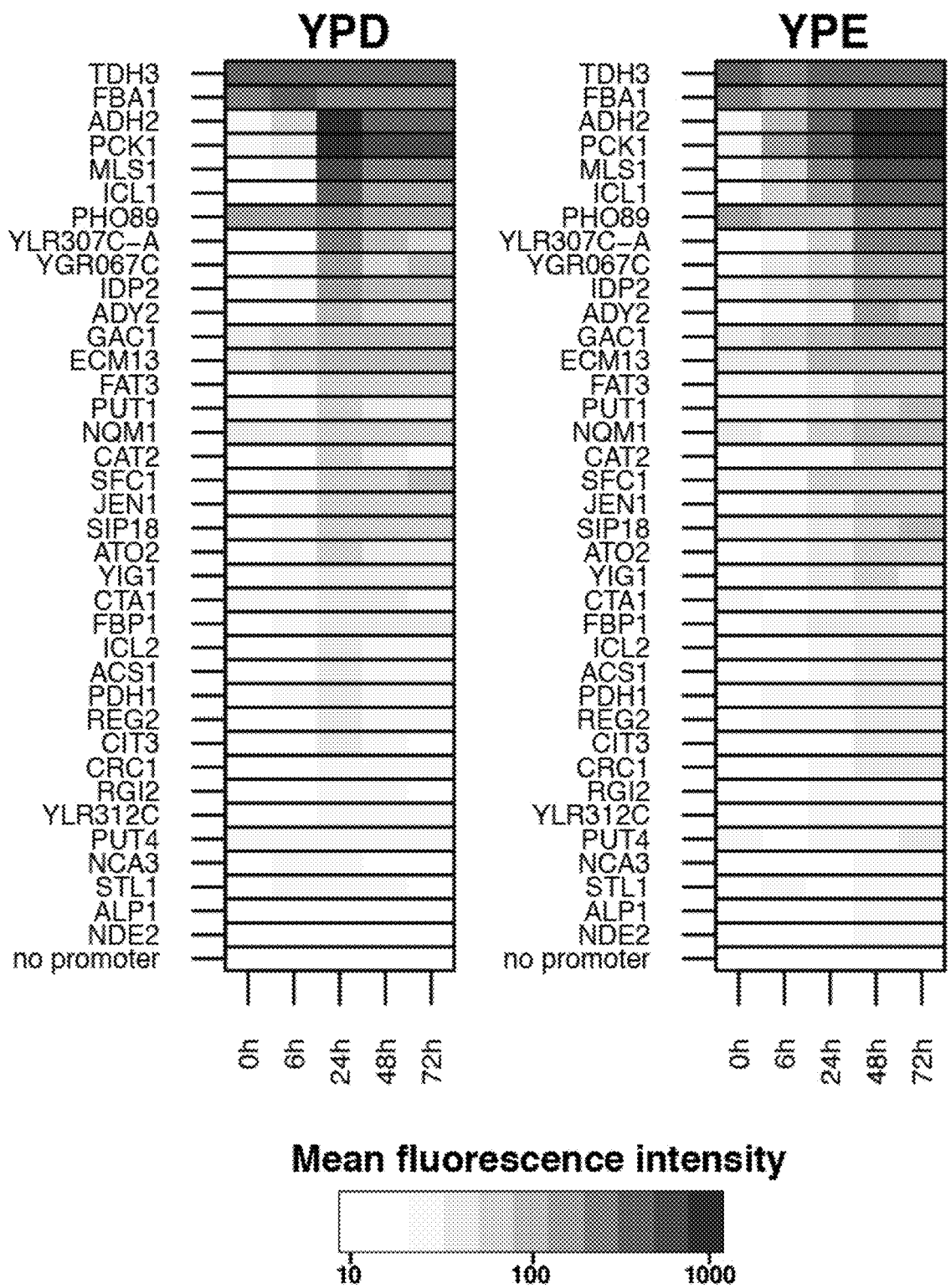
FIG. 5 is a heat map graphic generated in accordance with various embodiments of the invention with data of expression of enhanced-Green Fluorescent Protein driven by various *S. cerevisiae* promoters.
Figure 6:
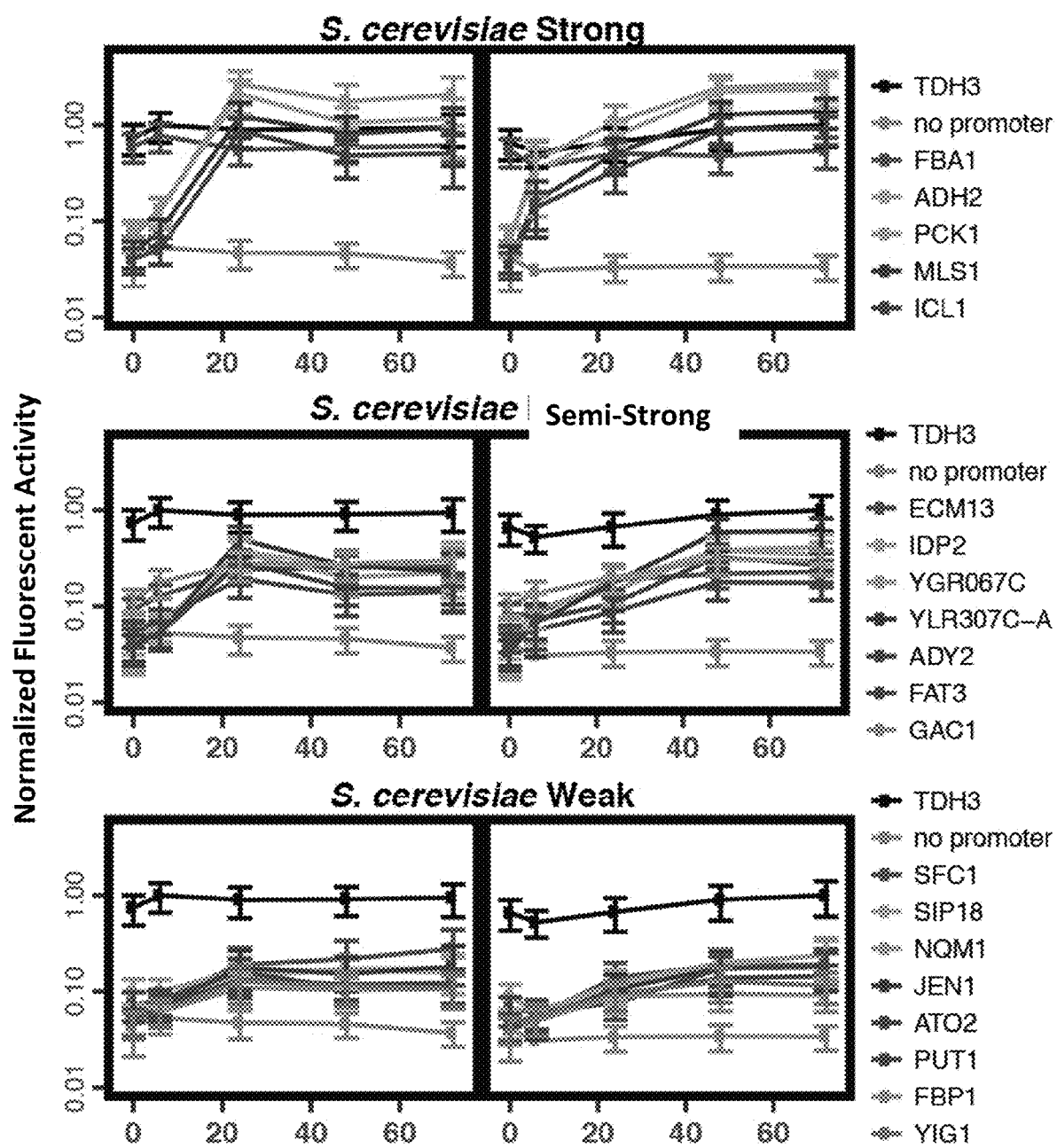
FIG. 6 is a data graph of enhanced-Green Fluorescent Protein expression driven by various *S. cerevisiae* promoters, generated in accordance with various embodiments of the invention.
Figure 7:
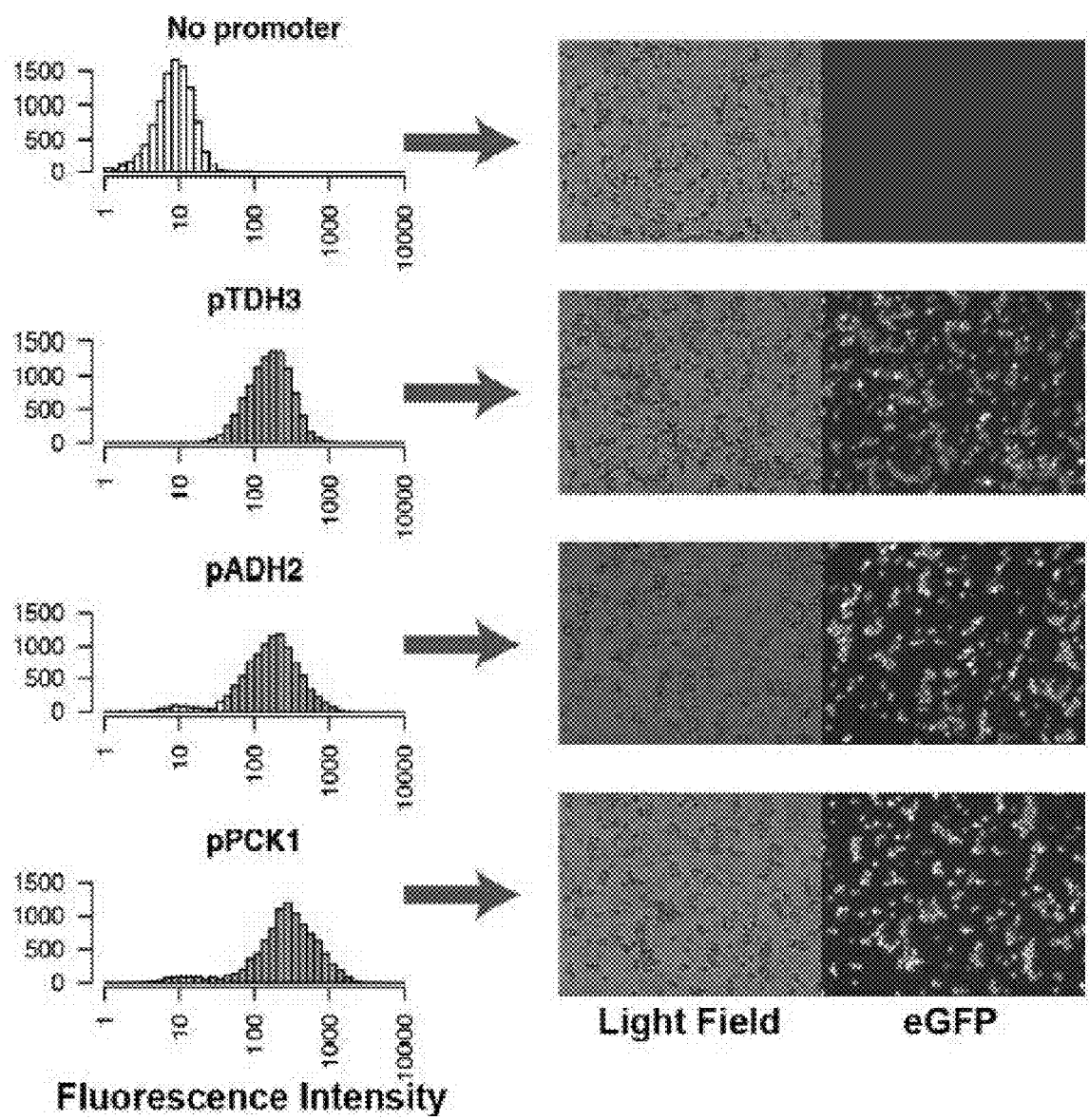
FIG. 7 illustrates fluorescence intensity of enhanced-Green Fluorescent Protein driven by various promoters, generated in accordance with various embodiments of the invention.

In order to compare the 35 putative production-phase promoters, the expression of eGFP protein was assessed over 72 hours in each strain by flow cytometry in media with both fermentable (YPD) and non-fermentable (YPE) carbon sources (FIGS. 5 and 6). All cultures were started in YPD media and analysis of eGFP expression began when cells were in the midst of exponential fermentative growth (OD600=0.4, 0 hrs). At this point, cells were either left to continue growth in YPD or spun-down and resuspended in YPE. Consistent with previous work, pADH2 was entirely repressed during exponential fermentative growth (0 hrs) unlike the constitutive promoters pTDH3 and pFBA1, which were expressed at near maximum levels regardless of phase. Moderate expression from pADH2 was observed after a further 6 hours in YPD culture or following a growth media switch to YPE. Within 24 hrs, expression reached levels exceeding those observed in the strong constitutive systems. Cytometry histograms and fluorescence microscopy demonstrated that within 48 hours, >95% of all cells with pADH2 and pPCK1 driven expression were fluorescing above background (FIG. 6). Protein expression levels spanned 50-15 fold, with most showing little or no expression until 24 hours into the culture (FIGS. 5 and 6). Transgene expression driven by the PCK1, MLS1, and ICL1 promoters (Seq. ID Nos. 2-4) not only showed the same timing of expression as pADH2, but also expressed at an equivalently high level. The promoters of genes YLR307C-A, YGRO67C, IDP2, ADY2, GAC1, ECM13 and FAT3 (Seq. ID Nos. 5-11) displayed semi-strong transgene expression (FIG. 5). In addition, the promoters of genes PUT1, NQM1, SFC1, JEN1, SIP18, ATO2, YIG1, and FBP1 (Seq. ID Nos. 12-19) displayed weak of transgene expression (FIGS. 5 and 6). The promoter PHO89 (Seq. ID No. 20) did not exhibit strong repression in during the growth phase (FIG. 5, 0 and 6 hours). The results of the other sequences are also depicted in FIG. 5 (Seq. ID Nos. 22-36). The constitutive promoters pTDH3 and pFBA1 (Seq. ID Nos. 50 and 52) were used as controls (FIGS. 5 and 6).

Figure 8:
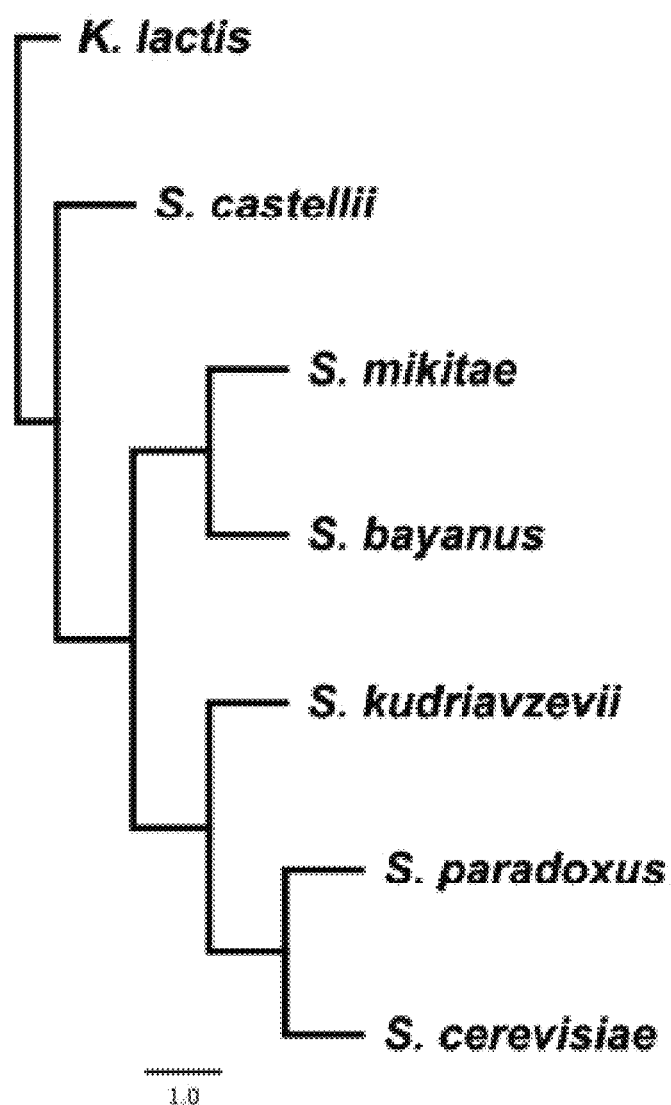
FIG. 8 illustrates a phylogenetic tree of *Saccharomyces sensu stricto* subgenus to provide reference for various embodiments of the invention.
Figure 9:
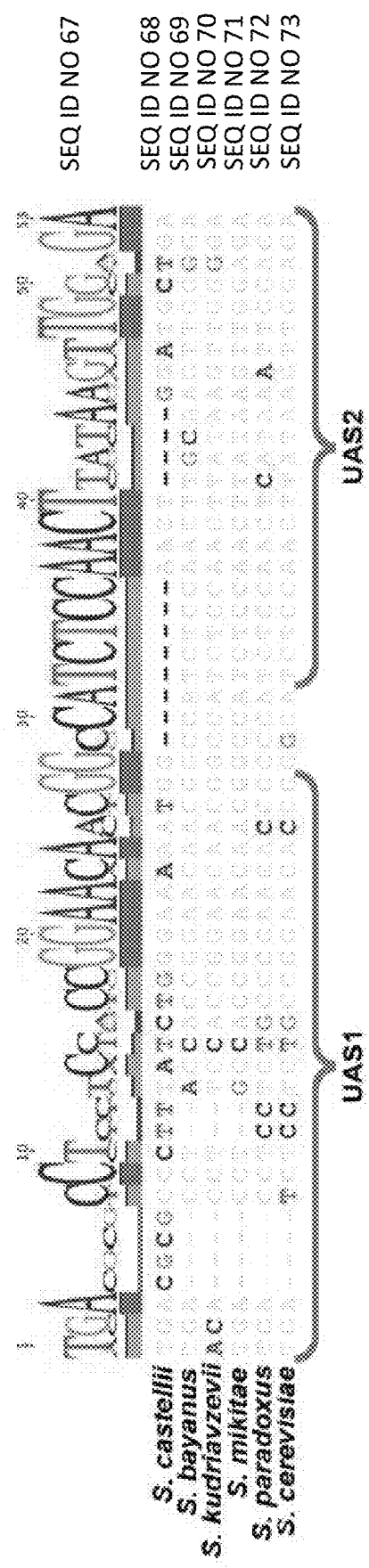
FIG. 9 illustrates a multiple sequence alignment of various *Saccharomyces sensu stricto* species' upstream activating sequences in ADH2 promoters to provide reference for various embodiments of the invention.
Figure 10:
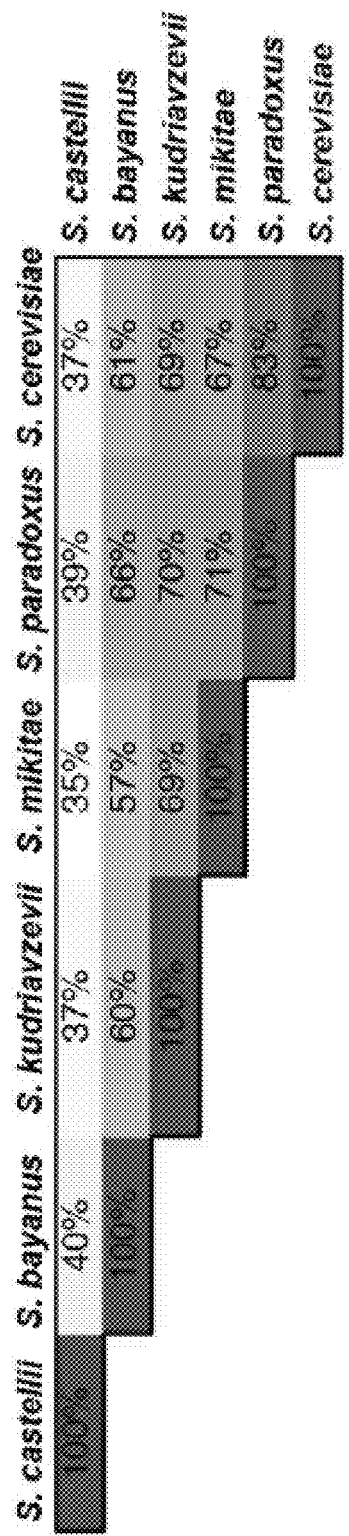
FIG. 10 illustrates homology between various *Saccharomyces sensu stricto* species' ADH2 promoters to provide reference for various embodiments of the invention.

The above analysis identified a large set of co-regulated promoters spanning a wide range of expression levels, three of which were as strong as pADH2. However, a more extensive set of strong production-phase promoters is desirable for assembly of constructs having multi-gene pathways, especially pathways having more than four genes. To identify other production-phase promoter candidates, the genomes of five closely related species within the *S. sensu stricto* complex were examined (FIG. 8). The promoter region was identified for the closest ADH2 gene homolog in the genomes of *Saccharomyces bayanus, Saccharomyces paradoxus, Saccharomyces mikitae, Saccharomyces kudriavzevii*, and *Saccharomyces castellii*. Multiple sequence alignment of the upstream activation sequences (UAS) revealed that nearly all sequences (except that from *S. castellii*) are highly conserved across this region, suggesting a potential for regulation similar to that of *S. cerevisiae* ADH2 (FIG. 9, Seq. ID Nos. 36-40). In order to be used for single-step pathway assembly, all promoter sequences must be sufficiently unique to prevent undesired recombination between each other. Therefore, the pairwise identities for each of the *Saccharomyces sensu stricto* ADH2 promoter pairs were analyzed (FIG. 10). The most similar promoter to the *S. cerevisiae* ADH2 promoter is that from *S. paradoxus*, with 83% identity, including a single 40 bp stretch located near the center of the promoter. This homology is significantly less than the 50-100 bp typically used for assembly by yeast homologous recombination, and recombination events between sequences with this level of identity occur at very low frequency, suggesting that these promoters should be compatible with a multi-gene assembly technique utilizing YHR as described above.

Figure 11:
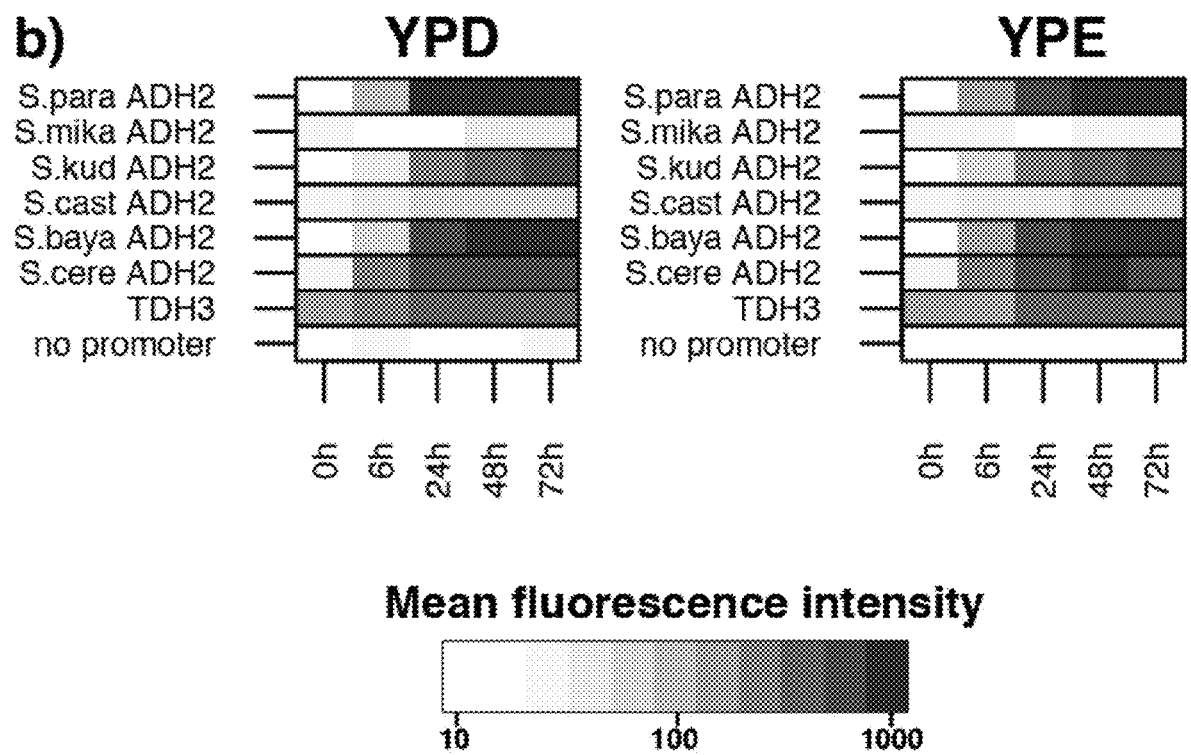
FIG. 11 is a heat map graphic generated in accordance with various embodiments of the invention with data of expression of enhanced-Green Fluorescent Protein driven by various *S. sensu stricto* ADH2 promoters.
Figure 12:
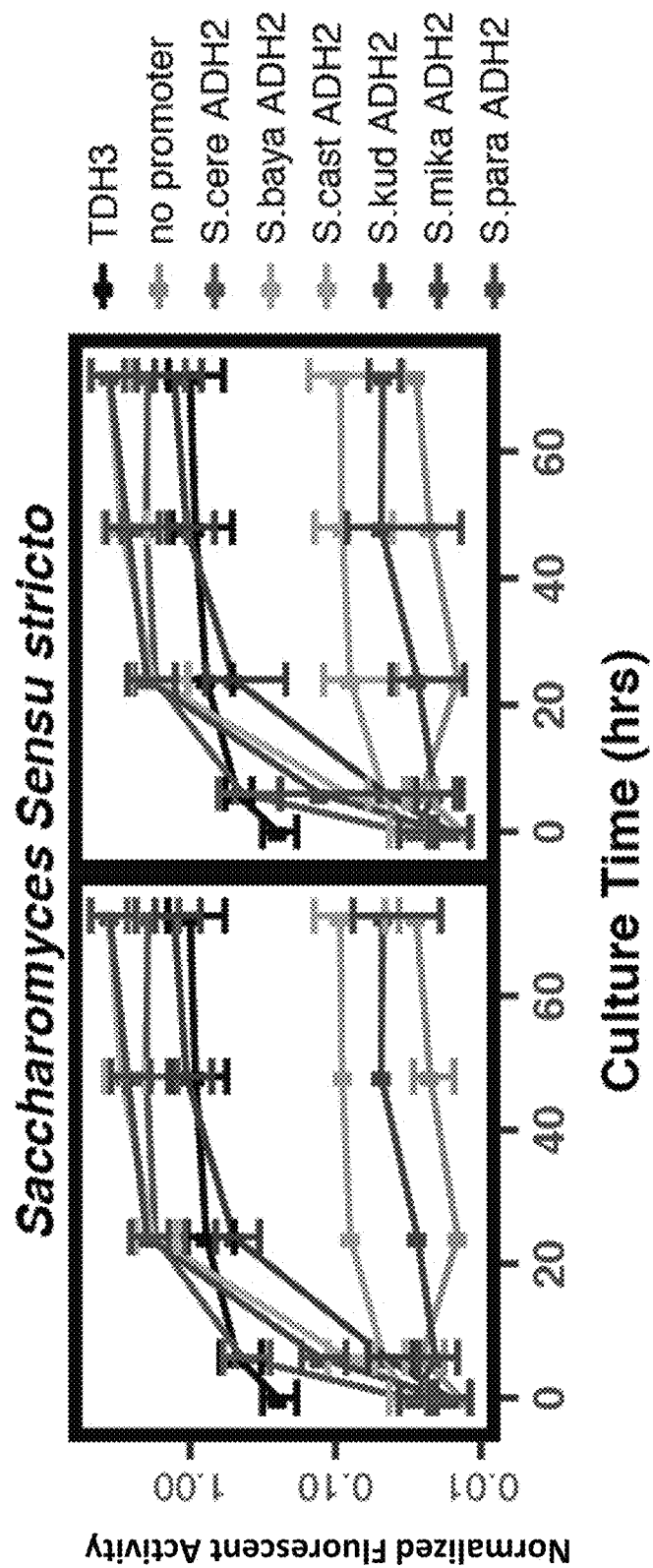
FIG. 12 is a data graph of enhanced-Green Fluorescent Protein expression driven by various *S. sensu stricto* ADH2 promoters, generated in accordance with various embodiments of the invention.

As with the endogenous yeast promoter candidates, these other putative *Saccharomyces* promoters required detailed characterization of induction profiles. DNA encoding each of these promoter sequences was obtained by commercial synthesis and characterized expression of eGFP from each promoter in the same manner as the endogenous yeast promoters (FIGS. 11 and 12). Of the five *Saccharomyces sensu stricto* pADH2s tested (Seq. ID Nos. 36-40), the promoters derived from *S. paradoxus, S. kudriavzevii*, and *S. bayanus* show timing and strength of expression equivalent to that of *S. cerevisiae* pADH2. In combination with the endogenous yeast promoters, these three additional *Saccharomyces* pADH2s expand the number of strong promoters with the desired induction profile.

Figure 13:
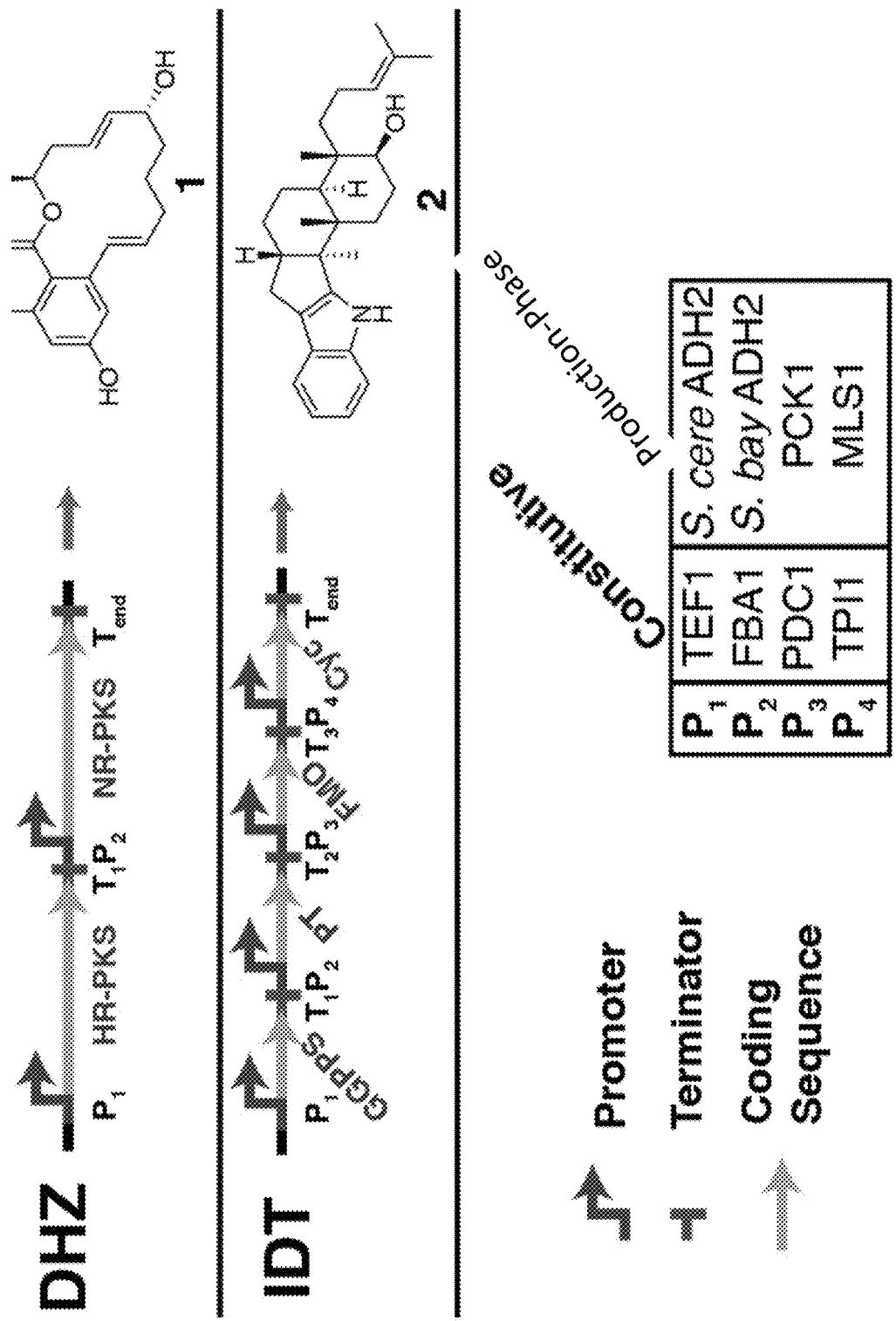
FIG. 13 illustrates four multi-gene expression vector constructs, each to generate a product compound, in accordance with an embodiment of the invention.
Figure 14:
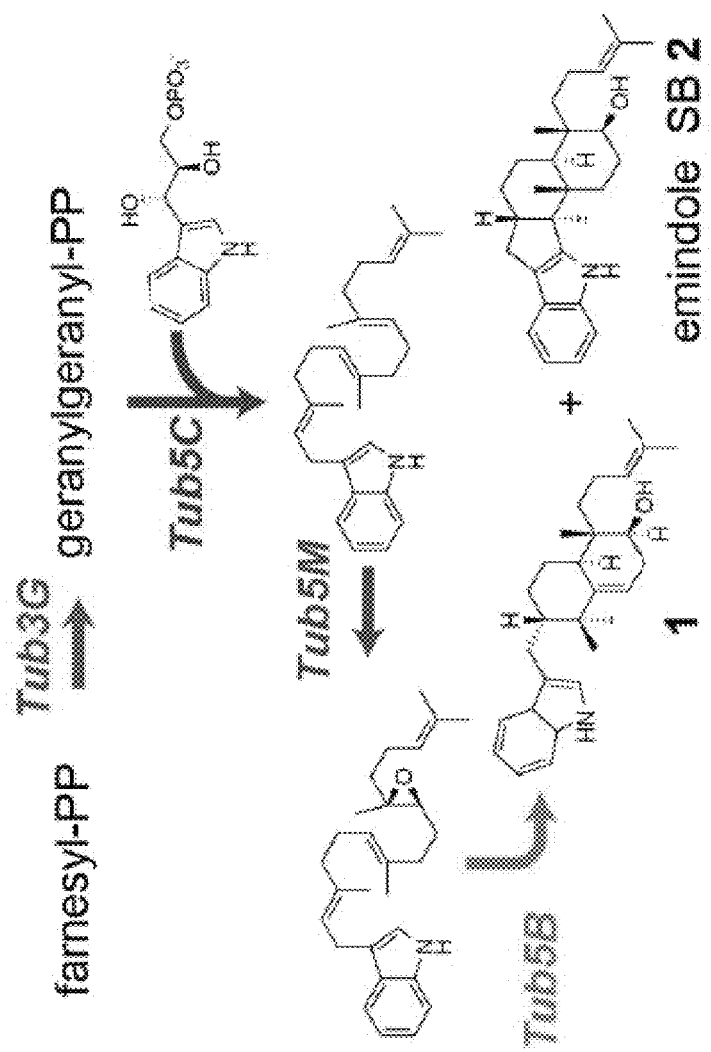
FIG. 14 illustrates a biosynthetic process that produces the compound emindole SB via a fungal four-gene cluster to provide reference for various embodiments of the invention.
Figure 15:
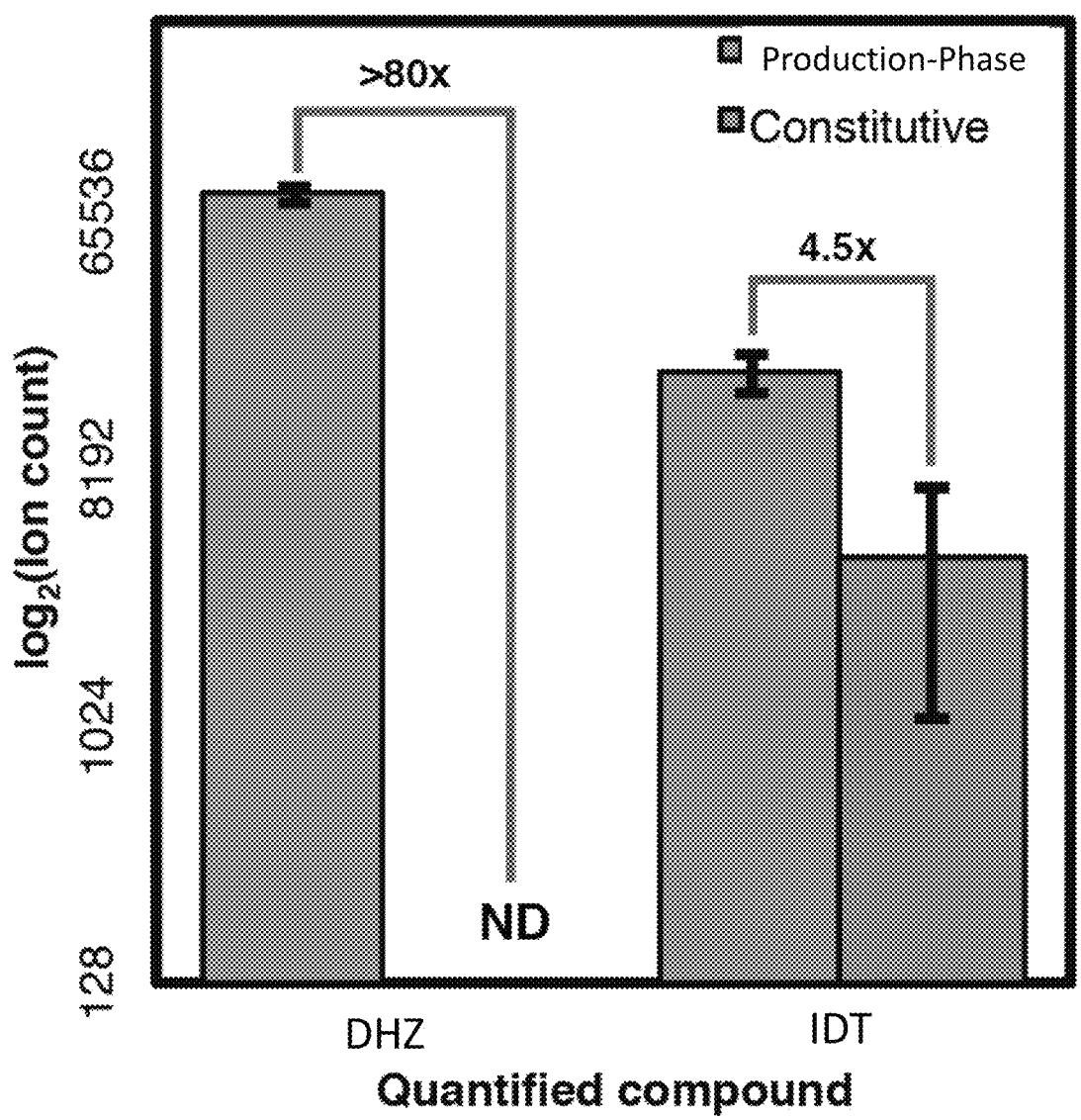
FIG. 15 is a data graph of the production results of two product compounds generated in accordance of an embodiment of the invention.

Expression of Compound Product Pathways Using the Production-Phase Promoter System To study the utility of the new promoter set for heterologous expression of a biosynthetic system, production of fungal derived deydrozearalenol (1) and indole-diterpene (2) was examined (FIG. 13, Compounds 1 & 2). The biosynthesis of the indole-diterpene compound the coordinated expression of four in *Aspergillus tubingensis* genes (FIG. 14, Seq ID Nos. 59-62). Two versions of each pathway were constructed: one having all production-phase promoters, and the other having all constitutive promoters (FIG. 14). The production-phase promoter system utilized the pADH2 from *S. cerevisiae* (Seq. ID No. 1), pADH2 from *S. bayanus* (Seq. ID No. 38), and pPCK1 (Seq. ID No. 2) and pMLS1 (Seq ID No. 3) from *S. cerevisiae*. In the constitutive system, transcription was driven by four frequently used strong constitutive promoters: pTEF1, pFBA1, pPCK1, and pTPI1 (Seq. ID Nos. 51-54). Each indole-diterpene system was constructed on a single plasmid harboring four expression cassettes: promoter::GGPPS::tADH2; promoter::PT::tPGI1; promoter::FMO::tENO2; and promoter::Cyc::tTEF1; wherein, the promoter sequences corresponded to either the production-phase or the constitutive promoters (FIG. 13). Similar constructs were built for the dehydrozearalenol compound with the two genes HR-PKS and NR-PKS (Seq. ID Nos. 63 and 64). All plasmids were constructed using yeast homologous recombination. It should be noted that pADH2 sequences from *S. cerevisiae* and *S. bayanus* (61% identity) are sufficiently unique for this type of assembly. The production of compounds 1 and 2 produced by *S. cerevisiae* BJ5464/npgA/pRS424 transformed with each of these plasmids were measured over seventy-two hours in YPD batch culture (FIG. 15). An 80-fold and 4.5-fold increase in titer of compound 1 and 2 was observed for the system using the production-phase promoters as compared to the constitutive system.

Materials and Methods Supporting the Production-Phase Promotor Experiments

General techniques, reagents, and strain information: Restriction enzymes were purchased from New England Biolabs (NEB, Ipswich, 25 MA). Cloning was performed in *E. coli* DH5a. PCR steps were performed using Q5® high-fidelity polymerase (NEB). Yeast dropout media was purchased from MP Biomedicals (Santa Ana, Calif.) and prepared according to manufacturer specifications. Promoter characterization experiments were performed in BY4741 (MATα, his3Δ1 leu2Δ0 met15Δ0 ura3Δ0) while all experiments involving the production of 1 were performed in BJ5464-npgA which is BJ5464 (MATαura3-52 his3Δ200 leu2Δ1 trp1 pep4::HIS3 prb1Δ1.6R can1 GAL) with two copies of pADH2-npgA integrated at δ elements. All Gibson assemblies were performed as previously described using 30 bp assembly overhangs.

Construction and characterization of promoter-eGFP reporter strains: All promoters were defined as the shorter of 500 base pairs upstream of a gene's start codon or the entire 5' intergenic region. All promoters from *S. cerevisiae* were amplified from genomic DNA, while ADH2 promoters from all *Saccharomyces sensu stricto* were ordered as gBlocks from Integrated DNA Technologies (IDT, Coralville, Iowa). Minimal alterations were made to promoters from *S. kudriavzevii* and *S. mikitae* in order to meet synthesis specifications. In all constructs, eGFP was cloned directly upstream of the terminator from the CYC1 gene (tCYC1). pRS415 was digested with SacI and SalI and a NotI-eGFP-tCYC1 cassette was inserted by Gibson assembly generating pCH600. Digestion of pCH600 with AccI and PmII removed the CEN/ARS origin, which was replaced by 500 bp sequences flanking the ho locus using Gibson assembly to yield plasmid pCH600-HOint. Each of the promoters to be analyzed was amplified with appropriate assembly overhangs using primers 9-92 Table S2 and inserted into pCH600-HOint digested with NotI to generate the pCH601 plasmid series. Digestion of the pCH601 plasmid series with AscI generated linear integration cassettes which were transformed into *S. cerevisiae* BY4741 by the LiAc/PEG method. Correct integration was confirmed by PCR amplification of promoters and Sanger sequencing.

For characterization, all strains were initially grown to saturation overnight in 100 μl of YPD media. These cells were then reinoculated at an OD600 of 0.1 into 1 ml of fresh YPD and allowed to grow to OD600=0.4 to reach mid-log phase growth (approximately 6 hrs). 500 μl of each culture was pelleted by centrifugation and resuspended in YPE broth for YPE data while the remaining 500 μl was used for YPD data. The 0 hour time point was collected immediately after resuspension. For each time point, 10 μl of culture was diluted in 2 ml of DI water and sonicated for three short pulses at 35% output on a Branson Sonifier. Expression data were collected for 10000 cells using a FACSCalibur flow cytometer (BD Bioscience) with the FL1 detector. Data were analyzed in R using the flowCore package.

Figure 16:
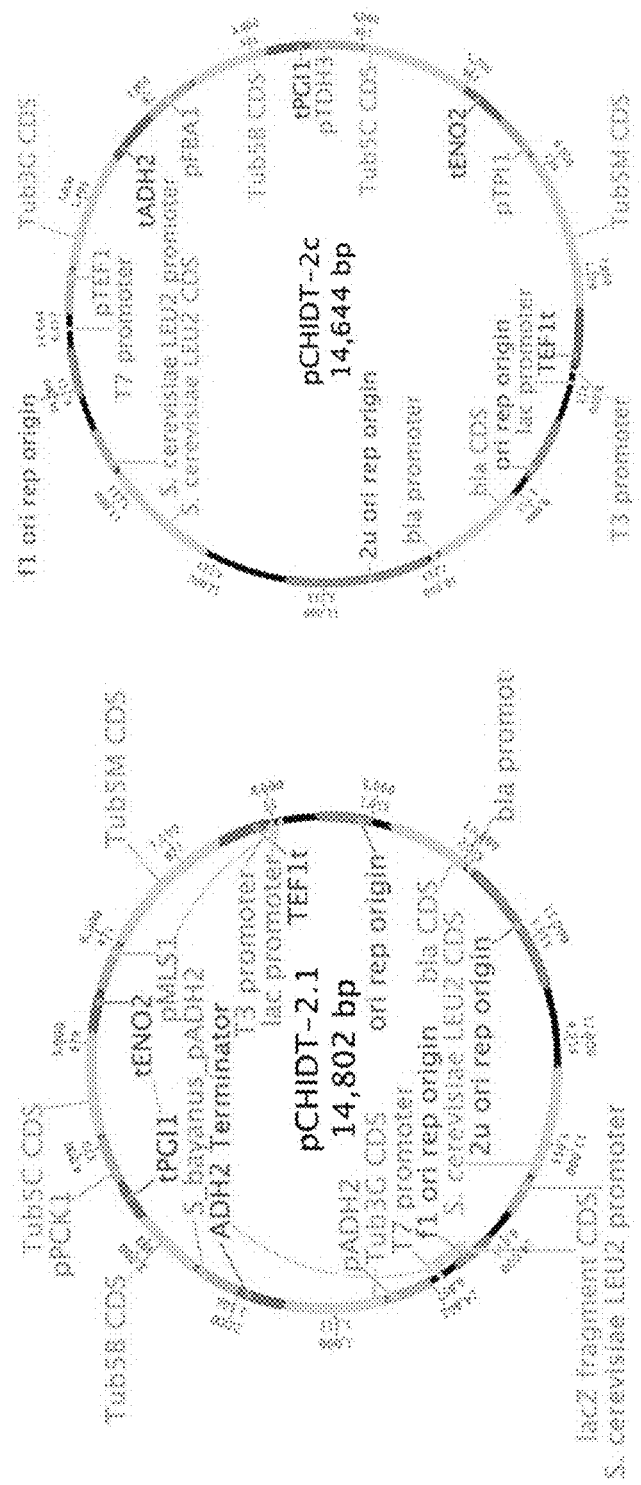
FIG. 16 illustrates two plasmid vector constructs in accordance with an embodiment of the invention.

Construction of plasmids to produce compounds in *S. cerevisiae*: The sequences for genes assembled on IDT producing plasmids are contained in the supporting information. Regulatory cassettes of promoters and terminators were fused using overlap extension PCR. All genes and regulatory cassettes were amplified by PCR, ensuring 60 bases of homology between all adjacent fragments. 500 ng of each purified fragment was combined with 100 ng of pRS425 linearized with Not1 and transformed into *S. cerevisiae* BJ5464/npgA. Sixteen clones were picked from each assembly plate and grown to saturation in 5 ml CSM-Leu medium. Plasmids were isolated, transformed into *E. coli* and purified prior to sequence confirmation using the Illumina MiSeq platform. Detailed plasmid maps for pCHIDT-2.1 and pCHIDT-2c are shown in FIG. 16 illustrates the primers used and the assembly strategy (Seq. ID Nos. 65 and 66).

Examining the productivity of indole diterpene generating systems Plasmids pCHIDT-2.1 and pCHIDT-2c were transformed into BJ5464InpgA with pRS424 as a source of tryptophan overproduction. Triplicates of each strain were inoculated into CSM-Leu/-Trp medium and grown overnight (OD600=2.5-3.0). Each culture was used to inoculate 20 ml cultures in YPD medium at an OD600=0.2 and incubated with shaking at 30° C. for 3 days. Every 24 hrs, 2 mls were sampled from each culture. Supernatants were clarified by centrifugation and extracted with 2 ml ethyl acetate (EtOAc). Cell pellets were extracted with 2 ml 50% EtOAc in acetone. 500 µl each of pellet and supernatant extracts were combined and dried in vacua. Samples were resuspended in 100 µl HPLC grade methanol and LC-MS analysis was conducted on a Shimadzu LC-MS-2020 liquid chromatography mass spectrometer with a Phenomenex Kinetex C18 reverse-phase column (1.7 µm, 100 Å, 100 mm×2.1 mm) with a linear gradient of 15% to 95% acetonitrile (v/v) in water (0.1% formic acid) over 10 min followed by 95% acetonitrile for 7 min at a flow rate of 0.3 ml/min.

TABLE 3

Summary of Sequence Listing

| Sequence ID No. | Description | Sequence |
|---|---|---|
| 1 | S. cerevisiae pADH2 | TATCTAAAAATTGCCTTATGATCCGTCTCTCCGGTTACAGCCTGTGTAACTGATTAATCC<br>TGCCTTTCTAATCACCATTCTAATGTTTTAATTAAGGGATTTTGTCTTCATTAACGGCTTT<br>CGCTCATAAAAATGTTATGACGTTTTGCCCGCAGGCGGGAAACCATCCACTTCACGAG<br>ACTGATCTCCTCTGCCGGAACACCGGGCATCTCCAACTTATAAGTTGGAGAAATAAGA<br>GAATTTCAGATTGAGAGAATGAAAAAAAAAAAAAAAAAAAGGCAGAGGAGAGCATAGA<br>AATGGGGTTCACTTTTTGGTAAAGCTATAGCATGCCTATCACATATAAATAGAGTGCCA<br>GTAGCGACTTTTTTCACACTCGAAATACTCTTACTACTGCTCTCTTGTTGTTTTTATCACT<br>TCTTGTTTCTTCTTGGTAAATAGAATATCAAGCTACAAAAAGCATACAATCAACTATCAA<br>CTATTAACTATATCGTAATACACA |
| 2 | S. cerevisiae pPCK1 | ATAGGAAAAAACCGAGCTTCCTTTCATCCGGCGCGGCTGTGTTCTACATATCACTGAAG<br>CTCCGGGTATTTTAAGTTATACAAGGGAAAGATGCCGGCTAGACTAGCAAGTTTTAGGC<br>TGCTTAACATTATGGATAGGCGGATAAAGGGCCCAAACAGGATTGTAAAGCTTAGACG<br>CTTCTGGTTGGACAATGGTACGTTTGTGTATTAAGTAAGGCTTGGCTGGGGATAGCAAC<br>ATTGGGCAGAGTATAGAAGACCACAAAAAAAAGGTATATAAGGGCAGAGAAGTCTTTGT<br>AATGTGTGTAACTTCTCTTCCATGTGTAATCAGTATTTCTACTTACTTCTTAAATATACAG<br>AAGTAAGACAGATAACCAACAGCCTTTCCCAGATATACATATATATCTTTATTTCAGCTT<br>AAACAATAATTATATTTGTTTAACTCAAAAATAAAAAAAAAAACCAAACTCACGCAACTA<br>ATTATTCCATAATAAAATAACAAC |
| 3 | S. cerevisiae pMLS1 | CCATTGGGCCGATGAAGTTAGTCGACGGATAGAAGCGGTTGTCCCCTTTCCCGGCGA<br>GCCGGCAGTCGGGCCGAGGTTCGGATAAATTTTGTATTGTGTTTTGATTCTGTCATGAG<br>TATTACTTATGTTCTCTTTAGGTAACCCCAGGTTAATCAATCACAGTTTCATACCGGCTA<br>GTATTCAAATTATGACTTTTCTTCTGCAGTGTCAGCCTTACGACGATTATCTATGAGCTT<br>TGAATATAGTTTGCCGTGATTCGTATCTTTAATTGGATAATAAAATGCGAAGGATCGATG<br>ACCCTTATTATTATTTTTCTACACTGGCTACCGATTTAACTCATCTTCTTGAAAGTATATA<br>AGTAACAGTAAAATATACCGTACTTCTGCTAATGTTATTTGTCCCTTATTTTTCTTTTCTT<br>GTCTTATGCTATAGTACCTAAGAATAACGACTATTGTTTTGAACTAAACAAAGTAGTAAA<br>AGCACATAAAAGAATTAAGAAA |
| 4 | S. cerevisiae pICL1 | ATTTATTGAAAAGTAAATATCTCGTAACCCGGATGCTTTGGGCGGTCGGGTTTTGCTAC<br>TCGTCATCCGATGAGAAAAACTGTTCCCTTTTGCCCCAGGTTTCCATTCATCCGAGCGA<br>TCACTTATCTGACTTCGTCACTTTTTCATTTCATCCGAAACAATCAAAACTGAAGCAAT<br>CACCACAAAATTAACACTCAACGTCATCTTTCACTACCCTTTACAGAAGAAAATATCCAT<br>AGTCCGGACTAGCATCCCAGTATGTGACTCAATATTGGTGCAAAAGAGAAAAGCATAAG<br>TCAGTCCAAAGTCCGCCCTTAACCAGGCACATCGGAATTCACAAAACGTTTCTTTATTA<br>TATAAAGGAGCTGCTTCACTGGCAAAATTCTTATTATTTGTCTTGGCTTGCTAATTTCAT<br>CTTATCCTTTTTTTCTTTTCACACCCAAATACCTAACAATTGAGAGAAAACTCTTAGCATA<br>ACATAACAAAAAGTCAACGAAAA |
| 5 | S. cerevisiae pYLR307C-A | CAAAAAAACAATGGAAGAACAAAGAAAATTTAGCGGAAGTAAAAATAACAGCCGAAAGC<br>CAAATTCAGGCTTATCTTGCCTACTCTTTCTTTTATCGAATTCCTTTAGGCCGTTGCAAT<br>AGAAAAGTAATAAAAACGCATATACGTAAGTTGTAGTCAGTGTAATTGCAATCTATTATG<br>CGCATCAGGTGCGCATACTACATCCATTGGTGCACAAAAAAAGGAACGCAGACAAGAA<br>AATTATTCAGTTTGCTGTTCGTGATGAGCCATCCCTGAATATGACTAATGTTAATGTTCA<br>ATTTGGGATCTTATTTTTTTTTGTGCAGTAATAAGAATCTTTGAAAAAAAACTATATAAGC<br>CTATATAGTTTGTAAGATATAAGACAAAACACACCTGCTTTTCCACTACACATTTTCGTT<br>ATTATATAAAAAGACAGCCAAGTATACTTGTCAACAAAATAAACTCATAGCAATTACAC<br>TATAAAAACAATAGCATCAAAA |
| 6 | S. cerevisiae pYGR067C | TGGCAATCCCCTCCGATCGTCCGCGGCAAAATGGTCGTCAATCGGACAAAGGGGGAT<br>GATGGGATCTGGTAATAGAAGAAAATATGGACTAAAGGTAGCCGCTAAAGCGATCCAG<br>GCATGTGTTGCCAATGATGTAAGTCAAGCGAAGGAAATGGTTCAGTAATATGATAGACA<br>GACTGCACTTCAAGGGTGCGCCCCTCCCCCGCGCATATGCTTACAACGCAAAT/stAT<br>TGACGTTTAATGTGGATACTTATCGTAATCGCTGCATTATAGATTTCGAGTCATGTTCAC<br>TTAACCCCACATATTTATATAGAACGCATCTTCAAAGTACTTATAAAGTTTAGTTTTACAT<br>TTTTCTGCTTTCTATTTCTTCTTTTTCGGTTCTTCTTCATGCCAGTTGGCATGGCTTAAGA<br>GCTTTACTTGTCGCTTTTATTTAAAACCTTCTCTCGGGAGAAGACAATTGTTGATATACA<br>GTAATTGTATTTGCATTATCACTGCT |

TABLE 3-continued

Summary of Sequence Listing

| Sequence ID No. | Description | Sequence |
|---|---|---|
| 7 | S. cerevisiae pIDP2 | AACGTCTATCTATTTATTTTTATAACTCCGGGATGTCATTGCCGGTGGTCCGAAAATCG<br>GCAAATAAGGAAATAAGGGAAGAATATGCAGTAGTCAAATCATCAGTGTTCTCTTTGAT<br>ACCTTTCAGGGCTAGGAATAGTGGGGGTGGAGTATAATATCAAAAACCGGACTTAACAT<br>TATTGGTTCGGTTGGAATTGGCTATAGGCAAACAGTCTCCGGCATGATATATAAATGA<br>CAGCCTGCAATTGTATGTTACTACACTCTTGACTTGTCGACTACAGTCGCTGCTCAGGC<br>ACGAGAATAGGAGGTAAGAAGGTAACGTACGTATATATATAAAATCGTA |
| 8 | S. cerevisiae pADY2 | GAGCTCCGTGGAATAGGCGAGCGGCTGAGTGGTTCTCCAAGCTACGGTTTTTACGTGT<br>AGCCCCATGTGAGCAAGCCAAACAAGGGCCCTTAAAGGCGTGACTACAAAAAGGGGC<br>GGGTTGGAAGGTCATCTGCAGCGAGATACGAAAAGATTTTTTGCCAGATTTGCGGTTG<br>GGCGGCTATTTCGGTATTGTTGGGGTAACAAACGTTGGGGAAGACTGCATTTTCTTACA<br>GCTTTTTTTCGTTATCGCGGGTTGGGCGGCTATGGCGCCTTCTCCTCTGTACTCCAACC<br>TGTCAGAGACACCAAGCTGTATATAAAGCACCTTGGTTGGATCGTATTTCCCTGAGATC<br>TTGCTATAGGTTCATTTTATATATCGTCCAATAGCAATAACAATACAACAGAAACTACTA<br>GCATCTGTTTATAAGAAAAAGGCAAATAGTCGACAGCTAACACAGATATAACTAAACAA<br>CCACAAAACAACTCATATACAAACAAATAAT |
| 9 | S. cerevisiae pGAC1 | CCCTATCTTTTTTTTTTCTCGCAATCTGGGGAAAGCTTTTCTCATGCTTATACGTGATTT<br>GTTATATAAGGGATTGCTATTTCAGGCATCATTCACCTCCTTTTGTATCCTTAGTTTCAC<br>TGCATTTGATATATATATATACGTATCTGTAGTTTCCTTCCATTACATAACGCATAATATA<br>CTATTTCCATAGTCTATCTTACATCTTTTTTCTTACTTTTGTTAAGGAACGGATAACGATA<br>AAACAAAAGAGAGATTTAAGATTACTTCTGTAACTTTTTTGATCCATTACCAAAACTATA<br>TTTTTTTTCTTTTCTCTCCTCTGGCATTAAACACAGTTATTGCTACAGCTAATCATCGATA<br>TAATAATACATCACATTAACTGTCTATAAGAGGCTGGTACTTAGTAGATGGTGAGAATTT<br>TTTATTTTTGTATTTTAACTTCATTTTTGTAAACAAGTTTGGAACTGGAACTTACTATAGAA<br>CAAGAGCTTAAACC |
| 10 | S. cerevisiae pECM13 | GTTGTATCCTATTGGATCACGGGCGACGGACAAGACCCGAAGTGCGGACCGGCATGG<br>TCAGCTTGCACGGAAGCTTTAAGGGTTTCCCTTGTTTCGGCATTAGAAGAGGCATTTCG<br>CACGTTTTACCGGGTCAGAAACTTCGAGGAAGCTGTGACAATTGGAAAAAAAGGCAAA<br>ACTAAATGCAATGTATCCGGTTGCCCATGCATTATTTGTGATGTTTTCGGATGTAGTTCG<br>CTGCGCTCCGCGGCGATATATCCTAGCGAGAGGCATATGTATAAATATATATATATA<br>TATCTAACAAAAGCATTCAAGTTTCTTTCTCTGGTGTTACGTCTTTGTTCGACTTTCTCT<br>GCTTACAGCCCTGTATGACCAAAGAAAAATAAAAAGACAGCTACATACCAGCAGAAAT<br>TTTTTTATAGTATTACACTATACATCCAAGTTTTTTCACAATTATTTATTGTTTTTCTCACAT<br>AGAAAATTCCGCATACTGCGATTATA |
| 11 | S. cerevisiae pFAT3 | GAAAGCTTATTACTGAGTTTTGCGGAGCATCGCTCGGAGCGGCGGAATTGAATCGAAC<br>CGCCGTGCTATTACCGAACAAAAAAATTCGAAAGCATAAACTCAGTAGTGAAAAACTTG<br>AGAATTTTCAGATGAGTGGCGACTTTCCAGTCCTTGCGGTTTTGTCACCTTAGTCAGCT<br>AGTAAGGAGGCCGTGTGGGTTAGAGTGGCTACAATCCTCAAAGGGCACTTCTAGAACC<br>CACGGTGAATTTTTTTGGCATGATAAATCGGTAGAATCGGTGAAGTAATTACCCAAAA<br>AAGGATCGGGATTGTGTTTCTCGTAATTCCGTATTATTGCCGATGGCATCGACTACTTC<br>TTTTTTCAGAAACCCCAACAAGGGTCTATTGTAATTGTATATAAACCTTTTTGTAATGGAT<br>ATATACATGTGGTACTATTTCTCCTCATCCTGCTCCATCGAAAATCCTCATACGAAGAGT<br>TAGGAAAGCAAAGAAAACAACAAAAAC |
| 12 | S. cerevisiae pPUT1 | AGACACAATGCGAAAAATCGCGCAGGGACATAATTTTTGTTTTCATTATTCTTTCGCTTA<br>TTCCCTCCGTTAGCTCCACCGCTTTTTTGATTGGAATTTCCTTTCGGCAATGGCTTTCC<br>GGTTACCACGCCTCGGGTTTCGCATCCCGAAAAGCATATCTACACAAGAAAAATGAATG<br>ATAAACAATTGATGAGTGGCGCTATTTCCCTTATCATCTCATTATTGTACTTAGTATCGT<br>CTATTATCAGGAGAAATCGCATGAACTAAGCCCATTTTCTCACCCTTCTGCCTTCTTATA<br>TAAAGCTTGCTGGGAACCGAACACAAACTCCACAAGTCCGTAGCAGCTCTTCTCTTTTG<br>TCTTTTATATATCATAAACATCGCTACATAGTAATAACACTAACGCACGCTAGAA |
| 13 | S. cerevisiae pNQM1 | AGGGGTAGCGGCTTTTTCATCAACTCGATTATTACCCTTTAGAGACCTTCCCTAAAGTG<br>AGCGGCAATTATTTCCGGATGTTAGTAGGGTAATATGGTTACGGATTTGTGACACAAA<br>GGGCTTTTCAACAGTCGGTCTGGGTTGAAGGATTTTCAGGATGACGAAGCTTTCAATAA<br>GAGGGACTGGACTGTTAACGCGGGGAATTATAGGTTACTTTCCTTGATCTGGCTCTGG<br>CTCTGGCTCTGATTTTGGCTCTTGTACTCCTCGGACTTCTTGACTTGTAACGAAATACG<br>TCTTTTGTCCTTCTCTTCTTCTTCCATAGTAGGGGCGAATGAGGGGAGCATAGTGGATC<br>CTTCTAACCATCTAGAATGGGGTGGACAACATATAAAAGAAGAGCAATCTTGCAGCGCA<br>GTCATATTTGCTAAGTATATCATTATTTCTTGCTAGCGTAAGTCATAAAAAATAGGAAA<br>TAATCACATATATACAAGAAATTAAAT |
| 14 | S. cerevisiae pSFC1 | AGCCTAGTCCCGGTAAACCGCAAACGGACCTTAATTGTGACGAAGGGCCCAAATTTGA<br>TGGGTCGGTGTTAATGATTAGTCCTCATTGTCATAATAAAGTGTGATGATGGAGGCAAT<br>GATGATATACGGTAGTACTACTGCTCGAGGTGCTATCTTTTAACCAATCCTTTGAGATTC<br>TTGTCGCCACGGAGTTACTACCTTTTACAAACCGTAATGTCACATTTTGCATATATCTTA<br>TGTATAAATATATAGTTCACTTACTACTTGTTCTCGTTTTGTTAACTTTCTTGTTGTAGTT<br>CTTCTTGTTCTTGGCGTTTCCCCCTTTGTTTTCTATCTGCTTCATAAGTAAAGTGCAAAG<br>CATTTTGGAAGATATTATCAATTGAGTCATTGAAAGAAACTTGGCATCTTCCCTATTACT<br>AAAACTAAGAATACTTGATTCAAGAAAGAAGTTTATATTAGTTTTAGCCGTAAGATAACA<br>TAACAAAGAAGAAGAAAGAAAA |

TABLE 3-continued

Summary of Sequence Listing

| Sequence ID No. | Description | Sequence |
| --- | --- | --- |
| 15 | S. cerevisiae pJEN1 | TCGATCAGCTCCAATTAAATGAAGACTATTCGCCGTACCGTTCCCAGATGGGTGCGAAA<br>GTCAGTGATCGAGGAAGTTATTGAGCGCGCGGCTTGAAACTATTTCTCCATCTCAGAG<br>CCGCCAAGCCTACCATTATTCTCCACCAGGAAGTTAGTTTGTAAGCTTCTGCACACCAT<br>CCGGACGTCCATAATTCTTCACTTAACGGTCTTTTGCCCCCCCTTCTACTATAATGCATT<br>AGAACGTTACCTGGTCATTTGGATGGAGATCTAAGTAACACTTACTATCTCCTATGGTA<br>CTATCCTTTACCAAAAAAAAAAAAAAAAAAAAAAAAAAAAAATCAGCAAAGTGAAGTAC<br>CCTCTTGATGTATAAATACATTGCACATCATTGTTGAGAATAGTTTTGGAAGTTGTCTA<br>GTTCCTTCTCCCTTAGATCTAAAAGGAAGAAGAGTAACAGTTTCAAAAGTTTTTCCTCAAA<br>GAGATTAAATACTGCTACTGAAAAT |
| 16 | S. cerevisiae pSIP18 | ACATAGTACTGTACGATTACTGTACGATTAATCTATCCACTTCAGATGTTCAACAATTCC<br>TTTTGGCATTACGTATTAATACTTCATAGGATCGGCACCCTCCCTTAAGCCTCCCCTAAA<br>TGCTTTTCGGTACCCCTTTAAGACAACTATCTCTTAACCTTCTGTATTTACTTGCATGTTA<br>CGTTGAGTCTCATTGGAGGTTTGCATCATATGTTTAGGTTTTTTTGGAAACGTGGACGG<br>CTCATAGTGATTGGTAAATGGGAGTTACGAATAAACGTATCTTAAAGGGAGCGGTATGT<br>AAAATGGATAGATGATCATGAATACAGTACGAGGTGTAAAGAATGATGGGACTGAGAG<br>GGCAATTATCATCCCTCAGAATCAACATCACAAACATATATAAAGCTCCCAATTCTGCCC<br>CAAAGTTTTGTCCCTAGGCATTTTTAATCTTTGTATCTGTGCTCTTTACTTTAGTAGAAAG<br>GTATATAAAAAGTATAGTCAAG |
| 17 | S. cerevisiae pAT02 | AAGTTCTTGACTACCCCTATCTCACACTAGTACGTAATTCAATGTATCATTCGTATTGTA<br>AGTAGATAGACGCAATACAGGAAAGCTGACCTTCCTTCCAATCACCACGGCTGAAA<br>TGCTTTGTTGACCAATTACGGACGCTTAAGAGCGGACGCGGCTGGAACGGCTCCATCC<br>TAAATCGGCGGAGGGAGAACTCCGATACCAGCCGACATGGCAATAATAGTGACAGTAG<br>ATGCTACCAGCCCCGCAATAATTTCACAGTAGATCATCAACAGTCTCCTCATTTCTGGA<br>AATGATCAGCAACTTCGACGGATTTAACTCTCAAGCAGTTACGCACTCCGAGAACAGCC<br>GTGATCATCTTTGAACAAGCAAAATATATAAAGCAGGAGAACTGTCCTACCTAGAGCTA<br>GAATAGCCATAACTAACTATGTAACATTCTACAGATCAATCAAAAACAATCTTCAATCAC<br>AGAAAAAAATAAAAGGC |
| 18 | S. cerevisiae pYIG1 | TTTTCTAGTTCTTCTTCTGCAATATTGCCTTTTGGGAAGAAGGATCGAAAGTAGCCATTT<br>GCAGACACGTTTTTACTATATTTACTGTATCTTCGATTGCGCGGCTAAAGTTGCCATATT<br>ATTATTATATTGCAGCTCAACCCCGCATTTCCGGAGTTTTCTTTTTTTTTATTTGGGGTAA<br>TTTGGAGGTCGGCGGCTATTGGTGGGGCCGGAAATGGTGACACACTTGTAATATATAAG<br>GAGGAAATCCTACATGTGTATAAGCGAAATCACAAGGATAATAATGTATTGCTAAACAC<br>CCTCAAGAAAGAAAATAATCATAACGAAATC |
| 19 | S. cerevisiae pFBP1 | CGGATGGAATCGCCGCTTTTGAATTCACCTCCGGGGTATTATTATTATTCTTAGTAGTC<br>GCGGTCGTGCGGACACCCGGAGTTATGCGGGCCCGAAAGCTCATTATGTAGTAAAGC<br>TAGGTAATGTTAAGGGCGTAAGAGCCAACGCAAGGCAGCAATAGCCTGGTATTCCCAC<br>ATATCAAGAAAGCTTAAAAAGTTGAGACAGGGAATTTGAAGGCGAAGATTGCCGAACT<br>GGCCAATACCCACTACTTTTTTTTTGGTTTGCTTGGTTTCTTCCTGTCGCTTGCCAACTT<br>GTGGCATCTTCCCCACACTATATTATAAGGATCGTCCTATGTATAGGCAATATTATCCAT<br>TTCACTCGCTAACAAATGTACGTATATATATGGAGCAACAAGTAGTGCAATTACAGACG<br>TGTATTTTGTCTTGATCTTGCTTTTTGTATGATAGGCCTAAGAATAACAGTGCGAACATA<br>TAAGAAACATCCCTCATACTACCACACAT |
| 20 | S. cerevisiae PHO89 | AGACCTTTTTTTCTTTTTCTGCTTTTTCGTCATCCCCACGTTGTGCCATTAATTTGTTAG<br>TGGGCCCTTAAATGTCGAAATATTGCTAAAAATTGGCCCGAGTCATTGAAAGGCTTTAA<br>GAATATACCGTACAAAGGAGTTTATGTAATCTTAATAAATTGCATATGACAATGCAGCAC<br>GTGGGAGACAAATAGTAATAATACTAATCTATCAATACTAGATGTCACAGCCACTTTGG<br>ATCCTTCTATTATGTAAATCATTAGATTAACTCAGTCAATAGCAGATTTTTTTTACAATGT<br>CTACTGGGTGGACATCTCCAAACAATTCATGTCACTAAGCCCGGTTTTCGATATGAAGA<br>AAATTATATATAAACCTGCTGAAGATGATCTTTACATTGAGGTTATTTTACATGAATTGTC<br>ATAGAATGAGTGACATAGATCAAAGGTGAGAATACTGGAGCGTATCTAATCGAATCAAT<br>ATAAACAAAGATTAAGCAAAA |
| 21 | S. cerevisiae CAT2 | TCCGAAGAGCGTGCTACCAATTCTTCATCTCGTTAACAAACTGGTTCTCCGTTAAAAATT<br>GTGCTATATGTCCTATAAGCCAACTCTATCTATATCTTTTCTTTTAGTCCTACTTTGGATA<br>CTGTTACCACCATTTTAGATTGCTTTTTCTTTTGCCGCTAGCCTTACAATATTTGGCAAA<br>CTTTTTTTTTTAGCCGGCCGAGACTCTTGATCTATGGCCGGGCGAAAGGGCAAATGACT<br>GCTTATCCCCGCCATCACTTCCCCCCGCCCAAGGGTTTAGAATTGGGGATTAAGTAAA<br>AACGAATGACTATTCCTCTCAAAGTCATCCTTGTTCGACAAAAAGAATGGAATATAACAT<br>ATTGGAACAATTTCATCCTCTTTTCCCCATTTTCGCATATAAGAGCAACTAAACGCCGGT<br>GAGTAAAGTGCCCTTCCCTACAGACTCTTTTACTCAGGTATATATATATATATATCCCTT<br>AAAAACTAAAAAGAAAGCACTC |
| 22 | S. cerevisiae CTA1 | AGCGGTTGTTCTAACCACTATTTAAAGCCGCAATTAGTAATGCAAAAAGTTGGCCGGAA<br>TTAGCCGCGCAAGTTGGTGGGGTCCCTTAATCCGAAAAAGGACGGCTTTAACAAATAT<br>AAACTCCGAAAATCCCCACAGTGACAGAATTGGAGAAACAACCAGTTTTGATATCGCCA<br>TACATATAAAGAGATGTAGAAAGCATTCTTCACTGTAATGTCCAAATCGTACATTTGAAT<br>TTCTTGTAGGTTTATTTAAAAGGTAAGTTAAATAAATATAATAGTACTTACAAATAAATTT<br>GGAACCCTAGAAG |

TABLE 3-continued

Summary of Sequence Listing

| Sequence ID No. | Description | Sequence |
|---|---|---|
| 23 | S. cerevisiae iCL2 | AATTTTTATTTTCTCCTTCCATATGAGCGACAGCGGTTACTAGCCGCTGTCCTCAGGTTA<br>ATGATCCAAGTCCGAGATCCGGGCCGAATATGCTTGCGGGGAAAGAAATAAAAGTGCA<br>TTGGAGAAGAAAAGGATATGCTCTTCAATTAGAAGCGCCGAAACACTAACATCATGCTA<br>GCGATATCATACGTACACTATATAATGTAAAAAATGGGCTTAAGAATAACTCTCTTATTT<br>CTTAACTTTTGTTGCGGTTGAAGAGCTTATAAAAGTACTAGTGGCCTAAAGAAGCTACA<br>GCGCCGATAATAATATCGATTTCGACTTTTCTAGTATTTCGCCG |
| 24 | S. cerevisiae ACS1 | TGTGCACATACGTCCAGAATGATATCAAGATAAATGGCACGTGTATGTACGGCTGTGTA<br>AATATGATAATCATCTCGGACGAACGGCGTAGCACTCTCCATCCCCTAAAAATGTTCAC<br>GTGTGACTGCTCCATTTCGCCGGATGTCGAGATGACCCCCCCCCCTCAAAAGGCACTC<br>ACCTGTTGACATGCCGTGGCAAATGATTGGGGTCATCCTTTTTTTCTGTTATCTCTAAGA<br>TCCAAAGAAAAGTAAAAAAAAAAGGTTGGGGTGCGAATTGCCGCCGAGCCTCCGATGC<br>CATTATTCAATGGGTATTGCAGTTGGGGTACAGTTCCTCGGTGGCAAATAGTTCTCCCT<br>TCATTTTGTATATAAACTGGGCGGCTATTCTAAGCATATTTCTCCCTTAGGTTATCTGGT<br>AGTACGTTATATCTTGTTCTTATATTTTCTATCTATAAGCAAAACCAAACATATCAAAACT<br>ACTAGAAAGACATTGCCCACTGTGCT |
| 25 | S. cerevisiae PDH1 | AATATAAATAAAATTCCATACAGCATGTCTAATCATAGCTAATTTATACATATTCATCATG<br>AAAACATATAGGGGAAAATATGGTCGGTTAACACACCTATCAAAAAATTATTCAGCAATT<br>CCAATCTCGTTAGTAAAATATATTCTTATTTTTTTTTTTTCTCTGATTGTATTATTTCTG<br>GAGTTTTGACTTATTTTTTTACCACATCGCGCTTTTCGTCCCCAATCTCTCTGATATATG<br>ATGCTGTCTATAGGTAGCCACTTCCCCGATGTCGGACCTCGGGCCGTTTACAAACTTTA<br>TTGAGATGACCTTATTTCTCCACATTCTAGTCATTCAACTTTTACCCTCATATGTTTACCT<br>TCACTAATGTGAAAGCATGACCAAAGAAAGTGTATAAGGTATATAAATCTGCCATAATGT<br>ATGTATAACTTATTAGGACTTTCTCAAATAGTATTTTGGTATTTTCTACTGTTCTCTGATG<br>ATCGAGAGCAAACAGA |
| 26 | S. cerevisiae REG2 | AAGTACGATATGGTATAACTGTAACATTGAAGGACTGAAGGACTGAAGGACTGAAGGA<br>CTATAGTCAAGGGCCAATGGGGAAGGTCCCTTCCAGGCCATTTGCCCGATAGTTTGTC<br>CTTCTCTTGCTTTTCCGACGGCCCGATTGCATGTGGCGGGGCAGCACTGGATAAAAAA<br>ACGTGGGGGGAGTGATTAAATTTATACGCTTATTGTGTCAACACGGAAACCTTATAGTT<br>ATCATTACTAACATCGCAACAAGCTGCTTTTTTACTCGTTTTTAGCCACACCATACCCCC<br>TTTAATTAACTAATAATGCATAAAATAGTTATTGCTTCTTGAGTTGCAGCTTCTTCCTGGA<br>CGTACTGTTATATATGGCATGTCTTCGCATGTCCGTCAAATTTAGCGTTGTCTCGAAACT<br>TAGGCTGTCGTTCTTGCTGTCTGTCTTCTGATAAAATAATATATTGGAATAAGAAAAAAA<br>AAATAGGAACAAGAAAGTGTGTGAGA |
| 27 | S. cerevisiae CIT3 | ATATTATTCAGTTGAAAGACAAAAAAACATAAATATTTCTATGAGCAAACAATTTGAACA<br>GAAAAATAAAATTGGGGAAGTGACACACCATGGTAGCGGTTCTAAAGCGAAATCGGCA<br>AAGCGGCTAAATAGCAGTTTTGATGACTTACTCCACACTGAAAATGGATGACCTTAAAT<br>AGGAGATAAAGCTTTTTCATCCCTATGTATTTAAGATGACTGGCTTGTCAAGCATTCTAA<br>TCATAAAAAAAAGATCGTATTTGATCAAGAATTTATACATAGACGCCGCTAAATAATTGA<br>ATACAAA |
| 28 | S. cerevisiae CFRC1 | CTCGTTTGCCGTTACATTGCATTGATGGTACAATAAAGGGCATGCTTTATATCGAGATG<br>TTTCAGTGTATATGAGGGGAAACAGAAAAGAGTCATTCCTGCCATTTTTGGTCACTGC<br>TTTTTCTGCTATGAGTAATGGTGAAGTTCCTTGTGGCTACACGCTTAATGTCATCGGGT<br>TACTGCTCCTAATATCCGCATATAAGCTTTATGCAGGGATCAGTTGGGCGGCTATTTAT<br>CTACACCCAGTCATCCGGCGTGACTGGATCTCCACTTGCCGCAATAAGTCGGTGGACA<br>AATGGAGATTTAAGAGTAAAGATGCATGATGGTATAATTCCTTTAGTCGAAATAGATATA<br>TTTCAAGCGCATATATAGGCAGACGCTTGTACTGTAGAAATAGCCGATATTCAATTGCG<br>CTCTATGTGTGTTTTTATTCCAGGTTTTCCTTGGATTCTACGTATTGTACGACTTTCTTAT<br>CCTCCACAAACGTCATCGTGTCAGTA |
| 29 | S. cerevisiae RGI2 | CCCAACAGATTTCAAGTCTGTCGCCTTAACCACTCGGCCATAGTGCCTAAAACAATGTA<br>GGTTATTTAAGCAAGTATTGTAGATACTTTTCGTAATAAACTACAATGCACCCACGACTC<br>GCGGTGTAATGATGGCATGAAATCATTGAACGAAGTTTTGCGGCTATACGGCTGAAGG<br>ACGAGACTAAAGGGACAGGAATTATTAATGCGGGGTATAATTTGAATAGTATTAACGGG<br>CACTGCCGTTTAGCCATCAAATGCTATTGTTGGGGTATTCTCTCTACTTTTTGTTCTTGG<br>CTTGAACCTTTTCGGCGTTGGCAATCGTCCGTATATAAGCATCGGCTGTCCCAATCCT<br>CTATTGCCCTTTTCCCTTGCACCTCCTTCTCAATTCTTCGTATCTTTCGCGTAAAGGTAG<br>ATCTTGATTCACCTATCTGTCGAAACACGATTAAGTGCAAACGAAACAACGTACAGTAT<br>ATAACAAAGTATTTTAAATAATAAGA |
| 30 | S. cerevisiae PUT4 | GCTATGACGTTTGGGTGGCCTAGCCGGTTCGCGTGTGCCTGTCGCTTTTGTCGCTTTT<br>CAACTTCTGCCCGATATTTCCTATCAAAGGAAAATGGGACGTTTTCAACCCCTCGCTAT<br>CATCGTGCCTGCACTCTGCCTATCGCCAACTACACCGGGGTTTTATCTGCTTCACCCCT<br>CCATCCAGTGCTGATAACAAGAAGAACCTTGCAGGGTAGGGCAGGACCTACGGCCAAA<br>ATACTAATTATGTCTGTTTATGTACATGCCCAATCTGAATATTCCATGAATGTAGGCAC<br>AGCATATCTCCATCCATGTACTGATACAGACGCATAAACATATATGTATATACATACTTA<br>TACACTCGAATATTTGTAGACTGATGTACTTCTATATATATAGGGGGTTTGTGTTCCT<br>CTTCCTTTCCTTTTTTTTCTCTCTTCCCTTCCAGTTTCTTTTATTCTTTGCTGTTTCGAAG<br>AATCACACCATCAATGAATAAATC |

TABLE 3-continued

Summary of Sequence Listing

| Sequence ID No. | Description | Sequence |
|---|---|---|
| 31 | S. cerevisiae NCA3 | TAGATGCGCCATCTCCGAGAAAAAATCTAGACAATAACAGCGACAATTAACCTAAAGAG GATAGAAGATCGAGCAAAAAATTTTTTTAATATGGGGTCAGTGGCGATATTATACTATA GGAGTTAAAGAGTAAGTTGAGTGTAAGGTGGTAGAATTATGATTGAACTCCGAAACTAA GCGCCGATTATGGGTGGCAAAGCGGACAGCTTTTGATATATAATCGATCGCTCTCGTA GTTGATATCCTCTCTCTTGCTTATCTTTTCCTGTATATAGTATATGTGTACATACAGATAC GAATATACCTCAGTTAGTTTGTTTTAACATTAAATATTCAACAGTTGCCAGTAGCAAAAA GAATATATCCATTCATTTCGAGCTTTTTCGTCTCATTACTGATATCCAACTAACAGTCTC CTCATAGACGGTACCTTACTTTCCTTTAATATTATAATACTAGTATAGTCGCACATACTTA ACTCGTCTCTCTAACACATA |
| 32 | S. cerevisiae STL1 | CTACGTCGCCTGTTCGAGCGGCTCTGTTCGTTGCATGAAACTAAAATAAGCGGAAAGT GTCCAGCCATCCACTACGTCAGAAAGAAATAATGGTTGTACACTGTTTCTCGGCTATAT ACCGTTTTTGGTTGGTTAATCCTCGCCAGGTGCAGCTATTGCGCTTGGCTGCTTCGCG ATAGTAGTAATCTGAGAAAGTGCAGATCCCGGTAAGGGAAACACTTTTGGTTCACCTTT GATAGGGCTTTCATTGGGGCATTCGTAACAAAAAGGAAGTAGATAGAGAAATTGAGAAA GCTTAAGTGAGATGTTTTAGCTTCAATTTTGTCCCCTTCAACGCTGCTTGGCCTTAGAG GGTCAGAATTGCAGTTCAGGAGTAGTCACACTCATAGTATATAAACAAGCCCTTTATTG ATTTTGAATAATTATTTTGTATACGTGTTCTAGCATACAAGTTAGAATAAATAAAAAATAG AAAAATAGAACATAGAAAGTTTTAGACC |
| 33 | S. cerevisiae ALP1 | GAGCTATAGTCTTTTGCGCTTTCAATACGTGTAGCGGTGTACCAAAAGTTGCACAAAAA TGTAGTTGTCAATGAAAGCGCACTACGTATATAATGACTATTTTTTTTTTCCTGGGTTGC ATGGGTAATTTGTTGTTAATATGCGATTTTCTTGGGGAAAAGGGTGTCATAGCGCCAAA AACTGCCGTGCGGCACAGTATGTATGTTTTTGAGTCGCGGCGTTTAAGGGCTTGGCAT AAAAAGTGGTTCAAGCGAGTGATAAGTTGGGCGAATGTCGTCTTTTTTGTAACCATGTC TTTCCTGAAAACAACCTGTAGGCAGCTCCACTCCACATAAGGGCTTTCTCCAATGGCAA TGGGAGCTCGGAACACCGGAGTAGAAATTTTTATAATGTGTATTGTATAAAACTTGCTT GTTATGCAGTTTTTGTTTTTTTTGTTACTCTTCCGTAGCACAATAGACATATATTAGCGG CAAAATTGTAGTGTTGCGATTATTGCC |
| 34 | S. cerevisiae NDE2 | GTGTAGTATTGATCTTGTTGGTATTGCTAGAAATGCTTCAGCAATACTGTATAAAATATG GAAACGTTGCCATGGCAAGACAAAAGAAGTGATCTTGAGTGAAATAATAGAGCCCGGA TGGCCGGGTAAATTCAACCGCTCGTACCGTTTATAATACGCATAAACGCCGAAAATGTC TCTATTTTAGTCATTCCCCAGAGTGCGGTATTGCGTACACCTGTCATGCGTTCCTTAGT GCCGATAGATATACTAATATCGATGCGTCACAGTAGCAGATCATCTCTGACACTTGTTT CCCCATTTTTTTTTTCATTTTTTAAAGGGTTTCTCTACAGCCTACAGGCCTCCCCTAATA AGTCAGCCCCTCCCTTTGGAGTGCGCTGTTGACCTGCTGTATATAAGAGGTATATCAGT GCCAGTAGGTAAACCCATCTTGCGGGGATTGTACCAGGAACATAGTAGAAAGACAAAA ACAACCACCGTACTTGCCATTCGTATAG |
| 35 | S. cerevisiae QNQ1 | CATCAATTAGGGCAAACTTGAATAGTCAGCTAGGTCATATATTTAAAATCTTAGCCCT ATGACTACATTAGGTTTATTGTTAGGTCTTTACGGCTGCATATTTGCTTTCGCCGTTCGG CGGGGTCCTGCGACGATTTCTGCGCGGTCTTGTATGGGTGGAGTTGACAGTTAACCCT CCGGACCCCCTACCCCGGTGTGCCCCCGGTCCATCTATCCATTTTGCGGTAACCCCTT TGCGCGACAGCTGCTTATCAAGGTACCTGGATCGAGCCATAAAAATTGATCTACACAGA TGAGATGGGGCATTGGGATATATTATTAGTCGGAGTATCATTATAGTTATTCAGTTTTAT GCAGGTTACTGGCCAAACGTTTTTCTTCATTTGGAATAATCGTTTAGGAGCTACTGTTC CGGTATAAAGTAACAAGCACAGTAGCAGAGTAATACGCAGTGACGATAATAGAGACTA GTAAAACAGTCGAGTTGTCGGACCTAAA |
| 36 | S. paradoxus pADH2 | TAGTCTTATCTAAAAATTGCCTTTATAGTCCGTCTCTCCAGTCACGGCCTGTGTAACTGA TTAATCCTGCCTTTCTAATCACCATTCTACTGTTTAATTAAGGGATTTTGTCTTCATCAAC GGCTTCCGCCCAAAAAAAAGTATGACGTTTTGCCCGCAGGCGTGAAGCTGCCCATCTT CACGGGCCTGACCTCCTCTGCCGGAACACCGGCCATCTCCAACTCATAAATTGGAGAA ATAAGAGAATTTCAGATTTTCAGAGGATGAAAAAAAAAAGGTAGAGAGCATAAAAATGG GGTTCACTTTTTGGCAAAGTTACAGTATGCTTATTACATATAAATAGAGTGCCGATAATG GCTTTTTTTTCATCTTCGAAATACGCTTGCTACTGCTCTTCCAGCGTTTTTATTACTTCTTT CTTGTTTCTCCTTAGTATATAAAATATCAAGCTACAACAAGCATACAATCAACTGTCAAC TGTCAATTATATTATAATACACT |
| 37 | S. kudriavzevii pADH2 | CTCTCAAATCTTTTAGCGCCAAGGACTCCAACTAATTGTATCTTGAATTTGCCTTTACGA TCCGTTTGTCCAGTCACGGCATGTATATCTTATTAATCCTGCCTTTCTAATCACGTATTC TAATGTTCAATTAAGGGATTTTATCTTCATCAACGGCTCCCACGCAAAAATGACGTTTT GCACACAGACACGAAATACACCTTCCACCGGAACAACGGCCATCTCCAACTTATAAGTT GGGGAAATAAGACAATTTCAGACTTCAGAGAATGAAAAAAAAAAGGTACATCACAGA TGGGGTTCAGGTTTGCTACAATTGCAGGGAGCCTGTCACATATAAATAGACCTCCAGT GATGATATCTTTCAGTCTTCAAACGTCTCTTGTCACAGTTCTGGTCGTTCTATATCACAT CTCTCTTGGTTCTACTTATTGTCTATAATATCAAGCTACAGCAAGCATACAATCAACTAT CTACCATACCATAATACACA |

TABLE 3-continued

Summary of Sequence Listing

| Sequence ID No. | Description | Sequence |
|---|---|---|
| 38 | S. bayanus pADH2 | GATCCAGTTCTCCAGTGACACAGCCTTTATCTGGTCAAACCTTTCTTTCTAATCACCTAT<br>GCTGATGCTTAATTAAGGGATTTTTGTCTCCATCAACGGCATGCGCCCAAAAATGACGT<br>TTTTTTTAACCCATAGACACGAAACTACCCATTTTCCACCGGCCTGACCTACCACCGGA<br>ACAACGGCCATCTCCAACTTGCAAGTTGGGGAAATTAAGAGCATCGCAGGTTTAATGG<br>AAGAAAAAAAAAAGGTACAGCACAGCGCAAATGGAGTTAGTTCCCTTATGTCACACACT<br>CACACACAGTCGGTCAGATCAAGCATACTGGGTGCGTATAAATAGAGTGGCCATTGCC<br>ACCCTGTTTATCTCAAAATCTGTCTTGTTAGTCTGTCTTCTCCCTTTTTCAGGTTACAATT<br>CTCTTGTTTCTACTTAGTATATAAGTATATCAAGCTATATTAAGCATACTATCAACTGTCA<br>ACTCTATCCTCAAAATACAATACAAA |
| 39 | S. mikitae pADH2 | TTTCCCAAAAAGTATTATTTTTAAGTGATAATTGATAAAAGGGGCAAAACGTAGACGCAA<br>ATAAAACGGAAATAATGATTCTCAGACCTTTTAGCGTCAAGAACTGCAACTAATCTTATC<br>TTAAAATTATCTTTATAATCCGTTTCTCCCGTCACAGTCTGTGTATCTGATTAATCCTGC<br>CTTTCTAATCACCTATTCTAATGTTCAATTAAGGGATTTTGTCTTCACCAACGGCTTCCA<br>CCCAAAAGTAAAAAATGACGTTGTACCCACAGACATCTTCACCGGCCTGACCTGCCAC<br>CGGAACAACGGCCATCTCCAACTCATAAATTGGAGAAATAAGAGAATTTCAGATTCTGG<br>AGGATGAAAAAAAAAGGTACAGCATAAATGGGGTTTTATGTGGGTACAATTACACTA<br>GGACTATCACATATAAATAGACGGGCAATGTAGGTTCTTTTCCACCCTTGAGACAGAGT<br>TATTC |
| 40 | S. castellii pADH2 | TGTCGTGGACGAAATACGCCACAATTTTGCCGAGAAGGTCATTAGTATGTCCAAGAAAC<br>CCTAGGTGTAAAGTCGGGAAATCCGAATCTCCGATTTTGGAGGGGCCCATGCCCTACT<br>TTTTTTCGCCAGGGGTGAAATTCCAAACCCGTGCGCGTTCTTGGAATTTGACAGCGCAT<br>TGAGTATGTGCTGCGTATTCCCACTATCATGACGCGCCCTTTATCTGGGAAAAATGGAA<br>CTGGATGCTGAAATATTTCACTCTCAGATCACATATCCCAAATCCIGTGAGTGAATTGTT<br>TGGTCAGGCGACCAAACAGGAATATGGAATAGATTCTATTCTCTGGATTCTACAATTAT<br>CCATTGTTAGCAAAACAAAAAAAAACTGGTGGTATATATATTCAGAGCCTAAAATTTAAAG<br>GTTGGATCTCAATTTTAAAAGTTTTCATTCTGTTTTGTTTTGTTTCTTCTTAGCTCACGA<br>ATAACCAAACAAAAAACAATCAATA |
| 41 | S. paradoxus pPCK1 | CAATAGGAAAAAACCAAGCTTCCTTTCATCCGGCACGGCTGTGTTGTACATATCACTGA<br>AGCTCCGGGTATTTTAAGTTATACAAGAGAAATATGCGGGCTAGACTAGCAAGATTCTG<br>GACTGTATAACGTTGTGGATAGGCGGATAAAGGGCCCAAACAGGATTGTAAAGCTTAG<br>ACGCCTCTGGTTGGGCAATGGCATGTTTGTGTATTAAGTAAGACTTGGCTGCGGGATA<br>GCAAAACTGAGCAGAATATAGAAGGCCACAAAAAAAAGGTATATAAGGGCAGCAAAGT<br>CTTTTATAATATATGTAGATTCTCTTCTCTGTGTAATTCATTCTTTGTGCTTACCACTCAAAT<br>ATACAGAAGTAAGACAGATAACCAACAGCCTTTCCCAGATATACATATATCTCATTGTTT<br>CAGTTTAAACAATAATCATATTTGTTCTCAAAAATAAAAAAAAACTAAACTCACTCAA<br>TCAATCATTCCATAAAAAAAAACAAT |
| 42 | S. kudriavzevii pPCK1 | CTTCCTTTCATCCGGCACGGCTGTGTCCCCACATCTCCCTAAAGCTCCGGGTATTTTAA<br>GTTATACAAGGGAAATATACGGGCTGGACTACAACTTGCAGGTTGCACAGCGTTATGG<br>ATAGGCGGATAAAGGGCCCAAGCAAGATCGTGAAGCTTGGACGCGTCTGGTTGGACA<br>ATGGTGACTTTTTGTGTATTAGATAATGCTTGACTGGAGAATATCAGGACTGAGCAGAG<br>TTAGGAAGACCACAAAAAAGGTATATAAGGGCAACGTCTCCGTGTATATGGATAGG<br>CTCTTCTCTCTGGTTACAATTCATTATTTCAGTTGTTTGCTAGATATAGAGATATAATACA<br>TCTAATAAACAGTCACTTCCAGAGATATATATATATACATATATCTATCTCCTCCTCCCA<br>GCTTAAATAATAACTATATTTGTTTAACTCGAAGAAAAAAAAAATTCAAATTTACTCTATC<br>AATTCAATTACCTCATAAAAAACAATA |
| 43 | S. bayanus pPCK1 | CTTCCTTTCATCCGGCACGGCTGTGTCCCCACATCTCCCTAAAGCTCCGGGTATTTTAA<br>GTTATACAAGGGAAATATACGGGCTGGACTACAACTTGCAGGTTGCACAGCGTTATGG<br>ATAGGCGGATAAAGGGCCCAAGCAAGATCGTGAAGCTTGGACGCGTCTGGTTGGACA<br>ATGGTGACTTTTTGTGTATTAGATAATGCTTGACTGGAGAATATCAGGACTGAGCAGAG<br>TTAGGAAGACCACAAAAAAGGTATATAAGGGCAACAAAGTCTCCGTGTATGGATAGG<br>CTCTTCTCTCTGGTTACAATTCATTATTTCAGTTGTTTGCTAGATATAGAGATATAATACA<br>TCTAATAAACAGTCACTTCCAGAGATATATATATATACATATATCTATCTCCTCCTCCCA<br>GCTTAAATAATAACTATATTTGTTTAACTCGAAGAAAAAAAAAATTCAAATTTACTCTATC<br>AATTCAATTACCTCATAAAAAACAATA |
| 44 | S. paradoxus pMLS1 | CGATACCACACGGTCCATTGGGCCGGTGGTGTTAGTCGACGGATATATGCATCTGTCC<br>CCTTTCCCGGCGAGCCGGCAGTCGGGCCGAGGTTCGGATAAATTTTTGCATTGTATTA<br>GTTTCTGTCATGAGTATTACTTATGGTTCCTTTAGAGCTAATCATTAGCTCGGTACCGGC<br>TGTTATGCAATTTATGACTTTTCTTCTACAGTGTCAGCCTTGTGACGATTATCTATGAAC<br>TTTGGATGTAGCGCATCGAGATTCGTATCTTTCATTGGATAGTAAATGGGAAGGATCGA<br>TGACCCTTATTACATTCTTTCCTATACTTAATATCCATTTAATCTATCTTCTTGAAAGTATA<br>TAAGTAACGGTAAATTTACCATACTTATGCTATTCTCATTTATCCCCTAATTTTCTTTTAA<br>CTTCTCGCCCTACAGTAACTAAGAATAACGGCTACTGTTTCGAATTAAGCAAAGTAGT<br>AAAGCACATAAAAGAATAAAGAA |

TABLE 3-continued

Summary of Sequence Listing

| Sequence ID No. | Description | Sequence |
|---|---|---|
| 45 | S. kudriavzevii praS1 | AGACCGAAGCGGGTAATGGACGGAATTAAGCAATTGTCCCCTCTCCCGGGGAGCCGA<br>CAGTCGGACCGAGCTTCGGATAAATTTCTGTATTGTTTFTGTTTCCGTCATGGGTATTAT<br>TTTCGGGATCCTTTTGCCAACCCCATAGTCAATCGTTAACATTTACCGGCTATGTA<br>GGATTATGACTATTCTCCTGCATGATCAGCGGAAGTGACGATTATCTATTAATTTTGAAC<br>TTCTACTTCGTGATCCGGAATTTAATTGGATAATAATGTGTCCGAAGGATCGAGTGACC<br>CTTATATTCTGTAGTTTTTTGTTACTGGCCATCCAATTCGTGTTCTTGGAAGTATATAAGT<br>TACAGTCGATTGACCTTTCTCAAGCTATTTTCATCTTTCTCCTACATTTACGTTTCTCTTC<br>TTCAATACAGCAGCTAGAAGTTACGATTACTCCTGTGATAAACAAAGTAATAGTAG<br>CCCACAAAAAGAGAGAAAGTAAAA |
| 46 | S. bayanus pMLS1 | GTAGCAGTCCGGAAATAAGCAAATGTCCCCTTTCCCGAGCTAACCAACGGTCGGGCCG<br>AGCCTCGGATAAATTTTTGCTTTGTTTTTGTTTCTGTCATGGGTATTATACATCATTTATT<br>TAGTTAACCCCTAGACTAATTAGCCGGCCATTAGTATGTAAGATTATGACTATAGTTTGT<br>ACCGGAACCCTGGTAGCAACTACTCATGAACTTTGGGCTCAGTATTTCGCAATCCCGG<br>TTTTAATTGGATAGCCTATCGCGAAGGATCGATGGATGACCCTTAGAATTGTCTCTTT<br>GTTACTACTCATTCAATGCGTGTGCTCTTGCAAGTTATATAAGTCACTCTAAATTAGTTTA<br>TACTTGAGCTTTTTACATTTCTCCCTTGATTGTTTCTTTCTTTTCCCCTTGTTCTGGTT<br>TATTGTAATAGCTAAGTGCAACGATTACCGCTGTTAAGTTAAAGAAGAGAGACAAGTAA<br>TAATAGTACACAGCAAGGAAAAAA |
| 47 | S. paradoxus pICL1 | TTACTAAATAGGCTGGCATCAGCTAACCCGGATGGTTGAATCCGGCTTTTGCTACTTGT<br>TGTCCGATGAAAAGGAGCGGCTTCCCTTTTGCCCCAGATTTCCATTCATCCGAGAGGT<br>CGCTTATCAGACTTCGTCATTTCTCATTTCATCCGAGATGATCAAATTGAAGCCAATCA<br>CCACAAAACTAACACTTAACGTCATGTTACACTACCCTTTACAGAAGAAAATATCCATAG<br>TCCGGACTAACATTCCAGTATGTGACTCAATATTGGTGCAAATGAGAAAATCATAGCAG<br>TCAGCCCAAGTCCGCCCTTTACCAGGGCACCGTAATTCACGAAACGTTTCTTTATTATA<br>TAAAGGAGCTACTTTACTAGCAAAATTCTTGTAATTCCTCTTCCCTTGCTAACTTCTTCTT<br>GTTTTCTTTTCCTTTTTACACACAGATATATAACAATTGAGAGAAAAACTCTAGTATAACA<br>TAACAAAAAGTCAACGAAAAA |
| 48 | S. kudriavzevii pICL1 | GTTACGGTGCCGCGCCGGTGGCCGGTGGTCTTCCGGTAAACAAAAAAGCTGCCTCC<br>CTTTCGCCCCAGATTTCCATTCATCCGAGGGCACCGCTTGTCAGACTTTATCGTTTTCC<br>TCATTTCATCCGAGAAGATCAATTCAAAGGCAATGACCACAAAAGCAACTCCTAACGTT<br>GTGTTACGCTACCCTTTACACAAAATATTCATAACCCGTAATGAATCCTAAGGTATGTGA<br>CTCAATTTTGGTGTAGAAAATGAGGAAAACGTAATACTAAGTTAAAGCTCGCCCTTTAAA<br>GTGAATATTCCTTGACCATTTGCGCAGGCACACCCGAATTCACAAACGTTTCTTTATTAT<br>ATAAAGGACCAGCTCTGCTAGTCAAATTTTTATAACTGCTTGTTCAGTTGCTGCTTCTTT<br>CTTGTCAATTTATTTCTTGTACTGTTCAACTACATAAAGCAAAGAGAAAACTCTCAGAAT<br>AACATAACAAAGAAGTCAACGAAAA |
| 49 | S. bayanus pICL1 | ACGAGGCTCGGCGTTTACTGCTGAATTTCCGGAAAGAAAGGGAAGGTTCCCTTTACCC<br>CAGATTTCCATTCATCCGAAGGACTGCTTATCAGAATTTGACATTTTTCTCATTTTATCC<br>GAGAAGATCAATTTAAGGCTAGTGACCACAAAACTAACTCTCATGCTGCGCTACCGCAA<br>GTTTCGCTCACAGAAAGAAAGCAAGCACCCATAGTCCGGACTACATCCTTGTATGTGAC<br>TCAAATTTTTGGCGTTGCCAATTAAACTGAAGTGTAAAGATTACTTCAAGCTCACCCTTT<br>AAAGTAGAATTCCTTAACGGTTTTAAATAGACACACCGAAATTAATAAACACTTTCTTTAT<br>TATATAAAGGACAGAGTTATTACTGGAATTCTCTTAACGCCTTCCTCCCTTACTATTGT<br>ATCTTTTCCTTTCACATAATCGCTACATAACTACATAGAGAAAACTCTCAGATTAACACA<br>GTAACAACGAAGAAAACAAAAA |
| 50 | S. cerevisiae pTDH3 | ACAGTTTATTCCTGGCATCCACTAAATATAATGGAGCCCGCTTTTTAAGCTGGCATCCA<br>GAAAAAAAAGAATCCCAGCACCAAAATATTGTTTTCTTCACCAACCATCAGTTCATAGG<br>TCCATTCTCTTAGCGCAACTACAGAGAACAGGGGCACAAACAGGCAAAAAACGGGCAC<br>AACCTCAATGGAGTGATGCAACCTGCCTGGAGTAAATGATGACACAAGGCAATTGACC<br>CACGCATGTATCTATCTCATTTTCTTACACCTTCTATTACCTTCTGCTCTCTCTGATTTGG<br>AAAAAGCTGAAAAAAAAGGTTGAAACCAGTTCCCTGAAATTATTCCCCTACTTGACTAAT<br>AAGTATATAAAGACGGTAGGTATTGATTGTAATTCTGTAAATCTATTTCTTAAACTTCTTA<br>AATTCTACTTTTATAGTTAGTCTTTTTTTTAGTTTTAAAACACCAAGAACTTAGTTTCGAAT<br>AAACACACATAAACAAACAAA |
| 51 | S. cerevisiae pTEF1 | ATAGCTTCAAAATGTTTCTACTCCTTTTTTACTCTTCCAGATTTTCTCGGACTCCGCGCA<br>TCGCCGTACCACTTCAAAACACCCAAGCACAGCATACTAAATTTCCCCTCTTTCTTCCT<br>CTAGGGTGTCGTTAATTACCCGTACTAAAGGTTTGGAAAAGAAAAAGAGACCGCCTC<br>GTTTCTTTTTCTTCGTCGAAAAAGGCAATAAAAATTTTTATCACGTTTCTTTTTCTTGAAA<br>ATTTTTTTTTTGATTTTTTTCTCTTTCGATGACCTCCCATTGATATTTAAGTTAATAAACG<br>GTCTTCAATTTCTCAAGTTTCAGTTTCATTTTTCTTGTTCTATTACAACTTTTTTACTTCT<br>TGCTCATTAGAAAGAAAGCATAGCAATCTAATCTAAGTTTTAATTACAAA |

TABLE 3-continued

Summary of Sequence Listing

| Sequence ID No. | Description | Sequence |
|---|---|---|
| 52 | S. cerevisiae pFBA1 | TGGGTCATTACGTAAATAATGATAGGAATGGGATTCTTCTATTTTTCCTTTTTCCATTCTA GCAGCCGTCGGGAAAACGTGGCATCCTCTCTTTCGGGCTCAATTGGAGTCACGCTGCC GTGAGCATCCTCTCTTTCCATATCTAACAACTGAGCACGTAACCAATGGAAAAGCATGA GCTTAGCGTTGCTCCAAAAAAGTATTGGATGGTTAATACCATTTGTCTGTTCTCTTCTGA CTTTGACTCCTCAAAAAAAAAAAATCTACAATCAACAGATCGCTTCAATTACGCCCTCAC AAAAACTTTTTTCCTTCTTCTTCGCCCACGTTAAATTTTATCCCTCATGTGTCTAACGGA TTTCTGCACTTGATTATTATAAAAAGACAAAGACATAATACTTCTCTATCAATTTCAGTT ATTGTTCTTCCTTGCGTTATTCTTCTGTTCTTCTTTTTCTTTTGTCATATATAACCATAACC AAGTAATACATATTCAAA |
| 53 | S. cerevisiae pPDC1 | CATGCGACTGGGTGAGCATATGTTCCGCTGATGTGATGTGCAAGATAAACAAGCAAGG CAGAAACTAACTTCTTCTTCATGTAATAAACACACCCCGCGTTTATTTACCTATCTCTAA ACTTCAACACCTTATATCATAACTAATATTTCTTGAGATAAGCACACTGCACCCATACCT TCCTTAAAAACGTAGCTTCCAGTTTTTGGTGGTTCCGGCTTCCTTCCCGATTCCGCCCG CTAAACGCATATTTTTGTTGCCTGGTGGCATTTGCAAAATGCATAACCTATGCATTTAAA AGATTATGTATGCTCTTCTGACTTTTCGTGTGATGAGGCTCGTGGAAAAAATGAATAATT TATGAATTTGAGAACAATTTTGTGTTGTTACGGTATTTTACTATGGAATAATCAATCAATT GAGGATTTTATGCAAATATCGTTTGAATATTTTTCCGACCCTTTGAGTACTTTTCTTCATA ATTGCATAATATTGTCCGCTGCCCCTTTTTCTGTTAGACGGTGTCTTGATCTACTTGCTA TCGTTCAACACCACCTTATTTTCTAACTATTTTTTTTTAGCTCATTTGAATCAGCTTATG GTGATGGCACATTTTTGCATAAACCTAGCTGTCCTCGTTGAACATAGGAAAAAAAAATAT ATAAACAAGGCTCTTTCACTCTCCTTGCAATCAGATTTGGGTTTGTTCCCTTTATTTTCA TATTTCTTGTCATATTCCTTTCTCAATTATTATTTTCTACTCATAACCTCACGCAAAATAA CACAGTCAAATCAATCAAA |
| 54 | S. cerevisiae pTPI1 | TATATCTAGGAACCCATCAGGTTGGTGGAAGATTACCCGTTCTAAGACTTTTCAGCTTC CTCTATTGATGTTACACCTGGACACCCCTTTTCTGGCATCCAGTTTTTAATCTTCAGTGG CATGTGAGATTCTCCGAAATTAATTAAAGCAATCACACAATTCTCTCGGATACCACCTC GGTTGAAACTGACAGGTGGTTTGTTACGCATGCTAATGCAAAGGAGCCTATATACCTTT GGCTCGGCTGCTGTAACAGGGAATATAAAGGGCAGCATAATTTAGGAGTTTAGTGAAC TTGCAACATTTACTATTTTCCCTTCTTACGTAAATATTTTTCTTTTTAATTCTAAATCAATC TTTTTCAATTTTTTGTTTGTATTCTTTTCTTGCTTAAATCTATAACTACAAAAAACACATAC ATAAACTAAAA |
| 55 | S. cerevisiae tADH2 | GCGGATCTCTTATGTCTTTACGATTTATAGTTTTCATTATCAAGTATGCCTATATTAGTAT ATAGCATCTTTAGATGACAGTGTTCGAAGTTTCACGAATAAAAGATAATATTCTACTTTTT GCTCCCACCGCGTTTGCTAGCACGAGTGAACACCATCCCTCGCCTGTGAGTTGTACCC ATTCCTCTAAACTGTAGACATGGTAGCTTCAGCAGTGTTCGTTATGTACGGCATCCTCC AACAAACAGTCGGTTATAGTTTGTCCTGCTCCTCTGAATCGTCTCCCTCGATATTTCTCA TTTTCCTTCGCATGCCAGCATTGAAATGATCGAAGTTCAATGATGAAACGGTAATTCTTC TGTCATTTACTCATCTCATCTCATCAAGTTATATAATTCTATACGGATGTAATTTTTCACT TTTCGTCTTGACGTCCACCCTATAATTTCAATTATTGAACCCTCAC |
| 56 | S. cerevisiae tPGI1 | ACAAATCGCTCTTAAATATATACCTAAAGAACATTAAAGCTATATTATAAGCAAAGATAC GTAAATTTTGCTTATATTATTATACACATATCATATTTCTATATTTTAAGATTTGGTTATA TAATGTACGTAATGCAAAGGAAATAAATTTTATACATTATTGAACAGCGTCCAAGTAACT ACATTATGTGCACTAATAGTTTAGCGTCGTGAAGACTTTATTGTGTCGCGAAAAGTAAAA ATTTTAAAAATTAGAGCACCTTGAACTTGCGAAAAAGGTTCTCATCAACTGTTTAAAAGG AGGATATCAGGTCCTATTTCTGACAAACAATATACAAATTTAGTTTCAAAGATGAATCAG TGCGCGAAGGACATAACTCA |
| 57 | S. cerevisiae tENO2 | AGTGCTTTTAACTAAGAATTATTAGTCTTTTCTGCTTATTTTTTCATCATAGTTTAGCA CTTTATATTAACGAATAGTTTATGAATCTATTTAGGTTTAAAAATTGATACAGTTTTATAA GTTACTTTTTCAAAGACTCGTGCTGTCTATTGCATAATGCACTGGAAGGGGAAAAAAA GGTGCACACGCGTGGCTTTTTCTTGAATTTGCAGTTTGAAAAATAACTACATGGATGAT AAGAAAACATGGAGTACAGTCACTTTGAGAACCTTCAATCAGCTGGTAACGTCTTCGTT AATTGGATACTCAAAAAAGATGGATAGCATGAATCACAAGATGGAAGGAAATGCGGGC CACGACCACAGTGATATGCATATGGGAGATGGAGATGATACCT |
| 58 | S. cerevisiae tTEF1 | GGAGATTGATAAGACTTTTCTAGTTGCATATCTTTTATATTTAAATCTTATCTATTAGTTA ATTTTTTGTAATTTATCCTTATATATAGTCTGGTTATTCTAAAATATCATTTCAGTATCTAA AAATTCCCCTCTTTTTTCAGTTATATCTTAACAGGCGACAGTCCAAATGTTGATTTATCC CAGTCCGATTCATCAGGGTTGTGAAGCATTTTGTCAATGGTCGAAATCACATCAGTAAT AGTGCCTCTTACTTGCCTCATAGAATTTCTTTCTCTTAACGTCACCGTTTGGTCTTTTAT AGTTTCGAAATCTATGGTGATACCAAATGGTGTTCCCAATTCATCGTTACGGGCGTATT TTTTACCAATTGAAGTATTGGAATCGTCAATTTTAAAGTATATCTCTCTTTTACGTAAAGC CTGCGAGATCCTCTTAAGTATAGCGGGGAAGCCATCGTTATTCGATATTGTCGTAACAA ATACTTTGATCGGCGCTAT |

TABLE 3-continued

Summary of Sequence Listing

| Sequence ID No. | Description | Sequence |
|---|---|---|
| 59 | A. tubingensis GGPPS | ATGCTGGGATTCCCAATGTTCAACCCAGCTACGCCTGATGTCTGGAAGATGAATACCC<br>CTTACTTTCCATTTGTTACACCGGGGTTATTTCCTGCCTCAGCACCCCCATCGCCCACC<br>AACGTAGATGCCGAAGCTGCCAGTTCCCAACAGTCGGAAGCAAGCTATCTGGATAAGG<br>AGAAAATTGTTCGAGGGCCACTTGATTATCTTCTCAAATCCCCTGGAAAAGACATTCGT<br>CGGAAATTCATTCACGCGTTCAATGAATGGCTGCGCATTCCTGAGGCAAGTTGAATAT<br>TATCACGGAAATTGTTGGATTGCTTCACACGGCCTCCCTTCTAATCGACGATATTCAGG<br>ACAATTCCAAGCTTCGACGCGGCCTCCCAGTGGCCCATAGCATATTTGGTATTGCGCA<br>GACAATTAACTCTGCCAATTATGCGTACTTTCTAGCCCAGGAAAGGCTCCGCGAACTGA<br>ATCATCCTGAAGCGTACGAAATATACACAGAGGAACTGCTTCGTCTGCACCGCGGTCA<br>AGGTATGGACTTGTACTGGCGGGACTGCCTAACCTGTCCCACAGAGGAGGACTATATT<br>GAGATGATCGCCAACAAGACTGGTGGCCTATTTCGACTGGCGATTAAGCTTATGCAGT<br>TGGAAAGCACTTTGTGCAGCAATGTCATTGAACTAGCAGACTTGTTGGGCGTGATCTTT<br>CAGATTCGGGATGATTACCAAAACTTACAGAGTGGACTATACGCCAAGAACAAGGGATT<br>TTGCGAGGATTTGACGGAGGGAAAATTTTCCTTTCTGATTATCCACAGTATTAACAGTAA<br>CCCGAACAATCACCATCTGCTAAATATACTACGGCAGCGGAGCGAGGACGATTCGGTG<br>AAGAAGTATGCTGTTGATTATATCGACTCGACGGGGAGTTTTGACTACTGCCGGGAAC<br>GGCTCGCTTCCTTATTGGAAGAGGCGGATCAAATGGTTAAGAAGTTGGAAAATGAGGG<br>GGGACAATCAAAGGGGATCTACGATATTCTGAGCTTTCTGTCGTGA |
| 60 | A. tubingensis PT | ATGGATGGGTTCGACCATTCTACIGCTCCACCAGGATATAACGAGCTAAAATGGCTCG<br>CCGATATCTTCGTCATCGGAATGGCTGTTGGCTGGGTTGCTCACTATATGGAGATGATT<br>CACACGTCGTTCAAGGACCAAACATACTGCATGACCATCGGGGGCCTTTGCATCAATTT<br>TGCCTGGGAAATCATATTCTGCACAATGTATCCTGCCAAAGGATTTGTCGAGCGGGTTG<br>CCTTTCTCATGGGCATTTCTCTCGACCTTGGGGTTATTTACGCGGGAATCAAGAACGCC<br>CCAAATGAATGGCACCACTCTGCAATGGTGAGGGACCATATGCCCCTTGTCTTCGCAG<br>CAACGACACTTTGTTGTCTGAGCGGTCATATGGCTCTTACTGCCCAGGTTGGTCCCGC<br>ACAAGCCTATACGTGGGGGGCAATTGCATGCCAGCTCTTTATCAGCATAGGGAATGTG<br>TTTCAATTGTTGAGTCGGGGAAACACACGAGGGGCGTCATGGACGCTATGGACCTCCA<br>GGTTTTTTTGGATCAACATCAGCCATTGGCTTTGCTCTTGTTCGATATATTCGCTGGTGG<br>GAGGCCTTTTCTTGGTTGAACTGCCCGCTTGTGATATGGTCCGTGGCCATGTTCTTTCT<br>GTTTGAAACACTCTATGGAGCCCTATTCTATTCTGTCAAGCGACAAGAAGGGAGATCCC<br>AGCGTGGAATCAAGCACAAAGAGAGGTAG |
| 61 | A. tubingensis FMO | ATGGCGGCACTTCCGGACGTTGCCTCCATTCCCATCCCTCTGGTGGCAACCCTAGGCA<br>TTGCCCCTCTAATTTTCTATCTCGTCCTTGATAGAATTAGCCCCTTGTGGCCAAATTCCA<br>AAGCTTTCCTGATTGGCAAGAAGACCGGAGACCGTGACATCGTTCGAGTGCCCATA<br>TGCCTACATCCGTCAGATCTATGGGAAGTATCACTGGGAGCCATTCGTACAGAAGCTG<br>TCTCCGAGGCTTAAGGATGAGGATCCGGCCAAATATAAGATGGTTCTGGAGATAATGG<br>ATGCAATCCACCTGTGTCTGATGCTAGTTGACGATATAACTGACAATAGCGACTATCGA<br>AAAGGCAAGCCAGCAGCCCACCGGATATATGGCCCTTCAGAGACAGCAAATCGCGCTT<br>ACTACCGAGTCACCCAGATTCTAAACAAGACCGTGCAAAAGTTCCCCAAGCTGGCCAA<br>GTTCCTGCTTCAGAATCTGGAAGAAATTCTCGAAGGCCAAGACCTGTCACTAATCTGGC<br>GACGGGATGGACTGGGTAGCCTTTCGACTGTTCCTGATGAGCGAGTTGCAGCCTATCG<br>CAAGATGGCGTCATTGAAAACTGGGGCGTTATTCCGGCTGCTGGGGCAATTGGTGATG<br>GAGGACCAATCGATGGACGGGACGATGACTACTCTTGCGTGGTGCTCTCAGCTGCAG<br>AATGACTGCAAGAATGTCTACTCATCTGAATATGCTAAGGCCAAAGGGGCGCTTGCCG<br>AAGACCTCCGAAATCGAGAGCTCTCATTTCCAATTATCCTCGCGCTGGAAGCTCCTGAA<br>GGGCATTGGGTCGCCAGTGCTTTGGAGACCAGCTCACCGCGCAACATTCGCAAGGCG<br>CTTGCTGTGATTCAGAGTGAGAGTGCGCAATGCTTGTTTCAAGGAGCTCAAGTCGG<br>CGAGTGCTTCGGTCCAGGACTGGTTGGCTATTTGGGGACGGAACGAGAAAATGAACTT<br>GAAGAGCCAGCAGACGTAG |
| 62 | A. tubingensis Cyc | ATGGCCAATGCCCAGCAACCCCCCTTTCGCATCCTTATTGTGGGCGGTTCTGTCGCAG<br>GCCTCATCCTTGCGCACTGTCTCGAACGCGCCAATATAGAGTACCTCATACTCGAAAAA<br>GGAGAAGATGTTGCTCCACAAGTTGGTGCCTCGATAGGTATCATGCCAAATGGCGGAC<br>GGATCCTCGAGCAACTGGGCCTATTTGGGGAGATTGAGCGTGTGATCGAGCCGTTGC<br>ATCAGGCGAATATCAGCTATCCAGATGGGTTCTGCTTTAGTAACGTCTATCCTAAGGTT<br>CTTGGCGACAGGTTCGGATACCCGGTTGCATTCTTGGACCGGCAGAAGTTCCTGCAGA<br>TTGCATATGAGGGGCTGAGAAGAAGCAGAATGTTCTCACCGGTAAAGGGTAGTTGG<br>ACTGCGACAGTCGGATCAAGGGACTGCTGTTTCTGTGGCTGACGGGACAGAGTATGA<br>GGCGGATCTCGTGGTTGGTGCTGATGGAGTACATAGTCGGGTGAGAAGTGAGATTTG<br>GAAGATGGCGGAAGAGAATCAGCCTGCATCAGTTTCGACACGTGAAAGAAGAAGCATG<br>ACTGTTGAATATGTCTGCGTTTTCGGGATTTCATCAGCCATCCCAGGGCTCGAGATAAG<br>CGAACAGATCAACGGTATTTTCGACCATCTATCCATTCTAACAATCCATGGCAGACATG<br>GTCGCGTGTTCTGGTTCGTGATCCAGAAGCTGGATAGGAAGTACGTCTATCCTGATGT<br>CCCGCGATTCTCAGACGAGGATGCCGTACAGCTCTTCGATCGGGTCAAACACGTGCG<br>GTTCTGGAAAACATCTGTGTGGGGACTTGTGGAAGAACAGAGAGGTGTCCTCGATG<br>ACAGCGCTGGAGGAGGGAGTGTTCGAGACATGGCATCATGATAGGATGGTTTTGATTG<br>GAGATAGCGTTCACAAGATGACGCCAACTTTGGCCAAGGAGCTAATTCAGCCATCGA<br>GGATGCTGCCGCGCTCTCTTCCCTTCTACATGATCTCGTCAACGCCCGTGGAGTTTGC<br>AAGCCATCGAATGTCCAGATTCAGCATCTCCTCAAGCAGTATCGGGAGACCCGATACA<br>CTCGCATGGTAGGCATGTGTCGCACCGCGGCTTCAGTCTCTCGGATTCAGGCCCGAG<br>ATGGCATCCTCAACACCGTCTTTGGACGATATTGGGCACCTTATGCTGGCAACCTGCC<br>TGCTGACCTGGCATCAAAAGTGATGGCAGATGCAGAGGTTGTTACTTTTCTGCCCTTGC |

TABLE 3-continued

Summary of Sequence Listing

| Sequence ID No. | Description | Sequence |
|---|---|---|
| | | CAGGGCGCTCAGGACCGGGCTGGGAGATGTACAGACGAAAGGGGAAGGGAGGGCAG GTGCAATGGGTGCTTATAATCTTAAGCTTACTTACGATTGGTGGATTGTGCATCTGGCT ACAAAGCAATGCGTTGAGTAGATAA |
| 63 | *H. subiculosis* hpm8 | ATGCCTTCTACCAGCAATCCATCTCACGTCCCTGTGGCCATCATCGGCCTGGCATGCC GATTCCCAGGCGAGGCCACCTCACCATCAAAATTCTGGGATCTTCTTAAGAATGGACG AGATGCCTACTCACCAAATACCGATCGATATAACGCTGATGCCTTTTACCATCCCAAGG CAAGCAACCGCCAAAACGTGCTGGCAACTAAGGGCGGCCACTTCCTCAAACAGGACC CATACGTTTTTGACGCCGCTTTCTTTAACATCACAGCCGCTGAGGCCATCTCCTTTGAC CCCAAGCAGCGAATTGCCATGGAAGTTGTCTACGAGGCTCTAGAAAATGCCGGAAAGA CACTACCCAAGGTGGCGGGCACACAAACTGCTTGCTATATCGGCTCTTCCATGAGTGA TTACCGAGACGCTGTTGTGCGTGACTTTGGAAACAGCCCCAAGTATCATATCCTGGGA ACATGCGAGGAGATGATTTCAAATCGTGTGTCCCATTTCTTGGATATTCACGGCCCCAG TGCCACCATTCATACAGCCTGCTCATCAAGTCTTGTTGCTACACACTTGGCTTGCCAAA GTTTGCAATCTGGAGAGTCAGAAATGGCCATCGCTGGTGGTGTTGGTATGATCATCAC CCCTGATGGTAATATGCATCTTACAACTTGGGATTCTTGAACCCCGAGGGCCACTCCC GGTCATTTGATGAGAATGCTGGTGGTTACGGTCGTGGTGAGGGTTGCGGTATCCTCAT CCTCAAGCGGCTAGACAGAGCTCTCGAAGATGGTGATTCCATTCGCGCCGTCATTCGA GCCTCTGGTGTCAACTCTGATGGCTGGACACAGGGTGTCACCATGCCCTCCAGCCAAG CCCAGTCTGCCCTTATCAAATACGTATACGAATCGCATGGCCTGGATTATGGTGCGACT CAATACGTTGAGGCTCACGGTACTGGTACCAAAGCCGGTGATCCCGCAGAGATTGGC GCCCTCCACCGCACAATTGGACAGGGCGCGTCCAAGTCTCGAAGGCTTTGGATTGGC AGTGTCAAGCCAAACATTGGCCATCTTGAAGCCGCCGCCGGTGTGGCTGGTATCATTA AGGGCGTCCTGTCCATGGAACACGGCATGATTCCTCCAAACATTTACTTCTCCAAGCC CAACCCTGCCATCCCTCTTGACGAGTGGAACATGGCCGTGCCTACCAAGTTGACTCCC TGGCCCGCCAGCCAAACTGGTCGCCGTATGAGTGTCAGCGGTTTCGGTATGGGTGGT ACCAACGGCCACGTCGTCCTTGAGGCCTACAAGCCCCAAGGAAAGCTCACCAACGGC CATACCAACGGCATCACCAATGGAATCCACAAGACTCGCCACAGCGGCAAGAGGCTTT TCGTCCTCAGCGCCCAGGATCAAGCTGGCTTCAAGCGTTTGGGTAACGCCCTGGTGG AGCATCTCGATGCCCTGGGCCCTGCCGCTGCCACCCCTGAGTTCCTCGCCAACCTCTC CCACACTCTTGCCGTTGGCAGATCTGGCTTGGCTTGGAGGTCCAGCATCATCGCTGAG AGCGCCCCTGATCTTCGGGAGAAGCTGGCAACTGATCCGGGTGAGGGAGCCGCTCGT TCTTCAGGCAGCGAGCCCCGTATTGGATTCGTCTTCACGGGTCAAGGTGCTCAGTGGG CCCGCATGGGCGTTGAGTTGTTGGAGCGCCCCGTCTTCAAGGCTTCCGTGATTAAGTC CGCGGAGACTTTGAAGGAGCTCGGCTGTGAATGGGACCCTATCGTTGAGCTTTCCAAG CCTCAAGCTGAGTCTCGACTTGGTGTTCCTGAAATCTCACAGCCCATCTGCACAGTCCT ACAAGTCGCCTTGGTTGATGAGTTGAAGCACTGGGGTGTATCACCTTCCAAGGTGGTC GGTCACTCCAGTGGTGAAATCGGTGCCGCATACAGCATTGGCGCTCTTTCTCACCGTG ACGCTGTCGCCGCTGCTTACTTCAGGGGCAAGTCTTCCAACGGAGCCAAGAAGCTTGG TGGTGGTATGATGGCTGTTGGGTGCTCTCGTGAGGACGCTGACAAGCTCCTCTCTGAG ACCAAGCTCAAGGGCGGTGTTGCTACCGTCGCATGTGTCAACTCCCCCTCCAGCGTGA CCATCTCAGGCGATGCCACTGCTCTCGAGGAACTCCGAGTTATTCTCGAGGAGAAGAG TGTGTTTGCTCGAAGACTCAAGGTCGACGTTGCCTACCACTCTGCCCACATGAACGCT GTCTTTGCCGAATACTCTGCTGCGATTGCCCACATTGAGCCCGCTCAGGCAGTTGAAG GTGGACCGATTATGGTCTCCAGTGTCACTGGTAGCGAAGTCGACTCTGAGCTTCTCGG CCCTTACTACTGGACCCGTAACTTGATCTCTCCCGTCTTATTCGCCGACGCTGTCAAGG AATTGGTTACCCCTGCTGATGGCGACGGCCAAAACACCGTCGATCTCCTGATTGAGAT TGGTCCTCACAGCGCTCTTGGTGGCCCTGTTGAGCAGATTCTGTCCCATAACGGCATC AAGAATGTTGCTTACAGATCTGCTCTTACTCGTGGCGAGAACGCTGTTGACTGCAGCCT CAAGCTTGCTGGCGAGCTCTTCCTTCTCGGCGTGCCCTTTGAGTTGCAAAAGGCCAAC GGTGACTCTGGTTCTCGCATGCTCACTAACCTACCTCCTTATCCTTGGAACCACTCCAA GTCATTCCGTGCCGACTCTCGTCTCCACCGTGAGCATCTGGAGCAGAAATTCCCTACT AGGAGTCTCATCGGTGCACCTGTCCCCATGATGGCAGAGAGCGAGTACACATGGCGC AACTTCATCCGTCTCGCTGACGAGCCTTGGCTCCGTGGTCACACTGTCGGTACCACCG TTCTGTTTCCTGGTGCCGGTATCGTGAGCATCATCTTGGAAGCTGCTCAACAGCTGGT GGATACCGGCAAGACCGTTCGGGGCTTCCGAATGCGCGATGTCAACCTCTTCGCCGC CATGGCTCTCCCCGAGGACCTGGCTACTGAGGTTATCATCCACATCCGACCTCACCTT ATCTCTACTGTTGGATCAACCGCCCCCGGTGGATGGTGGGAGTGGACTGTTTCCTCCT GCGTCGGAACTGACCAGCTGCGAGACAATGCTCGCGGTCTGGTAGCCATTGACTACG AAGAGAGCCGCAGCGAGCAGATCAACGCCGAGGACAAAGCGTTGGTTGCTTCTCAGG TCGCGGACTACCACAAGATCCTCAGCGAATGCCCTGAGCATTATGCTCATGACAAGTT CTACCAGCACATGACCAAGGCCTCTTGGAGCTACGGCGAGCTCTTCCAGGGTGTGGA GAATGTCCGTCCTGGATACGGAAAGACCATCTTTGACATCAGAGTCATTGACATTGGTG AGACCTTTAGCAAGGGACAACTTGAGCGACCTTTCCTCATCAACGCTGCCACTCTCGAT GCTGTATTCCAGAGCTGGCTCGGCAGTACCTACAACAACGGTGCTTTCGAGTTTGACA AGCCCTTCGTTCCCACCTCTATTGGCGAGTTGGAAATCTCTGTCAACATTCCCGGTGAT GGCGACTACCTCATGCCAGGCCACTGCCGCTCTGAGCGATACGGCTTCAACGAGTTGT CTGCTGATATTGCCATCTTCGACAAGGATCTGAAGAATGTGTTCCTTTCAGTGAAGGAT TTCCGAACTTCCGAGCTTGATATGGATTCCGGCAAGGGAGACGGAGATGCCGCTCACG TCGACCCTGCCGATATCAACTCGGAGGTTAAGTGGAACTACGCTCTTGGCCTCTCAA GTCCGAGGAAATCACCGAGCTGGTCACCAAGGTCGCCAGCAATGACAAGCTCGCCGA GCTTCTCCGTCTGACACTTCACAACAACCCTGCTGCCACTGTCATCGAGCTTGTTTCTG ATGAGAGCAAGATCTCTGGCGCATCTTCTGCCAAGCTGTCCAAGGGCCTTATCCTCCC CAGCCAGATCCGTTACGTAGTTGTCAACCCTGAGGCAGCGGACGCCGACTCTTTCTTC AAATTCTTCTCCCCTTGGTGAGGATGGTGCCCCTGTCGCTGCTGAAAGGGGCCCCGCC |

TABLE 3-continued

Summary of Sequence Listing

| Sequence ID No. | Description | Sequence |
|---|---|---|
| | | GAACTGTTGATCGCCTCCAGCGAAGTCACTGACGCGGCTGTCCTTGAGCGCCTGATTA
CCTTGGCCAAGCCTGATGCCAGCATTCTTGTTGCTGTCAACAACAAGACTACCGCCGC
TGCCCTCTCAGCCAAGGCGTTCCGTGTTGTCACCAGCATCCAGGACAGCAAGTCCATT
GCTCTCTACACTAGCAAGAAGGCGCCTGCCGCCGACACCTCCAAGCTCGAGGCCATC
ATCCTCAAGCCAACCACTGCTCAACCTGCCGCCCAGAATTTCGCCTCCATCCTCCAGA
AGGCACTCGAGCTCCAGGGCTACTCTGTCGTTTCTCAGCCATGGGGCACCGACATCGA
CGTCAACGATGCCAAGGGAAAGACCTACATTTCTCTGTTGGAGCTTGAGCAGCCTCTG
CTCGACAACCTCTCCAAGTCCGACTTCGAGAACCTCCGCGCAGTCGTTTTGAACTGCG
AGCGTCTCCTGTGGGTCACAGCAGGTGACAACCCATCTTTCGGCATGGTTGATGGTTT
CGCTCGCTGCATCATGAGCGAAATTGCCAGCACCAAGTTCCAGGTCCTGCATTTGAGC
GCTGCAACTGGTCTGAAGTACGGATCTTCTCTCGCCACCCGCATTCTCCAGTCGGATA
GCACCGACAACGAGTACCGGGAGGTCGATGGTGCTCTCCAGGTGGCCCGTATCTTCA
AGAGCTACAACGAGAACGAGAGTCTCCGCCACCACCTCGAGGATACCACCAGCGTTGT
GACTCTTGCTGACCAGGAGGATGCTCTGCGCCTCACTATTGGCAAGCCTGGTCTTTTG
GATACTTTGAAGTTTGTCCCCGATGAGCGTATGCTCCCACCTCTCCAGGATCACGAGG
TTGAAATCCAGGTCAAGGCTACTGGTCTGAACTTCCGAGACATCATGGCTTGCATGGG
TCTTATTCCTGTTCGATCTCTGGGCCAGGAGGCCAGTGGCATCGTCCTCAGAACCGGT
GCGAAGGCTACCAACTTCAAGCCTGGCGACCGTGTTTGCACCATGAACGTCGGAACAC
ATGCCACCAAGATCCGAGCCGACTACCGTGTCATGACAAAGATCCCCGACTCCATGAC
CTTTGAAGAAGCTGCCTCGGTTGCTGTTGTTCACACCACCGCCTACTACGCCTTCATCA
CCATCGCCAAGCTTCGCAAGGGCCAGTCCGTCTTGATCCACGCCGCCGCTGGTGGTG
TTGGCCAAGCAGCCATTCAGTTGGCCAAGCATCTCGGCCTCATCACCTATGTTACCGT
AGGTACTGAAGACAAGCGCCAGCTCATTCGGGAGCAGTATGGCATTCCCGACGAGCA
CATCTTCAACTCCCGTGATGCCAGCTTCGTCAAGGGTGTCCAGCGTGTTACCAACGGT
CGCGGTGTCGACTGCGTTCTCAACTCTCTATCCGGTGAGCTCCTGCGTGCTTCTTGGG
GATGCCTTGCTACCTTTGGTCATTTCATCGAAATTGGTCTCCGTGATATCACCAACAAC
ATGCGTCTTGACATGCGACCTTTCCGCAAGAGCACCTCCTTCACATTCATCAACACCCA
CACTCTCTTCGAGGAAGACCCCGCTGCGTTGGAGATATTCTCAACGAGTCCTTCAAG
CTCATGTTCGCTGGCGCCCTTACCGCTCCTAGCCCCTTGAATGCCTATCCCATTGGCC
AGGTCGAGGAGGCCTTCCGAACCATGCAGCAGGGCAAGCACCGCGGTAAGATGGTGC
TGTCCTTCTCCGATGACGCAAAGGCTCCCGTGTTGCGCAAAGCGAAGGATTCCTTGAA
ACTGGACCCTGACGCCACTTACCTCTTTGTTGGTGGTCTTGGTGGTCTGGGTCGCAGT
CTTGCCAAGGAGTTTGTTGCGTCTGGCGCCCGCAACATTGCCTTCTTATCCCGATCCG
GTGACACTACCGCCCAGGCCAAGGCTATCGTGGACGAATTGGCTGGCCAGGGTATCC
AGGTCAAGGCCTATCGTGGTGATATCGCCAGCGAGGCATCCTTCCTCCAGGCTATGGA
GCAATGCTCTCAGGATCTCCCGCCCGTAAAGGGTGTGATCCAGATGGCCATGGTTCTC
CGCGTATATCGTCTTTGAGAAGATGTCGTACGATGAGTGGACCGTCCCCGTTGGCCCCA
AGGTCCAAGGTTCATGGAACTTGCACAAGTACTTCAGTCATGAGCGACCTCTTGACTTC
ATGGTCATCTGCTCCTCAAGCTCCGGTATCTACGGTTATCCCAGTCAGGCTCAATACGC
CGCTGGCAACACTTACCAGGATGCCTTGGCTCACTACCGTCGCTCTCAGGGCCTGAAC
GCCATCTCCGTCAACTTGGGTATCATGCGAGATGTCGGTGTCCTGGCTGAGACGGGTA
CCACTGGTAACATCAAGCTCTGGGAAGAGGTCTTGGGCATCCGCGAGCCTGCCTTCCA
CGCTCTCATGAAGAGCTTGATCAACCATCAGCAGCGTGGGTCTGGGGACTACCCGGC
GCAGGTCTGCACTGGTCTTGGTACTGCTGACATTATGGCTACTCACGGCCTGGCCCGG
CCCGAGTATTTCAATGACCCCCGTTTTGGACCCCTTGCCGTCACCACTGTCGCGACCG
ATGCTTCAGCTGACGGCCAGGGCTCTGCTGTCTCGCTCGCCTCTAGGCTCTCCAAGGT
TTCCACCAAGGATGAAGCTGCCGAGATCATTACCGATGCTCTGGTCAACAAGACGGCA
GACATCCTGCAGATGCCCCCCTCTGAAGTCGACCCCGGCCGACCTCTGTACCGTTATG
GTGTTGACTCCCTTGTGGCGCTTGAGGTGCGAAACTGGATCACAAGGGAGATGAAGG
CGAACATGGCGCTGCTGGAGATTCTGGCAGCCGTCCCCATTGAGAGCTTCGCTGTCAA
GATTGCTGAGAAGAGCAAGTTGGTTACTGTTTAA |
| 64 | H. subiculosis hpm3 | ATGGTGACTGTACCACAGACTATCCTCTACTTTGGAGATCAGACAGACTCCTGGGTTGA
TTCCCTCGATCAGCTATACAGACAAGCCGCTACGATACCATGGCTACAGACGTTTCTCG
ACGACCTTGTAAAGGTCTTCAAGGAAGAGTCCCGGGGCATGGATCATGCGTTACAAGA
CAGTGTTGGTGAATACTCTACACTACTCGACTTGGCGGATAGATACCGCCATGGCACC
GACGAGATTGGTATGGTGCGTGCTGTCTTGCTACATGCCGCGAGAGGAGGCATGCTAT
TACAATGGGTGAAGAAAGAATCACAGCTTGTGGACCTCAATGGCTCCAAGCCTGAAGC
ACTCGGTATCTCTGGAGGACTCACCAACCTCGCAGCACTGGCGATATCCACAGACTTC
GAGTCTCTATATGACGCAGTCATTGAGGCTGCGAGAATATTTGTCAGATTATGCCGTTT
TACTTCGGTACGATCAAGAGCTATGGAGGACCGACCTGGCGTTTGGGGCTGGGCAGT
GCTGGGAATTACACCAGAGGAACTGAGCAAAGTGCTTGAGCAGTTCCAATCCAGCATG
GGGATTCCTGCCATCAAGAGAGCTAAGGTTGGCGTAACAGGAGACCGATGGAGCACC
GTTATTGGGCCACCCTCAGTCTTGGACCTATTCATCCACCAGTGTCCCGCTGTGCGCA
ACCTCCCCAAGAATGAATTGAGCATCCACGCCCTTCAGCACACAGTCACAGTCACAGA
GGCTGACCTCGACTTCATTGTCGGGAGTGCTGAGCTTCTTAGTCACCCCATTGTGCCA
GACTTCAAAGTCTGGGGAATGGATGATCCTGTGGCATCCTACCAGAACTGGGGAGAAA
TGCTAAGAGCAATCGTCACTCAAGTTTTGTCCAAGCCTTTGGACATTACCAAGGTGATT
GCGCAACTCAACACTCACCTCGGCCCTCGTCATGTCGACGTCCGAGTCATCGGACCTA
GCAGCCACACCCCCTACTTGGCGAGTTCGCTCAAAGCTGCTGGCAGCAAGGCTATTTT
CCAGACCGATAAGACTCTTGAGCAGTTACAGCCGAAGAAACTCCCCCCGGGCCGCATC
GCCATTGTCGGTATGGCTGGCCGTGGTCCTGGCTGCGAGAATGTTGATGAGTTCTGG
GACGTCATTATGGCGAAGCAGGATCGTTGTGAAGAGATTCCCAAAGATCGCTTCGACA
TCAATGAGTTCTACTGTACCGAGCACGGGAGGGTTGCACCACCACCACAAAATACGG
CTGCTTCATGAACAAGCCTGGAAACTTTGACTCCCGCTTCTTCCACGTGTCGCCTCGTG |

TABLE 3-continued

Summary of Sequence Listing

| Sequence ID No. | Description | Sequence |
|---|---|---|
| | | AGGCGCTGTTGATGGACCCCGGTCACAGGCAGTTCATGATGAGCACTTATGAAGCTCT
TGAGACGGCAGGATACTCTGATGGCCAGACTAGGGACGTTGATCCTAATAGGATCGCG
GCGTTCTATGGCCAGTCCAACGATGATTGGCATATGGTGAGCCATTATACCCTGGGTT
GTGATGCCTACACCCTGCAGGGGGCGCAAAGAGCCTTCGGCGCTGGTCGCATCGCCT
TCCACTTCAAGTGGGAGGGCCCAACATACTCGCTCGATTCTGCATGTGCCTCCACCTC
CTCTGCTATTCACCTGGCCTGCGTGAGTCTTCTATCCAAAGATGTGGACATGGCTGTTG
TGGGTGCTGCCAACGTCGTCGGGTATCCTCACTCCTGGACAAGTCTTAGCAAGTCTGG
TGTCTTGTCCGACACTGGAAACTGCAAAACCTACTGCGATGATGCTGATGGTTACTGCC
GAGCAGACTTTGTCGGCTCAGTTGTGCTGAAGCGTCTCGAAGATGCTGTCGAGCAAAA
CGACAACATCTTGGCTGTCGTGGCTGGTTCAGGCAGAAACCACTCCGGCAACTCTTCA
TCCATCACCACGTCGGATGCCGGTGCCCAGGAGAGACTGTTTCACAAGATTATGCACA
GCGCCAGAGTCTCTCCTGATGAGATCTCATATGTTGAGATGCACGGCACTGGAACTCA
GATTGGCGATCCGGCCGAGATGAGTGCTGTTACCAATGTCTTCAGGAAGAGGAAGGC
GAATAACCCCCTAACTGTTGGTGGAATCAAAGCGAACGTCGGGCATGCTGAAGCTTCT
GCTGGCATGGCCTCCCTGCTCAAATGCATACAGATGTTCCAGAAAGATATTATGCCCC
CTCAGGCTCGAATGCCCATACTCTCAACCCAAAGTATCCGAGTCTTTCTGAGCTTAAC
ATTCATATCCCCTCCGAGCCGAAGGAGTTCAAGGCTATCGGCGAGCGGCCACGACGC
ATCCTCCTTAATAACTTTGACGCAGCAGGTGGCAACGCCTCTCTCATTCTGGAAGACTT
CCCCTCCACCGTCAAGGAAAATGCGGACCCCAGGCCAAGCCATGTCATCGTTTCCTCT
GCCAAAACACAATCCTCATATCACGCGAATAAGCGTAACCTCCTGAAGTGGCTACGCA
AGAACAAAGATGCTAAACTCGAAGATGTTGCATACACAACCACCGCCCGCAGAATGCA
CCACCCCCTCAGATTCTCTTGCAGTGCCTCCACAACGGAGGAGCTCATTTCCAAGCTT
GAGGCAGACACGGCAGATGCAACTGCGTCTCGGGGCTCGCCCGTTGTCTTCGTATTC
ACGGGACAGGGCTCTCACTACGCCGGCATGGGTGCCGAGTTGTACAAGACATGCCCT
GCTTTCCGCGAGGAAGTCAACCTCTGTGCCAGCATCTCTGAGGAGCACGGGTTCCCC
CCGTACGTGGATATCATCACCAACAAAGATGTTGACATAACCACCAAGGACACCATGCA
GACACAGCTCGCTGTTGTCACGCTGGAGATCGCCCTCGCCGCATTCTGGAAGGCGTC
TGGTATCCAGCCGTCAGCAGTCATGGGTCACTCCCTGGGCGAGTATGTGGCTCTCCAG
GTCGCAGGGGTCCTATCTCTAGCTGATCTGCTCTACCTCGTCGGCAATCGGGCCCGTC
TCCTGCTGGAGCGCTGCGAAGCCGACACCTGCGCTATGTTGGCAGTATCAAGCTCTGC
TGCCTCCATCCGCGAGCTCATCGACCAGCGCCCGCAGTCATCCTTCGAGATTGCATGC
AAGAATAGCCCCAATGCCACGGTTATCAGCGGCAGCACTGATGAGATTTCTGAGCTCC
AGTCATCCTTCACGGCATCACGAGCCAGGGCTCTGTCTGTGCCCTATGGATTTCACTC
CTTCCAGATGGATCCCATGCTCGAGGATTACATCGTTCTTGCGGGTGGTGTAACCTACT
CGCCACCAAAGATTCCAGTTGCTTCAACCCTGCTCGCTTCGATTGTGGAGTCTTCAGG
GGTCTTCAACGCTTCCTACCTCGGTCAGCAAACCCGCCAAGCTGTCGACTTCGTCGGT
GCTCTTGGCGCCTTGAAGGAGAAGTTTGCTGACCCTCTCTGGCTGGAGATCGGACCCA
GCCAAATCTGCAGCTCCTTTGTCCGGGCGACTCTCTCACCCTCGCCGGGCAAAATCTT
GTCCACTTTGGAGGCAAATACCAACCCCTGGGCATCCATTTCCAAGTGCCTCGCCGGC
GCGTACAAGGATGGTGTCGCAGTTGACTGGTTGGCGGTGCATGCTCCATTCAAGGGC
GGCTTGAAGCTCGTGAAGTTGCCCGCCTATGCATGGGACCTCAAGGACTTCTGGATTG
TCTACTCTGAGGCCAACAAGGCTGCTCGAGCTTTGGCTCCCGCTCCCTCGTTCGAAAC
ACAGAGGATTTCTACATGTGCTCAACAGATTGTTGAAGAATCATCATCACCCAGCCTCC
ATGTCTCTGCCCGAGCTGCTATCTCCGATCCTGGCTTCATGGCCTTGGTCGACGGTCA
TCGCATGCGCGATGTGTCCATCTGCCCCGGAAGTGTCTTCTGCGAGGCAGGCCTTGC
CGTCTCCAAGTACGCACTGAAGTACAGTGGCCGAAAGGATACCGTGGAAACAAGACTT
ACAATCAACAACCTGTCTCTCAAGCGCCCGCTCACAAAGTCTCTTGTAGGCACCGATG
GCGAGCTTCTCACCACGGTTGTTGCAGACAAGGCCTCCAGCGATACCTTGCAGGTTTC
ATGGAAGGCTTCTTCCTCTCATGCATCATACGATCTTGGTAGCTGCGAGATCACCATTT
GTGATGCCCAGACTCTTCAAACTAGCTGGAACAGAAGCTCATACTTCGTCAAGGCTCG
TATGAACGAGTTGATCAAGAATGTCAAGAGCGGAAATGGTCACCGCATGCTCCCCAGT
ATCCTCTACACTCTCTTCGCTAGCACAGTTGATTATGACCCTACCTTCAAGTCTGTCAA
GGAGGCCTTCATCTCAAATGAGTTTGACGAAGCTGCTGCGGAGGTGGTGCTTCAGAAG
AACCCGGCTGGAACTCAGTTCTTTGCGTCCCCTTACTGGGGTGAGAGCGTAGTTCATC
TTGCCGGTTTCCTCGTGAACTCCAACCCTGCCCGCAAGACTGCTTCTCAGACGACCTT
CATGATGCAGAGTCTTGAGAGCGTCGAGCAGACCGCTGATCTCGAGGCTGGACGCAC
TTACTACACCTATGCTCGCGTTTTGCATGAGGAAGAAGACACAGTCAGCTGTGACTTGT
TCGTCTTCGACTCGGAGAAGATGGTAATGCAGTGCTCGGGACTCTCATTCCATGAGGT
CAGCAACAATGTTCTGGACAGACTTCTTGGAAAGGCATCACCGCCTGTGAAGCAAGTT
TCCCACCAGAAGGCGCCAGTGCTTGTGCCCGCAGAGTCAAAACCGGCCCTGAAAGCT
GCTGTCGAGGCGGCTCCCAAGGCGCCTGAGCCTGTGAAGACAGAGGTGAAGAAGATC
TCTTCGTCGGAGAGCGAATTGTTCCACACTATTCTTGAAAGCATCGCCAAGGAGACTG
GCACTCAGGTCTCTGACTTCACTGATGACATGGAACTGGCTGAACTTGGCGTTGATTC
CATCATGGGTATTGAGATCGCTGCCGGCGTCAGCAGCAGAACCGGCCTCGATGTTCTC
CTCCCCTCTTTTGTCGTAGATTATCCCACCATTGGAGATCTGCGAAACGAATTTGCGCG
CTCCTCTACATCTACACCTCCCAGCAAGACCTTTTCCGAGTTCTCCATCGTCGATGCCA
CTCCAGAGTCTACGCGCAGCTCGAGTCGAGCGCCTTCTGAGAAGAAGGAGCCTGCTC
CGGCTTCAGAGAAGTCTGAGGAGCTGGTGATCGTTCCGTCCGCGGTTGTCGAGGATT
CCTCTCCCCTCCCCAGTGCCAGAATCACCTTGATCCAGGGTCGATCTTCGAGTGGAAA
GCAGCCTTTCTACTTGATCGCCGATGGAGCTGGTAGCATTGCTACGTATATCCACCTG
GCTCCCTTCAAGGACAAGAGACCGGTTTATGGCATTGATTCGCCTTTCCTCCGTTGCC
CCAGCAGGCTGACCACCCAGGTGGGCATTGAAGGCGTCGCAAAGATCATCTTTGAGG
CGTTGATTAAGTGCCAGCCTGAGGGTCCCTTTGACTTGGGAGGATTCTCTGGCGGAGC
TATGCTCAGCTATGAGGTGTCTCGCCAACTCGCTGCCGCCGGTCGCGTCGTCTCCAGT
CTTCTCCTCATCGATATGTGTTCTCCCCGTCCTTTGGGTGTTGAGGACACAATCGAGGT |

TABLE 3-continued

Summary of Sequence Listing

| Sequence ID No. | Description | Sequence |
|---|---|---|
| | | CGGCTGGAAGGTCTACGAGACCATCGCTTCCCAAGATAAGCTCTGGAACGCCTCAAGT<br>AACACCCAGCAGCATCTCAAGGCCGTCTTCGCCTGCGTCGCAGCCTACCACCCTCCTC<br>CCATGACTCCCGCTCAACGACCCAAGCGAACAGCTATCATCTGGGCTAAAAAGGGCAT<br>GGTCGACCGTTGTTCTCGCGACGAGAAGGTGATGAAGTTCCTGGCCGACAAGGGCAT<br>CCCCACCGAGTCGTACCCAGGGTTCATGGAGGACCCCAAGCTGGGTGCCGTGGCGTG<br>GGGCCTTCCGCACAAGTCCGCTGCGGACTTGGGACCCAACGGATGGGACAAGTTCCT<br>TGGCGAGACTCTGTGCCTGTCTATCGATTCGGACCACTTGGATATGCCGATGCCGGGG<br>CATGTGCACTTGCTTCAGGCGGCGATGGAGGAGTCGTTCAAATATTTCAGCGAGGCAA<br>ATTAG |
| 65 | pCHIDT-2.1 | TATCTAAAAATTGCCTTATGATCCGTCTCTCCGGTTACAGCCTGTGTAACTGATTAATCC<br>TGCCTTTCTAATCACCATTCTAATGTTTTAATTAAGGGATTTTGTCTTCATTAACGGCTTT<br>CGCTCATAAAAATGTTATGACGTTTTGCCCGCAGGCGGGAAACCATCCACTTCACGAG<br>ACTGATCTCCTCTGCCGGAACACCGGGCATCTCCAACTTATAAGTTGGAGAAATAAGA<br>GAATTTCAGATTGAGAGAATGAAAAAAAAAAAAAAAAAAGGCAGAGGAGAGCATAGA<br>AATGGGGTTCACTTTTTGGTAAAGCTATAGCATGCCTATCACATATAAATAGAGTGCCA<br>GTAGCGACTTTTTTCACACTCGAAATACTCTTACTACTGCTCTCTTGTTGTTTTTATCACT<br>TCTTGTTTCTTCTTGGTAAATAGAATATCAAGCTACAAAAAGCATACAATCAACTATCAA<br>CTATTAACTATATCGTAATACACAATGCTGGGATTCCCAATGTTCAACCCAGCTACGCC<br>TGATGTCTGGAAGATGAATACCCCTTACTTTCCATTTGTTACACCGGGGTTATTTCCTG<br>CCTCAGCACCCCCATCGCCCACCAACGTAGATGCCGAAGCTGCCAGTTCCCAACAGTC<br>GGAAGCAAGCTATCTGGATAAGGAGAAATTGTTCGAGGGCCACTTGATTATCTTCTCA<br>AATCCCCTGGAAAAGACATTCGTCGGAAATTCATTCACGCGTTCAATGAATGGCTGCGC<br>ATTCCTGAGGACAAGTTGAATATTATCACGGAAATTGTTGGATTGCTTCACACGGCCTC<br>CCTTCTAATCGACGATATTCAGGACAATTCCAAGCTTCGACGCGGCCTCCCAGTGGCC<br>CATAGCATATTTGGTATTGCGCAGACAATTAACTCTGCCAATTATGCGTACTTTCTAGCC<br>CAGGAAAGGCTCCGCGAACTGAATCATCCTGAAGCGTACGAAATATACACAGAGGAAC<br>TGCTTCGTCTGCACCGCGGTCAAGGTATGGACTTGTACTGGCGGGACTGCCTAACCTG<br>TCCCACAGAGGAGGACTATATTGAGATGATCGCCAACAAGACTGGTGGCCTATTTCGA<br>CTGGCGATTAAGCTTATGCAGTTGGAAAGCACTTTGTGCAGCAATGTCATTGAACTAGC<br>AGACTTGTTGGGCGTGATCTTTCAGATTCGGGATGATTACCAAAACTTACAGAGTGGAC<br>TATACGCCAAGAACAAGGGATTTTGCGAGGATTTGACGGAGGGAAAATTTTCCTTTCTG<br>ATTATCCACAGTATTAACAGTAACCCGAACAATCACCATCTGCTAAATATACTACGGCA<br>GCGGAGCGAGGACGATTCGGTGAAGAAGTATGCTGTTGATTATATCGACTCGACGGG<br>GAGTTTTGACTACTGCCGGGAACGGCTCGCTTCCTTATTGGAAGAGGCGGATCAAATG<br>GTTAAGAAGTTGGAAAATGAGGGGGGACAATCAAAGGGGATCTACGATATTCTGAGCT<br>TTCTGTCGTGAGCGGATCTCTTATGTCTTTACGATTTATAGTTTTCATTATCAAGTATGC<br>CTATATTAGTATATAGCATCTTTAGATGACAGTGTTCGAAGTTTCACGAATAAAAGATAA<br>TATTCTACTTTTTGCTCCCACCGCGTTTGCTAGCACGAGTGAACACCATCCCTCGCCTG<br>TGAGTTGTACCCATTCCTCTAAACTGTAGACATGGTAGCTTCAGCAGTGTTCGTTATGT<br>ACGGCATCCTCCAACAAACAGTCGGTTATAGTTTGTCCTGCTCCTCTGAATCGTCTCCC<br>TCGATATTTCTCATTTTCCTTCGCATGCCAGCATTGAAATGATCGAAGTTCAATGATGAA<br>ACGGTAATTCTTCTGTCATTTACTCATCTCATCTCATCAAGTTATATAATTCTATACGGAT<br>GTAATTTTTCACTTTTCGTCTTGACGTCCACCCTATAATTTCAATTATTGAACCCTCACG<br>ATCCAGTTCTCCAGTGACACAGCCTTTATCTGGTCAAACCTTTCTTTCTAATCACCTATG<br>CTGATGCTTAATTAAGGGATTTTTGTCTCCATCAACGGCATGCGCCCAAAAATGACGTT<br>TTTTTTAACCCATAGACACGAAACTACCCATTTTCCACCGGCCTGACCTACCACCGGAA<br>CAACGGCCATCTCCAACTTGCAAGTTGGGGAAATTAAGAGCATCGCAGGTTTAATGGA<br>AGAAAAAAAAAAGGTACAGCACAGCGCAAATGGAGTTAGTTCCCTTATGTCACACACTC<br>ACACACAGTCGGTCAGATCAAGCATACTGGGTGCGTATAAATAGAGTGGCCATTGCCA<br>CCCTGTTTATCTCAAAATCTGTCTTGTTAGTGGTCTTCTCCCTTTTTCAGGTTACAATTCT<br>CTTGTTTCTACTTAGTATATAAGTATATCAAGCTATATTAAGCATACTATCAACTGTCAAC<br>TCTATCCTCAAAATACAATACAAAATGGATGGGTTCGACCATTCTACTGCTCCACCAGG<br>ATATAACGAGCTAAAATGGCTCGCCGATATCTTCGTCATCGGAATGGCTGTTGGCTGG<br>GTTGCTCACTATATGGAGATGATTCACACGTCGTTCAAGGACCAAACATACTGCATGAC<br>CATCGGGGGCCTTTGCATCAATTTTGCCTGGGAAATCATATTCTGCACAATGTATCCTG<br>CCAAAGGATTTGTCGAGCGGGTTGCCTTTCTCATGGGCATTTCTCTCGACCTTGGGGT<br>TATTTACGCGGGAATCAAGAACGCCCCAAATGAATGGCACCACTCTGCAATGGTGAGG<br>GACCATATGCCCCTTGTCTTCGCAGCAACGACACTTTGTTGTCTGAGCGGTCATATGG<br>CTCTTACTGCCCAGGTTGGTCCCGCACAAGCCTATACGTGGGGGGCAATTGCATGCCA<br>GCTCTTTATCAGCATAGGGAATGTGTTTCAATTGTTGAGTCGGGGAAACACACGAGGG<br>GCGTCATGGACGCTATGACCTCCAGGTTTTTTGGATCAACATCAGCCATTGGCTTTGC<br>TCTTGTTCGATATATTCGCTGGTGGGAGGCCTTTTCTTGGTTGAACTGCCCGCTTGTGA<br>TATGGTCCGTGGCCATGTTCTTTCTGTTTGAAACACTCTATGGAGCCCTATTCTATTCTG<br>TCAAGCGACAAGAAGGGAGATCCCAGCGTGGAATCAAGCACAAAGAGAGGTAGACAA<br>ATCGCTCTTAAATATATACCTAAAGAACATTAAAGCTATATTATAAGCAAAGATACGTAA<br>ATTTTGCTTATATTATTATACACATATCATATTTCTATATTTTTAAGATTTGGTTATATAAT<br>GTACGTAATGCAAAGGAAATAAATTTTATACATTATTGAACAGCGTCCAAGTAACTACAT<br>TATGTGCACTAATAGTTTAGCGTCGTGAAGACTTTATTGTGTCGCGAAAAGTAAAAATTT<br>TAAAAATTAGAGCACCTTGAACTTGCGAAAAAGGTTCTCATCAACTGTTTAAAAGGAGG<br>ATATCAGGTCCTATTTCTGACAAACAATATACAAATTTAGTTTCAAAGATGAATCAGTGC<br>GCGAAGGACATAACTCAATAGGAAAAAACCGAGCTTCCTTTCATCCGGCGCGGCTGTG<br>TTCTACATATCACTGAAGCTCCGGGTATTTTAAGTTATACAAGGGAAAGATGCCGGCTA<br>GACTAGCAAGTTTTAGGCTGCTTAACATTATGGATAGGCGGATAAAGGGCCCAAACAG<br>GATTGTAAAGCTTAGACGCTTCTGGTTGGACAATGGTACGTTTGTGTATTAAGTAAGGC |

TABLE 3-continued

Summary of Sequence Listing

| Sequence ID No. | Description | Sequence |
|---|---|---|
| | | TTGGCTGGGGATAGCAACATTGGGCAGAGTATAGAAGACCACAAAAAAAAGGTATATA<br>AGGGCAGAGAAGTCTTTGTTAATGTGTGTAACTTCTCTTCCATGTGTAATCAGTATTTCTA<br>CTTACTTCTTAAATATACAGAAGTAAGACAGATAACCAACAGCCTTTCCCAGATATACAT<br>ATATATCTTTATTTCAGCTTAAACAATAATTATATTTGTTTAACTCAAAAATAAAAAAAAAA<br>AACCAAACTCACGCAACTAATTATTCCATAATAAAATAACAACATGGCGGCACTTCCGG<br>ACGTTGCCTCCATTCCCATCCCTCTGGTGGCAACCCTAGGCATTGCCCCTCTAATTTTC<br>TATCTCGTCCTTGATAGAATTAGCCCCTTGTGGCCAAATTCCAAAGCTTTCCTGATTGG<br>CAAGAAGAAACCGGAGACCGTGACATCGTTCGAGTGCCCATATGCCTACATCCGTCAG<br>ATCTATGGGAAGTATCACTGGGAGCCATTCGTACAGAAGCTGTCTCCGAGGCTTAAGG<br>ATGAGGATCCGGCCAAATATAAGATGGTTCTGGAGATAATGGATGCAATCCACCTGTGT<br>CTGATGCTAGTTGACGATATAACTGACAATAGCGACTATCGAAAAGGCAAGCCAGCAG<br>CCCACCGGATATATGGCCCTTCAGAGACAGCAAATCGCGCTTACTACCGAGTCACCCA<br>GATTCTAAACAAGACCGTGCAAAAGTTCCCCAAGCTGGCCAAGTTCCTGCTTCAGAATC<br>TGGAAGAAATTCTCGAAGGCCAAGACCTGTCAGTAATCTGGCGACGGGATGGAGTGGG<br>TAGCCTTTCGACTGTTCCTGATGAGCGAGTTGCAGCCTATCGCAAGATGGCGTCATTG<br>AAAACTGGGGCGTTATTCCGGGTGCTGGGGCAATTGGTGATGGAGGACCAATCGATG<br>GACGGGACGATGACTACTCTTGCGTGGTGCTCTCAGCTGCAGAATGACTGCAAGAATG<br>TCTACTCATCTGAATATGCTAAGGCCAAAGGGGCGCTTGCCGAAGACCTCCGAAATCG<br>AGAGCTCTCATTTCCAATTATCCTCGCGCTGGAAGCTCCTGAAGGGCATTGGGTCGCC<br>AGTGCTTTGGAGACCAGCTCACCGCGCAACATTCGCAAGGCGCTTGCTGTGATTCAGA<br>GTGAGAGAGTGCGCAATGCTTGTTTCAAGGAGCTCAAGTCGGCGAGTGCTTCGGTCCA<br>GGACTGGTTGGCTATTTGGGGACGGAACGAGAAAATGAACTTGAAGAGCCAGCAGAC<br>GTAGAGTGCTTTTAACTAAGAATTATTAGTCTTTTCTGCTTATTTTTTCATCATAGTTTAG<br>AACACTTTATATTAACGAATAGTTTATGAATCTATTTAGGTTTAAAAATTGATACAGTTTT<br>ATAAGTTACTTTTTCAAAGACTCGTGCTGTCTATTGCATAATGCACTGGAAGGGGAAAA<br>AAAAGGTGCACACGCGTGGCTTTTTCTTGAATTTGCAGTTTGAAAAATAACTACATGGA<br>TGATAAGAAAACATGGAGTACAGTCACTTTGAGAACCTTCAATCAGCTGGTAACGTCTT<br>CGTTAATTGGATACTCAAAAAAGATGGATAGCATGAATCACAAGATGGAAGGAAATGCG<br>GGCCACGACCACAGTGATATGCATATGGGAGATGGAGATGATACCTCCATTGGGCCGA<br>TGAAGTTAGTCGACGGATAGAAGCGGTTGTCCCCTTTCCCGGCGAGCCGGCAGTCGG<br>GCCGAGGTTCGGATAAATTTTGTATTGTGTTTGATTCTGTCATGAGTATTACTTATGTT<br>CTCTTTAGGTAACCCCAGGTTAATCAATCACAGTTTCATACCGGCTAGTATTCAAATTAT<br>GACTTTTCTTCTGCAGTGTCAGCCTTACGACGATTATCTATGAGCTTTGAATATAGTTTG<br>CCGTGATTCGTATCTTTAATTGGATAATAAAATGCGAAGGATCGATGACCCTTATTATTA<br>TTTTTCTACACTGGCTACCGATTTAACTCATCTTCTTGAAAGTATATAAGTAACAGTAAAA<br>TATACCGTACTTCTGCTAATGTTATTTGTCCCTTATTTTTCTTTTCTTGTCTTATGCTATA<br>GTACCTAAGAATAACGACTATTGTTTTGAACTAAACAAAGTAGTAAAAGCACATAAAAGA<br>ATTAAGAAAATGGCCAATGCCCAGCAACCCCCCGTTTCGCATCCTTATTGTGGGCGGTTC<br>TGTCGCAGGCCTCATCCTTGCGCACTGTCTCGAACGCGCCAATATAGAGTACCTCATA<br>CTCGAAAAAGGAGAAGATGTTGCTCCACAAGTTGGTGCGTCGATAGGTATCATGCCAA<br>ATGGCGGACGGATCCTCGAGCAACTGGGCCTATTTGGGGAGATTGAGCGTGTGATCG<br>AGCCGTTGCATCAGGCGAATATCAGCTATCCAGATGGGTTCTGCTTTAGTAACGTCTAT<br>CCTAAGGTTCTTGGCGACAGGTTCGGATACCCGGTTGCATTCTTGGACCGGCAGAAGT<br>TCCTGCAGATTGCATATGAGGGGCTGAGAAAGAAGCAGAATGTTCTCACCGGTAAAAG<br>GGTAGTTGGACTGCGACAGTCGGATCAAGGGACTGCTGTTTCTGTGGCTGACGGGAC<br>AGAGTATGAGGCGGATCTCGTGGTTGGTGCTGATGGAGTACATAGTCGGGTGAGAAGT<br>GAGATTTGGAAGATGGCGGAAGAGAATCAGCCTGCATCAGTTTCGACACGTGAAAGAA<br>GAAGCATGACTGTTGAATATGTCTGCGTTTCGGGATTTCATCAGCCATCCCAGGGCTC<br>GAGATAAGCGAACAGATCAACGGTATTTTCGACCATCTATCCATTCTAACAATCCATGG<br>CAGACATGGTCGCGTGTTCTGGTTCGTGATCCAGAAGCTGGATAGGAAGTACGTCTAT<br>CCTGATGTCCCGCGATTCTCAGACGAGGATGCCGTACAGCTCTTCGATCGGGTCAAAC<br>ACGTGCGGTTCTGGAAAAACATCTGTGTGGGGACTTGTGGAAGAACAGAGAGGTGTC<br>CTCGATGACAGCGCTGGAGGAGGGAGTGTTCGAGACATGGCATCATGATAGGATGGT<br>TTTGATTGGAGATAGCGTTCACAAGATGACGCCCAACTTTGGCCAAGGAGCTAATTCAG<br>CCATCGAGGATGCTGCCGCGCTCTCTTCCCTTCTACATGATCTCGTCAACGCCCGTGG<br>AGTTTGCAAGCCATCGAATGCCAGATTCAGCATCTCCTCAAGCAGTATCGGGAGACC<br>CGATACACTCGCATGGTAGGCATGTGTCGCACCGCGGCTTCAGTCTCTCGGATTCAGG<br>CCCGAGATGGCATCCTCAACACCGTCTTTGGACGATATTGGGCACCTTATGCTGGCAA<br>CCTGCCTGCTGACCTGGCATCAAAAGTGATGGCAGATGCAGAGGTTGTTACTTTTCTG<br>CCCTTGCCAGGGCGCTCAGGACCGGGCTGGGAGATGTACAGACGAAAGGGGAAGGG<br>AGGGCAGGTGCAATGGGTGCTTATAATCTTAAGCTTACTTACGATTGGTGGATTGTGCA<br>TCTGGCTACAAAGCAATGCGTTGAGTAGATAAGGAGATTGATAAGACTTTTCTAGTTGC<br>ATATCTTTTATATTTAAATCTTATCTATTAGTTAATTTTTTGTAATTTATCCTTATATATAGT<br>CTGGTTATTCTAAAATATCATTTCAGTATCTAAAAATTCCCCTCTTTTTTCAGTTATATCTT<br>AACAGGCGACAGTCCAAATGTTGATTTATCCCAGTCCGATTCATCAGGGTTGTGAAGCA<br>TTTTGTCAATGGTCGAAATCACATCAGTAATAGTGCCTCTTACTTGCCTCATAGAATTTC<br>TTTCTCTTAACGTCACCGTTTGGTCTTTTATAGTTTCGAAATCTATGGTGATACCAAATG<br>GTGTTCCCAATTCATCGTTACGGGCGTATTTTTACCAATTGAAGTATTGGAATCGTCAA<br>TTTTAAAGTATATCTCTCTTTTACGTAAAGCCTGCGAGATCCTCTTAAGTATAGCGGGGA<br>AGCCATCGTTATTGTCGATATTGTCGTAACAAATACTTTGATCGGCGCTATGCGGCCGCCA<br>CCGCGGTGGAGCTCCAGCTTTTGTTCCCTTTAGTGAGGGTTAATTGCGCGCTTGGCGT<br>AATCATGGTCATAGCTGTTTCCTGTGTGAAATTGTTATCCGCTCACAATTCCACACAACA<br>TAGGAGCCGGAAGCATAAAGTGTAAAGCCTGGGGTGCCTAATGAGTGAGGTAACTCAC<br>ATTAATTGCGTTGCGCTCACTGCCCGCTTTCCAGTCGGGAAACCTGTCGTGCCAGCTG<br>CATTAATGAATCGGCCAACGCGCGGGGAGAGGCGGTTTGCGTATTGGGCGCTCTTCC |

TABLE 3-continued

Summary of Sequence Listing

| Sequence ID No. | Description | Sequence |
|---|---|---|
| | | GCTTCCTCGCTCACTGACTCGCTGCGGTCGGTCGTTCGGCTGCGGCGAGCGGTATCA
GCTCACTCAAAGGCGGTAATACGGTTATCCACAGAATCAGGGGATAACGCAGGAAAGA
ACATGTGAGCAAAAGGCCAGCAAAAGGCCAGGAACCGTAAAAAGGCCGCGTTGCTGG
CGTTTTTCCATAGGCTCCGCCCCCCTGACGAGCATCACAAAAATCGACGCTCAAGTCA
GAGGTGGCGAAACCCGACAGGACTATAAAGATACCAGGCGTTTCCCCCTGGAAGCTC
CCTCGTGCGCTCTCCTGTTCCGACCCTGCCGCTTACCGGATACCTGTCCGCCTTTCTC
CCTTCGGGAAGCGTGGCGCTTTCTCATAGCTCACGCTGTAGGTATCTCAGTTCGGTGT
AGGTCGTTCGCTCCAAGCTGGGCTGTGTGCACGAACCCCCCGTTCAGCCCGACCGCT
GCGCCTTATCCGGTAACTATCGTCTTGAGTCCAACCCGGTAAGACACGACTTATCGCC
ACTGGCAGCAGCCACTGGTAACAGGATTAGCAGAGCGAGGTATGTAGGCGGTGCTAC
AGAGTTCTTGAAGTGGTGGCCTAACTACGGCTACACTAGAAGGACAGTATTTGGTATCT
GCGCTCTGCTGAAGCCAGTTACCTTCGGAAAAAGAGTTGGTAGCTCTTGATCCGGCAA
ACAAACCACCGCTGGTAGCGGTGGTTTTTTTGTTTGCAAGCAGCAGATTACGCGCAGA
AAAAAAGGATCTCAAGAAGATCCTTTGATCTTTTCTACGGGGTCTGACGCTCAGTGGAA
CGAAAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACTTGGTC
TGACAGTTACCAATGCTTAATCAGTGAGGCACCTATCTCAGCGATCTGTCTATTTCGTT
CATCCATAGTTGCCTGACTCCCCGTCGTGTAGATAACTACGATACGGGAGGGCTTACC
ATCTGGCCCCAGTGCTGCAATGATACCGCGAGACCCACGCTCACCGGCTCCAGATTTA
TCAGCAATAAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGTTCGCCAGTT
AATAGTTTGCGCAACGTTGTTGCCATTGCTACAGGCATCGTGGTGTCACGCTCGTCGTT
TGGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAGTT
GGCCGCAGTGTTATCACTCATGGTTATGGCAGCACTGCATAATTCTCTTACTGTCATGC
CATCCGTAAGATGCTTTTCTGTGACTGGTGAGTACTCAACCAAGTCATTCTGAGAATAG
TGTATGCGGCGACCGAGTTGCTCTTGCCCGGCGTCAATACGGGATAATACCGCGCCA
CATAGCAGAACTTTAAAAGTGCTCATCATTGGAAAACGTTCTTCGGGGCGAAAACTCTC
AAGGATCTTACCGCTGTTGAGATCCAGTTCGATGTAACCCACTCGTGCACCCAACTGAT
CTTCAGCATCTTTTACTTTCACCAGCGTTTCTGGGTGAGCAAAAACAGGAAGGCAAAAT
GCCGCAAAAAAGGGAATAAGGGCGACACGGAAATGTTGAATACTCATACTCTTCCTTTT
TCAATATTATTGAAGCATTTATCAGGGTTATTGTCTCATGAGCGGATACATATTTGAATG
TATTTAGAAAAATAAACAAATAGGGGTTCCGCGCACATTTCCCCGAAAAGTGCCACCTG
AACGAAGCATCTGTGCTTCATTTTGTAGAACAAAAATGCAACGCGAGAGCGCTAATTTT
TCAAACAAAGAATCTGAGCTGCATTTTTACAGAACAGAAATGCAACGCGAAAGCGCTAT
TTTACCAACGAAGAATCTGTGCTTCATTTTTGTAAAACAAAAATGCAACGCGAGAGCGC
TAATTTTTCAAACAAAGAATCTGAGCTGCATTTTTACAGAACAGAAATGCAACGCGAGA
GCGCTATTTTACCAACAAAGAATCTATACTTCTTTTTTGTTCTACAAAAATGCATCCCGA
GAGCGCTATTTTCTAACAAAGCATCTTAGATTACTTTTTTTCTCCTTTGTGCGCTCTATA
ATGCAGTCTCTTGATAACTTTTTGCACTGTAGGTCCGTTAAGGTTAGAAGAAGGCTACT
TTGGTGTCTATTTTCTCTTCCATAAAAAAAGCCTGACTCCACTTCCCGCGTTTACTGATT
ACTAGCGAAGCTGCGGGTGCATTTTTTCAAGATAAAGGCATCCCCGATTATATTCTATA
CCGATGTGGATTGCGCATACTTTGTGAACAGAAAGTGATAGCGTTGATGATTCTTCATT
GGTCAGAAAATTATGAACGGTTTCTTCTATTTTGTCTCTATATACTACGTATAGGAAATG
TTTACATTTTCGTATTGTTTTCGATTCACTCTATGAATAGTTCTTACTACAATTTTTTTGTC
TAAAGAGTAATACTAGAGATAAACATAAAAAATGTAGAGGTCGAGTTTAGATGCAAGTT
CAAGGAGCGAAAGGTGGATGGGTAGGTTATATAGGGATATAGCACAGAGATATATAGC
AAAGAGATACTTTTGAGCAATGTTTGTGGAAGCGGTATTCGCAATATTTTAGTAGCTCG
TTACAGTCCGGTGCGTTTTTGGTTTTTTTGAAAGTGCGTCTTCAGAGCGCTTTTGGTTTC
AAAAGCGCTCTGAAGTTCCTATACTTTCTAGAGAATAGGAACTTCGGAATAGGAACTTC
AAAGCGTTTCCGAAAACGAGCGCTTCCGAAAATGCAACGCGAGCTGCGCACATACAGC
TCACTGTTCACGTCGCACCTATATCTGCGTGTTGCCTGTATATATATACATGAGAAGA
ACGGCATAGTGCGTGTTTATGCTTAAATGCGTACTTATATGCGTCTATTTATGTAGGATG
AAAGGTAGTCTAGTACCTCCTGTGATATTATCCCATTCCATGCGGGGTATCGTATGCTT
CCTTCAGCACTACCCTTTAGCTGTTCTATATGCTGCCACTCCTCAATTGGATTAGTCTCA
TCCTTCAATGCTATCATTTCCTTTGATATTGGATCATACTAAGAAACCATTATTATCATGA
CATTAACCTATAAAAATAGGCGTATCACGAGGCCCTTTCGTCTCGCGCGTTTCGGTGAT
GACGGTGAAAACCTCTGACACATGCAGCTCCCGGAGACGGTCACAGCTTGTCTGTAAG
CGGATGCCGGGAGCAGACAAGCCCGTCAGGGCGCGTCAGCGGGTGTTGGCGGGTGT
CGGGGCTGGCTTAACTATGCGGCATCAGAGCAGATTGTACTGAGAGTGCACCATATCG
ACTACGTCGTAAGGCCGTTTCTGACAGAGTAAAATTCTTGAGGGAACTTTCACCATTAT
GGGAAATGCTTCAAGAAGGTATTGACTTAAACTCCATCAAATGGTCAGGTCATTGAGTG
TTTTTTATTTGTTGTATTTTTTTTTTTAGAGAAAATCCTCCAATATCAAATTAGGAATCG
TAGTTTCATGATTTTCTGTTACACCTAACTTTTTGTGGTGCCCTCCTCCTTGTCAATA
TTAATGTTAAAGTGCAATTCTTTTTCCTTATCACGTTGAGCCATTAGTATCAATTTGCTTA
CCTGTATTCCTTACTATCCTCCTTTTTCTCCTTCTTGATAAATGTATGTAGATTGCGTAT
ATAGTTTCGTCTACCCTATGAACATATTCCATTTTGTAATTTCGTGTCGTTTCTATTATGA
ATTTCATTTATAAAGTTTATGTACAAATATCATAAAAAAAGAGAATCTTTTTAAGCAAGGA
TTTTCTTAACTTCTTCGGCGACAGCATCACCGACTTCGGTGGTACTGTTGGAACCACCT
AAATCACCAGTTCTGATACCTGCATCCAAAACCTTTTAACTGCATCTTCAATGGCCTTA
CCTTCTTCAGGCAAGTTCAATGACAATTTCAACATCATTGCAGCAGACAAGATAGTGGC
GATAGGGTCAACCTTATTCTTTGGCAAATCTGGAGCAGAACCGTGGCATGGTTCGTAC
AAACCAAATGCGGTGTTCTTGTCTGGCAAAGAGGCCAAGGACGCAGATGGCAACAAAC
CCAAGGAACCTGGGATAACGGAGGCTTCATCGGAGATGATATCACCAAACATGTTGCT
GGTGATTATAATACCATTTAGGTGGGTTGGGTTCTTAACTAGGATCATGGCGGCAGAAT |

TABLE 3-continued

Summary of Sequence Listing

| Sequence ID No. | Description | Sequence |
|---|---|---|
| | | CAATCAATTGATGTTGAACCTTCAATGTAGGGAATTCGTTCTTGATGGTTTCCTCCACAG<br>TTTTTCTCCATAATCTTGAAGAGGCCAAAAGATTAGCTTTATCCAAGGACCAAATAGGCA<br>ATGGTGGCTCATGTTGTAGGGCATGAAAGCGGCCATTCTTGTGATTCTTTGCACTTCT<br>GGAACGGTGTATTGTTCACTATCCCAAGCCACACCATCACCATCGTCTTCCTTTCTCTT<br>ACCAAAGTAAATACCTCCCACTAATTCTCTGACAACAACGAAGTCAGTACCTTTAGCAA<br>ATTGTGGCTTGATTGGAGATAAGTCTAAAAGAGAGTCGGATGCAAAGTTACATGGTCTT<br>AAGTTGGCGTACAATTGAAGTTCTTTACGGATTTTTAGTAAACCTTGTTCAGGTCTAACA<br>CTACCGGTACCCCATTTAGGACCAGCCACAGCACCTAACAAAACGGCATCAACCTTCTT<br>GGAGGCTTCCAGCGCCTCATCTGGAAGTGGGACACCTGTAGCATCGATAGCAGCACC<br>ACCAATTAAATGATTTTCGAAATCGAACTTGACATTGGAACGAACATCAGAAATAGCTTT<br>AAGAACCTTAATGGCTTCGGCTGTGATTTCTTGACCAACGTGGTCACCTGGCAAAACGA<br>CGATCTTCTTAGGGGCAGACATAGGGGCAGACATTAGAATGGTATATCCTTGAAATATA<br>TATATATATTGCTGAAATGTAAAAGGTAAGAAAAGTTAGAAAGTAAGACGATTGCTAACC<br>ACCTATTGGAAAAAACAATAGGTCCTTAAATAATATTGTCAACTTCAAGTATTGTGATGC<br>AAGCATTTAGTCATGAACGCTTCTCTATTCTATATGAAAAGCCGGTTCCGGCCTCTCAC<br>CTTTCCTTTTTCTCCCAATTTTTCAGTTGAAAAAGGTATATGCGTCAGGCGACCTCTGAA<br>ATTAACAAAAAATTTCCAGTCATCGAATTTGATTCTGTGCGATAGCGCCCCTGTGTGTTC<br>TCGTTATGTTGAGGAAAAAAATAATGGTTGCTAAGAGATTCGAACTCTTGCATCTTACGA<br>TACCTGAGTATTCCCACAGTTAACTGCGGTCAAGATATTTCTTGAATCAGGCGCCTTAG<br>ACCGCTCGGCCAAACAACCAATTACTTGTTGAGAAATAGAGTATAATTATCCTATAAATA<br>TAACGTTTTTGAACACACATGAACAAGGAAGTACAGGACAATTGATTTTGAAGAGAATG<br>TGGATTTTGATGTAATTGTTGGGATTCCATTTTTAATAAGGCAATAATATTAGGTATGTG<br>GATATACTAGAAGTTCTCCTCGACCGTCGATATGCGGTGTGAAATACCGCACAGATGC<br>GTAAGGAGAAAATACCGCATCAGGAAATTGTAAACGTTAATATTTTGTTAAAATTCGCGT<br>TAAATTTTTGTTAAATCAGCTCATTTTTTAACCAATAGGCCGAAATCGGCAAAATCCCTT<br>ATAAATCAAAAGAATAGACCGAGATAGGGTTGAGTGTTGTTCCAGTTTGGAACAAGAGT<br>CCACTATTAAAGAACGTGGACTCCAACGTCAAAGGGCGAAAAACCGTCTATCAGGGCG<br>ATGGCCCACTACGTGAACCATCACCCTAATCAAGTTTTTTGGGGTCGAGGTGCCGTAA<br>AGCACTAAATCGGAACCCTAAAGGGAGCCCCCGATTTAGAGCTTGACGGGGAAAGCC<br>GGCGAACGTGGCGAGAAAGGAAGGGAAGAAAGCGAAAGGAGCGGGCGCTAGGGCGC<br>TGGCAAGTGTAGCGGTCACGCTGCGCGTAACCACCACACCCGCCGCGCTTAATGCGC<br>CGCTACAGGGCGCGTCGCGCCATTCGCCATTCAGGCTGCGCAACTGTTGGGAAGGGC<br>GATCGGTGCGGGCCTCTTCGCTATTACGCCAGCTGGCGAAAGGGGGATGTGCTGCAA<br>GGCGATTAAGTTGGGTAACGCCAGGGTTTTCCCAGTCACGACGTTGTAAAACGACGGC<br>CAGTGAGCGCGCGTAATACGACTCACTATAGGGCGAATTGGGTACCGGGCCCCCCCT<br>CGAGGTCGACGGTATCGATAAGCTTGATATCGAATTCCTGCAGCCCGGGGGATCCACT<br>AGTTCTAGATTAATTAA |
| 66 | pCHIDT-2c | ATAGCTTCAAAATGTTTCTACTCCTTTTTTACTCTTCCAGATTTTCTCGGACTCCGCGCA<br>TCGCCGTACCACTTCAAAACACCCAAGCACAGCATACTAAATTTCCCCTCTTTCTTCCT<br>CTAGGGTGTCGTTAATTACCCGTACTAAAGGTTTGGAAAAGAAAAAAGAGACCGCCTC<br>GTTTCTTTTTCTTCGTCGAAAAAGGCAATAAAAATTTTTATCACGTTTCTTTTTCTTGAAA<br>ATTTTTTTTTTTGATTTTTTCTCTTTCGATGACCTCCCATTGATATTTAAGTTAATAAACG<br>GTCTTCAATTTCTCAAGTTTCAGTTTCATTTTTCTTGTTCTATTACAACTTTTTTTACTTCT<br>TGCTCATTAGAAAGAAAGCATAGCAATCTAATCTAAGTTTTAATTACAAAATGCTGGGAT<br>TCCCAATGTTCAACCCAGCTACGCCTGATGTCTGGAAGATGAATACCCCTTACTTTCCA<br>TTTGTTACACCGGGGTTATTTCCTGCCTCAGCACCCCCATCGCCCACCAACGTAGATG<br>CCGAAGCTGCCAGTTCCCAACAGTCGGAAGCAAGCTATCTGGATAAGGAGAAAATTGT<br>TCGAGGGCCACTTGATTATCTTCTCAAATCCCCTGGAAAAGACATTCGTCGGAAATTCA<br>TTCACGCGTTCAATGAATGGCTGCGCATTCCTGAGGACAAGTTGAATATTATCACGGAA<br>ATTGTTGGATTGCTTCACACGGCCTCCCTTCTAATCGACGATATTCAGGACAATTCCAA<br>GCTTCGACGCGGCCTCCCAGTGGCCCATAGCATATTTGGTATTGCGCAGACAATTAAC<br>TCTGCCAATTATGCGTACTTTCTAGCCCAGGAAAGGCTCCGCGAACTGAATCATCCTGA<br>AGCGTACGAAATATACACAGAGGAACTGCTTCGTCTGCACCGCGGTCAAGGTATGGAC<br>TTGTACTGGCGGGACTGCCTAACCTGTCCCACAGAGGAGGACTATATTGAGATGATCG<br>CCAACAAGACTGGTGGCCTATTTCGACTGGCGATTAAGCTTATGCAGTTGGAAAGCAC<br>TTTGTGCAGCAATGTCATTGAACTAGCAGACTTGTTGGGCGTGATCTTTTAGATTCGGG<br>ATGATTACCAAAACTTACAGAGTGGACTATACGCCAAGAACAAGGGATTTTGCGAGGAT<br>TTGACGGAGGGAAAATTTTCCTTTCTGATTATCCACAGTATTAACAGTAACCCGAACAAT<br>CACCATCTGCTAAATATACTACGGCAGCGGAGCGAGGACGATTCGGTGAAGAAGTATG<br>CTGTTGATTATATCGACTCGACGGGGAGTTTTGACTACTGCCGGGAACGGCTCGCTTC<br>CTTATTGGAAGAGGCGGATCAAATGGTTAAGAAGTTGGAAAATGAGGGGGACAATCA<br>AAGGGGATCTACGATATTCTGAGCTTTCTGTCGTGAGCGGATCTCTTATGTCTTTACGA<br>TTTATAGTTTTCATTATCAAGTATGCCTATATTAGTATATAGCATCTTTAGATGACAGTGT<br>TCGAAGTTTCACGAATAAAAGATAATATTCTACTTTTTGCTCCCACCGCGTTTGCTAGCA<br>CGAGTGAACACCATCCCTCGCCTGTGAGTTGTACCCATTCCTCTAAACTGTAGACATGG<br>TAGCTTCAGCAGTGTTCGTTATGTACGGCATCCTCCAACAAACAGTCGGTTATAGTTTG<br>TCCTGCTCCTCTGAATCGTCTCCCTCGATATTTCTCATTTTCTTCGCATGCCAGCATTG<br>AAATGATCGAAGTTCAATGATGAAACGGTAATTCTTCTGTCATTTACTCATCTCATCTCA<br>TCAAGTTATATAATTCTATACGGATGTAATTTTTCACTTTTCGTCTTGACGTCCACCCTAT<br>AATTTCAATTATTGAACCCTCACTGGGTCATTACGTAAATAATGATAGGAATGGGATTCT<br>TCTATTTTTCCTTTTTCCATTCTAGCAGCCGTCGGGAAAACGTGGCATCCTCTCTTTCG<br>GGCTCAATTGGAGTCACGCTGCCGTGAGCATCCTCTCTTTCCATATCTAACAACTGAGC<br>ACGTAACCAATGGAAAAGCATGAGCTTAGCGTTGCTCCAAAAAAGTATTGGATGGTTAA<br>TACCATTTGTCTGTTCTCTTCTGACTTTGACTCCTCAAAAAAAAAAATCTACAATCAACA |

TABLE 3-continued

Summary of Sequence Listing

| Sequence ID No. | Description | Sequence |
|---|---|---|
| | | GATCGCTTCAATTACGCCCTCACAAAAACTTTTTTCCTTCTTCTTCGCCCACGTTAAATT
TTATCCCTCATGTTGTCTAACGGATTTCTGCACTTGATTTATTATAAAAAGACAAAGACA
TAATACTTCTCTATCAATTTCAGTTATTGTTCTTCCTTGCGTTATTCTTCTGTTCTTCTTTT
TCTTTTGTCATATATAACCATAACCAAGTAATACATATTCAAATGGATGGGTTCGACCA
TTCTACTGCTCCACCAGGATATAACGAGCTAAAATGGCTCGCCGATATCTTCGTCATCG
GAATGGCTGTTGGCTGGGTTGCTCACTATATGGAGATGATTCACACGTCGTTCAAGGA
CCAAACATACTGCATGACCATCGGGGGCCTTTGCATCAATTTTGCCTGGGAAATCATAT
TCTGCACAATGTATCCTGCCAAAGGATTTGTCGAGCGGGTTGCCTTTCTCATGGGCATT
TCTCTCGACCTTGGGGTTATTTACGCGGGAATCAAGAACGCCCCAAATGAATGGCACC
ACTCTGCAATGGTGAGGGACCATATGCCCCTTGTCTTCGCAGCAACGACACTTTGTTGT
CTGAGCGGTCATATGGCTCTTACTGCCCAGGTTGGTCCCGCACAAGCCTATACGTGGG
GGGCAATTGCATGCCAGCTCTTTATCAGCATAGGGAATGTGTTTCAATTGTTGAGTCGG
GGAAACACACGAGGGGCGTCATGGACGCTATGGACCTCCAGGTTTTTTGGATCAACAT
CAGCCATTGGCTTTGCTCTTGTTCGATATATTCGCTGGTGGGAGGCCTTTTCTTGGTTG
AACTGCCCGCTTGTGATATGGTCCGTGGCCATGTTCTTTCTGTTTGAAACACTCTATGG
AGCCCTATTCTATTCTGTCAAGCGACAAGAAGGGAGATCCCAGCGTGGAATCAAGCAC
AAAGAGAGGTAGACAAATCGCTCTTAAATATATACCTAAAGAACATTAAAGCTATATTAT
AAGCAAAGATACGTAAATTTTGCTTATATTATTATACACATATCATATTTCTATATTTTAA
GATTTGGTTATATAATGTACGTAATGCAAAGGAAATAAATTTTATACATTATTGAACAGC
GTCCAAGTAACTACATTATGTGCACTAATAGTTTAGCGTCGTGAAGACTTTATTGTGTCG
CGAAAAGTAAAAATTTTAAAAATTAGAGCACCTTGAACTTGCGAAAAAGGTTCTCATCAA
CTGTTTAAAAGGAGGATATCAGGTCCTATTTCTGACAAACAATATACAAATTTAGTTTCA
AAGATGAATCAGTGCGCGAAGGACATAACTCAACAGTTTATTCCTGGCATCCACTAAAT
ATAATGGAGCCCGCTTTTTAAGCTGGCATCCAGAAAAAAAAAGAATCCCAGCACCAAA
TATTGTTTTCTTCACCAACCATCAGTTCATAGGTCCATTCTCTTAGCGCAACTACAGAGA
ACAGGGGCACAAACAGGCAAAAACGGGCACAACCTCAATGGAGTGATGCAACCTGC
CTGGAGTAAATGATGACACAAGGCAATTGACCCACGCATGTATCTATCTCATTTTCTTA
CACCTTCTATTACCTTCTGCTCTCTCTGATTTGGAAAAAGCTGAAAAAAAAGGTTGAAAC
CAGTTCCCTGAAATTATTCCCCTACTTGACTAATAAGTATATAAAGACGGTAGGTATTGA
TTGTAATTCTGTAAATCTATTTCTTAAACTTCTTAAATTCTACTTTTATAGTTAGTCTTTTT
TTTTAGTTTTAAAACACCAAGAACTTAGTTTCGAATAAACACACATAAACAAACAAAATGG
CGGCACTTCCGGACGTTGCCTCCATTCCCATCCCTCTGGTGGCAACCCTAGGCATTGC
CCCTCTAATTTTCTATCTCGTCCTTGATAGAATTAGCCCCTTGTGGCCAAATTCCAAAGC
TTTCCTGATTGGCAAGAAGAAACCGGAGACCGTGACATCGTTCGAGTGCCCATATGCC
TACATCCGTCAGATCTATGGGAAGTATCACTGGGAGCCATTCGTACAGAAGCTGTCTC
CGAGGCTTAAGGATGAGGATCCGGCCAAATATAAGATGGTTCTGGAGATAATGGATGC
AATCCACCTGTGTCTGATGCTAGTTGACGATATAACTGACAATAGCGACTATCGAAAAG
GCAAGCCAGCAGCCCACCGGATATATGGCCCTTCAGAGACAGCAAATCGCGCTTACTA
CCGAGTCACCCAGATTCTAAACAAGACCGTGCAAAAGTTCCCCAAGCTGGCCAAGTTC
CTGCTTCAGAATCTGGAAGAAATTCTCGAAGGCCAAGACCTGTCACTAATCTGGCGAC
GGGATGGACTGGGTAGCCTTTCGACTGTTCCTGATGAGCGAGTTGCAGCCTATCGCAA
GATGGCGTCATTGAAAACTGGGGCGTTATTCCGGCTGCTGGGGCAATTGGTGATGGA
GGACCAATCGATGGACGGGACGATGACTACTCTTGCGTGGTGCTCTCAGCTGCAGAAT
GACTGCAAGAATGTCTACTCATCTGAATATGCTAAGGCCAAAGGGGCGCTTGCCGAAG
ACCTCCGAAATCGAGAGCTCTCATTTCCAATTATCCTCGCGCTGGAAGCTCCTGAAGG
GCATTGGGTCGCCAGTGCTTTGGAGACCAGCTCACCGCGCAACATTCGCAAGGCGCT
TGCTGTGATTCAGAGTGAGAGTGCGCAATGCTTGTTTCAAGGAGCTCAAGTCGGCG
AGTGCTTCGGTCCAGGACTGGTTGGCTATTTGGGGACGGAACGAGAAAATGAACTTGA
AGAGCCAGCAGACGTAGAGTGCTTTTAACTAAGAATTATTAGTCTTTTCTGCTTATTTTT
TCATCATAGTTTAGAACACTTTATATTAACGAATAGTTTATGAATCTATTTAGGTTTAAAA
ATTGATACAGTTTTATAAGTTACTTTTTCAAAGACTCGTGCTGTCTATTGCATAATGCACT
GGAAGGGGAAAAAAAAGGTGCACACGCGTGGCTTTTTCTTGAATTTGCAGTTTGAAAAA
TAACTACATGGATGATAAGAAAACATGGAGTACAGTCACTTTGAGAACCTTCAATCAGC
TGGTAACGTCTTCGTTAATTGGATACTCAAAAAAGATGGATAGCATGAATCACAAGATG
GAAGGAAATGCGGGCCACGACCACAGTGATATGCATATGGGAGATGGAGATGATACCT
TATATCTAGGAACCCATCAGGTTGGTGGAAGATTACCCGTTCTAAGACTTTTCAGCTTC
CTCTATTGATGTTACACCTGGACACCCCTTTTCTGGCATCCAGTTTTTAATCTTCAGTGG
CATGTGAGATTCTCCGAAATTAATTAAAGCAATCACATTCTCTCGGATACCACCTC
GGTTGAAACTGACAGGTGGTFGTTACGCATGCTAATGCAAAGGAGCCTATATACCTTT
GGCTCGGCTGCTGTAACAGGGAATATAAAGGGCAGCATAATTTAGGAGTTTAGTGAAC
TTGCAACATTTACTATTTTCCCTTCTTACGTAAATATTTTTCTTTTTAATTCTAAATCAATC
TTTTTCAATTTTTTGTTTGTATTCTTTTCTTGCTTAAATCTATAACTACAAAAAACACATAC
ATAAACTAAAAATGGCCAATGCCCAGCAACCCCCCTTTCGCATCCTTATTGTGGGCGGT
TCTGTCGCAGGCCTCATCCTTGCGCACTGTCTCGAACGCGCCAATATAGAGTACCTCA
TACTCGAAAAGGAGAAGATGTTGCTCCACAAGTTGGTGCCTCGATAGGTATCATGCC
AAATGGCGGACGATCCTCGAGCAACTGGGCCTATTTGGGGAGATTGAGCGTGTGAT
CGAGCCGTTGCATCAGGCGAATATCAGCTATCCAGATGGGTTCTGCTTTAGTAACGTCT
ATCCTAAGGTTCTTGGCGACAGGTTCGGATACCCGGTTGCATTCTTGGACCGGCAGAA
GTTCCTGCAGATTGCATATGAGGGGCTGAGAAAGAAGCAGAATGTTCTCACCGGTAAA
AGGGTAGTTGGACTGCGACAGTCGGATCAAGGGACTGCTGTTTCTGTGGCTGACGGG
ACAGAGTATGAGGCGGATCTCGTGGTTGGTGCTGATGGAGTACATAGTCGGGTGAGAA
GTGAGATTTGGAAGATGCGGAAGAGAATCAGCCTGCATCAGTTTCGACACGTGAAAG
AAGAAGCATGACTGTTGAATATGTCTGCGTTTTCGGGATTTCATCAGCCATCCCAGGGC
TCGAGATAAGCGAACAGATCAACGGTATTTTCGACCATCTATCCATTCTAACAATCCAT
GGCAGACATGGTCGCGTGTTCTGGTTCGTGATCCAGAAGCTGGATAGGAAGTACGTCT |

TABLE 3-continued

Summary of Sequence Listing

| Sequence ID No. | Description | Sequence |
|---|---|---|
| | | ATCCTGATGTCCCGCGATTCTCAGACGAGGATGCCGTACAGCTCTTCGATCGGGTCAA
ACACGTGCGGTTCTGGAAAAACATCTGTGTGGGGACTTGTGGAAGAACAGAGAGGT
GTCCTCGATGACAGCGCTGGAGGAGGGAGTGTTCGAGACATGGCATCATGATAGGAT
GGTTTTGATTGGAGATAGCGTTCACAAGATGACGCCCAACTTTGGCCAAGGAGCTAATT
CAGCCATCGAGGATGCTGCCGCGCTCTCTTCCCTTCTACATGATCTCGTCAACGCCCG
TGGAGTTTGCAAGCCATCGAATGTCCAGATTCAGCATCTCCTCAAGCAGTATCGGGAG
ACCCGATACACTCGCATGGTAGGCATGTGTCGCACCGCGGCTTCAGTCTCTCGGATTC
AGGCCCGAGATGGCATCCTCAACACCGTCTTTGGACGATATTGGGCACCTTATGCTGG
CAACCTGCCTGCTGACCTGGCATCAAAAGTGATGGCAGATGCAGAGGTTGTTACTTTT
CTGCCCTTGCCAGGGCGCTCAGGACCGGGCTGGGAGATGTACAGACGAAAGGGGAA
GGGAGGGCAGGTGCAATGGGTGCTTATAATCTTAAGCTTACTTACGATTGGTGGATTG
TGCATCTGGCTACAAAGCAATGCGTTGAGTAGATAAGGAGATTGATAAGACTTTTCTAG
TTGCATATCTTTTATATTTAAATCTTATCTATTAGTTAATTTTTTGTAATTTATCCTTATATA
TAGTCTGGTTATTCTAAAATATCATTTCAGTATCTAAAAATTCCCCTCTTTTTTCAGTTAT
ATCTTAACAGGCGACAGTCCAAATGTTGATTTATCCCAGTCCGATTCATCAGGGTTGTG
AAGCATTTTGTCAATGGTCGAAATCACATCAGTAATAGTGCCTCTTACTTGCCTCATAGA
ATTTCTTTCTCTTAACGTCACCGTTTGGTCTTTTATAGTTTCGAAATCTATGGTGATACCA
AATGGTGTTCCCAATTCATCGTTACGGGCGTATTTTTTACCAATTGAAGTATTGGAATCG
TCAATTTTAAAGTATATCTCTCTTTTACGTAAAGCCTGCGAGATCCTCTTAAGTATAGCG
GGGAAGCCATCGTTATTCGATATTGTCGTAACAAATACTTTGATCGGCGCTATGCGGCC
GCCACCGCGGTGGAGCTCCAGCTTTTGTTCCCTTTAGTGAGGGTTAATTGCGCGCTTG
GCGTAATCATGGTCATAGCTGTTTCCTGTGTGAAATTGTTATCCGCTCACAATTCCACA
CAACATAGGAGCCGGAAGCATAAAGTGTAAAGCCTGGGGTGCCTAATGAGTGAGGTAA
CTCACATTAATTGCGTTGCGCTCACTGCCCGCTTTCCAGTCGGGAAACCTGTCGTGCC
AGCTGCATTAATGAATCGGCCAACGCGCGGGGAGAGGCGGTTTGCGTATTGGGCGCT
CTTCCGCTTCCTCGCTCACTGACTCGCTGCGCTCGGTCGTTCGGCTGCGGCGAGCGG
TATCAGCTCACTCAAAGGCGGTAATACGGTTATCCACAGAATCAGGGGATAACGCAGG
AAAGAACATGTGAGCAAAAGGCCAGCAAAAGGCCAGGAACCGTAAAAAGGCCGCGTT
GCTGGCGTTTTTCCATAGGCTCCGCCCCCCTGACGAGCATCACAAAAATCGACGCTCA
AGTCAGAGGTGGCGAAACCCGACAGGACTATAAAGATACCAGGCGTTTCCCCCTGGAA
GCTCCCTCGTGCGCTCTCCTGTTCCGACCCTGCCGCTTACCGGATACCTGTCCGCCTT
TCTCCCTTCGGGAAGCGTGGCGCTTTCTCATAGCTCACGCTGTAGGTATCTCAGTTCG
GTGTAGGTCGTTCGCTCCAAGCTGGGCTGTGTGCACGAACCCCCCGTTCAGCCCGAC
CGCTGCGCCTTATCCGGTAACTATCGTCTTGAGTCCAACCCGGTAAGACACGACTTAT
CGCCACTGGCAGCAGCCACTGGTAACAGGATTAGCAGAGCGAGGTATGTAGGCGGTG
CTACAGAGTTCTTGAAGTGGTGGCCTAACTACGGCTACACTAGAAGGACAGTATTTGGT
ATCTGCGCTCTGCTGAAGCCAGTTACCTTCGGAAAAAGAGTTGGTAGCTCTTGATCCG
GCAAACAAACCACCGCTGGTAGCGGTGGTTTTTTTGTTTGCAAGCAGCAGATTACGCG
CAGAAAAAAAGGATCTCAAGAAGATCCTTTGATCTTTTCTACGGGGTCTGACGCTCAGT
GGAACGAAAACTCACGTTAAGGGATTTTGGTCATGAGATTATCAAAAGGATCTTCACC
TAGATCCTTTTAAATTAAAAATGAAGTTTTAAATCAATCTAAAGTATATATGAGTAAACTT
GGTCTGACAGTTACCAATGCTTAATCAGTGAGGCACCTATCTCAGCGATCTGTCTATTT
CGTTCATCCATAGTTGCCTGACTCCCCGTCGTGTAGATAACTACGATACGGGAGGGCT
TACCATCTGGCCCCAGTGCTGCAATGATACCGCGAGACCCACGCTCACCGGCTCCAG
ATTTATCAGCAATAAACCAGCCAGCCGGAAGGGCCGAGCGCAGAAGTGGTCCTGCAA
CTTTATCCGCCTCCATCCAGTCTATTAATTGTTGCCGGGAAGCTAGAGTAAGTAGTTCG
CCAGTTAATAGTTTGCGCAACGTTGTTGCCATTGCTACAGGCATCGTGGTGTCACGCTC
GTCGTTTGGTATGGCTTCATTCAGCTCCGGTTCCCAACGATCAAGGCGAGTTACATGAT
CCCCCATGTTGTGCAAAAAAGCGGTTAGCTCCTTCGGTCCTCCGATCGTTGTCAGAAG
TAAGTTGGCCGCAGTGTTATCACTCATGGTTATGGCAGCACTGCATAATTCTCTTACTG
TCATGCCATCCGTAAGATGCTTTTCTGTGACTGGTGAGTACTCAACCAAGTCATTCTGA
GAATAGTGTATGCGGCGACCGAGTTGCTCTTGCCCGGCGTCAATACGGGATAATACCG
CGCCACATAGCAGAACTTTAAAAGTGCTCATCATTGGAAAACGTTCTTCGGGGCGAAAA
CTCTCAAGGATCTTACCGCTGTTGAGATCCAGTTCGATGTAACCCACTCGTGCACCCAA
CTGATCTTCAGCATCTTTTACTTTCACCAGCGTTTCTGGGTGAGCAAAAACAGGAAGGC
AAAATGCCGCAAAAAAGGGAATAAGGGCGACACGGAAATGTTGAATACTCATACTCTTC
CTTTTTCAATATTATTGAAGCATTTATCAGGGTTATTGTCTCATGAGCGGATACATATTT
GAATGTATTTAGAAAAATAAACAAATAGGGGTTCCGCGCACATTTCCCCGAAAAGTGCC
ACCTGAACGAAGCATCTGTGCTTCATTTTGTAGAACAAAAATGCAACGCGAGAGCGCTA
ATTTTTCAAACAAGAATCTGAGCTGCATTTTTACAGAACAGAAATGCAACGCGAAAGC
GCTATTTTACCAACGAAGAATCTGTGCTTCATTTTGTAAAACAAAAATGCAACGCGAGA
GCGCTAATTTTTCAAACAAAGAATCTGAGCTGCATTTTTACAGAACAGAAATGCAACGC
GAGAGCGCTATTTTACCAACAAAGAATCTATACTTCTTTTTTGTTCTACAAAAATGCATC
CCGAGAGCGCTATTTTTCTAACAAAGCATCTTAGATTACTTTTTTTCTCCTTTGTGCGCT
CTATAATGCAGTCTCTTGATAACTTTTTGCACTGTAGGTCCGTTAAGGTTAGAAGAAGG
CTACTTTGGTGTCTATTTTCTCTTCCATAAAAAAAGCCTGACTCCACTTCCCGCGTTTAC
TGATTACTAGCGAAGCTGCGGGTGCATTTTTTCAAGATAAAGGCATCCCCGATTATATT
CTATACCGATGTGGATTGCGCATACTTTGTGAACAGAAAGTGATAGCGTTGATGATTCT
TCATTGGTCAGAAAATTATGAACGGTTTCTTCTATTTTGTCTCTATATACTACGTATAGG
AAATGTTTACATTTTCGTATTGTTTTCGATTCACTCTATGAATAGTTCTTACTACAATTTT
TTGTCTAAAGAGTAATACTAGAGATAAACATAAAAAATGTAGAGGTCGAGTTTAGATGC
AAGTTCAAGGAGCGAAAGGTGGATGGGTAGGTTATATAGGGATATAGCACAGAGATAT
ATAGCAAAGAGATACTTTTGAGCAATGTTTGTGGAAGCGGTATTCGCAATATTTTAGTA
GCTCGTTACAGTCCGGTGCGTTTTTGGTTTTTTGAAAGTGCGTCTTCAGAGCGCTTTTG
GTTTTCAAAAGCGCTCTGAAGTTCCTATACTTTCTAGAGAATAGGAACTTCGGAATAGG |

TABLE 3-continued

Summary of Sequence Listing

| Sequence ID No. | Description | Sequence |
|---|---|---|
| | | AACTTCAAAGCGTTTCCGAAAACGAGCGCTTCCGAAAATGCAACGCGAGCTGCGCACA<br>TACAGCTCACTGTTCACGTCGCACCTATATCTGCGTGTTGCCTGTATATATATACATG<br>AGAAGAACGGCATAGTGCGTGTTTATGCTTAAATGCGTACTTATATGCGTCTATTTATGT<br>AGGATGAAAGGTAGTCTTAGTACCTCCTGTGATATTATCCCATTCCATGCGGGGTATCGT<br>ATGCTTCCTTCAGCACTACCCTTTAGCTGTTCTATATGCTGCCACTCCTCAATTGGATTA<br>GTCTCATCCTTCAATGCTATCATTTCCTTTGATATTGGATCATACTAAGAAACCATTATTA<br>TCATGACATTAACCTATAAAAATAGGCGTATCACGAGGCCCTTTCGTCTCGCGCGTTTC<br>GGTGATGACGGTGAAAACCTCTGACACATGCAGCTCCCGGAGACGGTCACAGCTTGTC<br>TGTAAGCGGATGCCGGGAGCAGACAAGCCCGTCAGGGCGCGTCAGCGGGTGTTGGC<br>GGGTGTCGGGGCTGGCTTAACTATGCGGCATCAGAGCAGATTGTACTGAGAGTGCAC<br>CATATCGACTACGTCGTAAGGCCGTTTCTGACAGAGTAAAATTCTTGAGGGAACTTTCA<br>CCATTATGGGAAATGCTTCAAGAAGGTATTGACTTAAACTCCATCAAATGGTCAGGTCA<br>TTGAGTGTTTTTTATTTGTTGTATTTTTTTTTTTAGAGAAAATCCTCCAATATCAAATTA<br>GGAATCGTAGTTTCATGATTTTCTGTTACACCTAACTTTTTGTGTGGTGCCCTCCTCCTT<br>GTCAATATTAATGTTAAAGTGCAATTCTTTTTCCTTATCACGTTGAGCCATTAGTATCAAT<br>TTGCTTACCTGTATTCCTTTACTATCCTCCTTTTTCTCCTTCTTGATAAATGTATGTAGAT<br>TGCGTATATAGTTTCGTCTACCCTATGAACATATTCCATTTTGTAATTTCGTGTCGTTTCT<br>ATTATGAATTTCATTTATAAAGTTTATGTACAAATATCATAAAAAAAGAGAATCTTTTTAA<br>GCAAGGATTTTCTTAACTTCTTCGGCGACAGCATCACCGACTTCGGTGGTACTGTTGGA<br>ACCACCTAAATCACCAGTTCTGATACCTGCATCCAAAACCTTTTTAACTGCATCTTCAAT<br>GGCCTTACCTTCTTCAGGCAAGTTCAATGACAATTTCAACATCATTGCAGCAGACAAGA<br>TAGTGGCGATAGGGTCAACCTTATTCTTTGGCAAATCTGGAGCAGAACCGTGGCATGG<br>TTCGTACAAACCAAATGCGGTGTTCTTGTCTGGCAAAGAGGCCAAGGACGCAGATGGC<br>AACAAACCCAAGGAACCTGGGATAACGGAGGCTTCATCGGAGATGATATCACCAAACA<br>TGTTGCTGGTGATTATAATACCATTTAGGTGGGTTGGGTTCTTAACTAGGATCATGGCG<br>GCAGAATCAATCAATTGATGTTGAACCTTCAATGTAGGGAATTCGTTCTTGATGGTTTCC<br>TCCACAGTTTTTCTCCATAATCTTGAAGAGGCCAAAAGATTAGCTTTATCCAAGGACCAA<br>ATAGGCAATGGTGGCTCATGTTGTAGGGCCATGAAAGCGGCCATTCTTGTGATTCTTTG<br>CACTTCTGGAACGGTGTATTGTTCACTATCCCAAGCGACACCATCACCATCGTCTTCCT<br>TTCTCTTACCAAAGTAAATACCTCCCACTAATTCTCTGACAACAACGAAGTCAGTACCTT<br>TAGCAAATTGTGGCTTGATTGGAGATAAGTCTAAAAGAGAGTCGGATGCAAAGTTACAT<br>GGTCTTAAGTTGGCGTACAATTGAAGTTCTTTACGGATTTTTAGTAAACCTTGTTCAGGT<br>CTAACACTACCGGTACCCCATTTAGGACCAGCCACAGCACCTAACAAAACGGCATCAA<br>CCTTCTTGGAGGCTTCCAGCGCCTCATCTGGAAGTGGGACACCTGTAGCATCGATAGC<br>AGCACCACCAATTAAATGATTTTCGAAATCGAACTTGACATTGGAACGAACATCAGAAA<br>TAGCTTTAAGAACCTTAATGGCTTCGGCTGTGATTTCTTGACCAACGTGGTCACCTGGC<br>AAAACGACGATCTTCTTAGGGGCAGACATAGGGGCAGACATTAGAATGGTATATCCTT<br>GAAATATATATATATATTGCTGAAATGTAAAAGGTAAGAAAAGTTAGAAAGTAAGACGAT<br>TGCTAACCACCTATTGGAAAAAACAATAGGTCCTTAAATAATATTGTCAACTTCAAGTAT<br>TGTGATGCAAGCATTTAGTCATGAACGCTTCTTCTATTCTTATATGAAAAGCCGGTTCCGG<br>CCTCTCACCTTTCCTTTTTCTCCCAATTTTTCAGTTGAAAAAGGTATATGCGTCAGGCGA<br>CCTCTGAAATTAACAAAAAATTTCCAGTCATCGAATTTGATTCTGTGCGATAGCGCCCCT<br>GTGTGTTCTCGTTATGTTGAGGAAAAAAATAATGGTTGCTAAGAGATTCGAACTCTTGC<br>ATCTTACGATACCTGAGTATTCCCACAGTTAACTGCGGTCAAGATATTTCTTGAATCAG<br>GCGCCTTAGACCGCTCGGCCAAACAACCAATTACTTGTTGAGAAATAGAGTATAATTAT<br>CCTATAAATATAACGTTTTTGAACACACATGAACAAGGAAGTACAGGACAATTGATTTTG<br>AAGAGAATGTGGATTTTGATGTAATTGTTGGGATTCCATTTTTAATAAGGCAATAATATT<br>AGGTATGTGGATATACTAGAAGTTCTCCTCGACCGTCGATATGCGGTGTGAAATACCG<br>CACAGATGCGTAAGGAGAAAATACCGCATCAGGAAATTGTAAACGTTAATATTTTGTTA<br>AAATTCGCGTTAAATTTTTGTTAAATCAGCTCATTTTTTAACCAATAGGCCGAAATCGGC<br>AAAATCCCTTATAAATCAAAAGAATAGACCGAGATAGGGTTGAGTGTTGTTCCAGTTTG<br>GAACAAGAGTCCACTATTAAAGAACGTGGACTCCAACGTCAAAGGGCGAAAAACCGTC<br>TATCAGGGCGATGGCCCACTACGTGAACCATCACCCTAATCAAGTTTTTTGGGGTCGA<br>GGTGCCGTAAAGCACTAAATCGGAACCCTAAAGGGAGCCCCCGATTTAGAGCTTGACG<br>GGGAAAGCCGGCGAACGTGGCGAGAAAGGAAGGGAAGAAAGCGAAAGGAGCGGGCG<br>CTAGGGCGCTGGCAAGTGTAGCGGTCACGCTGCGCGTAACCACCACACCCGCCGCGC<br>TTAATGCGCCGCTACAGGGCGCGTCGCGCCATTCGCCATTCAGGCTGCGCAACTGTT<br>GGGAAGGGCGATCGGTGCGGGCCTCTTCGCTATTACGCCAGCTGGCGAAAGGGGGAT<br>GTGCTGCAAGGCGATTAAGTTGGGTAACGCCAGGGTTTTCCCAGTCACGACGTTGTAA<br>AACGACGGCCAGTGAGCGCGCGTAATACGACTCACTATAGGGCGAATTGGGTACCGG<br>GCCCCCCCTCGAGGTCGACGGTATCGATAAGCTTGATATCGAATTCCTGCAGCCCGGG<br>GGATCCACTAGTTCTAGATTAATTAA |

Doctrine of Equivalents

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A host cell comprising a DNA vector that comprises at least two different production-phase promoters and at least two genes exogenous to the host cell, wherein each of the at least two genes exogenous to the host cell is situated proximately downstream of one of the two different production-phase promoters such that expression of the gene can be repressed and induced by the production-phase promoter that is proximately upstream from the gene;
   wherein the at least two different production-phase promoters are each capable of repressing expression of the gene in a *Saccharomyces cerevisiae* host cell when the *S. cerevisiae* host cell predominantly exhibits anaerobic energy metabolism; and
   wherein the at least two different production-phase promoters are each also capable of inducing expression of the gene in the *S. cerevisiae* host cell when the *S. cerevisiae* host cell predominantly exhibits aerobic energy metabolism.

2. The host cell of claim 1, wherein the anaerobic energy metabolism is defined by the catabolism of a fermentable carbon source.

3. The host cell of claim 2, wherein the fermentable carbon source is glucose or dextrose.

4. The host cell of claim 1, wherein the aerobic energy metabolism is defined by the catabolism of a nonfermentable carbon source.

5. The host cell of claim 4, wherein the nonfermentable carbon source is ethanol or glycerol.

6. The host cell of claim 1, wherein the host cell is a *S. cerevisiae* cell.

7. The host cell of claim 1, wherein at least one of the at least two different production-phase promoters comprises a production-phase promoter of *S. cerevisiae*.

8. The host cell of claim 7, wherein at least one of the at least two different production-phase promoters is selected from the group consisting of the *S. cerevisiae* ADH2 promoter (SEQ ID NO: 1), the *S. cerevisiae* PCK1 promoter (SEQ ID NO: 2), the *S. cerevisiae* MLS1 promoter (SEQ ID NO: 3), the *S. cerevisiae* ICL1 promoter (SEQ ID NO: 4), the *S. cerevisiae* YLR307C-A promoter (SEQ ID NO:5), the *S. cerevisiae* YGR067C promoter (SEQ ID NO: 6), the *S. cerevisiae* IDP2 promoter (SEQ ID NO: 7), the *S. cerevisiae* ADY2 promoter (SEQ ID NO: 8), the *S. cerevisiae* GAC1 promoter (SEQ ID NO: 9), the *S. cerevisiae* ECM13 promoter (SEQ ID NO: 10), the *S. cerevisiae* FAT3 promoter (SEQ ID NO: 11), the *S. cerevisiae* PUT1 promoter (SEQ ID NO: 12), the *S. cerevisiae* NQM1 promoter (SEQ ID NO: 13), the *S. cerevisiae* SFC1 promoter (SEQ ID NO: 14), the *S. cerevisiae* JEN1 promoter (SEQ ID NO: 15), the *S. cerevisiae* SIP18 promoter (SEQ ID NO: 16), the *S. cerevisiae* ATO2 promoter (SEQ ID NO: 17), the *S. cerevisiae* YIG1 promoter (SEQ ID NO: 18), and the *S. cerevisiae* FBP1 promoter (SEQ ID NO: 19).

9. The host cell of claim 8, wherein at least one of the at least two production-phase promoters is the *S. cerevisiae* PCK1 promoter sequence (SEQ ID NO: 2).

10. The host cell of claim 8, wherein at least one of the at least two production-phase promoters is the *S. cerevisiae* MLS1 promoter sequence (SEQ ID NO: 3).

11. The host cell of claim 8, wherein at least one of the at least two production-phase promoters is the *S. cerevisiae* ICL1 promoter sequence (SEQ ID NO: 4).

12. The host cell of claim 1, wherein at least one of the at least two different production-phase promoters comprises a production-phase promoter that is not from *S. cerevisiae*.

13. The host cell of claim 12, wherein at least one of the at least two different production-phase promoters is selected from the group consisting of the *S. paradoxus* ADH2 promoter (SEQ ID NO: 36), the *S. kudriavzevii* ADH2 promoter (SEQ ID NO: 37), the *S. bayanus* ADH2 promoter (SEQ ID NO: 38), the *S. paradoxus* PCK 1 promoter (SEQ ID NO: 41), the *S. kudriavzevii* PCK1 promoter (SEQ ID NO: 42), the *S. bayanus* PCK1 promoter (SEQ ID NO: 43), the *S. paradoxus* MLS1 promoter (SEQ ID NO: 44), the *S. kudriavzevii* MLS1 promoter (SEQ ID NO: 45), the *S. bayanus* MLS1 promoter (SEQ ID NO: 46), the *S. paradoxus* ICL1 promoter (SEQ ID NO: 47), the *S. kudriavzevii* ICL1 promoter (SEQ ID NO: 48), and the *S. bayanus* ICL1 promoter (SEQ ID NO: 49).

14. The host cell of claim 13, wherein at least one of the at least two production-phase promoters is a sequence selected from the group consisting of the *S. paradoxus* ADH2 promoter (SEQ ID NO: 36), the *S. kudriavzevii* ADH2 promoter (SEQ ID NO: 37), and the *S. bayanus* ADH2 promoter (SEQ ID NO: 38).

15. The host cell of claim 13, wherein at least one of the at least two production-phase promoters is a sequence selected from the group consisting of the *S. paradoxus* PCK1 promoter (SEQ ID NO: 41), the *S. kudriavzevii* PCK1 promoter (SEQ ID NO: 42), the *S. bayanus* PCK1 promoter (SEQ ID NO: 43), the *S. paradoxus* MLS1 promoter (SEQ ID NO: 44), the *S. kudriavzevii* MLS1 promoter (SEQ ID NO: 45), the *S. bayanus* MLS1 promoter (SEQ ID NO: 46), the *S. paradoxus* ICL1 promoter (SEQ ID NO: 47), the *S. kudriavzevii* ICL1 promoter (SEQ ID NO: 48), and the *S. bayanus* ICL1 promoter (SEQ ID NO: 49).

\* \* \* \* \*

```
                           SEQUENCE LISTING

<160> NUMBER OF SEQ ID NOS: 66

<210> SEQ ID NO 1
<211> LENGTH: 500
<212> TYPE: DNA
<213> ORGANISM: Saccharomyces cerevisiae

<400> SEQUENCE: 1
tatctaaaaa ttgccttatg atccgtctct ccggttacag cctgtgtaac tgattaatcc    60
tgcctttcta atcaccattc taatgtttta attaagggat tttgtcttca ttaacggctt   120
tcgctcataa aaatgttatg acgttttgcc cgcaggcggg aaaccatcca cttcacgaga   180
ctgatctcct ctgccggaac accgggcatc tccaacttat aagttggaga aataagagaa   240
tttcagattg agagaatgaa aaaaaaaaaa aaaaaaaagg cagaggagag catagaaatg   300
gggttcactt tttggtaaag ctatagcatg cctatcacat ataaatagag tgccagtagc   360 gactttttc acactcgaaa tactcttact actgctctct tgttgttttt atcacttctt    420
gtttcttctt ggtaaataga atatcaagct acaaaaagca tacaatcaac tatcaactat   480
taactatatc gtaatacaca                                                500

<210> SEQ ID NO 2
<211> LENGTH: 500
<212> TYPE: DNA
<213> ORGANISM: Saccharomyces cerevisiae

<400> SEQUENCE: 2
ataggaaaaa accgagcttc ctttcatccg gcgcggctgt gttctacata tcactgaagc    60
tccgggtatt ttaagttata caagggaaag atgccggcta gactagcaag ttttaggctg   120
cttaacatta tggataggcg gataaagggc ccaaacagga ttgtaaagct tagacgcttc   180
tggttggaca atggtacgtt tgtgtattaa gtaaggcttg gctggggata gcaacattgg   240
gcagagtata gaagaccaca aaaaaaaggt atataagggc agagaagtct ttgtaatgtg   300
tgtaacttct cttccatgtg taatcagtat ttctacttac ttcttaaata tacagaagta   360
agacagataa ccaacagcct ttcccagata tacatatata tcttttatttc agcttaaaca   420 ataattatat ttgtttaact caaaaataaa aaaaaaaaac caaactcacg caactaatta   480
ttccataata aaataacaac                                                500

<210> SEQ ID NO 3
<211> LENGTH: 500
<212> TYPE: DNA
<213> ORGANISM: Saccharomyces cerevisiae

<400> SEQUENCE: 3
ccattgggcc gatgaagtta gtcgacggat agaagcggtt gtccccttc ccggcgagcc     60 ggcagtcggg ccgaggttcg gataaatttt gtattgtgtt ttgattctgt catgagtatt   120
acttatgttc tctttaggta accccaggtt aatcaatcac agtttcatac cggctagtat   180
tcaaattatg acttttcttc tgcagtgtca gccttacgac gattatctat gagctttgaa   240
tatagtttgc cgtgattcgt atctttaatt ggataataaa atgcgaagga tcgatgaccc   300
```

```
ttattattat ttttctacac tggctaccga tttaactcat cttcttgaaa gtatataagt    360
aacagtaaaa tataccgtac ttctgctaat gttatttgtc ccttattttt cttttcttgt    420
cttatgctat agtacctaag ataacgact attgttttga actaaacaaa gtagtaaaag     480
cacataaaag aattaagaaa                                                500
```

<210> SEQ ID NO 4
<211> LENGTH: 500
<212> TYPE: DNA
<213> ORGANISM: Saccharomyces cerevisiae

<400> SEQUENCE: 4

```
atttattgaa aagtaaatat ctcgtaaccc ggatgctttg ggcggtcggg ttttgctact    60
cgtcatccga tgagaaaaac tgttcccttt tgccccaggt ttccattcat ccgagcgatc   120
acttatctga cttcgtcact ttttcatttc atccgaaaca atcaaaactg aagccaatca   180
ccacaaaatt aacactcaac gtcatctttc actacccttt acagaagaaa atatccatag   240
tccggactag catcccagta tgtgactcaa tattggtgca aaagagaaaa gcataagtca   300
gtccaaagtc cgcccttaac caggcacatc ggaattcaca aaacgtttct ttattatata   360
aaggagctgc ttcactggca aaattcttat tatttgtctt ggcttgctaa tttcatctta   420
tccttttttt cttttcacac ccaaatacct aacaattgag agaaaactct tagcataaca   480
taacaaaaag tcaacgaaaa                                                500
```

<210> SEQ ID NO 5
<211> LENGTH: 500
<212> TYPE: DNA
<213> ORGANISM: Saccharomyces cerevisiae

<400> SEQUENCE: 5

```
caaaaaaaca atggaagaac aaagaaaatt tagcggaagt aaaaataaca gccgaaagcc    60
aaattcaggc ttatcttgcc tactctttct tttatcgaat tcctttaggc cgttgcaata   120
gaaaagtaat aaaaacgcat atacgtaagt tgtagtcagt gtaattgcaa tctattatgc   180
gcatcaggtg cgcatactac atccattggt gcacaaaaaa aggaacgcag acaagaaaat   240
tattcagttt gctgttcgtg atgagccatc cctgaatatg actaatgtta atgttcaatt   300
tgggatctta ttttttttg tgcagtaata agaatctttg aaaaaaaact atataagcct   360
atatagtttg taagatataa gacaaaacac acctgctttt ccactacaca ttttcgttat   420
tatataaaaa agacagccaa gtatacttgt caacaaaata aactcatagc aattacacta   480
taaaaacaat agcatcaaaa                                                500
```

<210> SEQ ID NO 6
<211> LENGTH: 500
<212> TYPE: DNA
<213> ORGANISM: Saccharomyces cerevisiae

<400> SEQUENCE: 6

```
tggcaatccc ctccgatcgt ccgcggcaaa atggtcgtca atcggacaaa ggggatgat    60 gggatctggt aatagaagaa aatatggact aaaggtagcc gctaaagcga tccaggcatg   120
tgttgccaat gatgtaagtc aagcgaagga aatggttcag taatatgata gacagactgc   180
acttcaaggg tgcgcccct cccccgcgca tatgcttaca acgcaaaata attgacgttt    240
aatgtggata cttatcgtaa tcgctgcatt atagatttcg agtcatgttc acttaacccc   300
acatatttat atagaacgca tcttcaaagt acttataaag tttagttttta catttttctg   360
```

```
ctttctatttt cttcttttc ggttcttctt catgccagtt ggcatggctt aagagcttta      420
cttgtcgctt ttatttaaaa ccttctctcg ggagaagaca attgttgata tacagtaatt      480
gtatttgcat tatcactgct                                                   500
```

<210> SEQ ID NO 7
<211> LENGTH: 344
<212> TYPE: DNA
<213> ORGANISM: Saccharomyces cerevisiae

<400> SEQUENCE: 7

```
aacgtctatc tatttatttt tataactccg ggatgtcatt gccggtggtc cgaaaatcgg       60
caaataagga ataagggaa gaatatgcag tagtcaaatc atcagtgttc tctttgatac       120
ctttcagggc taggaatagt gggggtggag tataatatca aaaaccggac ttaacattat      180
tggttcggtt ggaattggct ataggcaaac tagtctccgg catgatatat aaatgacagc      240
ctgcaattgt atgttactac actcttgact tgtcgactac agtcgctgct caggcacgag      300
aataggaggt aagaaggtaa cgtacgtata tatataaaat cgta                        344
```

<210> SEQ ID NO 8
<211> LENGTH: 500
<212> TYPE: DNA
<213> ORGANISM: Saccharomyces cerevisiae

<400> SEQUENCE: 8

```
gagctccgtg gaataggcga gcggctgagt ggttctccaa gctacggttt ttacgtgtag       60
ccccatgtga gcaagccaaa caagggccct taaaggcgtg actacaaaaa ggggcgggtt      120
ggaaggtcat ctgcagcgag atacgaaaag attttttgcc agatttgcgg ttgggcggct      180
atttcggtat tgttgggta acaaacgttg gggaagactg cattttctta cagcttttt      240 tcgttatcgc gggttgggcg gctatggcgc cttctcctct gtactccaac ctgtcagaga      300
caccaagctg tatataaagc accttggttg gatcgtattt ccctgagatc ttgctatagg      360 ttcatttat atatcgtcca atagcaataa caatacaaca gaaactacta gcatctgttt      420
ataagaaaaa ggcaaatagt cgacagctaa cacagatata actaaacaac cacaaaacaa      480
ctcatataca aacaaataat                                                   500
```

<210> SEQ ID NO 9
<211> LENGTH: 500
<212> TYPE: DNA
<213> ORGANISM: Saccharomyces cerevisiae

<400> SEQUENCE: 9

```
ccctatcttt ttttttttct cgcaatctgg ggaaagcttt tctcatgctt atacgtgatt       60
tgttatataa gggattgcta tttcaggcat cattcacctc cttttgtatc cttagtttca      120
ctgcatttga tatatatata tacgtatctg tagtttcctt ccattacata acgcataata      180
tactatttcc atagtctatc ttacatcttt tttcttactt tgttaaggaa acggataacg      240
ataaaacaaa aagagagatt taagattact tctgtaactt ttttgatcca ttaccaaaac      300
tatatttttt ttcttttctc tcctctggca ttaaacacag ttattgctac agctaatcat      360
cgatataata atacatcaca ttaactgtct ataagaggct ggtacttagt agatggtgag      420
aattttttat ttttgtatt taacttcatt tttgtaaaca agttggaact ggaacttact      480
atagaacaag agcttaaacc                                                   500
```

<210> SEQ ID NO 10
<211> LENGTH: 499
<212> TYPE: DNA
<213> ORGANISM: Saccharomyces cerevisiae

<400> SEQUENCE: 10

| | | |
|---|---|---|
| gttgtatcct attggatcac gggcgacgga caagacccga agtgcggacc ggcatggtca | 60 |
| gcttgcacgg aagctttaag ggtttcccct gtttcggcat tagaagaggc atttcgcacg | 120 |
| ttttaccggg tcagaaactt cgaggaagct gtgacaattg gaaaaaaagg caaaactaaa | 180 |
| tgcaatgtat ccggttgccc atgcattatt tgtgatgttt tcggatgtag ttcgctgcgc | 240 |
| tccgcggcga tatatcctct agcgagaggc atatgtataa atatatatat atatatctaa | 300 |
| caaaagcatt caagtttctt tctctggtgt tacgtctttg ttcgactttc tctgcttaca | 360 |
| gccctgtatg accaaagaaa aaataaaaag acagctacat accagcagaa attttttata | 420 |
| gtattacact atacatccaa gttttttcac aattatttat tgttttttctc acatagaaaa | 480 |
| ttccgcatac tgcgattat | 499 |

<210> SEQ ID NO 11
<211> LENGTH: 500
<212> TYPE: DNA
<213> ORGANISM: Saccharomyces cerevisiae

<400> SEQUENCE: 11

| | | |
|---|---|---|
| gaaagcttat tactgagttt tgcggagcat cgctcggagc ggcggaattg aatcgaaccg | 60 |
| ccgtgctatt accgaacaaa aaattcgaa agcataaact cagtagtgaa aaacttgaga | 120 |
| attttcagat gagtggcgac tttccagtcc ttgcggtttt gtcaccttag tcagctagta | 180 |
| aggaggccgt gtgggttaga gtggctacaa tcctcaaagg gcacttctag aacccacggt | 240 |
| gaattttttt tggcatgata aatcggtaga atcggtgaag taattaccca aaaaaggatc | 300 |
| gggattgtgt ttctcgtaat tccgtattat tgccgatggc atcgactact tcttttttca | 360 |
| gaaaccccaa caagggtcta ttgtaattgt atataaacct ttttgtaatg gatatataca | 420 |
| tgtggtacta tttctcctca tcctgctcca tcgaaaatcc tcatacgaag agttaggaaa | 480 |
| gcaaagaaaa caacaaaaac | 500 |

<210> SEQ ID NO 12
<211> LENGTH: 412
<212> TYPE: DNA
<213> ORGANISM: Saccharomyces cerevisiae

<400> SEQUENCE: 12

| | | |
|---|---|---|
| agacacaatg cgaaaaatcg cgcagggaca taatttttgt tttcattatt ctttcgctta | 60 |
| ttccctccgt tagctccacc gctttttttga ttggaatttc ctttcggcaa tggctttccg | 120 |
| gttaccacgc ctcgggtttc gcatcccgaa aagcatatct acacaagaaa aatgaatgat | 180 |
| aaacaattga tgagtggcgc tatttccctt atcatctcat tattgtactt agtatcgtct | 240 |
| attatcagga gaaatcgcat gaactaagcc cattttctca cccttctgcc ttcttatata | 300 |
| aagcttgctg ggaaccgaac acaaactcca caagtccgta gcagctcttc tcttttgtct | 360 |
| tttatatatc ataaacatcg ctacatagta ataacactaa cgcacgctag aa | 412 |

<210> SEQ ID NO 13
<211> LENGTH: 500
<212> TYPE: DNA
<213> ORGANISM: Saccharomyces cerevisiae

<400> SEQUENCE: 13

```
aggggtagcg gcttttcat caactcgatt attacccttt agagaccttc cctaaagtga        60
gcggcaatta tttccggatg ttagtagggt aatatggtta cggatttgtg acacaaaagg       120
gcttttcaac agtcggtctg ggttgaagga ttttcaggat gacgaagctt caataagag        180
ggactggact gttaacgcgg ggaattatag gttactttcc ttgatctggc tctggctctg       240
gctctgattt tggctcttgt actcctcgga cttcttgact tgtaacgaaa tacgtctttt       300
gtccttctct tcttcttcca tagtagggc gaatgagggg agcatagtgg atccttctaa        360
ccatctagaa tggggtggac aacatataaa agaagagcaa tcttgcagcg cagtcatatt       420
tatgctaagt atatcattat ttcttgctag cgtaagtcat aaaaaatagg aaataatcac       480
atatatacaa gaaattaaat                                                   500
```

<210> SEQ ID NO 14
<211> LENGTH: 500
<212> TYPE: DNA
<213> ORGANISM: Saccharomyces cerevisiae

<400> SEQUENCE: 14

```
agcctagtcc cggtaaaccg caaacggacc ttaattgtga cgaagggccc aaatttgatg        60
ggtcggtgtt aatgattagt cctcattgtc ataataaagt gtgatgatgg aggcaatgat       120
gatatacggt agtactactg ctcgaggtgc tatctttaa ccaatccttt gagattcttg        180
tcgccacgga gttactacct tttacaaacc gtaatgtcac attttgcata tatcttatgt       240
ataaatatat agttcactta ctacttgttc tcgttttgtt aactttcttg ttgtagttct       300
tcttgttctt ggcgtttccc cctttgtttt ctatctgctt cataagtaaa gtgcaaagca       360
ttttggaaga tattatcaat tgagtcattg aaagaaactt ggcatcttcc ctattactaa       420
aactaagaat acttgattca agaaagaagt ttatattagt tttagccgta agataacata       480
acaaagaaga agaaagaaaa                                                   500
```

<210> SEQ ID NO 15
<211> LENGTH: 500
<212> TYPE: DNA
<213> ORGANISM: Saccharomyces cerevisiae

<400> SEQUENCE: 15

```
tcgatcagct ccaattaaat gaagactatt cgccgtaccg ttcccagatg ggtgcgaaag        60
tcagtgatcg aggaagttat tgagcgcgcg gcttgaaact atttctccat ctcgagccg        120
ccaagcctac cattattctc caccaggaag ttagtttgta agcttctgca caccatccgg       180
acgtccataa ttcttcactt aacggtcttt tgccccccct tctactataa tgcattagaa       240
cgttacctgg tcatttggat ggagatctaa gtaacactta ctatctccta tggtactatc       300
ctttaccaaa aaaaaaaaaa aaaaaaaaa aaaaaaatc agcaaagtga agtaccctct        360
tgatgtataa atacattgca catcattgtt gagaaatagt tttggaagtt gtctagtcct       420
tctcccttag atctaaaagg aagaagagta acagtttcaa aagttttttcc tcaaagagat       480
taaatactgc tactgaaaat                                                   500
```

<210> SEQ ID NO 16
<211> LENGTH: 500
<212> TYPE: DNA
<213> ORGANISM: Saccharomyces cerevisiae

```
<400> SEQUENCE: 16
acatagtact gtacgattac tgtacgatta atctatccac ttcagatgtt caacaattcc    60
ttttggcatt acgtattaat acttcatagg atcggcaccc tcccttaagc ctcccctaaa   120
tgctttcggt accccttttaa gacaactatc tcttaacctt ctgtatttac ttgcatgtta   180
cgttgagtct cattggaggt ttgcatcata tgtttaggtt ttttttggaaa cgtggacggc   240 tcatagtgat tggtaaatgg gagttacgaa taaacgtatc ttaaagggag cggtatgtaa   300
aatggataga tgatcatgaa tacagtacga ggtgtaaaga atgatgggac tgagagggca   360
attatcatcc ctcagaatca acatcacaaa catatataaa gctcccaatt ctgccccaaa   420
gttttgtccc taggcatttt taatctttgt atctgtgctc tttactttag tagaaaggta   480
tataaaaaag tatagtcaag                                                500

<210> SEQ ID NO 17
<211> LENGTH: 488
<212> TYPE: DNA
<213> ORGANISM: Saccharomyces cerevisiae

<400> SEQUENCE: 17
aagttcttga ctaccctat ctcacactag tacgtaattc aatgtatcat tcgtattgta    60
agtagataga gacgcaatac aggaaagctg accttccttc caatcaccac ggctgaaatg   120
ctttgttgac caattacgga cgcttaagag cggacgcggc tggaacggct ccatcctaaa   180
tcggcggagg gagaactccg ataccagccg acatggcaat aatagtgaca gtagatgcta   240
ccagccccgc aataatttca cagtagatca tcaacagtct cctcatttct ggaaatgatc   300
agcaacttcg acggatttaa ctctcaagca gttacgcact ccgagaacag ccgtgatcat   360
ctttgaacaa gcaaaatata taagcagga gaactgtcct acctagagct agaatagcca    420
taactaacta tgtaacattc tacagatcaa tcaaaaacaa tcttcaatca cagaaaaaaa   480
taaaaggc                                                            488

<210> SEQ ID NO 18
<211> LENGTH: 329
<212> TYPE: DNA
<213> ORGANISM: Saccharomyces cerevisiae

<400> SEQUENCE: 18
ttttctagtt cttcttctgc aatattgcct tttgggaaga aggatcgaaa gtagccattt    60
gcagacacgt ttttactata tttactgtat cttcgattgc gcggctaaag ttgccatatt   120
attattatat tgcagctcaa ccccgcattt ccggagtttt cttttttttt atttggggta   180
atttggaggt cggcggctat tggtgggccg gaaatggtga cacacttgta atatataagg   240
aggaaatcct acatgtgtat aagcgaaatc acaaggataa taatgtattg ctaaacaccc   300
tcaagaaaga aaataatcat aacgaaatc                                     329

<210> SEQ ID NO 19
<211> LENGTH: 500
<212> TYPE: DNA
<213> ORGANISM: Saccharomyces cerevisiae

<400> SEQUENCE: 19
cggatggaat cgccgctttt gaattcacct ccggggtatt attattattc ttagtagtcg    60
cggtcgtgcg gacacccgga gttatgcggg cccgaaagct cattatgtag taaagctagg   120
taatgttaag ggcgtaagag ccaacgcaag gcagcaatag cctggtattc ccacatatca   180
```

```
agaaagctta aaaagttgag acagggaatt tgaaggcgaa gattgccgaa ctggccaata      240
cccactactt tttttttggt ttgcttggtt tcttcctgtc gcttgccaac ttgtggcatc      300
ttccccacac tatattataa ggatcgtcct atgtataggc aatattatcc atttcactcg      360
ctaacaaatg tacgtatata tatggagcaa caagtagtgc aattacagac gtgtattttg      420
tcttgatctt gcttttgta tgataggcct aagaataaca gtgcgaacat ataagaaaca       480
tccctcatac taccacacat                                                  500
```

<210> SEQ ID NO 20
<211> LENGTH: 442
<212> TYPE: DNA
<213> ORGANISM: Saccharomyces cerevisiae

<400> SEQUENCE: 20

```
agacctttt tttcttttc tgcttttcg tcatccccac gttgtgccat taatttgtta        60
gtgggccctt aaatgtcgaa atattgctaa aaattggccc gagtcattga aaggctttaa      120
gaatataccg tacaaaggag tttatgtaat cttaataaat tgcatatgac aatgcagcac      180
gtgggagaca aatagtaata atactaatct atcaatacta gatgtcacag ccactttgga     240
tccttctatt atgtaaatca ttagattaac tcagtcaata gcagattttt tttacaatgt      300
ctactgggtg gacatctcca aacaattcat gtcactaagc ccggttttcg atatgaagaa      360
aattatatat aaacctgctg aagatgatct ttacattgag gttattttac atgaattgtc      420
atagaatgag tgacatagat ca                                               442
```

<210> SEQ ID NO 21
<211> LENGTH: 500
<212> TYPE: DNA
<213> ORGANISM: Saccharomyces cerevisiae

<400> SEQUENCE: 21

```
tccgaagagc gtgctaccaa ttcttcatct cgttaacaaa ctggttctcc gttaaaaatt     60
gtgctatatg tcctataagc caactctatc tatatctttt cttttagtcc tactttggat     120
actgttacca ccatttttaga ttgcttttc ttttgccgct agcctacaa tatttggcaa     180 acttttttt tttagccgcc gagactcttg atctatggcc gggcgaaagg gcaaatgact    240
gcttatcccc gccatcactt cccccccgccc aagggtttag aattgggat taagtaaaaa    300 cgaatgacta ttcctctcaa agtcatcctt gttcgacaaa agaatggaa tataacatat    360 tggaacaatt tcatcctctt tccccatttt tcgcatataa gagcaactaa acgccggtga    420
gtaaagtgcc cttccctaca gactctttta ctcaggtata tatatatata tatcccttaa    480
aaactaaaaa gaaagcactc                                                 500
```

<210> SEQ ID NO 22
<211> LENGTH: 310
<212> TYPE: DNA
<213> ORGANISM: Saccharomyces cerevisiae

<400> SEQUENCE: 22

```
agcggttgtt ctaaccacta tttaaagccg caattagtaa tgcaaaaagt tggccggaat     60
tagccgcgca agttggtggg gtcccttaat ccgaaaaagg acggctttaa caaatataaa     120
ctccgaaaat ccccacagtg acagaattgg agaaacaacc agttttgata tcgccataca     180
tataaagaga tgtagaaagc attcttcact gtaatgtcca atcgtacat ttgaatttct      240
```

```
tgtaggttta tttaaaaggt aagttaaata aatataatag tacttacaaa taaatttgga    300
accctagaag                                                           310

<210> SEQ ID NO 23
<211> LENGTH: 340
<212> TYPE: DNA
<213> ORGANISM: Saccharomyces cerevisiae

<400> SEQUENCE: 23 aattttatt  ttctccttcc atatgagcga cagcggttac tagccgctgt cctcaggtta    60
atgatccaag tccgagatcc gggccgaata tgcttgcggg gaaagaaata aaagtgcatt   120
ggagaagaaa aggatatgct cttcaattag aagcgccgaa acactaacat catgctagcg   180
atatcatacg tacactatat aatgtaaaaa atgggcttaa gaataactct cttatttctt   240
aacttttgtt gcggttgaag agcttataaa agtactagtg gcctaaagaa gctacagcgc   300
cgataataat atcgatttcg acttttctag tatttcgccg                         340

<210> SEQ ID NO 24
<211> LENGTH: 500
<212> TYPE: DNA
<213> ORGANISM: Saccharomyces cerevisiae

<400> SEQUENCE: 24
tgtgcacata cgtccagaat gatatcaaga taaatggcac gtgtatgtac ggctgtgtaa    60
atatgataat catctcggac gaacggcgta gcactctcca tcccctaaaa atgttcacgt   120
gtgactgctc catttcgccg gatgtcgaga tgacccccccc ccctcaaaag gcactcacct   180
gttgacatgc cgtggcaaat gattggggtc atccttttt  tctgttatct ctaagatcca   240
aagaaaagta aaaaaaaaag gttggggtac gaattgccgc cgagcctccg atgccattat   300
tcaatgggta ttgcagttgg ggtacagttc ctcggtggca aatagttctc ccttcatttt   360
gtatataaac tgggcggcta ttctaagcat atttctccct taggttatct ggtagtacgt   420
tatatcttgt tcttatattt tctatctata agcaaaacca aacatatcaa aactactaga   480
aagacattgc ccactgtgct                                               500

<210> SEQ ID NO 25
<211> LENGTH: 500
<212> TYPE: DNA
<213> ORGANISM: Saccharomyces cerevisiae

<400> SEQUENCE: 25
aatataaata aaattccata cagcatgtct aatcatagct aatttataca tattcatcat    60
gaaaacatat aggggaaaat atggtcggtt aacacaccta tcaaaaaatt attcagcaat   120
tccaatctcg ttagtaaaat atattcttat tttttttttt tttctctgat tgtattattt   180
ctggagtttt gacttatttt tttaccacat cgcgctttc  gtccccaatc tctctgatat   240
atgatgctgt ctataggtag ccacttcccc gatgtcggac ctcgggccgt ttacaaactt   300
tattgagatg accttatttc tccacattct agtcattcaa cttttaccct catatgttta   360
ccttcactaa tgtgaaagca tgaccaaaga aagtgtataa ggtatataaa tctgccataa   420
tgtatgtata acttattagg actttctcaa atagtatttt ggtattttct actgttctct   480
gatgatcgag agcaaacaga                                               500

<210> SEQ ID NO 26
<211> LENGTH: 500
```

<212> TYPE: DNA
<213> ORGANISM: Saccharomyces cerevisiae

<400> SEQUENCE: 26

```
aagtacgata tggtataact gtaacattga aggactgaag gactgaagga ctgaaggact      60
atagtcaagg gccaatgggg aaggtccctt ccaggccatt tgcccgatag tttgtccttc     120
tcttgctttt ccgacggccc gattgcatgt ggcggggcag cactggataa aaaacgtgg     180
ggggagtgat taaatttata cgcttattgt gtcaacacgg aaaccttata gttatcatta    240
ctaacatcgc aacaagctgc ttttttactc gttttagcc acaccatacc cctttaatt     300
aactaataat gcataaaata gttattgctt cttgagttgc agcttcttcc tggacgtact    360
gttatatatg gcatgtcttc gcatgtccgt caaatttagc gttgtctcga aacttaggct    420
gtcgttcttg ctgtctgtct tctgataaaa taatatattg gaataagaaa aaaaaaatag    480
gaacaagaaa gtgtgtgaga                                                 500
```

<210> SEQ ID NO 27
<211> LENGTH: 304
<212> TYPE: DNA
<213> ORGANISM: Saccharomyces cerevisiae

<400> SEQUENCE: 27

```
atattattca gttgaaagac aaaaaaacat aaatatttct atgagcaaac aatttgaaca      60
gaaaaataaa attggggaag tgacacacca tggtagcggt tctaaagcga aatcggcaaa    120
gcggctaaat agcagttttg atgacttact ccacactgaa aatggatgac cttaaatagg    180
agataaagct ttttcatccc tatgtattta agatgactgg cttgtcaagc attctaatca    240
taaaaaaaag atcgtatttg atcaagaatt tatacataga cgccgctaaa taattgaata    300
caaa                                                                 304
```

<210> SEQ ID NO 28
<211> LENGTH: 500
<212> TYPE: DNA
<213> ORGANISM: Saccharomyces cerevisiae

<400> SEQUENCE: 28

```
ctcgtttgcc gttacattgc attgatggta caataaaggg catgctttat atcgagatgt      60
ttcagtgtat atgaggggaa acagaaaaga gtcattcctg ccattttttg gtcactgctt    120
tttctgctat gagtaatggt gaagttcctt gtggctacac gcttaatgtc atcgggttac    180
tgctcctaat atccgcatat aagctttatg cagggatcag ttgggcggct atttatctac    240
acccagtcat ccggcgtgac tggatctcca cttgccgcaa taagtcggtg gacaaatgga    300
gatttaagag taaagatgca tgatggtata attcctttag tcgaaataga tatatttcaa    360
gcgcatatat aggcagacgc ttgtactgta gaaatagccg atattcaatt gcgctctatg    420
tgtgttttta ttccaggttt tccttggatt ctacgtattg tacgactttc ttatcctcca    480
caaacgtcat cgtgtcagta                                                500
```

<210> SEQ ID NO 29
<211> LENGTH: 500
<212> TYPE: DNA
<213> ORGANISM: Saccharomyces cerevisiae

<400> SEQUENCE: 29

```
cccaacagat ttcaagtctg tcgccttaac cactcggcca tagtgcctaa aacaatgtag      60
```

```
gttatttaag caagtattgt agatactttt cgtaataaac tacaatgcac ccacgactcg      120
cggtgtaatg atggcatgaa atcattgaac gaagttttgc ggctatacgg ctgaaggacg      180
agactaaagg gacaggaatt attaatgcgg ggtataattt gaatagtatt aacgggcact      240
gccgtttagc catcaaatgc tattgttggg gtattctctc tacttttgt tcttggcttg       300 aaccttttcg gcggttggca atcgtccgta tataagcatc ggctgtccca atcctctatt      360 gccctttttcc cttgcacctc cttctcaatt cttcgtatct ttcgcgtaaa ggtagatctt     420
gattcaccta tctgtcgaaa cacgattaag tgcaaacgaa acaacgtaca gtatataaca     480
aagtatttta aataataaga                                                  500

<210> SEQ ID NO 30
<211> LENGTH: 500
<212> TYPE: DNA
<213> ORGANISM: Saccharomyces cerevisiae

<400> SEQUENCE: 30
gctatgacgt ttgggtggcc tagccggttc gcgtgtgcct gtcgcttttg tcgcttttca      60
acttctgccc gatatttcct atcaaaggaa aatgggacgt tttcaacccc tcgctatcat      120
cgtgcctgca ctctgcctat cgccaactac accggggttt tatctgcttc accctccat      180 ccagtgctga taacaagaag aaccttgcag ggtagggcag gacctacggc caaaatacta     240
attatgtctg tttatgtaca tgccccaatc tgaatattcc atgaatgtag gcacagcata     300
tctccatcca tgtactgata cagacgcata acatatatg tatatacata cttatacact      360
cgaatatttg tagactgatg tacttctata tatatatagg gggtttgtgt tcctcttcct     420 ttccttttttt tttctctctt cccttccagt ttctttttatt ctttgctgtt tcgaagaatc   480
acaccatcaa tgaataaatc                                                  500

<210> SEQ ID NO 31
<211> LENGTH: 500
<212> TYPE: DNA
<213> ORGANISM: Saccharomyces cerevisiae

<400> SEQUENCE: 31
tagatgcgcc atctccgaga aaaaatctag acaataacag cgacaattaa cctaaagagg      60
atagaagatc gagcaaaaaa attttttttaa tatggggtca gtggcgatat tatactatag    120
gagttaaaga gtaagttgag tgtaaggtgg tagaattatg attgaactcc gaaactaagc     180
gccgattatg ggtggcaaag cggacagctt ttgatatata atcgatcgct ctcgtagttg     240
atatcctctc tcttgcttat cttttcctgt atatagtata tgtgtacata cagatacgaa     300
tatacctcag ttagtttgtt ttaacattaa atattcaaca gttgccagta gcaaaaagaa     360
tatatccatt catttcgagc ttttttcgtct cattactgat atccaactaa cagtctcctc    420
atagacggta ccttactttc ctttaatatt ataatactag tatagtcgca catacttaac    480
tcgtctctct ctaacacata                                                  500

<210> SEQ ID NO 32
<211> LENGTH: 500
<212> TYPE: DNA
<213> ORGANISM: Saccharomyces cerevisiae

<400> SEQUENCE: 32
ctacgtcgcc tgttcgagcg gctctgttcg ttgcatgaaa ctaaaataag cggaaagtgt      60
ccagccatcc actacgtcag aaagaaataa tggttgtaca ctgtttctcg gctatatacc     120
```

```
gttttttggtt ggttaatcct cgccaggtgc agctattgcg cttggctgct tcgcgatagt        180
agtaatctga gaaagtgcag atcccggtaa gggaaacact tttggttcac ctttgatagg        240
gctttcattg gggcattcgt aacaaaaagg aagtagatag agaaattgag aaagcttaag        300
tgagatgttt tagcttcaat tttgtcccct tcaacgctgc ttggccttag agggtcagaa        360
ttgcagttca ggagtagtca cactcatagt atataaacaa gccctttatt gattttgaat        420
aattattttg tatacgtgtt ctagcataca agttagaata ataaaaaat agaaaaatag         480 aacatagaaa gttttagacc                                                    500

<210> SEQ ID NO 33
<211> LENGTH: 500
<212> TYPE: DNA
<213> ORGANISM: Saccharomyces cerevisiae

<400> SEQUENCE: 33
gagctatagt cttttgcgct ttcaatacgt gtagcggtgt accaaaagtt gcacaaaaat         60
gtagttgtca atgaaagcgc actacgtata taatgactat ttttttttc ctggggttgca       120 tgggtaattt gttgttaata tgcgattttc ttggggaaaa gggtgtcata gcgccaaaaa       180
ctgccgtgcg gcacagtatg tatgttttg agtcgcggcg tttaagggct tggcataaaa        240
agtggttcaa gcgagtgata agttgggcga atgtcgtctt ttttgtaacc atgtctttcc       300
tgaaaacaac ctgtaggcag ctccactcca cataagggct ttctccaatg gcaatgggag       360
ctcggaacac cggagtagaa attttttataa tgtgtattgt ataaaacttg cttgttatgc      420 agttttgtt tttttgtta ctcttccgta gcacaataga catatattag cggcaaaatt         480
gtagtgttgc gattattgcc                                                    500

<210> SEQ ID NO 34
<211> LENGTH: 500
<212> TYPE: DNA
<213> ORGANISM: Saccharomyces cerevisiae

<400> SEQUENCE: 34
gtgtagtatt gatcttgttg gtattgctag aaatgcttca gcaatactgt ataaaatatg         60
gaaacgttgc catggcaaga caaaagaagt gatcttgagt gaaataatag agcccggatg       120
gccgggtaaa ttcaaccgct cgtaccgttt ataatacgca taaacgccga aaatgtctct       180
attttagtca ttccccagag tgcggtattg cgtacacctg tcatgcgttc cttagtgccg       240
atagatatac taatatcgat gcgtcacagt agcagatcat ctctgacact tgtttcccca       300
tttttttttt tcatttttta aagggtttct ctacagccta caggcctccc ctaataagtc       360
agcccctccc tttggagtgc gctgttgacc tgcgtatata agaggtatat cagtgccagt       420
aggtaaaccc atcttgcggg gattgtacca ggaacatagt agaaagacaa aaacaaccac       480
cgtacttgcc attcgtatag                                                    500

<210> SEQ ID NO 35
<211> LENGTH: 500
<212> TYPE: DNA
<213> ORGANISM: Saccharomyces cerevisiae

<400> SEQUENCE: 35
catcaattag ggcaaacttg aatagtcagc taggtcatat atttaaaatc aattagccct         60
atgactacat taggtttatt gttaggtctt tacggctgca tatttgcttt cgccgttcgg       120
```

```
cggggtcctg cgacgatttc tgcgcggtct tgtatgggtg gagttgacag ttaaccctcc    180
ggaccccta ccccggtgtg ccccggtcc atctatccat tttgcggtaa ccccttcgcg     240
cgacagctgc ttatcaaggt acctggatcg agccataaaa attgatctac acagatgaga    300
tggggcattg ggatatatta ttagtcggag tatcattata gttattcagt tttatgcagg    360
ttactggcca aacgttttc ttcatttgga ataatcgttt aggagctact gttccggtat     420
aaagtaacaa gcacagtagc agagtaaatac gcagtgacga taatagagac tagtaaaaca   480
gtcgagttgt cggacctaaa                                                500

<210> SEQ ID NO 36
<211> LENGTH: 500
<212> TYPE: DNA
<213> ORGANISM: Saccharomyces paradoxus

<400> SEQUENCE: 36
tagtcttatc taaaaattgc ctttatagtc cgtctctcca gtcacggcct gtgtaactga     60
ttaatcctgc ctttctaatc accattctac tgtttaatta agggattttg tcttcatcaa    120
cggcttccgc ccaaaaaaaa gtatgacgtt ttgcccgcag gcgtgaagct gcccatcttc    180
acgggcctga cctcctctgc cggaacaccg gccatctcca actcataaat tggagaaata    240
agagaatttc agattttcag aggatgaaaa aaaaaggta gagagcataa aaatggggtt     300
cacttttggg caaagttaca gtatgcttat tacatataaa tagagtgccg ataatggctt    360
tttttcatct tcgaaatacg cttgctactg ctcttccagc gttttttatta cttctttctt   420
gtttctcctt agtatataaa atatcaagct acaacaagca tacaatcaac tgtcaactgt    480
caattatatt ataatacact                                                500

<210> SEQ ID NO 37
<211> LENGTH: 496
<212> TYPE: DNA
<213> ORGANISM: Saccharomyces kudriavzevii

<400> SEQUENCE: 37
ctctcaaatc tttagcgcc aaggactcca actaattgta tcttgaattt gcctttacga      60
tccgtttgtc cagtcacggc atgtatatct tattaatcct gcctttctaa tcacgtattc    120
taatgttcaa ttaagggatt ttatcttcat caacggctcc cacgcaaaaa atgacgtttt    180
gcacacagac acgaaataca ccttccaccg gaacaacggc catctccaac ttataagttg    240
gggaaataag acaatttcag acttcagaga atgaaaaaaa aaaaggtac atcacagatg     300
gggttcaggt ttgctacaat tgcagggagc ctgtcacata taaatagacc tccagtgatg    360
atatctttca gtcttcaaac gtctcttgtc acagttctgg tcgttctata tcacatctct    420
cttggttcta cttattgtct ataatatcaa gctacagcaa gcatacaatc aactatctac    480
cataccataa tacaca                                                    496

<210> SEQ ID NO 38
<211> LENGTH: 441
<212> TYPE: DNA
<213> ORGANISM: Saccharomyces bayanus

<400> SEQUENCE: 38
gatccagttc tccagtgaca cagcctttat ctggtcaaac ctttctttct aatcacctat     60
gctgatgctt aattaaggga ttttgtctc catcaacggc atgcgcccaa aaatgacgtt    120
ttttttaacc catagacacg aaactaccca ttttccaccg gcctgaccta ccaccggaac    180
```

```
aacggccatc tccaacttgc aagttgggga aattaagagc atcgcaggtt taatggaaga    240
aaaaaaaaag gtacagcaca gcgcaaatgg agttagttcc cttatgtcac acactcacac    300
acagtcggtc agatcaagca tactgggtgc gtataaatag agtggccatt gccaccctgt    360
ttatctcaaa atctgtcttg ttagtggtct tctcccttt  tcaggttaca attctcttgt    420
ttctacttag tatataagta t                                              441

<210> SEQ ID NO 39
<211> LENGTH: 480
<212> TYPE: DNA
<213> ORGANISM: Saccharomyces mikitae

<400> SEQUENCE: 39
tttcccaaaa agtattattt ttaagtgata attgataaaa ggggcaaaac gtagacgcaa     60
ataaaacgga aataatgatt ctcagacctt ttagcgtcaa gaactgcaac taatcttatc    120
ttaaaattat ctttataatc cgtttctccc gtcacagtct gtgtatctga ttaatcctgc    180 cttctaatc  acctattcta atgttcaatt aagggatttt gtcttcacca acggcttcca    240
cccaaaagta aaaaatgacg ttgtacccac agacatcttc accggcctga cctgccaccg    300
gaacaacggc catctccaac tcataaattg gagaaataag agaatttcag attctggagg    360
atgaaaaaaa aaaggtaca  gcataaatgg ggttttatgt gggtacaatt acactaggac    420
tatcacatat aaatagacgg gcaatgtagg ttcttttcca cccttgagac agagttattc    480

<210> SEQ ID NO 40
<211> LENGTH: 500
<212> TYPE: DNA
<213> ORGANISM: Saccharomyces castellii

<400> SEQUENCE: 40
tgtcgtggac gaaatacgcc acaattttgc cgagaaggtc attagtatgt ccaagaaacc     60
ctaggtgtaa agtcgggaaa tccgaatctc cgattttgga ggggcccatg ccctactttt    120
tttcgccagg ggtgaaattc caaacccgtg cgcgttcttg gaatttgaca gcgcattgag    180
tatgtgctgc gtattcccac tatcatgacg cgcccttat  ctgggaaaaa tggaactgga    240
tgctgaaata tttcactctc agatcacata tcccaaatcc tgtgagtgaa ttgtttggtc    300
aggcgaccaa acaggaatat ggaatagatt ctattctctg gattctacaa ttatccattg    360
ttagcaaaac aaaaaaaact ggtggtatat atattcagag cctaaaattt aaaggttgga    420
tctcaatttt aaagttttc  attctgtttt gttttttgttt cttcttagct cacgaataac    480
caaacaaaaa acaatcaata                                                500

<210> SEQ ID NO 41
<211> LENGTH: 500
<212> TYPE: DNA
<213> ORGANISM: Saccharomyces paradoxus

<400> SEQUENCE: 41
caataggaaa aaaccaagct tcctttcatc cggcacggct gtgttgtaca tatcactgaa     60
gctccgggta ttttaagtta tacaagagaa atatgcgggc tagactagca agattctgga    120
ctgtataacg ttgtggatag gcggataaag ggcccaaaca ggattgtaaa gcttagacgc    180
ctctggttgg gcaatggcat gttttgtgtat taagtaagac ttggctgcgg gatagcaaaa    240
ctgagcagaa tatagaaggc cacaaaaaaa aggtatataa gggcagcaaa gtcttttataa    300
```

```
tatatgtaga ttctcttctc tgtgtaattc attcttgtgc ttaccactca aatatacaga    360
agtaagacag ataaccaaca gcctttccca gatatacata tatctcattg tttcagttta    420
aacaataatc atatttgttt aactcaaaaa taaaaaaaaa ctaaactcac tcaatcaatc    480
attccataaa aaaaaacaat                                                500

<210> SEQ ID NO 42
<211> LENGTH: 500
<212> TYPE: DNA
<213> ORGANISM: Saccharomyces kudriavzevii

<400> SEQUENCE: 42
cttcctttca tccggcacgg ctgtgtcccc acatctccct aaagctccgg gtattttaag    60
ttatacaagg gaaatatacg ggctggacta caacttgcag gttgcacagc gttatggata    120
ggcggataaa gggcccaagc aagatcgtga agcttggacg cgtctggttg gacaatggtg    180 acttttgtg tattagataa tgcttgactg gagaatatca ggactgagca gagttaggaa    240
gaccacaaaa aaggtatata agggcaacaa agtctccgtg atatggatag gctcttctct    300
ctggttacaa ttcattattt cagttgtttg ctagatatag agatataata catctaataa    360
acagtcactt ccagagatat atatatatac atatatctat ctcctcctcc cagcttaaat    420
aataactata tttgtttaac tcgaagaaaa aaaaaattca aatttactct atcaattcaa    480
ttacctcata aaaaacaata                                                500

<210> SEQ ID NO 43
<211> LENGTH: 500
<212> TYPE: DNA
<213> ORGANISM: Saccharomyces bayanus

<400> SEQUENCE: 43
cttcctttca tccggcacgg ctgtgtcccc acatctccct aaagctccgg gtattttaag    60
ttatacaagg gaaatatacg ggctggacta caacttgcag gttgcacagc gttatggata    120
ggcggataaa gggcccaagc aagatcgtga agcttggacg cgtctggttg gacaatggtg    180 acttttgtg tattagataa tgcttgactg gagaatatca ggactgagca gagttaggaa    240
gaccacaaaa aaggtatata agggcaacaa agtctccgtg atatggatag gctcttctct    300
ctggttacaa ttcattattt cagttgtttg ctagatatag agatataata catctaataa    360
acagtcactt ccagagatat atatatatac atatatctat ctcctcctcc cagcttaaat    420
aataactata tttgtttaac tcgaagaaaa aaaaaattca aatttactct atcaattcaa    480
ttacctcata aaaaacaata                                                500

<210> SEQ ID NO 44
<211> LENGTH: 500
<212> TYPE: DNA
<213> ORGANISM: Saccharomyces paradoxus

<400> SEQUENCE: 44
cgataccaca cggtccattg ggccggtggt gttagtcgac ggatatatgc atctgtcccc    60
tttcccggcg agccggcagt cgggccgagg ttcggataaa tttttgcatt gtattagttt    120
ctgtcatgag tattacttat ggttcccttta gagctaatca ttagctcggt accggctgtt    180
atgcaattta tgacttttct tctacagtgt cagccttgtg acgattatct atgaactttg    240
gatgtagcgc atcgagattc gtatctttca ttggatagta aatgggaagg atcgatgacc    300
cttattacat tctttcctat acttaatatc catttaatct atcttcttga agtatataa    360
```

| gtaacggtaa atttaccata cttatgctat tctcatttat cccctaattt tcttttaact | 420 |
| tctcgcccta cagtaactaa gaataacggc tactgtttcg aaattaagca aagtagtaaa | 480 |
| gcacataaaa gaataaagaa | 500 |

<210> SEQ ID NO 45
<211> LENGTH: 500
<212> TYPE: DNA
<213> ORGANISM: Saccharomyces kudriavzevii

<400> SEQUENCE: 45

| agaccgaagc gggtaatgga cggaattaag caattgtccc ctctcccggg gagccgacag | 60 |
| tcggaccgag cttcggataa atttctgtat tgttttgtt tccgtcatgg gtattatttt | 120 |
| cgggatcctt ttgccaaccc catagtcaat cgttaacatt taccggccaa tatgtaggat | 180 |
| tatgactatt ctcctgcatg atcagcggaa gtgacgatta tctattaatt ttgaacttct | 240 |
| acttcgtgat ccggaattta attggataat aatgtgtccg aaggatcgag tgacccttat | 300 |
| attctgtagt tttttgttac tggccatcca attcgtgttc ttggaagtat ataagttaca | 360 |
| gtcgattgac ctttctcaag ctattttcat ctttctccta catttacgtt tctcttcttc | 420 |
| aatacagcag ctagaagtta cgattactcc tgtgaagata aacaaagtaa tagtagccca | 480 |
| caaaaagaga gaaagtaaaa | 500 |

<210> SEQ ID NO 46
<211> LENGTH: 500
<212> TYPE: DNA
<213> ORGANISM: Saccharomyces bayanus

<400> SEQUENCE: 46

| gtagcagtcc ggaaataagc aaatgtcccc tttcccgagc taaccaacgg tcgggccgag | 60 |
| cctcggataa attttgctt tgttttgtt tctgtcatgg gtattataca tcatttattt | 120 |
| agttaacccc tagactaatt agccggccat tagtatgtaa gattatgact atagtttgta | 180 |
| ccggaaccct ggtagcaact actcatgaac tttgggctca gtatttcgca atcccggttt | 240 |
| taattggata gcctatcgcg aaggatcgat ggatgaccct tagaattgtc tcttttgtta | 300 |
| ctactcattc aatgcgtgtg ctcttgcaag tatataagtc actctaaatt agtttatact | 360 |
| tgagctttt acatttctcc cttgattgtt tctttctctt ttccccttgt tctggtttat | 420 |
| tgtaatagct aagtgcaacg attaccgctg ttaagttaaa gaagagagac aagtaataat | 480 |
| agtacacagc aaggaaaaaa | 500 |

<210> SEQ ID NO 47
<211> LENGTH: 500
<212> TYPE: DNA
<213> ORGANISM: Saccharomyces paradoxus

<400> SEQUENCE: 47

| ttactaaata ggctggcatc agctaacccg gatggttgaa tccggctttt gctacttgtt | 60 |
| gtccgatgaa aaggagcggc ttccctttg ccccagattt ccattcatcc gagaggtcgc | 120 |
| ttatcagact tcgtcatttc tcatttcatc cgagatgatc aaaattgaag ccaatcacca | 180 |
| caaaactaac acttaacgtc atgttacact acccttaca gaagaaaata tccatagtcc | 240 |
| ggactaacat tccagtatgt gactcaatat tggtgcaaat gagaaaatca tagcagtcag | 300 |
| cccaagtccg cccttacca gggcaccgta attcacgaaa cgtttcttta ttatataaag | 360 |

```
gagctacttt actagcaaaa ttcttgtaat tcctcttccc ttgctaactt cttcttgttt    420
tcttttcctt tttacacaca gatatataac aattgagaga aaaactctag tataacataa    480
caaaaaagtc aacgaaaaaa                                                500
```

<210> SEQ ID NO 48
<211> LENGTH: 500
<212> TYPE: DNA
<213> ORGANISM: Saccharomyces kudriavzevii
<400> SEQUENCE: 48

```
gttacggtgc cgcgccggtg gccggtggtc ttccggtaaa caaaaaaagc tgcctcccct     60
tcgccccaga tttccattca tccgagggca ccgcttgtca gactttatcg tttttcctcat   120 ttcatccgag aagatcaatt caaaggcaat gaccacaaaa gcaactccta acgttgtgtt   180
acgctaccct ttacacaaaa tattcataac ccgtaatgaa tcctaaggta tgtgactcaa   240
ttttggtgta gaaaatgagg aaaacgtaat actaagttaa agctcgccct ttaaagtgaa   300
tattccttga ccatttgcgc aggcacaccc gaattcacaa acgtttcttt attatataaa   360
ggaccagctc tgctagtcaa attttttataa ctgcttgttc agttgctgct tctttcttgt   420
caatttattt cttgtactgt tcaactacat aaagcaaaga gaaaactctc agaataacat   480
aacaaagaag tcaacgaaaa                                               500
```

<210> SEQ ID NO 49
<211> LENGTH: 500
<212> TYPE: DNA
<213> ORGANISM: Saccharomyces bayanus
<400> SEQUENCE: 49

```
acgaggctcg gcgtttactg ctgaattttcc ggaaagaaag ggaaggttcc ctttaccccca    60 gatttccatt catccgaagg actgcttatc agaatttgac attttttctca ttttatccga   120 gaagatcaat ttaaggctag tgaccacaaa actaactctc atgctgcgct accgcaagtt   180
tcgctcacag aaagaaagca agcacccata gtccggacta catccttgta tgtgactcaa   240
atttttggcg ttgccaatta aactgaagtg taaagattac ttcaagctca cccttttaaag   300 tagaattcct taacggtttt aaatagacac accgaaatta ataaacactt tctttattat   360
ataaaggaca gagtttatta ctggaattct cttaacgcct tcctccctta ctattgtatc   420
ttttcctttc acataatcgc tacataacta catagagaaa actctcagat taacacagta   480
acaacgaaga aaacaaaaaa                                               500
```

<210> SEQ ID NO 50
<211> LENGTH: 500
<212> TYPE: DNA
<213> ORGANISM: Saccharomyces cerevisiae
<400> SEQUENCE: 50

```
acagtttatt cctggcatcc actaaatata atggagcccg cttttttaagc tggcatccag     60 aaaaaaaaag aatcccagca ccaaaatatt gttttcttca ccaaccatca gttcataggt    120
ccattctctt agcgcaacta cagagaacag gggcacaaac aggcaaaaaa cgggcacaac   180
ctcaatggag tgatgcaacc tgcctggagt aaatgatgac acaaggcaat tgacccacgc   240
atgtatctat ctcattttct tacaccttct attaccttct gctctctctg atttggaaaa   300
agctgaaaaa aaaggttgaa accagttccc tgaaattatt ccctacttg actaataagt    360 atataaagac ggtaggtatt gattgtaatt ctgtaaatct atttcttaaa cttcttaaat   420
```

```
tctacttta tagttagtct ttttttagt tttaaaacac caagaactta gtttcgaata      480
aacacacata aacaaacaaa                                                500

<210> SEQ ID NO 51
<211> LENGTH: 412
<212> TYPE: DNA
<213> ORGANISM: Saccharomyces cerevisiae

<400> SEQUENCE: 51
atagcttcaa aatgtttcta ctccttttt actcttccag attttctcgg actccgcgca      60
tcgccgtacc acttcaaaac acccaagcac agcatactaa atttcccctc tttcttcctc    120
tagggtgtcg ttaattaccc gtactaaagg tttggaaaag aaaaaagaga ccgcctcgtt    180 tcttttctt cgtcgaaaaa ggcaataaaa attttatca cgtttctttt tcttgaaaat      240 ttttttttt gattttttc tctttcgatg acctcccatt gatatttaag ttaataaacg      300
gtcttcaatt tctcaagttt cagtttcatt tttcttgttc tattacaact ttttttactt    360
cttgctcatt agaaagaaag catagcaatc taatctaagt tttaattaca aa            412

<210> SEQ ID NO 52
<211> LENGTH: 500
<212> TYPE: DNA
<213> ORGANISM: Saccharomyces cerevisiae

<400> SEQUENCE: 52
tgggtcatta cgtaaataat gataggaatg ggattcttct atttttcctt tttccattct     60
agcagccgtc gggaaaacgt ggcatcctct ctttcgggct caattggagt cacgctgccg    120
tgagcatcct ctcttttccat atctaacaac tgagcacgta accaatggaa aagcatgagc    180
ttagcgttgc tccaaaaaag tattggatgg ttaataccat ttgtctgttc tcttctgact    240
ttgactcctc aaaaaaaaaa aatctacaat caacagatcg cttcaattac gccctcacaa    300
aaactttttt ccttcttctt cgcccacgtt aaatttatc cctcatgttg tctaacggat     360
ttctgcactt gatttattat aaaagacaa agacataata cttctctatc aatttcagtt     420
attgttcttc cttgcgttat tcttctgttc ttctttttct tttgtcatat ataaccataa    480
ccaagtaata catattcaaa                                                500

<210> SEQ ID NO 53
<211> LENGTH: 800
<212> TYPE: DNA
<213> ORGANISM: Saccharomyces cerevisiae

<400> SEQUENCE: 53
catgcgactg ggtgagcata tgttccgctg atgtgatgtg caagataaac aagcaaggca     60
gaaactaact tcttcttcat gtaataaaca cacccgcgt ttatttacct atctctaaac     120
ttcaacacct tatatcataa ctaatatttc ttgagataag cacactgcac ccataccttc    180
cttaaaaacg tagcttccag ttttttggtgg ttccggcttc cttcccgatt ccgcccgcta   240
aacgcatatt tttgttgcct ggtggcattt gcaaaatgca taacctatgc atttaaaaga    300
ttatgtatgc tcttctgact tttcgtgtga tgaggctcgt ggaaaaaatg aataatttat    360
gaatttgaga acaattttgt gttgttacgg tattttacta tggaataatc aatcaattga    420 ggatttttatg caaatatcgt ttgaatattt ttccgaccct ttgagtactt ttcttcataa   480
ttgcataata ttgtccgctg cccctttttc tgttagacgg tgtcttgatc tacttgctat    540
```

```
cgttcaacac cacctttattt tctaactatt ttttttttag ctcatttgaa tcagcttatg    600
gtgatggcac attttttgcat aaacctagct gtcctcgttg aacataggaa aaaaaaatat    660
ataaacaagg ctctttcact ctccttgcaa tcagatttgg gtttgttccc tttattttca    720
tatttcttgt catattcctt tctcaattat tattttctac tcataacctc acgcaaaata    780
acacagtcaa atcaatcaaa                                                 800

<210> SEQ ID NO 54
<211> LENGTH: 430
<212> TYPE: DNA
<213> ORGANISM: Saccharomyces cerevisiae

<400> SEQUENCE: 54
tatatctagg aacccatcag gttggtggaa gattacccgt tctaagactt ttcagcttcc     60
tctattgatg ttacacctgg acaccccttt tctggcatcc agttttttaat cttcagtggc   120 atgtgagatt ctccgaaatt aattaaagca atcacacaat tctctcggat accacctcgg   180
ttgaaactga caggtggttt gttacgcatg ctaatgcaaa ggagcctata tacctttggc   240
tcggctgctg taacagggaa tataaagggc agcataattt aggagtttag tgaacttgca   300
acatttacta ttttcccttc ttacgtaaat attttttcttt ttaattctaa atcaatcttt   360 ttcaatttttt tgtttgtatt cttttcttgc ttaaatctat aactacaaaa aacacataca   420
taaactaaaa                                                           430

<210> SEQ ID NO 55
<211> LENGTH: 466
<212> TYPE: DNA
<213> ORGANISM: Saccharomyces cerevisiae

<400> SEQUENCE: 55
gcggatctct tatgtctttta cgatttatag ttttcattat caagtatgcc tatattagta    60
tatagcatct ttagatgaca gtgttcgaag tttcacgaat aaaagataat attctacttt   120
ttgctcccac cgcgtttgct agcacgagtg aacaccatcc ctcgcctgtg agttgtaccc   180
attcctctaa actgtagaca tggtagcttc agcagtgttc gttatgtacg gcatcctcca   240
acaaacagtc ggttatagtt tgtcctgctc ctctgaatcg tctccctcga tatttctcat   300
tttccttcgc atgccagcat tgaaatgatc gaagttcaat gatgaaacgg taattcttct   360
gtcatttact catctcatct catcaagtta tataattcta tacggatgta atttttcact   420
tttcgtcttg acgtccaccc tataatttca attattgaac cctcac                  466

<210> SEQ ID NO 56
<211> LENGTH: 382
<212> TYPE: DNA
<213> ORGANISM: Saccharomyces cerevisiae

<400> SEQUENCE: 56
acaaatcgct cttaaatata tacctaaaga acattaaagc tatattataa gcaaagatac    60
gtaaattttg cttatattat tatacacata tcatatttct atattttttaa gatttggtta   120 tataatgtac gtaatgcaaa ggaaataaat tttatacatt attgaacagc gtccaagtaa   180
ctacattatg tgcactaata gtttagcgtc gtgaagactt tattgtgtcg cgaaaagtaa   240
aaattttaaa aattagagca ccttgaactt gcgaaaaagg ttctcatcaa ctgttttaaaa  300 ggaggatatc aggtcctatt tctgacaaac aatatacaaa tttagtttca aagatgaatc   360
agtgcgcgaa ggacataact ca                                            382
```

<210> SEQ ID NO 57
<211> LENGTH: 400
<212> TYPE: DNA
<213> ORGANISM: Saccharomyces cerevisiae

<400> SEQUENCE: 57

```
agtgctttta actaagaatt attagtcttt tctgcttatt ttttcatcat agtttagaac      60
actttatatt aacgaatagt ttatgaatct atttaggttt aaaaattgat acagttttat     120
aagttacttt ttcaaagact cgtgctgtct attgcataat gcactggaag gggaaaaaaa     180
aggtgcacac gcgtggcttt ttcttgaatt tgcagtttga aaaataacta catggatgat     240
aagaaaacat ggagtacagt cactttgaga accttcaatc agctggtaac gtcttcgtta     300
attggatact caaaaaagat ggatagcatg aatcacaaga tggaaggaaa tgcgggccac     360
gaccacagtg atatgcatat gggagatgga gatgatacct                           400
```

<210> SEQ ID NO 58
<211> LENGTH: 500
<212> TYPE: DNA
<213> ORGANISM: Saccharomyces cerevisiae

<400> SEQUENCE: 58

```
ggagattgat aagactttc tagttgcata tctttatat ttaaatctta tctattagtt        60
aattttttgt aatttatcct tatatatagt ctggttattc taaaatatca tttcagtatc     120
taaaaattcc cctcttttt cagttatatc ttaacaggcg acagtccaaa tgttgattta      180
tcccagtccg attcatcagg gttgtgaagc attttgtcaa tggtcgaaat cacatcagta     240
atagtgcctc ttacttgcct catagaattt ctttctctta acgtcaccgt ttggtctttt     300
atagtttcga atctatggt gataccaaat ggtgttccca attcatcgtt acgggcgtat      360
ttttttaccaa ttgaagtatt ggaatcgtca attttaaagt atatctctct tttacgtaaa    420
gcctgcgaga tcctcttaag tatagcgggg aagccatcgt tattcgatat tgtcgtaaca     480
aatactttga tcggcgctat                                                  500
```

<210> SEQ ID NO 59
<211> LENGTH: 1041
<212> TYPE: DNA
<213> ORGANISM: Aspergillus tubingensis

<400> SEQUENCE: 59

```
atgctgggat tcccaatgtt caacccagct acgcctgatg tctggaagat gaataccct       60
tactttccat ttgttacacc ggggttattt cctgcctcag cacccccatc gcccaccaac     120
gtagatgccg aagctgccag ttcccaacag tcggaagcaa gctatctgga taaggagaaa     180
attgttcgag ggccacttga ttatcttctc aaatcccctg aaaagacat cgtcggaaa      240
ttcattcacg cgttcaatga atggctgcgc attcctgagg acaagttgaa tattatcacg     300
gaaattgttg gattgcttca cacggcctcc cttctaatcg acgatattca ggacaattcc     360
aagcttcgac gcggcctccc agtggcccat agcatatttg gtattgcgca gacaattaac     420
tctgccaatt atgcgtactt tctagcccag gaaaggctcc gcgaactgaa tcatcctgaa     480
gcgtacgaaa tatacacaga ggaactgctt cgtctgcacc gcggtcaagg tatggacttg     540
tactggcggg actgcctaac ctgtcccaca gaggaggact atattgagat gatcgccaac     600
aagactggtg gcctatttcg actggcgatt aagcttatgc agttggaaag cactttgtgc     660
```

| | |
|---|---|
| agcaatgtca ttgaactagc agacttgttg ggcgtgatct ttcagattcg ggatgattac | 720 |
| caaaacttac agagtggact atacgccaag aacaagggat tttgcgagga tttgacggag | 780 |
| ggaaaatttt cctttctgat tatccacagt attaacagta acccgaacaa tcaccatctg | 840 |
| ctaaatatac tacggcagcg gagcgaggac gattcggtga agaagtatgc tgttgattat | 900 |
| atcgactcga cggggagttt tgactactgc cgggaacggc tcgcttcctt attggaagag | 960 |
| gcggatcaaa tggttaagaa gttggaaaat gagggggac aatcaaaggg gatctacgat | 1020 |
| attctgagct ttctgtcgtg a | 1041 |

<210> SEQ ID NO 60
<211> LENGTH: 732
<212> TYPE: DNA
<213> ORGANISM: Aspergillus tubingensis

<400> SEQUENCE: 60

| | |
|---|---|
| atggatgggt tcgaccattc tactgctcca ccaggatata acgagctaaa atggctcgcc | 60 |
| gatatcttcg tcatcggaat ggctgttggc tgggttgctc actatatgga gatgattcac | 120 |
| acgtcgttca aggaccaaac atactgcatg accatcgggg gcctttgcat caattttgcc | 180 |
| tgggaaatca tattctgcac aatgtatcct gccaaaggat ttgtcgagcg ggttgccttt | 240 |
| ctcatgggca tttctctcga ccttggggtt atttacgcgg gaatcaagaa cgccccaaat | 300 |
| gaatggcacc actctgcaat ggtgagggac catatgcccc ttgtcttcgc agcaacgaca | 360 |
| ctttgttgtc tgagcggtca tatggctctt actgcccagg ttggtcccgc acaagcctat | 420 |
| acgtgggggg caattgcatg ccagctcttt atcagcatag gaatgtgtt tcaattgttg | 480 |
| agtcggggaa acacacgagg ggcgtcatgg acgctatgga cctccaggtt ttttggatca | 540 |
| acatcagcca ttggctttgc tcttgttcga tatattcgct ggtgggaggc cttttccttgg | 600 |
| ttgaactgcc cgcttgtgat atggtccgtg ccatgttct ttctgtttga aacactctat | 660 |
| ggagccctat tctattctgt caagcgacaa gaagggagat cccagcgtgg aatcaagcac | 720 |
| aaagagaggt ag | 732 |

<210> SEQ ID NO 61
<211> LENGTH: 1008
<212> TYPE: DNA
<213> ORGANISM: Aspergillus tubingensis

<400> SEQUENCE: 61

| | |
|---|---|
| atggcggcac ttccggacgt tgcctccatt cccatccctc tggtggcaac cctaggcatt | 60 |
| gcccctctaa ttttctatct cgtccttgat agaattagcc ccttgtggcc aaattccaaa | 120 |
| gctttcctga ttggcaagaa gaaaccggag accgtgacat cgttcgagtg cccatatgcc | 180 |
| tacatccgtc agatctatgg gaagtatcac tgggagccat tcgtacagaa gctgtctccg | 240 |
| aggcttaagg atgaggatcc ggccaaatat aagatggttc tggagataat ggatgcaatc | 300 |
| cacctgtgtc tgatgctagt tgacgatata actgacaata gcgactatcg aaaaggcaag | 360 |
| ccagcagccc accggatata tggcccttca gagacagcaa atcgcgctta ctaccgagtc | 420 |
| acccagattc taaacaagac cgtgcaaaag ttccccaagc tggccaagtt cctgcttcag | 480 |
| aatctggaag aaattctcga aggccaagac ctgtcactaa tctggcgacg ggatggactg | 540 |
| ggtagccttt cgactgttcc tgatgagcga gttcagcct atcgcaagat ggcgtcattg | 600 |
| aaaactgggg cgttattccg gctgctgggg caattggtga tggaggacca atcgatggac | 660 |
| gggacgatga ctactcttgc gtggtgctct cagctgcaga atgactgcaa gaatgtctac | 720 |

```
tcatctgaat atgctaaggc caaaggggcg cttgccgaag acctccgaaa tcgagagctc    780
tcatttccaa ttatcctcgc gctggaagct cctgaagggc attgggtcgc cagtgctttg    840
gagaccagct caccgcgcaa cattcgcaag gcgcttgctg tgattcagag tgagagagtg    900
cgcaatgctt gtttcaagga gctcaagtcg gcgagtgctt cggtccagga ctggttggct    960
atttggggac ggaacgagaa aatgaacttg aagagccagc agacgtag              1008
```

```
<210> SEQ ID NO 62
<211> LENGTH: 1416
<212> TYPE: DNA
<213> ORGANISM: Aspergillus tubingensis

<400> SEQUENCE: 62
atggccaatg cccagcaacc cccctttcgc atccttattg tgggcggttc tgtcgcaggc     60
ctcatccttg cgcactgtct cgaacgcgcc aatatagagt acctcatact cgaaaaagga    120
gaagatgttg ctccacaagt tggtgcctcg ataggtatca tgccaaatgg cggacggatc    180
ctcgagcaac tgggcctatt tggggagatt gagcgtgtga tcgagccgtt gcatcaggcg    240
aatatcagct atccagatgg gttctgcttt agtaacgtct atcctaaggt tcttggcgac    300
aggttcggat acccggttgc attcttggac cggcagaagt tcctgcagat tgcatatgag    360
gggctgagaa agaagcagaa tgttctcacc ggtaaaaggg tagttggact gcgcacagtcg   420 gatcaaggga ctgctgtttc tgtggctgac gggacagagt atgaggcgga tctcgtggtt    480
ggtgctgatg gagtacatag tcgggtgaga agtgagattt ggaagatggc ggaagagaat    540
cagcctgcat cagtttcgac acgtgaaaga agaagcatga ctgttgaata tgtctgcgtt    600
ttcgggattt catcagccat cccagggctc gagataagcg aacagatcaa cggtattttc    660
gaccatctat ccattctaac aatccatggc agacatggtc gcgtgttctg gttcgtgatc    720
cagaagctgg ataggaagta cgtctatcct gatgtcccgc gattctcaga cgaggatgcc    780
gtacagctct tcgatcgggt caaacacgtg cggttctgga aaaacatctg tgtgggggac    840
ttgtggaaga acagagaggt gtcctcgatg acagcgctgg aggagggagt gttcgagaca    900
tggcatcatg ataggatggt tttgattgga gatagcgttc acaagatgac gcccaacttt    960
ggccaaggag ctaattcagc catcgaggat gctgccgcgc tctcttccct tctacatgat   1020
ctcgtcaacg cccgtggagt ttgcaagcca tcgaatgtcc agattcagca tctcctcaag   1080
cagtatcggg agacccgata cactcgcatg gtaggcatgt gtcgcaccgc ggcttcagtc   1140
tctcggattc aggcccgaga tggcatcctc aacaccgtct tggacgata ttgggcacct   1200 tatgctggca acctgcctgc tgacctggca tcaaaagtga tggcagatgc agaggttgtt   1260
acttttctgc ccttgccagg cgctcagga ccgggctggg agatgtacag acgaaagggg   1320
aagggagggc aggtgcaatg ggtgcttata atcttaagct tacttacgat tggtggattg   1380
tgcatctggc tacaaaagcaa tgcgttgagt agataa                            1416
```

```
<210> SEQ ID NO 63
<211> LENGTH: 7050
<212> TYPE: DNA
<213> ORGANISM: Hypomyces subiculosis

<400> SEQUENCE: 63
atgccttcta ccagcaatcc atctcacgtc cctgtggcca tcatcggcct ggcatgccga     60
ttcccaggcg aggccaccte accatcaaaa ttctgggatc ttcttaagaa tggacgagat    120
```

```
gcctactcac caaataccga tcgatataac gctgatgcct tttaccatcc caaggcaagc    180
aaccgccaaa acgtgctggc aactaagggc ggccacttcc tcaaacagga cccatacgtt    240
tttgacgccg ctttctttaa catcacagcc gctgaggcca tctcctttga ccccaagcag    300
cgaattgcca tggaagttgt ctacgaggct ctagaaaatg ccggaaagac actacccaag    360
gtggcgggca cacaaactgc ttgctatatc ggctcttcca tgagtgatta ccgagacgct    420
gttgtgcgtg actttggaaa cagccccaag tatcatatcc tgggaacatg cgaggagatg    480
atttcaaatc gtgtgtccca tttcttggat attcacggcc ccagtgccac cattcataca    540
gcctgctcat caagtcttgt tgctacacac ttggcttgcc aaagtttgca atctggagag    600
tcagaaatgg ccatcgctgg tggtgttggt atgatcatca cccctgatgg taatatgcat    660
cttaacaact tgggattctt gaaccccgag ggccactccc ggtcatttga tgagaatgct    720
ggtggttacg gtcgtggtga gggttgcggt atcctcatcc tcaagcggct agacagagct    780
ctcgaagatg gtgattccat cgcgccgtc attcgagcct ctggtgtcaa ctctgatggc    840
tggacacagg gtgtcaccat gccctccagc caagcccagt ctgcccttat caaatacgta    900
tacgaatcgc atggcctgga ttatggtgcg actcaatacg ttgaggctca cggtactggt    960
accaaagccg tgatcccgc agagattggc gccctccacc gcacaattgg acagggcgcg   1020
tccaagtctc gaaggctttg gattggcagt gtcaagccaa acattggcca tcttgaagcc   1080
gccgccggtg tggctggtat cattaagggc gtcctgtcca tggaacacgg catgattcct   1140
ccaaacattt acttctccaa gcccaaccct gccatccctc ttgacgagtg aacatggcc    1200 gtgcctacca agttgactcc ctggcccgcc agccaaactg tcgccgtat gagtgtcagc   1260 ggtttcggta tgggtggtac caacggccac gtcgtccttg aggcctacaa gccccaagga   1320
aagctcacca acgccatac caacggcatc accaatggaa tccacaagac tcgccacagc   1380
ggcaagaggc ttttcgtcct cagcgcccag gatcaagctg gcttcaagcg tttgggtaac   1440
gccctggtgg agcatctcga tgccctgggc cctgccgctg ccaccccga gttcctcgcc   1500 aacctctccc acactcttgc cgttggcaga tctggcttgg cttggaggtc cagcatcatc   1560
gctgagagcg cccctgatct tcgggagaag ctggcaactg atccgggtga gggagccgct   1620
cgttcttcag gcagcgagcc ccgtattgga ttcgtcttca cgggtcaagg tgctcagtgg   1680
gcccgcatgg gcgttgagtt gttggagcgc cccgtcttca aggcttccgt gattaagtcc   1740
gcggagactt tgaaggagct cggctgtgaa tgggacccta tcgttgagct ttccaagcct   1800
caagctgagt ctcgacttgg tgttcctgaa atctcacagc ccatctgcac agtcctacaa   1860
gtcgccttgg ttgatgagtt gaagcactgg ggtgtatcac cttccaaggt ggtcggtcac   1920
tccagtggtg aaatcggtgc cgcatacagc attggcgctc tttctcaccg tgacgctgtc   1980
gccgctgctt acttcagggg caagtcttcc aacggagcca agaagcttgg tggtggtatg   2040
atggctgttg ggtgctctcg tgaggacgct gacaagctcc tctctgagac caagctcaag   2100
ggcggtgttg ctaccgtcgc atgtgtcaac tcccctcca gcgtgaccat ctcaggcgat   2160
gccactgctc tcgaggaact ccgagttatt ctcgaggaga agagtgtgtt tgctcgaaga   2220
ctcaaggtcg acgttgccta ccactctgcc cacatgaacg ctgtctttgc cgaatactct   2280
gctgcgattg cccacattga gcccgctcag gcagttgaag gtggaccgat tatggtctcc   2340
agtgtcactg gtagcgaagt cgactctgag cttctcggcc cttactactg gacccgtaac   2400
ttgatctctc ccgtcttatt cgccgacgct gtcaaggaat tggttacccc tgctgatggc   2460
gacggccaaa acaccgtcga tctcctgatt gagattggtc ctcacagcgc tcttggtggc   2520
```

```
cctgttgagc agattctgtc ccataacggc atcaagaatg ttgcttacag atctgctctt    2580
actcgtggcg agaacgctgt tgactgcagc ctcaagcttg ctggcgagct cttccttctc    2640
ggcgtgccct ttgagttgca aaaggccaac ggtgactctg gttctcgcat gctcactaac    2700
ctacctcctt atccttggaa ccactccaag tcattccgtg ccgactctcg tctccaccgt    2760
gagcatctgg agcagaaatt ccctactagg agtctcatcg gtgcacctgt ccccatgatg    2820
gcagagagcg agtacacatg gcgcaacttc atccgtctcg ctgacgagcc ttggctccgt    2880
ggtcacactg tcggtaccac cgttctgttt cctggtgccg gtatcgtgag catcatcttg    2940
gaagctgctc aacagctggt ggataccggc aagaccgttc ggggcttccg aatgcgcgat    3000
gtcaacctct tcgccgccat ggctctcccc gaggacctgg ctactgaggt tatcatccac    3060
atccgacctc accttatctc tactgttgga tcaaccgccc ccggtggatg gtgggagtgg    3120
actgtttcct cctgcgtcgg aactgaccag ctgcgagaca atgctcgcgg tctggtagcc    3180
attgactacg aagagagccg cagcgagcag atcaacgccg aggacaaagc gttggttgct    3240
tctcaggtcg cggactacca caagatcctc agcgaatgcc ctgagcatta tgctcatgac    3300
aagttctacc agcacatgac caaggcctct tggagctacg gcgagctctt ccagggtgtg    3360
gagaatgtcc gtcctggata cggaaagacc atctttgaca tcagagtcat tgacattggt    3420 gagacctta gcaagggaca acttgagcga cctttcctca tcaacgctgc cactctcgat    3480
gctgtattcc agagctggct cggcagtacc tacaacaacg gtgctttcga gtttgacaag    3540
cccttcgttc ccacctctat tggcgagttg gaaatctctg tcaacattcc cggtgatggc    3600
gactacctca tgccaggcca ctgccgctct gagcgatacg gcttcaacga gttgtctgct    3660
gatattgcca tcttcgacaa ggatctgaag aatgtgttcc tttcagtgaa ggatttccga    3720
acttccgagc ttgatatgga ttccggcaag ggagacggag atgccgctca cgtcgaccct    3780
gccgatatca actcggaggt taagtggaac tacgctcttg gcctcctcaa gtccgaggaa    3840
atcaccgagc tggtcaccaa ggtcgccagc aatgacaagc tcgccgagct tctccgtctg    3900
acacttcaca caaaccctgc tgccactgtc atcgagcttg tttctgatga gagcaagatc    3960
tctggcgcat cttctgccaa gctgtccaag ggccttatcc tccccagcca gatccgttac    4020
gtagttgtca accctgaggc agcggacgcc gactctttct tcaaattctt ctcccttggt    4080
gaggatggtg cccctgtcgc tgctgaaagg ggccccgccg aactgttgat cgcctccagc    4140
gaagtcactg acgcggctgt ccttgagcgc tgattaccct tggccaagcc tgatgccagc    4200
attcttgttg ctgtcaacaa caagactacc gccgctgccc tctcagccaa ggcgttccgt    4260
gttgtcacca gcatccagga cagcaagtcc attgctctct acactagcaa gaaggcgcct    4320
gccgccgaca cctccaagct cgaggccatc atcctcaagc caaccactgc tcaacctgcc    4380
gcccagaatt tcgcctccat cctccagaag gcactcgagc tccagggcta ctctgtcgtt    4440
tctcagccat ggggcaccga catcgacgtc aacgatgcca agggaaagac ctacatttct    4500
ctgttggagc ttgagcagcc tctgctcgac aacctctcca agtccgactt cgagaacctc    4560
cgcgcagtcg ttttgaactg cgagcgtctc ctgtgggtca cagcaggtga caacccatct    4620
ttcggcatgg ttgatggttt cgctcgctgc atcatgagcg aaattgccag caccaagttc    4680
caggtcctgc atttgagcgc tgcaactggt ctgaagtacg atcttctct cgccacccgc    4740 attctccagt cggatagcac cgacaacgag taccggagg tcgatggtgc tctccaggtg    4800
gcccgtatct tcaagagcta caacgagaac gagagtctcc gccaccacct cgaggatacc    4860
```

```
accagcgttg tgactcttgc tgaccaggag gatgctctgc gcctcactat tggcaagcct    4920
ggtcttttgg atactttgaa gtttgtcccc gatgagcgta tgctcccacc tctccaggat    4980
cacgaggttg aaatccaggt caaggctact ggtctgaact tccgagacat catggcttgc    5040
atgggtctta ttcctgttcg atctctgggc caggaggcca gtggcatcgt cctcagaacc    5100
ggtgcgaagg ctaccaactt caagcctggc gaccgtgttt gcaccatgaa cgtcggaaca    5160
catgccacca agatccgagc cgactaccgt gtcatgacaa agatccccga ctccatgacc    5220
tttgaagaag ctgcctcggt tgctgttgtt cacaccaccg cctactacgc cttcatcacc    5280
atcgccaagc ttcgcaaggg ccagtccgtc ttgatccacg ccgccgctgg tggtgttggc    5340
caagcagcca ttcagttggc caagcatctc ggcctcatca cctatgttac cgtaggtact    5400
gaagacaagc gccagctcat tcgggagcag tatggcattc ccgacgagca catcttcaac    5460
tcccgtgatg ccagcttcgt caagggtgtc cagcgtgtta ccaacggtcg cggtgtcgac    5520
tgcgttctca actctctatc cggtgagctc ctgcgtgctt cttggggatg ccttgctacc    5580
tttggtcatt tcatcgaaat tggtctccgt gatatccacg acaacatgcg tcttgacatg    5640
cgacctttcc gcaagagcac ctccttcaca ttcatcaaca cccacactct cttcgaggaa    5700
gaccccgctg cgttgggaga tattctcaac gagtccttca agctcatgtt cgctggcgcc    5760
cttaccgctc ctagcccctt gaatgcctat cccattggcc aggtcgagga ggccttccga    5820
accatgcagc agggcaagca ccgcggtaag atggtgctgt ccttctccga tgacgcaaag    5880
gctcccgtgt gcgcaaagc gaaggattcc ttgaaactgg accctgacgc cacttacctc    5940
tttgttggtg gtcttggtgg tctgggtcgc agtcttgcca aggagtttgt tgcgtctggc    6000
gcccgcaaca ttgccttctt atcccgatcc ggtgacacta ccgcccaggc caaggctatc    6060
gtggacgaat tggctggcca gggtatccag gtcaaggcct atcgtggtga tatcgccagc    6120
gaggcatcct tcctccaggc tatggagcaa tgctctcagg atctcccgcc cgtaaagggt    6180
gtgatccaga tggccatggt tctccgcgat atcgtctttg agaagatgtc gtacgatgag    6240
tggaccgtcc ccgttggccc caaggtccaa ggttcatgga acttgcacaa gtacttcagt    6300
catgagcgac ctcttgactt catggtcatc tgctcctcaa gctccggtat ctacggttat    6360
cccagtcagg ctcaatacgc cgctggcaac acttaccagg atgccttggc tcactaccgt    6420
cgctctcagg gcctgaacgc catctccgtc aacttgggta tcatgcgaga tgtcggtgtc    6480
ctggctgaga cgggtaccac tggtaacatc aagctctggg aagaggtctt gggcatccgc    6540
gagcctgcct tccacgctct catgaagagc ttgatcaacc atcagcagcg tgggtctggg    6600
gactacccgg cgcaggtctg cactggtctt ggtactgctg acattatggc tactcacggc    6660
ctggcccggc ccgagtattt caatgacccc cgttttggac cccttgccgt caccactgtc    6720
gcgaccgatg cttcagctga cggccagggc tctgctgtct cgctcgcctc taggctctcc    6780
aaggtttcca ccaaggatga agctgccgag atcattaccg atgctctggt caacaagacg    6840
gcagacatcc tgcagatgcc ccctctgaa gtcgacccg ccgacctct gtaccgttat    6900 ggtgttgact cccttgtggc gcttgaggtg cgaaactgga tcacaaggga gatgaaggcg    6960
aacatggcgc tgctggagat tctggcagcc gtccccattg agagcttcgc tgtcaagatt    7020
gctgagaaga gcaagttggt tactgtttaa                                    7050
```

<210> SEQ ID NO 64
<211> LENGTH: 6150
<212> TYPE: DNA
<213> ORGANISM: Hypomyces subiculosis

<400> SEQUENCE: 64

```
atggtgactg taccacagac tatcctctac tttggagatc agacagactc ctgggttgat      60
tccctcgatc agctatacag acaagccgct acgataccat ggctacagac gtttctcgac     120
gaccttgtaa aggtcttcaa ggaagagtcc cggggcatgg atcatgcgtt acaagacagt     180
gttggtgaat actctacact actcgacttg gcggatagat accgccatgg caccgacgag     240
attggtatgg tgcgtgctgt cttgctacat gccgcgagag gaggcatgct attacaatgg     300
gtgaagaaag aatcacagct tgtggacctc aatggctcca agcctgaagc actcggtatc     360
tctggaggac tcaccaacct cgcagcactg gcgatatcca cagacttcga gtctctatat     420
gacgcagtca ttgaggctgc gagaatattt gtcagattat gccgttttac ttcggtacga     480
tcaagagcta tggaggaccg acctggcgtt tggggctggg cagtgctggg aattacacca     540
gaggaactga gcaaagtgct tgagcagttc aatccagca tggggattcc tgccatcaag      600
agagctaagg ttggcgtaac aggagaccga tggagcaccg ttattgggcc accctcagtc     660
ttggacctat tcatccacca gtgtcccgct gtgcgcaacc tccccaagaa tgaattgagc     720
atccacgccc ttcagcacac agtcacagtc acagaggctg acctcgactt cattgtcggg     780
agtgctgagc ttcttagtca ccccattgtg ccagacttca aagtctgggg aatggatgat     840
cctgtggcat cctaccagaa ctggggagaa atgctaagag caatcgtcac tcaagttttg     900
tccaagcctt tggacattac caaggtgatt gcgcaactca cactcacct cggccctcgt      960
catgtcgacg tccgagtcat cggacctagc agccacaccc cctacttggc gagttcgctc    1020
aaagctgctg gcagcaaggc tatttttccag accgataaga ctcttgagca gttacagccg    1080
aagaaactcc ccccgggccg catcgccatt gtcggtatgg ctggccgtgg tcctggctgc    1140
gagaatgttg atgagttctg ggacgtcatt atggcgaagc aggatcgttg tgaagagatt    1200
cccaaagatc gcttcgacat caatgagttc tactgtaccg agcacgggga gggttgcacc    1260
accaccacaa aatacggctg cttcatgaac aagcctggaa actttgactc ccgcttcttc    1320
cacgtgtcgc ctcgtgaggc gctgttgatg accccggtc acaggcagtt catgatgagc    1380
acttatgaag ctcttgagac ggcaggatac tctgatggcc agactaggga cgttgatcct    1440
aataggatcg cggcgttcta tggccagtcc aacgatgatt ggcatatggt gagccattat    1500
accctgggtt gtgatgccta caccctgcag ggggcgcaaa gagccttcgg cgctggtcgc    1560
atcgccttcc acttcaagtg gaagggccca acatactcgc tcgattctgc atgtgcctcc    1620
acctcctctg ctattcacct ggcctgcgtg agtcttctat ccaaagatgt ggacatggct    1680
gttgtgggtg ctgccaacgt cgtcgggtat cctcactcct ggacaagtct tagcaagtct    1740
ggtgtcttgt ccgacactgg aaactgcaaa acctactgcg atgatgctga tggttactgc    1800
cgagcagact ttgtcggctc agttgtgctg aagcgtctcg aagatgctgt cgagcaaaac    1860
gacaacatct tggctgtcgt ggctggttca ggcagaaacc actccggcaa ctcttcatcc    1920
atcaccacgt cggatgccgg tgcccaggag agactgtttc acaagattat gcacagcgcc    1980
agagtctctc ctgatgagat ctcatatgtt gagatgcacg gcactggaac tcagattggc    2040
gatccggccg agatgagtgc tgttaccaat gtcttcagga agaggaaggc gaataacccc    2100
ctaactgttg gtggaatcaa agcgaacgtc gggcatgctg aagcttctgc tggcatggcc    2160
tccctgctca aatgcataca gatgttccag aaagatatta tgccccctca ggctcgaatg    2220
ccccatactc tcaacccaaa gtatccgagt ctttctgagc ttaacattca tatcccctcc    2280
```

```
gagccgaagg agttcaaggc tatcggcgag cggccacgac gcatcctcct taataacttt    2340
gacgcagcag gtggcaacgc ctctctcatt ctggaagact tcccctccac cgtcaaggaa    2400
aatgcggacc ccaggccaag ccatgtcatc gtttcctctg ccaaaacaca atcctcatat    2460
cacgcgaata agcgtaacct cctgaagtgg ctacgcaaga acaaagatgc taaactcgaa    2520
gatgttgcat acacaaccac cgcccgcaga atgcaccacc ccctcagatt ctcttgcagt    2580
gcctccacaa cggaggagct catttccaag cttgaggcag acacggcaga tgcaactgcg    2640
tctcggggct cgcccgttgt cttcgtattc acgggacagg gctctcacta cgccggcatg    2700
ggtgccgagt tgtacaagac atgccctgct ttccgcgagg aagtcaacct ctgtgccagc    2760
atctctgagg agcacggggtt ccccccgtac gtggatatca tcaccaacaa agatgttgac    2820
ataaccacca aggacaccat gcagacacag ctcgctgttg tcacgctgga gatcgccctc    2880
gccgcattct ggaaggcgtc tggtatccag ccgtcagcag tcatgggtca ctccctgggc    2940
gagtatgtgg ctctccaggt cgcaggggtc ctatctctag ctgatctgct ctacctcgtc    3000
ggcaatcggg cccgtctcct gctggagcgc tgcgaagccg acacctgcgc tatgttggca    3060
gtatcaagct ctgctgcctc catccgcgag ctcatcgacc agcgcccgca gtcatccttc    3120
gagattgcat gcaagaatag ccccaatgcc acggttatca gcggcagcac tgatgagatt    3180
tctgagctcc agtcatcctt cacggcatca cgagccaggg ctctgtctgt gccctatgga    3240
tttcactcct tccagatgga tcccatgctc gaggattaca tcgttcttgc gggtggtgta    3300
acctactcgc caccaaagat tccagttgct tcaaccctgc tcgcttcgat tgtggagtct    3360 tcagggg tct tcaacgcttc ctacctcggt cagcaaaccc gccaagctgt cgacttcgtc    3420
ggtgctcttg gcgccttgaa ggagaagttt gctgaccctc tctggctgga gatcggaccc    3480
agccaaatct gcagctcctt tgtccgggcg actctctcac cctcgccggg caaaatcttg    3540
tccactttgg aggcaaatac caaccccctgg gcatccattt ccaagtgcct cgccggcgcg    3600
tacaaggatg gtgtcgcagt tgactggttg gcggtgcatg ctccattcaa gggcggcttg    3660
aagctcgtga agttgcccgc ctatgcatgg gacctcaagg acttctggat tgtctactct    3720
gaggccaaca aggctgctcg agctttggct cccgctccct cgttcgaaac acagaggatt    3780
tctacatgtg ctcaacagat tgttgaagaa tcatcatcac ccagcctcca tgtctctgcc    3840
cgagctgcta tctccgatcc tggcttcatg gccttggtcg acggtcatcg catgcgcgat    3900
gtgtccatct gccccggaag tgtcttctgc gaggcaggcc ttgccgtctc caagtacgca    3960
ctgaagtaca gtggccgaaa ggataccgtg gaaacaagac ttacaatcaa caacctgtct    4020
ctcaagcgcc cgctcacaaa gtctcttgta ggcaccgatg gcgagcttct caccacggtt    4080
gttgcagaca aggcctccag cgatacccttg caggtttcat ggaaggcttc ttcctctcat    4140
gcatcatacg atcttggtag ctgcgagatc accatttgtg atgcccagac tcttcaaact    4200
agctggaaca gaagctcata cttcgtcaag gctcgtatga acgagttgat caagaatgtc    4260
aagagcggaa atggtcaccg catgctcccc agtatcctct acactctctt cgctagcaca    4320
gttgattatg accctacctt caagtctgtc aaggaggcct tcatctcaaa tgagtttgac    4380
gaagctgctg cggaggtggt gcttcagaag aacccggctg gaactcagtt ctttgcgtcc    4440
ccttactggg gtgagagcgt agttcatctt gccggtttcc tcgtgaactc caaccctgcc    4500
cgcaagactg cttctcagac gaccttcatg atgcagagtc ttgagagcgt cgagcagacc    4560
gctgatctcg aggctggacg cacttactac acctatgctc gcgttttgca tgaggaagaa    4620
gacacagtca gctgtgactt gttcgtcttc gactcggaga agatggtaat gcagtgctcg    4680
```

```
ggactctcat tccatgaggt cagcaacaat gttctggaca gacttcttgg aaaggcatca    4740
ccgcctgtga agcaagtttc ccaccagaag gcgccagtgc ttgtgcccgc agagtcaaaa    4800
ccggccctga agctgctgt cgaggcggct cccaaggcgc ctgagcctgt gaagacagag    4860
gtgaagaaga tctcttcgtc ggagagcgaa ttgttccaca ctattcttga aagcatcgcc    4920
aaggagactg gcactcaggt ctctgacttc actgatgaca tggaactggc tgaacttggc    4980
gttgattcca tcatgggtat tgagatcgct gccggcgtca gcagcagaac cggcctcgat    5040
gttctcctcc cctcttttgt cgtagattat cccaccattg gagatctgcg aaacgaattt    5100
gcgcgctcct ctacatctac acctcccagc aagacctttt ccgagttctc catcgtcgat    5160
gccactccag agtctacgcg cagctcgagt cgagcgcctt ctgagaagaa ggagcctgct    5220
ccggcttcag agaagtctga ggagctggtg atcgttccgt ccgcggttgt cgaggattcc    5280
tctcccctcc ccagtgccag aatcaccttg atccagggtc gatcttcgag tggaaagcag    5340
cctttctact tgatcgccga tggagctggt agcattgcta cgtatatcca cctggctccc    5400
ttcaaggaca agagaccggt ttatggcatt gattcgcctt cctccgttg ccccagcagg    5460 ctgaccaccc aggtgggcat tgaaggcgtc gcaaagatca tctttgaggc gttgattaag    5520
tgccagcctg agggtcccctt tgacttggga ggattctctg gcggagctat gctcagctat    5580
gaggtgtctc gccaactcgc tgccgccggt cgcgtcgtct ccagtcttct cctcatcgat    5640
atgtgttctc cccgtccttt gggtgttgag gacacaatcg aggtcggctg gaaggtctac    5700
gagaccatcg cttcccaaga taagctctgg aacgcctcaa gtaacaccca gcagcatctc    5760
aaggccgtct tcgcctgcgt cgcagcctac caccctcctc ccatgactcc cgctcaacga    5820
cccaagcgaa cagctatcat ctgggctaaa aagggcatgg tcgaccgttg ttctcgcgac    5880
gagaaggtga tgaagttcct ggccgacaag ggcatcccca ccgagtcgta cccagggttc    5940
atggaggacc ccaagctggg tgccgtggcg tggggccttc cgcacaagtc cgctgcggac    6000
ttgggaccca acggatggga caagttcctt ggcgagactc tgtgcctgtc tatcgattcg    6060
gaccacttgg atatgccgat gccggggcat gtgcacttgc ttcaggcggc gatggaggag    6120
tcgttcaaat atttcagcga ggcaaattag                                    6150
```

<210> SEQ ID NO 65
<211> LENGTH: 14802
<212> TYPE: DNA
<213> ORGANISM: Artificial Sequence
<220> FEATURE:
<223> OTHER INFORMATION: synthesized in lab

<400> SEQUENCE: 65

```
tatctaaaaa ttgccttatg atccgtctct ccggttacag cctgtgtaac tgattaatcc     60
tgcctttcta atcaccattc taatgttttta attagggat tttgtcttca ttaacggctt    120
tcgctcataa aaatgttatg acgttttgcc cgcaggcggg aaaccatcca cttcacgaga    180
ctgatctcct ctgccggaac accgggcatc tccaacttat aagttggaga ataagagaa    240 tttcagattg agagaatgaa aaaaaaaaaa aaaaaaaagg cagaggagag catagaaatg    300
gggttcactt tttggtaaag ctatagcatg cctatcacat ataaatagag tgccagtagc    360 gactttttttc acactcgaaa tactcttact actgctctct tgttgttttt atcacttctt    420
gtttcttctt ggtaaataga atatcaagct acaaaaagca tacaatcaac tatcaactat    480
taactatatc gtaatacaca atgctgggat tcccaatgtt caacccagct acgcctgatg    540
```

| | |
|---|---|
| tctggaagat gaatacccct tactttccat tgttacacc ggggttattt cctgcctcag | 600 |
| caccccatc gcccaccaac gtagatgccg aagctgccag ttcccaacag tcggaagcaa | 660 |
| gctatctgga taaggagaaa attgttcgag ggccacttga ttatcttctc aaatcccctg | 720 |
| gaaaagacat tcgtcggaaa ttcattcacg cgttcaatga atggctgcgc attcctgagg | 780 |
| acaagttgaa tattatcacg gaaattgttg gattgcttca cacggcctcc cttctaatcg | 840 |
| acgatattca ggacaattcc aagcttcgac gcggcctccc agtggcccat agcatatttg | 900 |
| gtattgcgca gacaattaac tctgccaatt atgcgtactt tctagcccag gaaaggctcc | 960 |
| gcgaactgaa tcatcctgaa gcgtacgaaa tatacacaga ggaactgctt cgtctgcacc | 1020 |
| gcggtcaagg tatggacttg tactggcggg actgcctaac ctgtcccaca gaggaggact | 1080 |
| atattgagat gatcgccaac aagactggtg gcctatttcg actggcgatt aagcttatgc | 1140 |
| agttggaaag cactttgtgc agcaatgtca ttgaactagc agacttgttg ggcgtgatct | 1200 |
| ttcagattcg ggatgattac caaaacttac agagtggact atacgccaag aacaagggat | 1260 |
| tttgcgagga tttgacggag ggaaaatttt cctttctgat tatccacagt attaacagta | 1320 |
| acccgaacaa tcaccatctg ctaaatatac tacggcagcg gagcgaggac gattcggtga | 1380 |
| agaagtatgc tgttgattat atcgactcga cggggagttt tgactactgc cgggaacggc | 1440 |
| tcgcttcctt attggaagag gcggatcaaa tggttaagaa gttggaaaat gagggggac | 1500 |
| aatcaaaggg gatctacgat attctgagct ttctgtcgtg agcggatctc ttatgtcttt | 1560 |
| acgatttata gttttcatta tcaagtatgc ctatattagt atatagcatc tttagatgac | 1620 |
| agtgttcgaa gtttcacgaa taaaagtaaa tattctactt tttgctccca ccgcgtttgc | 1680 |
| tagcacgagt gaacaccatc cctcgcctgt gagttgtacc cattcctcta aactgtagac | 1740 |
| atggtagctt cagcagtgtt cgttatgtac ggcatcctcc aacaaacagt cggttatagt | 1800 |
| ttgtcctgct cctctgaatc gtctccctcg atatttctca ttttccttcg catgccagca | 1860 |
| ttgaaatgat cgaagttcaa tgatgaaacg gtaattcttc tgtcatttac tcatctcatc | 1920 |
| tcatcaagtt atataattct atacggatgt aattttttcac ttttcgtctt gacgtccacc | 1980 |
| ctataatttc aattattgaa ccctcacgat ccagttctcc agtgacacag cctttatctg | 2040 |
| gtcaaacctt tctttctaat cacctatgct gatgcttaat taagggattt ttgtctccat | 2100 |
| caacggcatg cgcccaaaaa tgacgttttt tttaacccat agacacgaaa ctacccattt | 2160 |
| tccaccggcc tgacctacca ccggaacaac ggccatctcc aacttgcaag ttggggaaat | 2220 |
| taagagcatc gcaggtttaa tggaagaaaa aaaaaaggta cagcacagcg caaatggagt | 2280 |
| tagttcccctt atgtcacaca ctcacacaca gtcggtcaga tcaagcatac tgggtgcgta | 2340 |
| taaatagagt ggccattgcc accctgttta tctcaaaatc tgtcttgtta gtggtcttct | 2400 |
| ccctttttca ggttacaatt ctcttgtttc tacttagtat ataagtatat caagctatat | 2460 |
| taagcatact atcaactgtc aactctatcc tcaaaataca atacaaaatg gatgggttcg | 2520 |
| accattctac tgctccacca ggatataacg agctaaaatg gctcgccgat atcttcgtca | 2580 |
| tcggaatggc tgttggctgg gttgctcact atatggagat gattcacacg tcgttcaagg | 2640 |
| accaaacata ctgcatgacc atcgggggcc tttgcatcaa ttttgcctgg gaaatcatat | 2700 |
| tctgcacaat gtatcctgcc aaaggatttg tcgagcgggt tgccttttctc atgggcattt | 2760 |
| ctctcgacct tggggttatt tacgcgggaa tcaagaacgc cccaaatgaa tggcaccact | 2820 |
| ctgcaatggt gagggaccat atgccccttg tcttcgcagc aacgcacctt tgttgtctga | 2880 |
| gcggtcatat ggctcttact gcccaggttg gtcccgcaca agcctatacg tgggggggcaa | 2940 |

```
ttgcatgcca gctctttatc agcataggga atgtgtttca attgttgagt cggggaaaca    3000
cacgaggggc gtcatggacg ctatggacct ccaggttttt tggatcaaca tcagccattg    3060
gctttgctct tgttcgatat attcgctggt gggaggcctt tcttggttg aactgcccgc     3120 ttgtgatatg gtccgtggcc atgttctttc tgtttgaaac actctatgga gccctattct    3180
attctgtcaa gcgacaagaa gggagatccc agcgtggaat caagcacaaa gagaggtaga    3240
caaatcgctc ttaaatatat acctaaagaa cattaaagct atattataag caaagatacg    3300
taaattttgc ttatattatt atacacatat catatttcta tattttaag atttggttat     3360 ataatgtacg taatgcaaag gaaataaatt ttatacatta ttgaacagcg tccaagtaac    3420
tacattatgt gcactaatag tttagcgtcg tgaagacttt attgtgtcgc gaaaagtaaa    3480
aattttaaaa attagagcac cttgaacttg cgaaaaaggt tctcatcaac tgtttaaaag    3540
gaggatatca ggtcctattt ctgacaaaca atatacaaat ttagtttcaa agatgaatca    3600
gtgcgcgaag gacataactc aataggaaaa aaccgagctt cctttcatcc ggcgcggctg    3660
tgttctacat atcactgaag ctccgggtat tttaagttat acaagggaaa gatgccggct    3720
agactagcaa gttttaggct gcttaacatt atggataggc ggataaaggg cccaaacagg    3780
attgtaaagc ttagacgctt ctggttggac aatggtacgt ttgtgtatta agtaaggctt    3840
ggctggggat agcaacattg gcagagtat agaagaccac aaaaaaaagg tatataaggg     3900
cagagaagtc tttgtaatgt gtgtaacttc tcttccatgt gtaatcagta tttctactta    3960
cttcttaaat atacagaagt aagacagata accaacagcc tttcccagat atacatatat    4020
atctttattt cagcttaaac aataattata tttgtttaac tcaaaataa aaaaaaaaa      4080 ccaaactcac gcaactaatt attccataat aaaataacaa catggcgcca cttccggacg    4140
ttgcctccat tcccatccct ctggtggcaa ccctaggcat tgcccctcta attttctatc    4200
tcgtccttga tagaattagc cccttgtggc caaattccaa agctttcctg attggcaaga    4260
agaaaccgga gaccgtgaca tcgttcgagt gcccatatgc ctacatccgt cagatctatg    4320
ggaagtatca ctgggagcca ttcgtacaga agctgtctcc gaggcttaag gatgaggatc    4380
cggccaaata taagatggtt ctggagataa tggatgcaat ccacctgtgt ctgatgctag    4440
ttgacgatat aactgacaat agcgactatc gaaaaggcaa gccagcagcc caccggatat    4500
atggcccttc agagacagca aatcgcgctt actaccgagt cacccagatt ctaaacaaga    4560
ccgtgcaaaa gttccccaag ctggccaagt tcctgcttca gaatctggaa gaaattctcg    4620
aaggccaaga cctgtcacta atctggcgac gggatggact gggtagcctt tcgactgttc    4680
ctgatgagcg agttgcagcc tatcgcaaga tggcgtcatt gaaaactggg gcgttattcc    4740
ggctgctggg gcaattggtg atggaggacc aatcgatgga cggacgatg actactcttg     4800 cgtggtgctc tcagctgcag aatgactgca agaatgtcta ctcatctgaa tatgctaagg    4860 ccaaggggc gcttgccgaa gacctccgaa atcgagagct ctcatttcca attatcctcg     4920
cgctggaagc tcctgaaggg cattgggtcg ccagtgcttt ggagaccagc tcaccgcgca    4980
acattcgcaa ggcgcttgct gtgattcaga gtgagagagt gcgcaatgct tgtttcaagg    5040
agctcaagtc ggcgagtgct tcggtccagg actggttggc tatttgggga cggaacgaga    5100
aaatgaactt gaagagccag cagacgtaga gtgcttttaa ctaagaatta ttagtctttt    5160
ctgcttattt tttcatcata gtttagaaca ctttatatta acgaatagtt tatgaatcta    5220
tttaggttta aaaattgata cagttttata agttactttt tcaaagactc gtgctgtcta    5280
```

```
ttgcataatg cactggaagg ggaaaaaaaa ggtgcacacg cgtggctttt tcttgaattt    5340
gcagtttgaa aaataactac atggatgata agaaaacatg gagtacagtc actttgagaa    5400
ccttcaatca gctggtaacg tcttcgttaa ttggatactc aaaaaagatg gatagcatga    5460
atcacaagat ggaaggaaat gcgggccacg accacagtga tatgcatatg ggagatggag    5520
atgataccto cattgggccg atgaagttag tcgacggata gaagcggttg tccccttttcc   5580
cggcgagccg gcagtcgggc cgaggttcgg ataaattttg tattgtgttt tgattctgtc    5640
atgagtatta cttatgttct cttttaggtaa ccccaggtta atcaatcaca gtttcatacc    5700
ggctagtatt caaattatga cttttcttct gcagtgtcag ccttacgacg attatctatg    5760
agctttgaat atagtttgcc gtgattcgta tcttttaattg gataataaaa tgcgaaggat    5820
cgatgacccct tattattatt tttctacact ggctaccgat ttaactcatc ttcttgaaag    5880
tataagta acagtaaaat ataccgtact tctgctaatg ttatttgtcc cttatttttc       5940
ttttcttgtc ttatgctata gtacctaaga ataacgacta ttgttttgaa ctaaacaaag    6000
tagtaaaagc acataaaaga attaagaaaa tggccaatgc ccagcaaccc cccttttcgca    6060
tccttattgt gggcggttct gtcgcaggcc tcatccttgc gcactgtctc gaacgcgcca    6120
atatagagta cctcatactc gaaaaaggag aagatgttgc tccacaagtt ggtgcctcga    6180
taggtatcat gccaaatggc ggacggatcc tcgagcaact gggcctatttt ggggagattg   6240
agcgtgtgat cgagccgttg catcaggcga atatcagcta ccagatggg ttctgcttta     6300
gtaacgtcta tcctaaggtt cttggcgaca ggttcggata cccggttgca ttcttggacc    6360
ggcagaagtt cctgcagatt gcatatgagg ggctgagaaa aagcagaat gttctcaccg     6420
gtaaaagggt agttggactg cgacagtcgg atcaagggac tgctgtttct gtggctgacg    6480
ggacagagta tgaggcggat ctcgtggttg gtgctgatgg agtacatagt cgggtgagaa    6540
gtgagatttg aagatggcg gaagagaatc agcctgcatc agtttcgaca cgtgaaagaa     6600
gaagcatgac tgttgaatat gtctgcgttt tcgggatttc atcagccatc ccagggctcg    6660
agataagcga acagatcaac ggtattttcg accatctatc cattctaaca atccatggca    6720
gacatggtcg cgtgttctgg ttcgtgatcc agaagctgga taggaagtac gtctatcctg    6780
atgtcccgcg attctcagac gaggatgccg tacagctctt cgatcgggtc aaacacgtgc    6840
ggttctggaa aaacatctgt gtgggggact tgtggaagaa cagagaggtg tcctcgatga    6900
cagcgctgga ggagggagtg ttcgagacat ggcatcatga taggatggtt ttgattggag    6960
atagcgttca caagatgacg cccaactttg gccaaggagc taattcagcc atcgaggatg    7020
ctgccgcgct ctcttccctt ctacatgatc tcgtcaacgc ccgtggagtt tgcaagccat    7080
cgaatgtcca gattcagcat ctcctcaagc agtatcggga gacccgatac actcgcatgg    7140
taggcatgtg tcgcaccgcg gcttcagtct ctcggattca ggcccgagat ggcatcctca    7200
acaccgtctt tggacgatat tgggcacctt atgctggcaa cctgcctgct gacctggcat    7260
caaaagtgat ggcagatgca gaggttgtta ctttttctgcc cttgccaggg cgctcaggac    7320
cgggctggga gatgtacaga cgaaagggga agggagggca ggtgcaatgg gtgcttataa    7380
tcttaagctt acttacgatt ggtggattgt gcatctggct acaaagcaat gcgttgagta    7440
gataaggaga ttgataagac ttttctagtt gcatatcttt tatatttaaa tcttatctat    7500
tagttaatttt tttgtaattt atccttatat atagtctggt tattctaaaa tatcatttca    7560
gtatctaaaa attcccctct tttttcagtt atatcttaac aggcgacagt ccaaatgttg    7620
atttatccca gtccgattca tcagggttgt gaagcatttt gtcaatggtc gaaatcacat    7680
```

```
cagtaatagt gcctcttact tgcctcatag aatttctttc tcttaacgtc accgtttggt   7740
cttttatagt ttcgaaatct atggtgatac caaatggtgt tcccaattca tcgttacggg   7800 cgtattttt accaattgaa gtattggaat cgtcaatttt aaagtatatc tctcttttac    7860
gtaaagcctg cgagatcctc ttaagtatag cggggaagcc atcgttattc gatattgtcg   7920
taacaaatac tttgatcggc gctatgcggc cgccaccgcg gtggagctcc agcttttgtt   7980 cccttagtg agggttaatt gcgcgcttgg cgtaatcatg gtcatagctg tttcctgtgt    8040
gaaattgtta tccgctcaca attccacaca acataggagc cggaagcata aagtgtaaag   8100
cctggggtgc ctaatgagtg aggtaactca cattaattgc gttgcgctca ctgcccgctt   8160
tccagtcggg aaacctgtcg tgccagctgc attaatgaat cggccaacgc gcggggagag   8220
gcggtttgcg tattgggcgc tcttccgctt cctcgctcac tgactcgctg cgctcggtcg   8280
ttcggctgcg gcgagcggta tcagctcact caaaggcggt aatacggtta ccacagaat    8340 caggggataa cgcaggaaag aacatgtgag caaaaggcca gcaaaaggcc aggaaccgta   8400
aaaaggccgc gttgctggcg tttttccata ggctccgccc cctgacgag catcacaaaa    8460 atcgacgctc aagtcagagg tggcgaaacc cgacaggact ataaagatac caggcgtttc   8520 ccctggaag ctccctcgtg cgctctcctg ttccgaccct gccgcttacc ggatacctgt    8580
ccgcctttct cccttcggga agcgtggcgc tttctcatag ctcacgctgt aggtatctca   8640
gttcggtgta ggtcgttcgc tccaagctgg gctgtgtgca cgaaccccc gttcagcccg     8700 accgctgcgc cttatccggt aactatcgtc ttgagtccaa cccggtaaga cacgacttat   8760
cgccactggc agcagccact ggtaacagga ttagcagagc gaggtatgta ggcggtgcta   8820
cagagttctt gaagtggtgg cctaactacg gctacactag aaggacagta tttggtatct   8880
gcgctctgct gaagccagtt accttcggaa aaagagttgg tagctcttga tccggcaaac   8940
aaaccaccgc tggtagcggt ggtttttttg tttgcaagca gcagattacg cgcagaaaaa   9000
aaggatctca agaagatcct ttgatctttt ctacggggtc tgacgctcag tggaacgaaa   9060
actcacgtta agggattttg gtcatgagat tatcaaaaag gatcttcacc tagatccttt   9120
taaattaaaa atgaagtttt aaatcaatct aaagtatata tgagtaaact tggtctgaca   9180
gttaccaatg cttaatcagt gaggcaccta tctcagcgat ctgtctattt cgttcatcca   9240
tagttgcctg actccccgtc gtgtagataa ctacgatacg ggagggctta ccatctggcc   9300
ccagtgctgc aatgataccg cgagacccac gctcaccggc tccagattta tcagcaataa   9360
accagccagc cggaagggcc gagcgcagaa gtggtcctgc aactttatcc gcctccatcc   9420
agtctattaa ttgttgccgg gaagctagag taagtagttc gccagttaat agtttgcgca   9480
acgttgttgc cattgctaca ggcatcgtgg tgtcacgctc gtcgtttggt atggcttcat   9540
tcagctccgg ttcccaacga tcaaggcgag ttacatgatc ccccatgttg tgcaaaaaag   9600
cggttagctc cttcggtcct ccgatcgttg tcagaagtaa gttggccgca gtgttatcac   9660
tcatggttat ggcagcactg cataattctc ttactgtcat gccatccgta agatgctttt   9720
ctgtgactgg tgagtactca accaagtcat tctgagaata gtgtatgcgg cgaccgagtt   9780
gctcttgccc ggcgtcaata cgggataata ccgcgccaca tagcagaact ttaaaagtgc   9840
tcatcattgg aaaacgttct tcggggcgaa aactctcaag gatcttaccg ctgttgagat   9900
ccagttcgat gtaacccact cgtgcaccca actgatcttc agcatctttt actttcacca   9960
gcgtttctgg gtgagcaaaa acaggaaggc aaaatgccgc aaaaaaggga ataagggcga   10020
```

```
cacggaaatg ttgaatactc atactcttcc tttttcaata ttattgaagc atttatcagg    10080
gttattgtct catgagcgga tacatatttg aatgtattta gaaaaataaa caaatagggg    10140
ttccgcgcac atttccccga aaagtgccac ctgaacgaag catctgtgct tcattttgta    10200
gaacaaaaat gcaacgcgag agcgctaatt tttcaaacaa agaatctgag ctgcattttt    10260
acagaacaga aatgcaacgc gaaagcgcta ttttaccaac gaagaatctg tgcttcattt    10320
ttgtaaaaca aaaatgcaac gcgagagcgc taattttttca aacaaagaat ctgagctgca    10380
tttttacaga acagaaatgc aacgcgagag cgctatttta ccaacaaaga atctatactt    10440 ctttttttgtt ctacaaaaat gcatcccgag agcgctattt ttctaacaaa gcatcttaga    10500
ttactttttt tctcctttgt gcgctctata atgcagtctc ttgataactt tttgcactgt    10560
aggtccgtta aggttagaag aaggctactt tggtgtctat tttctcttcc ataaaaaaag    10620
cctgactcca cttcccgcgt ttactgatta ctagcgaagc tgcgggtgca ttttttcaag    10680
ataaaggcat ccccgattat attctatacc gatgtggatt gcgcatactt tgtgaacaga    10740
aagtgatagc gttgatgatt cttcattggt cagaaaatta tgaacggttt cttctatttt    10800
gtctctatat actacgtata ggaaatgttt acattttcgt attgttttcg attcactcta    10860
tgaatagttc ttactacaat ttttttgtct aaagagtaat actagagata aacataaaaa    10920
atgtagaggt cgagtttaga tgcaagttca aggagcgaaa ggtggatggg taggttatat    10980
agggatatag cacagagata tatagcaaag agatactttt gagcaatgtt tgtggaagcg    11040
gtattcgcaa tatttttagta gctcgttaca gtccggtgcg ttttttggttt tttgaaagtg    11100 cgtcttcaga gcgcttttgg ttttcaaaag cgctctgaag ttcctatact ttctagagaa    11160
taggaacttc ggaataggaa cttcaaagcg tttccgaaaa cgagcgcttc cgaaaatgca    11220
acgcgagctg cgcacataca gctcactgtt cacgtcgcac ctatatctgc gtgttgcctg    11280
tatatatata tacatgagaa gaacggcata gtgcgtgttt atgcttaaat gcgtacttat    11340
atgcgtctat ttatgtagga tgaaaggtag tctagtacct cctgtgatat tatcccattc    11400
catgcggggt atcgtatgct tccttcagca ctaccctttta gctgttctat atgctgccac    11460
tcctcaattg gattagtctc atccttcaat gctatcattt cctttgatat tggatcatac    11520
taagaaacca ttattatcat gacattaacc tataaaaata ggcgtatcac gaggcccttt    11580
cgtctcgcgc gtttcggtga tgacggtgaa aacctctgac acatgcagct cccggagacg    11640
gtcacagctt gtctgtaagc ggatgccggg agcagacaag cccgtcaggg cgcgtcagcg    11700
ggtgttggcg ggtgtcgggg ctggcttaac tatgcggcat cagagcagat tgtactgaga    11760
gtgcaccata tcgactacgt cgtaaggccg tttctgacag agtaaaattc ttgagggaac    11820
tttcaccatt atgggaaatg cttcaagaag gtattgactt aaactccatc aaatggtcag    11880
gtcattgagt gtttttttatt tgttgtattt tttttttttt agagaaaatc ctccaatatc    11940
aaattaggaa tcgtagtttc atgattttct gttcaccta actttttgtg tggtgccctc    12000
ctccttgtca atattaatgt taaagtgcaa ttcttttttcc ttatcacgtt gagccattag    12060
tatcaatttg cttacctgta ttcctttact atcctccttt ttctccttct tgataaatgt    12120
atgtagattg cgtatatagt ttcgtctacc ctatgaacat attccatttt gtaatttcgt    12180
gtcgtttcta ttatgaattt catttataaa gtttatgtac aaatatcata aaaaagaga    12240 atcttttttaa gcaaggattt tcttaacttc ttcggcgaca gcatcaccga cttcggtggt    12300
actgttggaa ccacctaaat caccagttct gatacctgca tccaaaacct ttttaactgc    12360
atcttcaatg gccttacctt cttcaggcaa gttcaatgac aatttcaaca tcattgcagc    12420
```

```
agacaagata gtggcgatag ggtcaacctt attctttggc aaatctggag cagaaccgtg    12480
gcatggttcg tacaaaccaa atgcggtgtt cttgtctggc aaagaggcca aggacgcaga    12540
tggcaacaaa cccaaggaac ctgggataac ggaggcttca tcggagatga tatcaccaaa    12600
catgttgctg gtgattataa taccatttag gtgggttggg ttcttaacta ggatcatggc    12660
ggcagaatca atcaattgat gttgaacctt caatgtaggg aattcgttct tgatggtttc    12720
ctccacagtt tttctccata atcttgaaga ggccaaaaga ttagctttat ccaaggacca    12780
aataggcaat ggtggctcat gttgtagggc catgaaagcg gccattcttg tgattctttg    12840
cacttctgga acggtgtatt gttcactatc ccaagcgaca ccatcaccat cgtcttcctt    12900
tctcttacca aagtaaatac ctcccactaa ttctctgaca acaacgaagt cagtaccttt    12960
agcaaattgt ggcttgattg gagataagtc taaaagagag tcggatgcaa agttacatgg    13020
tcttaagttg gcgtacaatt gaagttcttt acggattttt agtaaacctt gttcaggtct    13080
aacactaccg gtaccccatt taggaccagc cacagcacct aacaaaacgg catcaacctt    13140
cttggaggct tccagcgcct catctggaag tgggacacct gtagcatcga tagcagcacc    13200
accaattaaa tgattttcga aatcgaactt gacattggaa cgaacatcag aaatagcttt    13260 aagaaccttca atggcttcgg ctgtgatttc ttgaccaacg tggtcacctg gcaaaacgac    13320
gatcttctta ggggcagaca taggggcaga cattagaatg gtatatcctt gaaatatata    13380
tatatattgc tgaaatgtaa aaggtaagaa aagttagaaa gtaagacgat tgctaaccac    13440
ctattgaaaa aaacaatagg tccttaaata atattgtcaa cttcaagtat tgtgatgcaa    13500
gcatttagtc atgaacgctt ctctattcta tatgaaaagc cggttccggc ctctcacctt    13560
tcctttttct cccaatttttt cagttgaaaa aggtatatgc gtcaggcgac ctctgaaatt    13620
aacaaaaaat ttccagtcat cgaatttgat tctgtgcgat agcgccctg tgtgttctcg    13680 ttatgttgag gaaaaaaata atggttgcta agagattcga actcttgcat cttacgatac    13740
ctgagtattc ccacagttaa ctgcggtcaa gatatttctt gaatcaggcg ccttagaccg    13800
ctcggccaaa caaccaatta cttgttgaga aatagagtat aattatccta taaatataac    13860 gttttgaac acacatgaac aaggaagtac aggacaattg attttgaaga gaatgtggat    13920
tttgatgtaa ttgttgggat tccattttta ataaggcaat aatattaggt atgtggatat    13980
actagaagtt ctcctcgacc gtcgatatgc ggtgtgaaat accgcacaga tgcgtaagga    14040
gaaaataccg catcaggaaa ttgtaaacgt taatattttg ttaaaattcg cgttaaattt    14100
ttgttaaatc agctcatttt ttaaccaata ggccgaaatc ggcaaaatcc cttataaatc    14160 aaagaatag accgagatag ggttgagtgt tgttccagtt tggaacaaga gtccactatt    14220
aaagaacgtg gactccaacg tcaaagggcg aaaaaccgtc tatcagggcg atggcccact    14280
acgtgaacca tcaccctaat caagtttttt ggggtcgagg tgccgtaaag cactaaatcg    14340
gaaccctaaa gggagccccc gatttagagc ttgacgggga agccggcga acgtggcgag    14400 aaaggaaggg aagaaagcga aaggagcggg cgctagggcg ctggcaagtg tagcggtcac    14460
gctgcgcgta accaccacac ccgccgcgct taatgcgccg ctacagggcg cgtcgcgcca    14520
ttcgccattc aggctgcgca actgttggga agggcgatcg gtgcgggcct cttcgctatt    14580
acgccagctg gcgaaagggg gatgtgctgc aaggcgatta agttgggtaa cgccagggtt    14640
ttcccagtca cgacgttgta aaacgacggc cagtgagcgc gcgtaatacg actcactata    14700
gggcgaattg ggtaccgggc cccccctcga ggtcgacggt atcgataagc ttgatatcga    14760
```

| attcctgcag cccgggggat ccactagttc tagattaatt aa | 14802 |

<210> SEQ ID NO 66
<211> LENGTH: 14644
<212> TYPE: DNA
<213> ORGANISM: Artificial Sequence
<220> FEATURE:
<223> OTHER INFORMATION: synthesized in lab

<400> SEQUENCE: 66

| | |
|---|---|
| atagcttcaa aatgtttcta ctcctttttt actcttccag attttctcgg actccgcgca | 60 |
| tcgccgtacc acttcaaaac acccaagcac agcatactaa atttccctc tttcttcctc | 120 |
| tagggtgtcg ttaattaccc gtactaaagg tttggaaaag aaaaagaga ccgcctcgtt | 180 |
| tcttttctt cgtcgaaaaa ggcaataaaa attttttatca cgtttctttt tcttgaaaat | 240 |
| ttttttttt gatttttttc tctttcgatg acctcccatt gatatttaag ttaataaacg | 300 |
| gtcttcaatt tctcaagttt cagtttcatt tttcttgttc tattacaact tttttttactt | 360 |
| cttgctcatt agaaagaaag catagcaatc taatctaagt tttaattaca aaatgctggg | 420 |
| attcccaatg ttcaacccag ctacgcctga tgtctggaag atgaataccc cttactttcc | 480 |
| atttgttaca ccggggttat ttcctgcctc agcaccccca tcgcccacca acgtagatgc | 540 |
| cgaagctgcc agttcccaac agtcggaagc aagctatctg gataaggaga aaattgttcg | 600 |
| agggccactt gattatcttc tcaaatcccc tggaaaagac attcgtcgga aattcattca | 660 |
| cgcgttcaat gaatggctgc gcattcctga ggacaagttg aatattatca cggaaattgt | 720 |
| tggattgctt cacacggcct cccttctaat cgacgatatt caggacaatt ccaagcttcg | 780 |
| acgcggcctc ccagtggccc atagcatatt tggtattgcg cagacaatta actctgccaa | 840 |
| ttatgcgtac tttctagccc aggaaaggct ccgcgaactg aatcatcctg aagcgtacga | 900 |
| aatatacaca gaggaactgc ttcgtctgca ccgcggtcaa ggtatggact tgtactggcg | 960 |
| ggactgccta acctgtccca cagaggagga ctatattgag atgatcgcca acaagactgg | 1020 |
| tggcctattt cgactggcga ttaagcttat gcagttggaa agcactttgt gcagcaatgt | 1080 |
| cattgaacta gcagacttgt tgggcgtgat ctttcagatt cgggatgatt accaaaactt | 1140 |
| acagagtgga ctatacgcca agaacaaggg attttgcgag gatttgacgg agggaaaatt | 1200 |
| ttcctttctg attatccaca gtattaacag taacccgaac aatcaccatc tgctaaaatat | 1260 |
| actacggcag cggagcgagg acgattcggt gaagaagtat gctgttgatt atatcgactc | 1320 |
| gacggggagt tttgactact gccgggaacg gctcgcttcc ttattggaag aggcggatca | 1380 |
| aatggttaag aagttggaaa atgaggggggg acaatcaaag gggatctacg atattctgag | 1440 |
| cttttctgtcg tgagcggatc tcttatgtct ttacgattta tagttttcat tatcaagtat | 1500 |
| gcctatatta gtatatagca tctttagatg acagtgttcg aagtttcacg aataaaagat | 1560 |
| aatattctac ttttttgctcc caccgcgttt gctagcacga gtgaacacca tccctcgcct | 1620 |
| gtgagttgta cccattcctc taaactgtag acatggtagc ttcagcagtg ttcgttatgt | 1680 |
| acggcatcct ccaacaaaca gtcggttata gtttgtcctg ctcctctgaa tcgtctccct | 1740 |
| cgatatttct cattttcctt cgcatgccag cattgaaatg atcgaagttc aatgatgaaa | 1800 |
| cggtaattct tctgtcattt actcatctca tctcatcaag ttatataatt ctatacggat | 1860 |
| gtaatttttc acttttcgtc ttgacgtcca ccctataatt tcaattattg aaccctcact | 1920 |
| gggtcattac gtaaataatg ataggaatgg gattcttcta ttttttccttt ttccattcta | 1980 |
| gcagccgtcg ggaaaacgtg gcatcctctc tttcgggctc aattggagtc acgctgccgt | 2040 |

```
gagcatcctc tctttccata tctaacaact gagcacgtaa ccaatggaaa agcatgagct   2100
tagcgttgct ccaaaaaagt attggatggt taataccatt tgtctgttct cttctgactt   2160
tgactcctca aaaaaaaaaa atctacaatc aacagatcgc ttcaattacg ccctcacaaa   2220 aactttttc cttcttcttc gcccacgtta aattttatcc ctcatgttgt ctaacggatt   2280
tctgcacttg atttattata aaaagacaaa gacataatac ttctctatca atttcagtta   2340
ttgttcttcc ttgcgttatt cttctgttct tcttttctt ttgtcatata taaccataac   2400
caagtaatac atattcaaaa tggatgggtt cgaccattct actgctccac caggatataa   2460
cgagctaaaa tggctcgccg atatcttcgt catcggaatg gctgttggct gggttgctca   2520
ctatatggag atgattcaca cgtcgttcaa ggaccaaaca tactgcatga ccatcggggg   2580
cctttgcatc aattttgcct gggaaatcat attctgcaca atgtatcctg ccaaaggatt   2640
tgtcgagcgg gttgcctttc tcatgggcat ttctctcgac cttggggtta tttacgcggg   2700
aatcaagaac gccccaaatg aatggcacca ctctgcaatg gtgagggacc atatgcccct   2760
tgtcttcgca gcaacgacac tttgttgtct gagcggtcat atggctctta ctgcccaggt   2820
tggtcccgca caagcctata cgtgggggc aattgcatgc cagctcttta tcagcatagg   2880
gaatgtgttt caattgttga gtcggggaaa cacacgaggg gcgtcatgga cgctatggac   2940
ctccaggttt tttggatcaa catcagccat tggctttgct cttgttcgat atattcgctg   3000
gtgggaggcc ttttcttggt tgaactgccc gcttgtgata tggtccgtgg ccatgttctt   3060
tctgtttgaa acactctatg gagccctatt ctattctgtc aagcgacaag aagggagatc   3120
ccagcgtgga atcaagcaca agagaggta gacaaatcgc tcttaaatat atacctaaag   3180
aacattaaag ctatattata agcaaagata cgtaaatttt gcttatatta ttatacacat   3240
atcatatttc tatatttta agatttggtt atataatgta cgtaatgcaa aggaaataaa   3300
ttttatacat tattgaacag cgtccaagta actacattat gtgcactaat agtttagcgt   3360
cgtgaagact ttattgtgtc gcgaaaagta aaaattttaa aaattagagc accttgaact   3420
tgcgaaaaag gttctcatca actgtttaaa aggaggatat caggtcctat ttctgacaaa   3480
caatatacaa atttagtttc aaagatgaat cagtgcgcga aggacataac tcaacagttt   3540
attcctggca tccactaaat ataatggagc ccgctttta agctggcatc cagaaaaaaa   3600
aagaatccca gcaccaaaat attgttttct tcaccaacca tcagttcata ggtccattct   3660
cttagcgcaa ctacagagaa caggggcaca acaggcaaa aaacgggcac aacctcaatg   3720
gagtgatgca acctgcctgg agtaaatgat gacacaaggc aattgaccca cgcatgtatc   3780
tatctcattt tcttcacct tctattacct tctgctctct ctgatttgga aaaagctgaa   3840
aaaaaaggtt gaaaccagtt ccctgaaatt attcccctac ttgactaata agtatataaa   3900
gacggtaggt attgattgta attctgtaaa tctatttctt aaacttctta aattctactt   3960
ttatagttag tcttttttt agttttaaaa caccaagaac ttagtttcga ataaacacac   4020
ataaacaaac aaaatggcgg cacttccgga cgttgcctcc attcccatcc ctctggtggc   4080
aaccctaggc attgcccctc taattttcta tctcgtcctt gatagaatta gccccttgtg   4140
gccaaattcc aaagctttcc tgattggcaa gaagaaaccg gagaccgtga catcgttcga   4200
gtgcccatat gcctacatcc gtcagatcta tgggaagtat cactgggagc cattcgtaca   4260
gaagctgtct ccgaggctta aggatgagga tccggccaaa tataagatgg ttctggagat   4320
aatggatgca atccacctgt gtctgatgct agttgacgat ataactgaca atagcgacta   4380
```

```
tcgaaaaggc aagccagcag cccaccggat atatggccct tcagagacag caaatcgcgc    4440
ttactaccga gtcacccaga ttctaaacaa gaccgtgcaa aagttcccca agctggccaa    4500
gttcctgctt cagaatctgg aagaaattct cgaaggccaa gacctgtcac taatctggcg    4560
acgggatgga ctgggtagcc tttcgactgt tcctgatgag cgagttgcag cctatcgcaa    4620
gatggcgtca ttgaaaactg gggcgttatt ccggctgctg gggcaattgg tgatggagga    4680
ccaatcgatg gacgggacga tgactactct tgcgtggtgc tctcagctgc agaatgactg    4740
caagaatgtc tactcatctg aatatgctaa ggccaaaggg gcgcttgccg aagacctccg    4800
aaatcgagag ctctcatttc caattatcct cgcgctggaa gctcctgaag gcattgggt    4860 cgccagtgct ttggagacca gctcaccgcg caacattcgc aaggcgcttg ctgtgattca    4920
gagtgagaga gtgcgcaatg cttgtttcaa ggagctcaag tcggcgagtg cttcggtcca    4980
ggactggttg gctatttggg gacggaacga gaaaatgaac ttgaagagcc agcagacgta    5040
gagtgctttt aactaagaat tattagtctt ttctgcttat tttttcatca tagtttagaa    5100
cactttatat taacgaatag tttatgaatc tatttaggtt taaaaattga tacagttta    5160 taagttactt tttcaaagac tcgtgctgtc tattgcataa tgcactggaa ggggaaaaaa    5220
aaggtgcaca cgcgtggctt tttcttgaat ttgcagtttg aaaataact acatggatga    5280 taagaaaaca tggagtacag tcactttgag aaccttcaat cagctggtaa cgtcttcgtt    5340
aattggatac tcaaaaaaga tggatagcat gaatcacaag atggaaggaa atgcgggcca    5400
cgaccacagt gatatgcata tgggagatgg agatgatacc ttatatctag gaacccatca    5460
ggttggtgga agattacccg ttctaagact tttcagcttc ctctattgat gttacacctg    5520
gacacccctt ttctggcatc cagttttaa tcttcagtgg catgtgagat tctccgaaat    5580
taattaaagc aatcacacaa ttctctcgga taccacctcg gttgaaactg acaggtggtt    5640
tgttacgcat gctaatgcaa aggagcctat ataccttggg ctcggctgct gtaacaggga    5700
atataaaggg cagcataatt taggagtta gtgaacttgc aacattact attttccctt    5760 cttacgtaaa tattttttctt tttaattcta aatcaatctt tttcaatttt ttgtttgtat    5820
tcttttcttg cttaaatcta taactacaaa aaacacatac ataaactaaa atgggccaat    5880
gcccagcaac ccccctttcg catccttatt gtgggcggtt ctgtcgcagg cctcatcctt    5940
gcgcactgtc tcgaacgcgc caatatagag tacctcatac tcgaaaaagg agaagatgtt    6000
gctccacaag ttggtgcctc gataggtatc atgccaaatg gcggacggat cctcgagcaa    6060
ctgggcctat tgggggagat tgagcgtgtg atcgagccgt tgcatcaggc gaatatcagc    6120
tatccagatg ggttctgctt tagtaacgtc tatcctaagg ttcttggcga caggttcgga    6180
tacccggttg cattcttgga ccggcagaag ttcctgcaga ttgcatatga ggggctgaga    6240
aagaagcaga atgttctcac cggtaaaagg gtagttggac tgcgacagtc ggatcaaggg    6300
actgctgttt ctgtggctga cgggacagag tatgaggcgg atctcgtggt tggtgctgat    6360
ggagtacata gtcgggtgag aagtgagatt tggaagatgg cggaagagaa tcagcctgca    6420
tcagtttcga cacgtgaaag aagaagcatg actgttgaat atgtctgcgt tttcgggatt    6480
tcatcagcca tcccagggct cgagataagc gaacagatca acggtattt cgaccatcta    6540 tccattctaa caatccatgg cagacatggt cgcgtgttct ggttcgtgat ccagaagctg    6600
gataggaagt acgtctatcc tgatgtcccg cgattctcag acgaggatgc cgtacagctc    6660
ttcgatcggg tcaaacacgt gcggttctgg aaaaacatct gtgtggggga cttgtggaag    6720
aacagagagg tgtcctcgat gacagcgctg gaggagggag tgttcgagac atggcatcat    6780
```

```
gataggatgg ttttgattgg agatagcgtt cacaagatga cgcccaactt tggccaagga    6840
gctaattcag ccatcgagga tgctgccgcg ctctcttccc ttctacatga tctcgtcaac    6900
gcccgtggag tttgcaagcc atcgaatgtc cagattcagc atctcctcaa gcagtatcgg    6960
gagacccgat acactcgcat ggtaggcatg tgtcgcaccg cggcttcagt ctctcggatt    7020
caggcccgag atggcatcct caacaccgtc tttggacgat attgggcacc ttatgctggc    7080
aacctgcctg ctgacctggc atcaaaagtg atggcagatg cagaggttgt tacttttctg    7140
cccttgccag ggcgctcagg accgggctgg gagatgtaca gacgaaaggg gaagggaggg    7200
caggtgcaat gggtgcttat aatcttaagc ttacttacga ttggtggatt gtgcatctgg    7260
ctacaaagca atgcgttgag tagataagga gattgataag acttttctag ttgcatatct    7320
tttatattta aatcttatct attagttaat tttttgtaat ttatccttat atatagtctg    7380
gttattctaa aatatcattt cagtatctaa aaattcccct ctttttttcag ttatatctta    7440
acaggcgaca gtccaaatgt tgatttatcc cagtccgatt catcagggtt gtgaagcatt    7500
ttgtcaatgg tcgaaatcac atcagtaata gtgcctctta cttgcctcat agaatttctt    7560
tctcttaacg tcaccgtttg gtcttttata gtttcgaaat ctatggtgat accaaatggt    7620
gttcccaatt catcgttacg ggcgtatttt ttaccaattg aagtattgga atcgtcaatt    7680
ttaaagtata tctctctttt acgtaaagcc tgcgagatcc tcttaagtat agcggggaag    7740
ccatcgttat tcgatattgt cgtaacaaat actttgatcg gcgctatgcg gccgccaccg    7800
cggtggagct ccagcttttg ttcccttttag tgagggttaa ttgcgcgctt ggcgtaatca    7860
tggtcatagc tgtttcctgt gtgaaattgt tatccgctca caattccaca aacatagga    7920
gccggaagca taaagtgtaa agcctggggt gcctaatgag tgaggtaact cacattaatt    7980
gcgttgcgct cactgcccgc tttccagtcg ggaaacctgt cgtgccagct gcattaatga    8040
atcggccaac gcgcggggag aggcggtttg cgtattgggc gctcttccgc ttcctcgctc    8100
actgactcgc tgcgctcggt cgttcggctg cggcgagcgg tatcagctca ctcaaaggcg    8160
gtaatacggt tatccacaga atcagggga acgcaggaa agaacatgtg agcaaaaggc    8220
cagcaaaagg ccaggaaccg taaaaaggcc gcgttgctgg cgtttttcca taggctccgc    8280
ccccctgacg agcatcacaa aaatcgacgc tcaagtcaga ggtggcgaaa cccgacagga    8340
ctataaagat accaggcgtt tccccctgga agctccctcg tgcgctctcc tgttccgacc    8400
ctgccgctta ccggatacct gtccgccttt ctcccttcgg gaagcgtggc gctttctcat    8460
agctcacgct gtaggtatct cagttcggtg taggtcgttc gctccaagct gggctgtgtg    8520
cacgaacccc ccgttcagcc cgaccgctgc gccttatccg gtaactatcg tcttgagtcc    8580
aacccggtaa gacacgactt atcgccactg gcagcagcca ctggtaacag gattagcaga    8640
gcgaggtatg taggcggtgc tacagagttc ttgaagtggt ggcctaacta cggctacact    8700
agaaggacag tatttggtat ctgcgctctg ctgaagccag ttaccttcgg aaaaagagtt    8760
ggtagctctt gatccggcaa acaaaccacc gctggtagcg tggtttttt tgtttgcaag    8820
cagcagatta cgcgcagaaa aaaggatct caagaagatc ctttgatctt ttctacgggg    8880
tctgacgctc agtggaacga aaactcacgt taagggattt tggtcatgag attatcaaaa    8940
aggatcttca cctagatcct ttaaattaa aaatgaagtt ttaaatcaat ctaaagtata    9000
tatgagtaaa cttggtctga cagttaccaa tgcttaatca gtgaggcacc tatctcagcg    9060
atctgtctat ttcgttcatc catagttgcc tgactccccg tcgtgtagat aactacgata    9120
```

```
cgggagggct taccatctgg ccccagtgct gcaatgatac cgcgagaccc acgctcaccg    9180
gctccagatt tatcagcaat aaaccagcca gccggaaggg ccgagcgcag aagtggtcct    9240
gcaactttat ccgcctccat ccagtctatt aattgttgcc gggaagctag agtaagtagt    9300
tcgccagtta atagtttgcg caacgttgtt gccattgcta caggcatcgt ggtgtcacgc    9360
tcgtcgtttg gtatggcttc attcagctcc ggttcccaac gatcaaggcg agttacatga    9420
tcccccatgt tgtgcaaaaa agcggttagc tccttcggtc ctccgatcgt tgtcagaagt    9480
aagttggccg cagtgttatc actcatggtt atggcagcac tgcataattc tcttactgtc    9540
atgccatccg taagatgctt ttctgtgact ggtgagtact caaccaagtc attctgagaa    9600
tagtgtatgc ggcgaccgag ttgctcttgc ccggcgtcaa tacgggataa taccgcgcca    9660
catagcagaa ctttaaaagt gctcatcatt ggaaaacgtt cttcggggcg aaaactctca    9720
aggatcttac cgctgttgag atccagttcg atgtaaccca ctcgtgcacc caactgatct    9780
tcagcatctt ttactttcac cagcgtttct gggtgagcaa aaacaggaag gcaaaatgcc    9840
gcaaaaaagg gaataagggc gacacggaaa tgttgaatac tcatactctt ccttttcaa    9900 tattattgaa gcatttatca gggttattgt ctcatgagcg gatacatatt tgaatgtatt    9960
tagaaaaata aacaaatagg ggttccgcgc acatttcccc gaaaagtgcc acctgaacga    10020
agcatctgtg cttcattttg tagaacaaaa atgcaacgcg agagcgctaa ttttcaaac     10080 aaagaatctg agctgcattt ttacagaaca gaaatgcaac gcgaaagcgc tattttacca    10140
acgaagaatc tgtgcttcat ttttgtaaaa caaaaatgca acgcgagagc gctaattttt    10200
caaacaaaga atctgagctg cattttacag aacagaaat gcaacgcgag agcgctattt     10260
taccaacaaa gaatctatac ttcttttttg ttctacaaaa atgcatcccg agagcgctat    10320
ttttctaaca aagcatctta gattacttt tttctccttt gtgcgctcta taatgcagtc      10380
tcttgataac ttttgcact gtaggtccgt taaggttaga agaaggctac tttggtgtct      10440
attttctctt ccataaaaaa agcctgactc cacttcccgc gtttactgat tactagcgaa    10500
gctgcgggtg cattttttca agataaaggc atccccgatt atattctata ccgatgtgga    10560
ttgcgcatac tttgtgaaca gaaagtgata gcgttgatga ttcttcattg gtcagaaaat    10620
tatgaacggt ttcttctatt ttgtctctat atactacgta taggaaatgt ttacattttc     10680
gtattgtttt cgattcactc tatgaatagt tcttactaca attttttgt ctaaagagta     10740 atactagaga taaacataaa aaatgtagag gtcgagttta gatgcaagtt caaggagcga    10800
aaggtggatg ggtaggttat atagggatat agcacagaga tatatagcaa agagatactt    10860
ttgagcaatg tttgtggaag cggtattcgc aatatttag tagctcgtta cagtccggtg     10920 cgttttggt tttttgaaag tgcgtcttca gagcgctttt ggttttcaaa agcgctctga    10980
agttcctata ctttctagag aataggaact tcggaatagg aacttcaaag cgtttccgaa    11040
aacgagcgct tccgaaaatg caacgcgagc tgcgcacata cagctcactg ttcacgtcgc    11100
acctatatct gcgtgttgcc tgtatatata tatacatgag aagaacggca tagtgcgtgt    11160
ttatgcttaa atgcgtactt atatgcgtct atttatgtag gatgaaaggt agtctagtac    11220
ctcctgtgat attatcccat tccatgcggg gtatcgtatg cttccttcag cactaccctt    11280
tagctgttct atatgctgcc actcctcaat tggattagtc tcatccttca atgctatcat    11340
ttcctttgat attggatcat actaagaaac cattattatc atgacattaa cctataaaaa    11400
taggcgtatc acgaggccct ttcgtctcgc gcgtttcggt gatgacgtg aaaacctctg     11460 acacatgcag ctcccggaga cggtcacagc ttgtctgtaa gcggatgccg ggagcagaca    11520
```

```
agcccgtcag ggcgcgtcag cgggtgttgg cgggtgtcgg ggctggctta actatgcggc   11580
atcagagcag attgtactga gagtgcacca tatcgactac gtcgtaaggc cgtttctgac   11640
agagtaaaat tcttgaggga actttcacca ttatgggaaa tgcttcaaga aggtattgac   11700
ttaaactcca tcaaatggtc aggtcattga gtgttttta tttgttgtat ttttttttt    11760 ttagagaaaa tcctccaata tcaaattagg aatcgtagtt tcatgatttt ctgttacacc   11820 taacttttg tgtggtgccc tcctccttgt caatattaat gttaaagtgc aattcttttt    11880
ccttatcacg ttgagccatt agtatcaatt tgcttacctg tattccttta ctatcctcct   11940 tttctcctt cttgataaat gtatgtagat tgcgtatata gtttcgtcta ccctatgaac    12000
atattccatt ttgtaatttc gtgtcgtttc tattatgaat ttcatttata aagtttatgt   12060
acaaatatca taaaaaaga gaatcttttt aagcaaggat tttcttaact tcttcggcga    12120
cagcatcacc gacttcggtg gtactgttgg aaccacctaa atcaccagtt ctgatacctg   12180
catccaaaac cttttaact gcatcttcaa tggccttacc ttcttcaggc aagttcaatg    12240
acaatttcaa catcattgca gcagacaaga tagtggcgat agggtcaacc ttattctttg   12300
gcaaatctgg agcagaaccg tggcatggtt cgtacaaacc aaatgcggtg ttcttgtctg   12360
gcaaagaggc caaggacgca gatggcaaca aacccaagga acctgggata acggaggctt   12420
catcggagat gatatcacca aacatgttgc tggtgattat aataccattt aggtgggttg   12480
ggttcttaac taggatcatg gcggcagaat caatcaattg atgttgaacc ttcaatgtag   12540
ggaattcgtt cttgatggtt tcctccacag tttttctcca taatcttgaa gaggccaaaa   12600
gattagcttt atccaaggac caaataggca atggtggctc atgttgtagg gccatgaaag   12660
cggccattct tgtgattctt tgcacttctg gaacggtgta ttgttcacta tcccaagcga   12720
caccatcacc atcgtcttcc tttctcttac caaagtaaat acctcccact aattctctga   12780
caacaacgaa gtcagtacct ttagcaaatt gtggcttgat tggagataag tctaaaagag   12840
agtcggatgc aaagttacat ggtcttaagt tggcgtacaa ttgaagttct ttacggattt    12900
ttagtaaacc ttgttcaggt ctaacactac cggtacccca tttaggacca gccacagcac   12960
ctaacaaaac ggcatcaacc ttcttggagg cttccagcgc ctcatctgga agtgggacac   13020
ctgtagcatc gatagcagca ccaccaatta aatgattttc gaaatcgaac ttgacattgg   13080
aacgaacatc agaaatagct ttaagaacct taatggcttc ggctgtgatt tcttgaccaa   13140
cgtggtcacc tggcaaaacg acgatcttct taggggcaga catagggca gacattagaa    13200 tggtatatcc ttgaaatata tatatatatt gctgaaatgt aaaaggtaag aaaagttaga   13260
aagtaagacg attgctaacc acctattgga aaaaacaata ggtccttaaa taatattgtc   13320
aacttcaagt attgtgatgc aagcatttag tcatgaacgc ttctctattc tatatgaaaa   13380
gccggttccg gcctctcacc tttccttttt ctcccaattt ttcagttgaa aaaggtatat   13440
gcgtcaggcg acctctgaaa ttaacaaaaa atttccagtc atcgaatttg attctgtgcg   13500
atagcgcccc tgtgtgttct cgttatgttg aggaaaaaaa taatggttgc taagagattc   13560
gaactcttgc atcttacgat acctgagtat tcccacagtt aactgcggtc aagatatttc   13620
ttgaatcagg cgccttagac cgctcggcca aacaaccaat tacttgttga gaaatagagt   13680
ataattatcc tataaatata acgttttga acacacatga acaaggaagt acaggacaat    13740
tgattttgaa gagaatgtgg atttttgatgt aattgttggg attccatttt taataaggca   13800
ataatattag gtatgtggat atactagaag ttctcctcga ccgtcgatat gcggtgtgaa    13860
```

```
ataccgcaca gatgcgtaag gagaaaatac cgcatcagga aattgtaaac gttaatattt   13920
tgttaaaatt cgcgttaaat ttttgttaaa tcagctcatt ttttaaccaa taggccgaaa   13980
tcggcaaaat cccttataaa tcaaaagaat agaccgagat agggttgagt gttgttccag   14040
tttggaacaa gagtccacta ttaaagaacg tggactccaa cgtcaaaggg cgaaaaaccg   14100
tctatcaggg cgatggccca ctacgtgaac catcaccta atcaagtttt ttggggtcga    14160
ggtgccgtaa agcactaaat cggaaccta aagggagccc ccgatttaga gcttgacggg    14220
gaaagccggc gaacgtggcg agaaaggaag ggaagaaagc gaaggagcg ggcgctaggg     14280 cgctggcaag tgtagcggtc acgctgcgcg taaccaccac acccgccgcg cttaatgcgc   14340
cgctacaggg cgcgtcgcgc cattcgccat tcaggctgcg caactgttgg gaagggcgat   14400
cggtgcgggc ctcttcgcta ttacgccagc tggcgaaagg gggatgtgct gcaaggcgat   14460
taagttgggt aacgccaggg ttttcccagt cacgacgttg taaaacgacg gccagtgagc   14520
gcgcgtaata cgactcacta tagggcgaat tgggtaccgg gccccccctc gaggtcgacg   14580
gtatcgataa gcttgatatc gaattcctgc agcccggggg atccactagt tctagattaa   14640
ttaa                                                                14644
```